(12) United States Patent
Frackenpohl et al.

(10) Patent No.: US 9,173,395 B2
(45) Date of Patent: Nov. 3, 2015

(54) USE OF SUBSTITUTED ISOQUINOLINONES, ISOQUINOLINDIONES, ISOQUINOLINTRIONES AND DIHYDROISOQUINOLINONES OR IN EACH CASE SALTS THEREOF AS ACTIVE AGENTS AGAINST ABIOTIC STRESS IN PLANTS

(75) Inventors: Jens Frackenpohl, Frankfurt (DE); Hans-Joachim Zeiss, I, Sulzbach (DE); Ines Heinemann, Hofheim (DE); Lothar Willms, Hofheim (DE); Thomas Mueller, Frankfurt (DE); Marco Busch, Lyons (FR); Pascal Von Koskull-Doering, Leverkusen (DE); Christopher Hugh Rosinger, Hofheim (DE); Jan Dittgen, Frankfurt (DE); Martin Jeffrey Hills, Idstein (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 0 days.

(21) Appl. No.: 14/130,640

(22) PCT Filed: Jul. 2, 2012

(86) PCT No.: PCT/EP2012/062809
§ 371 (c)(1),
(2), (4) Date: Jun. 4, 2014

(87) PCT Pub. No.: WO2013/004652
PCT Pub. Date: Jan. 10, 2013

(65) Prior Publication Data
US 2014/0302987 A1    Oct. 9, 2014

(30) Foreign Application Priority Data

Jul. 4, 2011  (EP) .................................... 11172477

(51) Int. Cl.
| | | |
|---|---|---|
| *A01N 25/32* | (2006.01) | |
| *A01N 43/42* | (2006.01) | |
| *A01N 43/90* | (2006.01) | |
| *A01N 43/38* | (2006.01) | |

(52) U.S. Cl.
CPC ................ *A01N 43/42* (2013.01); *A01N 43/38* (2013.01); *A01N 43/90* (2013.01)

(58) Field of Classification Search
None
See application file for complete search history.

(56) References Cited

U.S. PATENT DOCUMENTS

| 4,785,002 A | 11/1988 | Draber et al. |
| 5,201,931 A | 4/1993 | Abrams et al. |
| 7,323,475 B2 * | 1/2008 | Arend et al. .................... 514/310 |
| 8,188,117 B2 * | 5/2012 | Plettenburg et al. .......... 514/309 |
| 2005/0282848 A1 | 12/2005 | Jagtap et al. |
| 2008/0085890 A1 | 4/2008 | Tsou et al. |
| 2009/0069300 A1 | 3/2009 | Zhou et al. |
| 2011/0071141 A1 | 3/2011 | Murata et al. |
| 2013/0053341 A1 * | 2/2013 | Suzuki et al. .................... 514/63 |

FOREIGN PATENT DOCUMENTS

| DE | 3534948 | 4/1987 |
| DE | 4103253 | 8/1992 |
| EP | 1396488 | 3/2004 |
| WO | 97/23441 | 7/1997 |
| WO | 99/11649 | 3/1999 |
| WO | 00/04173 | 1/2000 |
| WO | 00/28055 | 5/2000 |
| WO | 02/44183 | 6/2002 |
| WO | 02/090334 | 11/2002 |
| WO | 02/094790 | 11/2002 |
| WO | 2004/009556 | 1/2004 |
| WO | 2004/024694 | 3/2004 |
| WO | 2004/031171 | 4/2004 |
| WO | 2004/090140 | 10/2004 |
| WO | 2009/112275 | 9/2009 |
| WO | 200/118765 | 10/2009 |
| WO | 2009/155402 | 12/2009 |
| WO | 2010/039079 | 4/2010 |

OTHER PUBLICATIONS

Johnson, M. Catherine et al., J. Comput. Aided Mol. Des. (2011), vol. 25 pp. 689-698.*
International Search Report for PCT/EP2012/062809 Mailed December 12, 2012.

* cited by examiner

*Primary Examiner* — Heidi Reese
(74) *Attorney, Agent, or Firm* — Miles and Stockbridge

(57) ABSTRACT

Use of substituted isoquinolinones, isoquinolinediones, isoquinolinetriones and dihydroisoquinolinones of the general formula (I) or their respective salts (I)

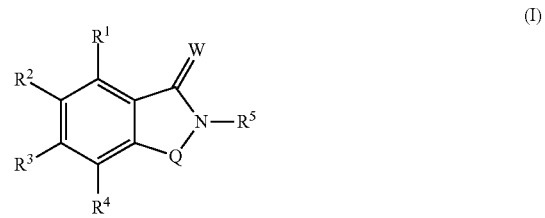

where the radicals in the general formula (I) correspond to the definitions given in the description,
for enhancing stress tolerance in plants to abiotic stress, for strengthening plant growth and/or for increasing plant yield, and selected processes for preparing the compounds mentioned above.

15 Claims, No Drawings ated to abiotic stress, for strengthening plant growth and/or for increasing plant yield, and selected processes for preparing the compounds mentioned above.

USE OF SUBSTITUTED ISOQUINOLINONES, ISOQUINOLINDIONES, ISOQUINOLINTRIONES AND DIHYDROISOQUINOLINONES OR IN EACH CASE SALTS THEREOF AS ACTIVE AGENTS AGAINST ABIOTIC STRESS IN PLANTS

The invention relates to the use of substituted isoquinolinones, isoquinolinediones, isoquinolinetriones and dihydroisoquinolinones or their respective salts for enhancing stress tolerance in plants to abiotic stress, for strengthening plant growth and/or for increasing plant yield, and selected processes for preparing the compounds mentioned above.

It is known that certain substituted isoquinolinones can be used as active compounds in connection with respiratory disorders (cf. WO2010039079). The antiinflammatory (cf. U.S. Pat. No. 7,393,955), histamine-3-antagonistic (cf. US20090069300) and β-secretase-inhibitory action (cf. WO2009044019) of substituted isoquinolinones has likewise been described. Moreover, it is known that substituted isoquinolinones can also be employed in cancer therapy, for stroke or for neurodegenerative disorders (cf. WO2002090334, WO2002094790, WO2004031171, WO2004009556, WO2004024694, EP1396488). Furthermore, it is known that fused thiazolyl- and oxazolylisoquinolinones can be used as active compounds for cardiovascular and degenerative disorders and inflammatory disorders (cf. WO2009155402), while the preparation of fused isoquinolinones of the phenanthridinone and azaphenanthridinone type and their use as pharmaceutically active compounds is described in WO200244183 and WO99/1649.

It is known that substituted isoquinolinediones and isoquinolinetriones can be used as pharmaceutically active compounds for cancer therapy (cf. U.S. Pat. No. 7,713,994). Furthermore, WO2009118765 and WO99/11649 describe the preparation of certain substituted dihydroisoquinolinones. The selectivity of certain substituted isoquinolinones and dihydroisoquinolinones at enzymes from the family of the poly(ADP-ribose) polymerase is described in Chem Med Chem 2008, 3, 914. Moreover, it is known that substituted dihydroisoquinolinones and isoquinolinediones can be used as calcium channel blockers (cf. 2010/017048).

It is also known that certain isoquinolinones and dihydroisoquinolinones substituted by partially saturated heterocycles having 5 ring members can be used as insecticidally active compounds (cf. WO 2009112275).

However, the use of the substituted isoquinolinones, isoquinolinediones, isoquinolinetriones and dihydroisoquinolinones described in the patent applications and publications cited above for increasing the stress tolerance of plants against biotic stress, for enhancing plant growth and/or for increasing plant yield has hitherto not been described.

It is known that plants can react to natural stress conditions, for example cold, heat, drought, injury, pathogenic attack (viruses, bacteria, fungi, insects), etc., but also to herbicides, with specific or unspecific defence mechanisms [Pflanzenbiochemie, p. 393-462, Spektrum Akademischer Verlag, Heidelberg, Berlin, Oxford, Hans W. Heldt, 1996; Biochemistry and Molecular Biology of Plants, p. 1102-1203, American Society of Plant Physiologists, Rockville, Md., eds. Buchanan, Gruissem, Jones, 2000].

In plants, there is knowledge of numerous proteins, and the genes which code for them, which are involved in defence reactions to abiotic stress (for example cold, heat, drought, salt, flooding). Some of these form part of signal transduction chains (for example transcription factors, kinases, phosphatases) or cause a physiological response of the plant cell (for example ion transport, deactivation of reactive oxygen species). The signalling chain genes of the abiotic stress reaction include inter alia transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and proline transporter (Hasegawa et al., 2000, Annu Rev Plant Physiol Plant Mol Biol 51: 463-499). The stress defence of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332).

Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of signalling substances which are endogenous to plants and are involved in stress tolerance or pathogenic defence are already known. Examples here include salicylic acid, benzoic acid, jasmonic acid or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defence reactions which cause elevated stress tolerance or pathogen tolerance of the plant [Sembdner, and Parthier, 1993, Ann. Rev. Plant Physiol. Plant Mol. Biol. 44: 569-589].

It is additionally known that chemical substances can increase the tolerance of plants to abiotic stress. Such substances are applied either by seed dressing, by leaf spraying or by soil treatment. For instance, an increase in the abiotic stress tolerance of crop plants by treatment with elicitors of systemic acquired resistance (SAR) or abscisic acid derivatives is described (Schading and Wei, WO200028055; Abrams and Gusta, U.S. Pat. No. 5,201,931; Abrams et al., WO97/23441, Churchill et al., 1998, Plant Growth Regul 25: 35-45). In addition, effects of growth regulators on the stress tolerance of crop plants have been described (Morrison and Andrews, 1992, J Plant Growth Regul 11: 113-117, RD-259027). In this context, it is likewise known that a growth-regulating naphthylsulphonamide (4-bromo-N-(pyridin-2-ylmethyl)naphthalene-1-sulphonamide) influences the germination of plant seeds in the same way as abscisic acid (Park et al. Science 2009, 324, 1068-1071). It is also known that a further naphthylsulphonamide, N-(6-aminohexyl)-5-chloronaphthalene-1-sulphonamide, influences the calcium level in plants which have been exposed to cold shock (Cholewa et al. Can. J. Botany 1997, 75, 375-382).

Similar effects are also observed on application of fungicides, especially from the group of the strobilurins or of the succinate dehydrogenase inhibitors, and are frequently also accompanied by an increase in yield (Draber et al., DE3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE4103253). The effect of antioxidants, for example naphthols and xanthines, to increase abiotic stress tolerance in plants has also already been described (Bergmann et al., DD277832, Bergmann et al., DD277835). However, the molecular causes of the antistress action of these substances are substantially unknown.

It is additionally known that the tolerance of plants to abiotic stress can be increased by a modification of the activity of endogeneous poly-ADP-ribose polymerases (PARP) or poly-(ADP-ribose)glycohydrolases (PARG) (de Block et al., The Plant Journal, 2004, 41, 95; Levine et al., FEBS Lett. 1998, 440, 1; WO0004173; WO04090140).

It is thus known that plants possess several endogenous reaction mechanisms which can bring about effective defence against a wide variety of different harmful organisms and/or natural abiotic stress.

Since the ecologic and economic demands on modern plant treatment compositions are increasing constantly, for example with respect to toxicity, selectivity, application rate, formation of residues and favourable manufacture, there is a constant need to develop novel plant treatment compositions which have advantages over those known, at least in some areas.

It was therefore an object of the present invention to provide further compounds which increase tolerance to abiotic stress in plants, bring about invigoration of plant growth and/or contribute to an increase in plant yield.

The present invention accordingly provides for the use of substituted isoquinolinones, isoquinolinediones, isoquinolinetriones and dihydroisoquinolinones of the general formula (I) or their respective salts (I)

for increasing tolerance to abiotic stress in plants, where Q represents

Q-1

Q-2

Q-3

Q-4

Q-5

Q-6

Q-7

Q-8

Q-9

Q-10

Q-11 or

Q-12 where $R^6$ to $R^{27}$ each have the meaning according to the definitions below and where the arrow represents a bond to the group N—$R^5$, W represents oxygen or sulphur, $A^1$ represents N—$R^{12}$ or the grouping $CHR^{13}$, where $R^{12}$ and $R^{13}$ in the groupings N—$R^{12}$ and $CHR^{13}$ each have the meaning according to the definition below, $A^2$ represents N (nitrogen) or the grouping C—$R^{16}$, where $R^{16}$ in the grouping C—$R^{16}$ in each case has the meaning according to the definition below, $A^3$ represents N (nitrogen) or the grouping C—$R^{24}$, where $R^{24}$ in the grouping C—$R^{24}$ in each case has the meaning according to the definition below, $A^4$ represents N (nitrogen) or the grouping C—$R^{25}$, where $R^{25}$ in the grouping C—$R^{25}$ in each case has the meaning according to the definition below, $R^1, R^2, R^3, R^4$ are each independently hydrogen, nitro, amino, hydroxyl, halogen, cyano, thiocyanato, isothiocyanato, alkyl, cycloalkyl, alkenyl, alkynyl, aryl, arylalkyl, arylalkenyl, arylalkynyl, heteroaryl, cycloalkylalkyl, cycloalkylalkenyl, cycloalkylalkynyl, heteroarylalkyl, heteroarylalkenyl, heteroarylalkynyl, cycloalkenyl, alkoxy(alkyl)phosphoryl, alkylthio(alkyl)phosphoryl, alkylamino(alkyl)phosphoryl, bisalkylamino(alkyl)phosphoryl, bisalkoxyphosphoryl, haloalkyl, halocycloalkyl, haloalkenyl, halocycloalkenyl, haloalkylalkynyl, hydroxyhaloalkylalkynyl, hydroxyalkylalkynyl, alkoxyalkylalkynyl, trisalkylsilylalkynyl, bisalkyl(aryl)silylalkynyl, bisaryl(alkyl)silylalkynyl, alkoxyalkyl, alkoxy, haloalkoxy, cycloalkyloxy, alkenyloxyalkyl, heteroarylalkoxy, arylalkoxy, alkoxycarbonyl, arylalkoxycarbonyl, cycloalkoxycarbonyl, cycloalkylalkoxycarbonyl, haloalkoxycarbonyl, hydroxycarbonyl, aminocarbonyl, alkylaminocarbonyl, cycloalkylaminocarbonyl, cycloalkylalkylaminocarbonyl, alkylamino, alkenylamino, alkynylamino, hydrothio, alkylthio, haloalkylthio, bisalkylamino, cycloalkylamino, alkylcarbonylamino, cycloalkylcarbonylamino, haloalkylcarbonylamino, alkoxycarbonylamino, alkoxycarbonylalkylamino, cycloalkoxycarbonylamino, cycloalkylalkoxycarbonylamino, arylalkoxycarbonylamino, alkylaminocarbonylamino, bis(alkyl)aminocarbonylamino, cycloalkylaminocarbonylamino, arylaminocarbonylamino, arylalkylaminocarbonylamino, arylaminocarbonylalkylcarbonylamino, heteroarylaminocarbonylamino, arylalkyliminoamino, alkylsulphonylamino, cycloalkylsulphonylamino, arylsulphonylamino, hetarylsulphonylamino, sulphonylhaloalkylamino, aminoalkylsulphonyl, aminohaloalkylsulphonyl, alkylsulphonyl, cycloalkylsulphonyl, arylsulphonyl, alkylsulphinyl, cycloalkylsulphinyl, arylsulphinyl, N,S-dialkylsulphonimidoyl, S-alkylsulphonimidoyl, alkylsulphonylaminocarbonyl, cycloalkylsulphonylaminocarbonyl, cycloalkylaminosulphonyl, cycloalkylalkoxy, alkynylalkoxy, alkenylalkoxy, alkenyloxyalkoxy, alkyloxyalkoxy, alkylaminoalkoxy, bisalkylaminoalkoxy, cycloalkylaminoalkoxy, heterocyclyl-N-alkoxy, arylaminocarbonylalkylcarbonylamino, alkylaminocarbonylalkylcarbonylamino, aryloxy, heteroaryloxy, aminoalkyl, aminoalkenyl, alkoxycarbonylaminoalkyl, tris(alkyl)silyl, bis(alkyl)arylsilyl, bis(alkyl)alkylsilyl, $R^2$ and $R^3$ with the atoms to which they are attached form a fully saturated, partially saturated or fully unsaturated 5- to 7-membered ring which is optionally interrupted by heteroatoms and optionally substituted further, $R^3$ and $R^4$ with the atoms to which they are attached form a fully saturated, partially saturated or fully unsaturated 5- to 7-membered ring which is optionally interrupted by heteroatoms and optionally substituted further, $R^5$ represents hydrogen, hydroxyl, alkyl, cycloalkyl, halogen, alkenylalkyl, alkynylalkyl, haloalkyl, alkoxyalkyl, alkynyl, alkenyl, cycloalkylalkyl, cyanoalkyl, nitroalkyl, arylalkyl, heteroarylalkyl, aryl, alkylamino, alkylaminoalkyl, bisalkylaminoalkyl, aminocarbonylalkyl, alkylaminocarbonylalkyl, bisalkylaminocarbonylalkyl, alkoxycarbonylalkyl, hydroxycarbonylalkyl, alkylcarbonyl, cycloalkylcarbonyl, haloalkylcarbonyl, alkoxycarbonyl, alkylsulphonyl, arylsulphonyl, cycloalkylsulphonyl, arylalkylsulphonyl, alkenylsulphonyl, heteroarylsulphonyl, alkynylsulphonyl, alkylsulphinyl, arylsulphinyl, cycloalkylsulphinyl, alkenylsulphinyl, alkynylsulphinyl, arylcarbonyl, heteroarylcarbonyl, alkoxycarbonylalkyl, cyanoalkylaminocarbonyl, alkynylaminocarbonyl, heterocyclylcarbonyl, hetaroarylalkylaminocarbonyl, alkenyloxycarbonyl, cycloalkylalkoxycarbonyl, cycloalkylalkoxycarbonylcarbonyl, alkoxycarbonylcarbonyl, cycloalkylalkylaminocarbonyl, arylalkylaminocarbonyl or a negative charge, $R^6$ represents hydrogen, hydroxyl, nitro, halogen, amino, alkyl, cycloalkyl, alkylcarbonyl, arylcarbonyl, alkylaminocarbonyl, bisalkylaminocarbonyl, cycloalkylaminocarbonyl, cycloalkenylaminocarbonyl, cycloalkyl(alkyl)aminocarbonyl, alkyl(alkyl)aminocarbonyl, cycloalkylalkylaminocarbonyl, cycloalkylalkyl(alkyl)aminocarbonyl, alkyl(alkynyl)aminocarbonyl, alkynylaminocarbonyl, arylaminocarbonyl, heteroarylaminocarbonyl, alkenylaminocarbonyl, cyanoalkylaminocarbonyl, arylalkylaminocarbonyl, aryl(alkyl)aminocarbonyl, heteroaryl(alkyl)aminocarbonyl, heterocyclyl-N-carbonyl, alkoxycarbonylheterocyclyl-N-carbonyl, alkoxycarbonylalkylaminocarbonyl, hydroxycarbonylheterocyclyl-N-carbonyl, hydroxycarbonylalkylaminocarbonyl, cycloalkoxycarbonylheterocyclyl-N-carbonyl, cycloalkoxycarbonylalkylaminocarbonyl, alkylaminocarbonylalkylaminocarbonyl, aminocarbonylalkylaminocarbonyl, cycloalkylaminocarbonylalkylaminocarbonyl, bisalkylaminoalkylaminocarbonyl, bisalkylaminocarbonylalkylaminocarbonyl, alkylaminocarbonylalkylaminocarbonyl, heterocyclyl-N-carbonylalkylaminocarbonyl, cycloalkyl-N-heterocyclyl-N-carbonyl, alkoxy(alkyl)aminocarbonyl, alkoxycarbonylamino, hydroxycarbonyl, alkoxycarbonyl, cycloalkyloxycarbonyl, cycloalkylalkoxycarbonyl, alkyloxyalkoxycarbonyl, alkoxycarbonylalkoxycarbonyl, alkenyloxycarbonyl, alkynyloxycarbonyl, hydroxycarbonylalkoxycarbonyl, haloalkoxycarbonyl, aryl(alkyl)aminocarbonylamino, arylaminocarbonylamino, alkylaminocarbonylamino, heteroarylaminocarbonylamino, alkoxy, alkylaminoalkoxy, alkylcarbonyloxy, arylcarbonyloxy, alkenylalkyl, alkynylalkyl, haloalkyl, alkoxyalkyl, alkynyl, alkenyl, aryl, heteroaryl, heterocyclyl, alkoxycarbonylalkyl, alkylamino, bisalkylamino, cycloalkylamino, arylalkylamino, $R^7$ represents hydrogen, halogen, amino, alkyl, haloalkyl, cycloalkyl, alkylcarbonyl, arylcarbonyl, heteroarylcarbonyl, cycloalkylcarbonyl, alkoxycarbonyl, hydroxycarbonyl, aryl, heteroaryl, arylcarbonylalkoxycarbonyl, alkylcarbonylalkoxycarbonyl, cycloalkylalkoxycarbonyl, heteroarylalkoxycarbonyl, heteroarylalkylalkoxycarbonyl, heteroarylheteroarylalkylalkoxycarbonyl, arylalkoxycarbonyl, alkylcarbonyloxy, arylaminocarbonyl, alkylaminocarbonyl, bisalkylaminocarbonyl, cycloalkylaminocarbonyl, heterocyclyl-N-carbonyl, arylalkylaminocarbonyl, cyanoalkylaminocarbonyl, alkenylaminocarbonyl, bis(alkoxycarbonyl)alkenylamino, biscyanoalkenylamino, alkoxycarbonyl(cyano)alkenylamino, alkylamino, arylamino, cycloalkylamino, aryl(alkyl)amino, bisalkylamino, $R^8$ represents hydrogen, alkyl, haloalkyl, cycloalkyl, halogen, $R^9$ represents hydrogen, alkyl, haloalkyl, cycloalkyl, halogen, $R^{10}$, $R^{11}$ independently of one another represent hydrogen, halogen, alkyl, cycloalkyl, haloalkyl, arylalkyl, heteroarylalkyl, alkylcarbonyl, arylalkylcarbonyl, cycloalkylcarbonyl, cycloalkylalkylcarbonyl, arylcarbonyl, heteroarylcarbonyl, arylaminocarbonyl, alkylaminocarbonyl, alkynyl, alkenyl, haloalkenyl, $R^{12}$ represents hydroxyl, alkoxy, alkenyloxy, arylalkoxy, alkylamino, arylamino, heteroarylamino, heteroarylcarbonylamino, arylcarbonylamino, $R^{13}$ represents hydrogen, alkoxy, alkenyloxy, aryl, heteroaryl, heteroarylamino, arylamino, bisalkylaminoalkylamino, alkylamino, $R^{14}$, $R^{15}$ independently of one another represent hydrogen, alkyl, cycloalkyl, haloalkyl, alkylcarbonyl, cycloalkylcarbonyl, cycloalkylalkylcarbonyl, arylcarbonyl, heteroarylcarbonyl, alkoxycarbonyl, hydroxycarbonyl, alkoxy, arylalkyl, heteroarylalkyl, alkylaminocarbonyl, alkenylaminocarbonyl, alkynylalkylaminocarbonyl, cyanoalkylaminocarbonyl, cycloalkylaminocarbonyl, $R^{16}$, $R^{17}$, $R^{18}$, $R^{19}$ independently of one another represent hydrogen, halogen, nitro, amino, cyano, thiocyanato, isothiocyanato, hydroxyl, hydrothio, alkyl, cycloalkyl, alkoxy, haloalkyl, haloalkylthio, alkylthio, haloalkoxy, alkylamino, heteroarylalkylamino, arylalkylamino, cycloalkylamino, alkylcarbonylamino, bis(alkyl)aminoalkylcarbonylamino, arylalkylcarbonylamino, cycloalkylcarbonylamino, cycloalkylalkylcarbonylamino, alkyl-N-heterocyclyl-N, alkyl-N-heterobicycloalkyl-N, bisalkylaminoalkylamino, hydroxycarbonyl, alkoxycarbonyl, alkylaminocarbonyl, cycloalkylaminocarbonyl, arylalkylaminocarbonyl, arylsulphonylamino, alkylsulphonylamino, cyclopropylsulphonylamino, alkoxycarbonylamino, alkoxycarbonylalkylamino, cycloalkoxycarbonylamino, cycloalkylalkoxycarbonylamino, arylalkoxycarbonylamino, alkylaminocarbonylamino, bis(alkyl)aminocarbonylamino, cycloalkylaminocarbonylamino, arylaminocarbonylamino, arylalkylaminocarbonylamino, arylaminocarbonylalkylcarbonylamino, heteroarylaminocarbonylamino, arylalkyliminoamino, heterocyclyl-N-carbonyl, alkoxycarbonylheterocyclyl-N-carbonyl, alkoxycarbonylalkylaminocarbonyl, hydroxycarbonylheterocyclyl-N-carbonyl, hydroxycarbonylalkylaminocarbonyl, cycloalkoxycarbonylheterocyclyl-N-carbonyl, cycloalkoxycarbonylalkylaminocarbonyl, alkylaminocarbonylalkylaminocarbonyl, aminocarbonylalkylaminocarbonyl, cycloalkylaminocarbonylalkylaminocarbonyl, bisalkylaminoalkylaminocarbonyl, bisalkylaminocarbonylalkylaminocarbonyl, alkylaminocarbonylalkylaminocarbonyl, heterocyclyl-N-carbonylalkylaminocarbonyl, cycloalkyl-N-heterocyclyl-N-carbonyl, alkoxy(alkyl)aminocarbonyl, $R^{20}$, $R^{21}$, $R^{22}$, $R^{23}$ independently of one another represent hydrogen, alkyl, cycloalkyl, haloalkyl, and $R^{24}$, $R^{25}$, $R^{26}$, $R^{27}$ independently of one another represent hydrogen, halogen, nitro, alkyl, cycloalkyl, alkoxy, haloalkyl, haloalkylthio, alkylthio, haloalkoxy, alkylamino, heteroarylalkylamino, arylalkylamino, cycloalkylamino, hydroxycarbonyl, alkoxycarbonyl, alkylaminocarbonyl, cycloalkylaminocarbonyl, arylalkylaminocarbonyl, aryl, heteroaryl, cycloalkoxycarbonyl, cycloalkylalkoxycarbonyl, alkenyloxycarbonyl, alkenylaminocarbonyl, alkynyloxycarbonyl, alkynylaminocarbonyl, alkenyl, alkynyl, aminosulphonyl, alkylsulphonylamino, cycloalkylsulphonylamino, arylsulphonylamino, hetarylsulphonylamino, sulphonylhaloalkylamino, aminoalkylsulphonyl, aminohaloalkylsulphonyl, alkylsulphonyl, cycloalkylsulphonyl, arylsulphonyl, alkylsulphinyl, cycloalkylsulphinyl, arylsulphinyl, cycloalkoxy.

The compounds of the general formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulphonic acids, for example p-toluenesulphonic acid, onto a basic group, for example amino, alkylamino, dialkylamino, piperidino, morpholino or pyridino. These salts then contain the conjugated base of the acid as anion.

Suitable substituents present in deprotonated form, such as, for example, sulphonic acids or carboxylic acids, may form inner salts with groups which for their part can be protonated, such as amino groups. The compounds of the formula (I) used in accordance with the invention and salts thereof are referred to hereinafter as "compounds of the general formula (I)".

Preference is given to the inventive use of compounds of the general formula (I) or salts thereof, in which Q represents

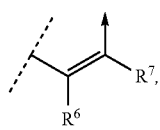
Q-1

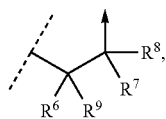
Q-2

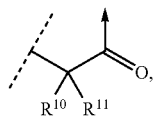
Q-3

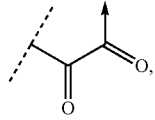
Q-4

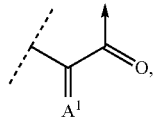
Q-5

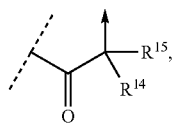
Q-6

-continued

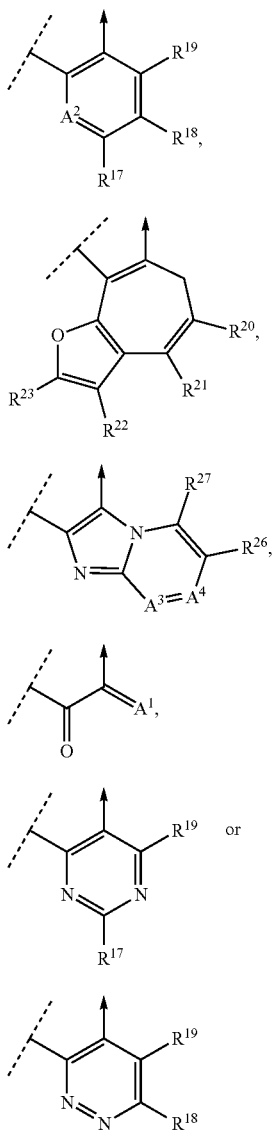

where R[6] to R[27] each have the meaning according to the definitions below and where the arrow represents a bond to the group N—R[5], W represents oxygen or sulphur, A[1] represents N—R[12] or the grouping CHR[13], where R[12] and R[13] in the groupings N—R[12] and CHR[13] each have the meaning according to the definition below, A[2] represents N (nitrogen) or the grouping C—R[16], where R[16] in the grouping C—R[16] in each case has the meaning according to the definition below, A[3] represents N (nitrogen) or the grouping C—R[24], where R[24] in the grouping C—R[24] in each case has the meaning according to the definition below, A[4] represents N (nitrogen) or the grouping C—R[25], where R[25] in the grouping C—R[25] in each case has the meaning according to the definition below, R[1], R[2], R[3], R[4] are each independently hydrogen, nitro, amino, hydroxyl, halogen, cyano, thiocyanato, isothiocyanato, $(C_1-C_8)$-alkyl, $(C_3-C_8)$-cycloalkyl, $(C_2-C_8)$-alkenyl, $(C_2-C_8)$-alkynyl, aryl, aryl-$(C_1-C_8)$-alkyl, aryl-$(C_2-C_8)$-alkenyl, aryl-$(C_2-C_8)$-alkynyl, heteroaryl, $(C_3-C_8)$-cycloalkyl-$(C_1-C_8)$-alkyl, $(C_{3-8})$-cycloalkyl-$(C_2-C_8)$-alkenyl, $(C_3-C_8)$-cycloalkyl-$(C_2-C_8)$-alkynyl, heteroaryl-$(C_1-C_8)$-alkyl, heteroaryl-$(C_2-C_8)$-alkenyl, heteroaryl-$(C_2-C_8)$-alkynyl, $(C_5-C_8)$-cycloalkenyl, $(C_1-C_8)$-alkoxy[$(C_1-C_8)$-alkyl]phosphoryl, $(C_1-C_8)$-alkylthio[$(C_1-C_8)$-alkyl]phosphoryl, $(C_1-C_8)$-alkylamino[$(C_1-C_8)$-alkyl]phosphoryl, bis-[$(C_1-C_8)$-alkyl]amino[$(C_1-C_8)$-alkyl]phosphoryl, bis-[$(C_1-C_8)$-alkoxy]phosphoryl, $(C_1-C_8)$-haloalkyl, $(C_3-C_8)$-halocycloalkyl, $(C_2-C_8)$-haloalkenyl, $(C_3-C_8)$-halocycloalkenyl, $(C_1-C_8)$-haloalkyl-$(C_2-C_8)$-alkynyl, hydroxy-$(C_1-C_8)$-haloalkyl-$(C_2-C_8)$-alkynyl, hydroxy-$(C_1-C_8)$-alkyl-$(C_2-C_8)$-alkynyl, $(C_1-C_8)$-alkoxy-$(C_1-C_8)$-alkyl-$(C_2-C_8)$-alkynyl, tris-[$(C_1-C_8)$-alkyl]silyl-$(C_1-C_8)$-alkynyl, bis-[$(C_1-C_8)$-alkyl]arylsilyl-$(C_2-C_8)$-alkynyl, bis-aryl-[$(C_1-C_8)$-alkyl]silyl-$(C_1-C_8)$-alkynyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, $(C_2-C_8)$-alkenyloxy-$(C_1-C_8)$-alkyl, heteroaryl-$(C_1-C_8)$-alkoxy, aryl-$(C_1-C_8)$-alkoxy, $(C_1-C_8)$-alkoxycarbonyl, aryl-$(C_1-C_8)$-alkoxycarbonyl, $(C_3-C_8)$-cycloalkoxycarbonyl, $(C_3-C_8)$-cycloalkyl-$(C_1-C_8)$-alkoxycarbonyl, $(C_1-C_8)$-haloalkoxycarbonyl, hydroxycarbonyl, aminocarbonyl, $(C_1-C_8)$-alkylaminocarbonyl, $(C_3-C_8)$-cycloalkylaminocarbonyl, $(C_3-C_8)$-cycloalkyl-$(C_1-C_8)$-alkylaminocarbonyl, $(C_1-C_8)$-alkylamino, $(C_2-C_8)$-alkenylamino, $(C_2-C_8)$-alkynylamino, hydrothio, $(C_1-C_8)$-alkylthio, $(C_1-C_8)$-haloalkylthio, bis-$(C_1-C_8)$-alkylamino, $(C_3-C_8)$-cycloalkylamino, $(C_1-C_8)$-alkylcarbonylamino, $(C_3-C_8)$-cycloalkylcarbonylamino, $(C_1-C_8)$-haloalkylcarbonylamino, $(C_1-C_8)$-alkoxycarbonylamino, $(C_1-C_8)$-alkoxycarbonyl-$(C_1-C_8)$-alkylamino, $(C_3-C_8)$-cycloalkoxycarbonylamino, $(C_3-C_8)$-cycloalkyl-$(C_1-C_8)$-alkoxycarbonylamino, aryl-$(C_1-C_8)$-alkoxycarbonylamino, $(C_1-C_8)$-alkylaminocarbonylamino, bis-[$(C_1-C_8)$-alkyl]aminocarbonylamino, $(C_3-C_8)$-cycloalkylaminocarbonylamino, arylaminocarbonylamino, aryl-$(C_1-C_8)$-alkylaminocarbonylamino, arylaminocarbonyl-$(C_1-C_8)$-alkylcarbonylamino, heteroarylaminocarbonylamino, aryl-$(C_1-C_8)$-alkyliminoamino, $(C_1-C_8)$-alkylsulphonylamino, $(C_3-C_8)$-cycloalkylsulphonylamino, arylsulphonylamino, hetarylsulphonylamino, sulphonyl-$(C_1-C_8)$-haloalkylamino, amino-$(C_1-C_8)$-alkylsulphonyl, amino-$(C_1-C_8)$-haloalkylsulphonyl, $(C_1-C_8)$-alkylsulphonyl, $(C_3-C_8)$-cycloalkylsulphonyl, arylsulphonyl, $(C_1-C_8)$-alkylsulphinyl, $(C_3-C_8)$-cycloalkylsulphinyl, arylsulphinyl, N,S-di-$(C_1-C_8)$-alkylsulphonimidoyl, S—$(C_1-C_8)$-alkylsulphonimidoyl, $(C_1-C_8)$-alkylsulphonylaminocarbonyl, $(C_3-C_8)$-cycloalkylsulphonylaminocarbonyl, $(C_3-C_8)$-cycloalkylaminosulphonyl, $(C_3-C_8)$-cycloalkyl-$(C_1-C_8)$-alkoxy, $(C_2-C_8)$-alkynyl-$(C_1-C_8)$-alkoxy, $(C_2-C_8)$-alkenyl-$(C_1-C_8)$-alkoxy, $(C_2-C_8)$-alkenyloxy-$(C_1-C_8)$-alkoxy, $(C_1-C_8)$-alkoxy-$(C_1-C_8)$-alkoxy, $(C_1-C_8)$-alkylamino-$(C_1-C_8)$-alkoxy, bis-$(C_1-C_8)$-alkylamino-$(C_1-C_8)$-alkoxy, $(C_3-C_8)$-cycloalkylamino-$(C_1-C_8)$-alkoxy, heterocyclyl-N—$(C_1-C_8)$-alkoxy, arylaminocarbonyl-$(C_1-C_8)$-alkylcarbonylamino, $(C_1-C_8)$-alkylaminocarbonyl-$(C_1-C_8)$-alkylcarbonylamino, aryloxy, heteroaryloxy, amino-$(C_1-C_8)$-alkyl, amino-$(C_2-C_8)$-alkenyl, $(C_1-C_8)$-alkoxycarbonylamino-$(C_1-C_8)$-alkyl, tris-[$(C_1-C_8)$-alkyl]silyl, bis-[$(C_1-C_8)$-alkyl]arylsilyl, bis-[$(C_1-C_8)$-alkyl]-$(C_1-C_8)$-alkylsilyl, R[2] and R[3] with the atoms to which they are attached form a fully saturated, partially saturated or fully unsaturated 5- to 7-membered ring which is optionally interrupted by heteroatoms and optionally substituted further, $R^3$ and $R^4$ with the atoms to which they are attached form a fully saturated, partially saturated or fully unsaturated 5- to 7-membered ring which is optionally interrupted by heteroatoms and optionally substituted further, $R^5$ represents hydrogen, hydroxy, $(C_1-C_8)$-alkyl, $(C_3-C_8)$-cycloalkyl, halogen, $(C_2-C_8)$-alkenyl-$(C_1-C_8)$-alkyl, $(C_2-C_8)$-alkynyl-$(C_1-C_8)$-alkyl, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, $(C_3-C_8)$-cycloalkyl-$(C_1-C_8)$-alkyl, cyano-$(C_1-C_8)$-alkyl, nitro-$(C_1-C_8)$-alkyl, aryl-$(C_1-C_8)$-alkyl, heteroaryl-$(C_1-C_8)$-alkyl, aryl, $(C_1-C_8)$-alkylamino, $(C_1-C_8)$-alkylamino-$(C_1-C_8)$-alkyl, bis-[$(C_1-C_8)$-alkyl]amino-$(C_1-C_8)$-alkyl, aminocarbonyl-$(C_1-C_8)$-alkyl, $(C_1-C_8)$-alkylaminocarbonyl-$(C_1-C_8)$-alkyl, bis-[$(C_1-C_8)$-alkyl]aminocarbonyl-$(C_1-C_8)$-alkyl, $(C_1-C_8)$-alkoxycarbonyl-$(C_1-C_8)$-alkyl, hydroxycarbonyl-$(C_1-C_8)$-alkyl, $(C_1-C_8)$-alkylcarbonyl, $(C_3-C_8)$-cycloalkylcarbonyl, $(C_1-C_8)$-haloalkylcarbonyl, $(C_1-C_8)$-alkoxycarbonyl, $(C_1-C_8)$-alkylsulphonyl, arylsulphonyl, $(C_3-C_8)$-cycloalkylsulphonyl, aryl-$(C_1-C_8)$-alkylsulphonyl, $(C_2-C_8)$-alkenylsulphonyl, heteroarylsulphonyl, $(C_2-C_8)$-alkynylsulphonyl, $(C_1-C_8)$-alkylsulphinyl, arylsulphinyl, $(C_3-C_8)$-cycloalkylsulphinyl, $(C_2-C_8)$-alkenylsulphinyl, $(C_2-C_8)$-alkynylsulphinyl, arylcarbonyl, heteroarylcarbonyl, $(C_1-C_8)$-alkoxycarbonyl-$(C_1-C_8)$-alkyl, cyano-$(C_1-C_8)$-alkylaminocarbonyl, $(C_2-C_8)$-alkynylaminocarbonyl, heterocyclylcarbonyl, hetaroaryl-$(C_1-C_8)$-alkylaminocarbonyl, $(C_2-C_8)$-alkenyloxycarbonyl, $(C_3-C_8)$-cycloalkyl-$(C_1-C_8)$-alkoxycarbonyl, $(C_3-C_8)$-cycloalkyl-$(C_1-C_8)$-alkoxycarbonylcarbonyl, $(C_1-C_8)$-alkoxycarbonylcarbonyl, $(C_3-C_8)$-cycloalkyl-$(C_1-C_8)$-alkylaminocarbonyl, aryl-$(C_1-C_8)$-alkylaminocarbonyl or a negative charge, $R^6$ represents hydrogen, hydroxy, nitro, halogen, amino, $(C_1-C_8)$-alkyl, $(C_3-C_8)$-cycloalkyl, $(C_1-C_8)$-alkylcarbonyl, arylcarbonyl, $(C_1-C_8)$-alkylaminocarbonyl, bis-$(C_1-C_8)$-alkylaminocarbonyl, $(C_3-C_8)$-cycloalkylaminocarbonyl, $(C_4-C_8)$-cycloalkenylaminocarbonyl, $(C_3-C_8)$-cycloalkyl-[$(C_1-C_8)$-alkyl]aminocarbonyl, $(C_1-C_8)$-alkyl-[$(C_1-C_8)$-alkyl]aminocarbonyl, $(C_3-C_8)$-cycloalkyl-$(C_1-C_8)$-alkylaminocarbonyl, $(C_3-C_8)$-cycloalkyl-$(C_1-C_8)$-alkyl[$(C_1-C_8)$-alkyl]aminocarbonyl, $(C_1-C_8)$-alkyl[$(C_2-C_8)$-alkynyl]aminocarbonyl, $(C_1-C_8)$-alkynylaminocarbonyl, arylaminocarbonyl, heteroarylaminocarbonyl, $(C_2-C_8)$-alkenylaminocarbonyl, cyano-$(C_1-C_8)$-alkylaminocarbonyl, aryl-$(C_1-C_8)$-alkylaminocarbonyl, aryl[$(C_1-C_8)$-alkyl]aminocarbonyl, heteroaryl[$(C_1-C_8)$-alkyl]aminocarbonyl, heterocyclyl-N-carbonyl, $(C_1-C_8)$-alkoxycarbonylheterocyclyl-N-carbonyl, $(C_1-C_8)$-alkoxycarbonyl-$(C_1-C_8)$-alkylaminocarbonyl, hydroxycarbonylheterocyclyl-N-carbonyl, hydroxycarbonyl-$(C_1-C_8)$-alkylaminocarbonyl, $(C_3-C_8)$-cycloalkoxycarbonylheterocyclyl-N-carbonyl, $(C_3-C_8)$-cycloalkoxycarbonyl-$(C_1-C_8)$-alkylaminocarbonyl, $(C_1-C_8)$-alkylaminocarbonyl-$(C_1-C_8)$-alkylaminocarbonyl, aminocarbonyl-$(C_1-C_8)$-alkylaminocarbonyl, $(C_3-C_8)$-cycloalkylaminocarbonyl-$(C_1-C_8)$-alkylaminocarbonyl, bis-$(C_1-C_8)$-alkylamino-$(C_1-C_8)$-alkylaminocarbonyl, bis-$(C_1-C_8)$-alkylaminocarbonyl-$(C_1-C_8)$-alkylaminocarbonyl, $(C_1-C_8)$-alkylaminocarbonyl-$(C_1-C_8)$-alkylaminocarbonyl, heterocyclyl-N-carbonyl-$(C_1-C_8)$-alkylaminocarbonyl, $(C_3-C_8)$-cycloalkyl-N-heterocyclyl-N-carbonyl, $(C_1-C_8)$-alkoxy[$(C_1-C_8)$-alkyl]aminocarbonyl, $(C_1-C_8)$-alkoxycarbonylamino, hydroxycarbonyl, $(C_1-C_8)$-alkoxycarbonyl, $(C_1-C_8)$-cycloalkoxycarbonyl, $(C_1-C_8)$-cycloalkyl-$(C_1-C_8)$-alkoxycarbonyl, $(C_1-C_8)$-alkoxy-$(C_1-C_8)$-alkoxycarbonyl, $(C_1-C_8)$-alkoxycarbonyl-$(C_1-C_8)$-alkoxycarbonyl, $(C_2-C_8)$-alkenyloxycarbonyl, $(C_2-C_8)$-alkynyloxycarbonyl, hydroxycarbonyl-$(C_1-C_8)$-alkoxycarbonyl, $(C_1-C_8)$-haloalkoxycarbonyl, aryl[$(C_1-C_8)$-alkyl]aminocarbonylamino, arylaminocarbonylamino, $(C_1-C_8)$-alkylaminocarbonylamino, heteroarylaminocarbonylamino, $(C_1-C_8)$-alkoxy, $(C_1-C_8)$-alkylamino-$(C_1-C_8)$-alkoxy, $(C_1-C_8)$-alkylcarbonyloxy, arylcarbonyloxy, $(C_2-C_8)$-alkenyl-$(C_1-C_8)$-alkyl, $(C_2-C_8)$-alkynyl-$(C_1-C_8)$-alkyl, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, aryl, heteroaryl, $(C_1-C_8)$-alkoxycarbonyl-$(C_1-C_8)$-alkyl, $(C_1-C_8)$-alkylamino, bis-$(C_1-C_8)$-alkylamino, $(C_3-C_8)$-cycloalkylamino, aryl-$(C_1-C_8)$-alkylamino, $R^7$ represents hydrogen, halogen, amino, $(C_1-C_8)$-alkyl, $(C_1-C_8)$-haloalkyl, $(C_3-C_8)$-cycloalkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, hydroxycarbonyl, aryl, heteroaryl, arylcarbonyl-$(C_1-C_8)$-alkoxycarbonyl, $(C_1-C_8)$-alkylcarbonyl-$(C_1-C_8)$-alkoxycarbonyl, $(C_3-C_8)$-cycloalkyl-$(C_1-C_8)$-alkoxycarbonyl, heteroaryl-$(C_1-C_8)$-alkoxycarbonyl, heteroarylheteroaryl$(C_1-C_8)$-alkyl-$(C_1-C_8)$-alkoxycarbonyl, heteroaryl$(C_1-C_8)$-alkyl-$(C_1-C_8)$-alkoxycarbonyl, aryl-$(C_1-C_8)$-alkoxycarbonyl, $(C_1-C_8)$-alkylcarbonyloxy, arylaminocarbonyl, $(C_1-C_8)$-alkylaminocarbonyl, bis-$(C_1-C_8)$-alkylaminocarbonyl, $(C_3-C_8)$-cycloalkylaminocarbonyl, heterocyclyl-N-carbonyl, aryl-$(C_1-C_8)$-alkylaminocarbonyl, cyano-$(C_1-C_8)$-alkylaminocarbonyl, $(C_2-C_8)$-alkenylaminocarbonyl, bis-[$(C_1-C_8)$-alkoxycarbonyl]-$(C_2-C_8)$-alkenylamino, bis-cyano-$(C_1-C_8)$-alkenylamino, $(C_1-C_8)$-alkoxycarbonyl (cyano)-$(C_2-C_8)$-alkenylamino, $(C_1-C_8)$-alkylamino, arylamino, $(C_3-C_8)$-cycloalkylamino, aryl[$(C_1-C_8)$-alkyl]amino, bis-$(C_1-C_8)$-alkylamino, $R^8$ represents hydrogen, $(C_1-C_8)$-alkyl, $(C_1-C_8)$-haloalkyl, $(C_3-C_8)$-cycloalkyl, halogen, $R^9$ represents hydrogen, $(C_1-C_8)$-alkyl, $(C_1-C_8)$-haloalkyl, $(C_3-C_8)$-cycloalkyl, halogen, $R^{10}$, $R^{11}$ independently of one another represent hydrogen, halogen, $(C_1-C_8)$-alkyl, $(C_3-C_8)$-cycloalkyl, $(C_1-C_8)$-haloalkyl, aryl-$(C_1-C_8)$-alkyl, heteroaryl-$(C_1-C_8)$-alkyl, $(C_1-C_8)$-alkylcarbonyl, aryl-$(C_1-C_8)$-alkylcarbonyl, $(C_3-C_8)$-cycloalkylcarbonyl, $(C_3-C_8)$-cycloalkyl-$(C_1-C_8)$-alkylcarbonyl, arylcarbonyl, heteroarylcarbonyl, arylaminocarbonyl, $(C_1-C_8)$-alkylaminocarbonyl, $(C_2-C_8)$-alkynyl, $(C_2-C_8)$-alkenyl, $(C_2-C_8)$-haloalkenyl, $R^{12}$ represents hydroxyl, $(C_1-C_8)$-alkoxy, $(C_2-C_8)$-alkenyloxy, aryl-$(C_1-C_8)$-alkoxy, $(C_1-C_8)$-alkylamino, arylamino, heteroarylamino, heteroarylcarbonylamino, arylcarbonylamino, $R^{13}$ represents hydrogen, $(C_1-C_8)$-alkoxy, $(C_2-C_8)$-alkenyloxy, aryl, heteroaryl, heteroarylamino, arylamino, bis-$(C_1-C_8)$-alkylamino-$(C_1-C_8)$-alkylamino, $(C_1-C_8)$-alkylamino, $R^{14}$, $R^{15}$ independently of one another represent hydrogen, $(C_1-C_8)$-alkyl, $(C_3-C_8)$-cycloalkyl, $(C_1-C_8)$-haloalkyl, $(C_1-C_8)$-alkylcarbonyl, $(C_3-C_8)$-cycloalkylcarbonyl, $(C_3-C_8)$-cycloalkyl-$(C_1-C_8)$-alkylcarbonyl, arylcarbonyl, heteroarylcarbonyl, $(C_1-C_8)$-alkoxycarbonyl, hydroxycarbonyl, $(C_1-C_8)$-alkoxy, aryl-$(C_1-C_8)$-alkyl, heteroaryl-$(C_1-C_8)$-alkyl, $(C_1-C_8)$-alkylaminocarbonyl, $(C_2-C_8)$-alkenylaminocarbonyl, $(C_2-C_8)$-alkynyl-$(C_1-C_8)$-alkylaminocarbonyl, cyano-$(C_1-C_8)$-alkylaminocarbonyl, $(C_3-C_8)$-cycloalkylaminocarbonyl, $R^{16}$, $R^{17}$, $R^{18}$, $R^{19}$ independently of one another represent hydrogen, halogen, nitro, amino, cyano, thiocyanato, isothiocyanato, hydroxy, hydrothio, $(C_1-C_8)$-alkyl, $(C_3-C_8)$-cycloalkyl, $(C_1-C_8)$-alkoxy, $(C_1-C_8)$-haloalkyl, $(C_1-$ $C_8$)-haloalkylthio, $(C_1-C_8)$-alkylthio, $(C_1-C_8)$-haloalkoxy, $(C_1-C_8)$-alkylamino, heteroaryl-$(C_1-C_8)$-alkylamino, aryl-$(C_1-C_8)$-alkylamino, $(C_3-C_8)$-cycloalkylamino, $(C_1-C_8)$-alkylcarbonylamino, bis-[$(C_1-C_8)$-alkyl]amino-$(C_1-C_8)$-alkylcarbonylamino, aryl-$(C_1-C_8)$-alkylcarbonylamino, $(C_3-C_8)$-cycloalkylcarbonylamino, $(C_3-C_8)$-cycloalkyl-$(C_1-C_8)$-alkylcarbonylamino $(C_1-C_8)$-alkyl-N-heterocyclyl-N, $(C_1-C_8)$-alkyl-N-heterobicyclyl-N, bis-$(C_1-C_8)$-alkylamino-$(C_1-C_8)$-alkylamino, hydroxycarbonyl, $(C_1-C_8)$-alkoxycarbonyl, $(C_1-C_8)$-alkylaminocarbonyl, $(C_3-C_8)$-cycloalkylaminocarbonyl, aryl-$(C_1-C_8)$-alkylaminocarbonyl, arylsulphonylamino, $(C_1-C_8)$-alkylsulphonylamino, $(C_3-C_8)$-cycloalkylsulphonylamino, $(C_1-C_8)$-alkoxycarbonylamino, $(C_1-C_8)$-alkoxycarbonyl-$(C_1-C_8)$-alkylamino, $(C_3-C_8)$-cycloalkoxycarbonylamino, $(C_3-C_8)$-cycloalkyl-$(C_1-C_8)$-alkoxycarbonylamino, aryl-$(C_1-C_8)$-alkoxycarbonylamino, $(C_1-C_8)$-alkylaminocarbonylamino, bis-[$(C_1-C_8)$-alkyl]aminocarbonylamino, $(C_3-C_8)$-cycloalkylaminocarbonylamino, arylaminocarbonylamino, aryl-$(C_1-C_8)$-alkylaminocarbonylamino, arylaminocarbonyl-$(C_1-C_8)$-alkylcarbonylamino, heteroarylaminocarbonylamino, aryl-$(C_1-C_8)$-alkyliminoamino, heterocyclyl-N-carbonyl, $(C_1-C_8)$-alkoxycarbonylheterocyclyl-N-carbonyl, $(C_1-C_8)$-alkoxycarbonyl-$(C_1-C_8)$-alkylaminocarbonyl, hydroxycarbonylheterocyclyl-N-carbonyl, hydroxycarbonyl-$(C_1-C_8)$-alkylaminocarbonyl, $(C_3-C_8)$-cycloalkoxycarbonylheterocyclyl-N-carbonyl, $(C_3-C_8)$-cycloalkoxycarbonyl-$(C_1-C_8)$-alkylaminocarbonyl, $(C_1-C_8)$-alkylaminocarbonyl-$(C_1-C_8)$-alkylaminocarbonyl, aminocarbonyl-$(C_1-C_8)$-alkylaminocarbonyl, $(C_3-C_8)$-cycloalkylaminocarbonyl-$(C_1-C_8)$-alkylaminocarbonyl, bis-$(C_1-C_8)$-alkylamino-$(C_1-C_8)$-alkylaminocarbonyl, bis-$(C_1-C_8)$-alkylaminocarbonyl-$(C_1-C_8)$-alkylaminocarbonyl, $(C_1-C_8)$-alkylaminocarbonyl-$(C_1-C_8)$-alkylaminocarbonyl, heterocyclyl-N-carbonyl-$(C_1-C_8)$-alkylaminocarbonyl, $(C_3-C_8)$-cycloalkyl-N-heterocyclyl-N-carbonyl, $(C_1-C_8)$-alkoxy[$(C_1-C_8)$-alkyl]aminocarbonyl, $R^{20}$, $R^{21}$, $R^{22}$, $R^{23}$ independently of one another represent hydrogen, $(C_1-C_8)$-alkyl, $(C_3-C_8)$-cycloalkyl, $(C_1-C_8)$-haloalkyl, and $R^{24}$, $R^{25}$, $R^{26}$, $R^{27}$ independently of one another represent hydrogen, halogen, nitro, $(C_1-C_8)$-alkyl, $(C_3-C_8)$-cycloalkyl, $(C_1-C_8)$-alkoxy, $(C_1-C_8)$-haloalkyl, $(C_1-C_8)$-haloalkylthio, $(C_1-C_8)$-alkylthio, $(C_1-C_8)$-haloalkoxy, $(C_1-C_8)$-alkylamino, heteroaryl-$(C_1-C_8)$-alkylamino, aryl-$(C_1-C_8)$-alkylamino, $(C_3-C_8)$-cycloalkylamino, hydroxycarbonyl, $(C_1-C_8)$-alkoxycarbonyl, $(C_1-C_8)$-alkylaminocarbonyl, $(C_3-C_8)$-cycloalkylaminocarbonyl, aryl-$(C_1-C_8)$-alkylaminocarbonyl, aryl, heteroaryl, $(C_3-C_8)$-cycloalkoxycarbonyl, $(C_3-C_8)$-cycloalkyl-$(C_1-C_8)$-alkoxycarbonyl, $(C_2-C_8)$-alkenyloxycarbonyl, $(C_2-C_8)$-alkenylaminocarbonyl, $(C_2-C_8)$-alkynyloxycarbonyl, $(C_2-C_8)$-alkynylaminocarbonyl, $(C_2-C_8)$-alkenyl, $(C_2-C_8)$-alkynyl, aminosulphonyl, $(C_1-C_8)$-alkylsulphonylamino, $(C_3-C_8)$-cycloalkylsulphonylamino, arylsulphonylamino, hetarylsulphonylamino, sulphonyl-$(C_1-C_8)$-haloalkylamino, amino-$(C_1-C_8)$-alkylsulphonyl, amino-$(C_1-C_8)$-haloalkylsulphonyl, $(C_1-C_8)$-alkylsulphonyl, $(C_3-C_8)$-cycloalkylsulphonyl, arylsulphonyl, $(C_1-C_8)$-alkylsulphinyl, $(C_3-C_8)$-cycloalkylsulphinyl, arylsulphinyl, $(C_3-C_8)$-cycloalkoxy.

Particular preference is given to the inventive use of compounds of the general formula (I) or salts thereof, in which Q represents

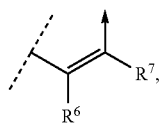
Q-1

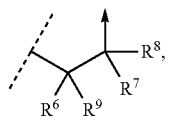
Q-2

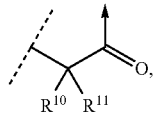
Q-3

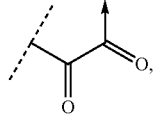
Q-4

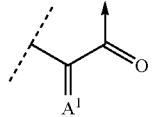
Q-5

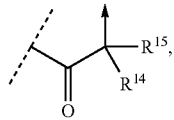
Q-6

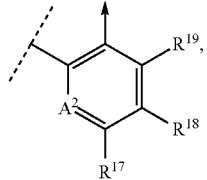
Q-7

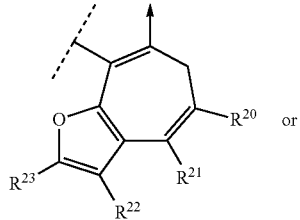
Q-8
or

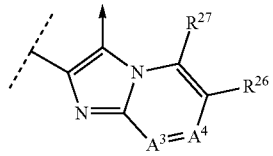
Q-9 where $R^6$ to $R^{27}$ each have the meaning according to the definitions below and where the arrow represents a bond to the group N—$R^5$, W represents oxygen or sulphur, $A^1$ represents N—$R^{12}$ or the grouping CHR$^{13}$, where $R^{12}$ and $R^{13}$ in the groupings N—$R^{12}$ and CHR$^{13}$ each have the meaning according to the definition below, A² represents N (nitrogen) or the grouping C—R¹⁶, where R¹⁶ in the grouping C—R¹⁶ in each case has the meaning according to the definition below, A³ represents N (nitrogen) or the grouping C—R²⁴, where R²⁴ in the grouping C—R²⁴ in each case has the meaning according to the definition below, A⁴ represents N (nitrogen) or the grouping C—R²⁵, where R²⁵ in the grouping C—R²⁵ in each case has the meaning according to the definition below, R¹, R², R³, R⁴ each independently represent hydrogen, nitro, amino, hydroxyl, halogen, cyano, thiocyanato, isothiocyanato, $(C_1-C_7)$-alkyl, $(C_3-C_7)$-cycloalkyl, $(C_2-C_7)$-alkenyl, $(C_2-C_7)$-alkynyl, optionally substituted phenyl, aryl-$(C_1-C_7)$-alkyl, aryl-$(C_2-C_7)$-alkenyl, aryl-$(C_2-C_7)$-alkynyl, heteroaryl, $(C_3-C_7)$-cycloalkyl-$(C_1-C_7)$-alkyl, $(C_3-C_7)$-cycloalkyl-$(C_2-C_7)$-alkenyl, $(C_3-C_7)$-cycloalkyl-$(C_2-C_7)$-alkynyl, heteroaryl-$(C_1-C_7)$-alkyl, heteroaryl-$(C_2-C_7)$-alkenyl, heteroaryl-$(C_2-C_7)$-alkynyl, $(C_5-C_7)$-cycloalkenyl, $(C_1-C_7)$-alkoxy[$(C_1-C_7)$-alkyl]phosphoryl, $(C_1-C_7)$-alkylthio[$(C_1-C_7)$-alkyl]phosphoryl, $(C_1-C_7)$-alkylamino[$(C_1-C_7)$-alkyl]phosphoryl, bis-[$(C_1-C_7)$-alkyl]amino[$(C_1-C_7)$-alkyl]phosphoryl, bis-[$(C_1-C_7)$-alkoxy]phosphoryl, $(C_1-C_7)$-haloalkyl, $(C_3-C_7)$-halocycloalkyl, $(C_2-C_7)$-haloalkenyl, $(C_3-C_7)$-halocycloalkenyl, $(C_1-C_7)$-haloalkyl-$(C_2-C_7)$-alkynyl, hydroxy-$(C_1-C_7)$-haloalkyl-$(C_2-C_7)$-alkynyl, hydroxy-$(C_1-C_7)$-alkyl-$(C_2-C_7)$-alkynyl, $(C_1-C_7)$-alkoxy-$(C_1-C_7)$-alkyl-$(C_2-C_7)$-alkynyl, tris-[$(C_1-C_7)$-alkyl]silyl-$(C_1-C_7)$-alkynyl, bis-[$(C_1-C_7)$-alkyl]arylsilyl-$(C_2-C_7)$-alkynyl, bis-aryl-[$(C_1-C_7)$-alkyl]silyl-$(C_1-C_7)$-alkynyl, $(C_1-C_7)$-alkoxy-$(C_1-C_7)$-alkyl, $(C_1-C_7)$-alkoxy, $(C_1-C_7)$-haloalkoxy, $(C_3-C_7)$-cycloalkyloxy, $(C_2-C_7)$-alkenyloxy-$(C_1-C_7)$-alkyl, heteroaryl-$(C_1-C_7)$-alkoxy, aryl-$(C_1-C_7)$-alkoxy, $(C_1-C_7)$-alkoxycarbonyl, aryl-$(C_1-C_7)$-alkoxycarbonyl, $(C_3-C_7)$-cycloalkoxycarbonyl, $(C_3-C_7)$-cycloalkyl-$(C_1-C_7)$-alkoxycarbonyl, $(C_1-C_7)$-haloalkoxycarbonyl, hydroxycarbonyl, aminocarbonyl, $(C_1-C_7)$-alkylaminocarbonyl, $(C_3-C_7)$-cycloalkylaminocarbonyl, $(C_3-C_7)$-cycloalkyl-$(C_1-C_7)$-alkylaminocarbonyl, $(C_1-C_7)$-alkylamino, $(C_2-C_7)$-alkenylamino, $(C_2-C_7)$-alkynylamino, hydrothio, $(C_1-C_7)$-alkylthio, $(C_1-C_7)$-haloalkylthio, bis-$(C_1-C_7)$-alkylamino, $(C_3-C_7)$-cycloalkylamino, $(C_1-C_7)$-alkylcarbonylamino, $(C_3-C_7)$-cycloalkylcarbonylamino, $(C_1-C_7)$-haloalkylcarbonylamino, $(C_1-C_7)$-alkoxycarbonylamino, $(C_1-C_7)$-alkoxycarbonyl-$(C_1-C_7)$-alkylamino, $(C_3-C_7)$-cycloalkoxycarbonylamino, $(C_3-C_7)$-cycloalkyl-$(C_1-C_7)$-alkoxycarbonylamino, aryl-$(C_1-C_7)$-alkoxycarbonylamino, $(C_1-C_7)$-alkylaminocarbonylamino, bis-[$(C_1-C_7)$-alkyl]aminocarbonylamino, $(C_3-C_7)$-cycloalkylaminocarbonylamino, arylaminocarbonylamino, aryl-$(C_1-C_7)$-alkylaminocarbonylamino, arylaminocarbonyl-$(C_1-C_7)$-alkylcarbonylamino, heteroarylaminocarbonylamino, aryl-$(C_1-C_7)$-alkyliminoamino, $(C_1-C_7)$-alkylsulphonylamino, $(C_3-C_7)$-cycloalkylsulphonylamino, arylsulphonylamino, hetarylsulphonylamino, sulphonyl-$(C_1-C_7)$-haloalkylamino, amino-$(C_1-C_7)$-alkylsulphonyl, amino-$(C_1-C_7)$-haloalkylsulphonyl, $(C_1-C_7)$-alkylsulphonyl, $(C_3-C_7)$-cycloalkylsulphonyl, arylsulphonyl, $(C_1-C_7)$-alkylsulphinyl, $(C_3-C_7)$-cycloalkylsulphinyl, arylsulphinyl, N,S-di-$(C_1-C_7)$-alkylsulphonimidoyl, S—$(C_1-C_7)$-alkylsulphonimidoyl, $(C_1-C_7)$-alkylsulphonylaminocarbonyl, $(C_3-C_7)$-cycloalkylsulphonylaminocarbonyl, $(C_3-C_7)$-cycloalkylaminosulphonyl, $(C_3-C_7)$-cycloalkyl-$(C_1-C_7)$-alkoxy, $(C_2-C_7)$-alkynyl-$(C_1-C_7)$-alkoxy, $(C_2-C_7)$-alkenyl-$(C_1-C_7)$-alkoxy, $(C_2-C_7)$-alkenyloxy-$(C_1-C_7)$-alkoxy, $(C_1-C_7)$-alkoxy-$(C_1-C_7)$-alkoxy, $(C_1-C_7)$-alkylamino-$(C_1-C_7)$-alkoxy, bis-$(C_1-C_7)$-alkylamino-$(C_1-C_7)$-alkoxy, $(C_3-C_7)$-cycloalkylamino-$(C_1-C_7)$-alkoxy, heterocyclyl-N—$(C_1-C_7)$-alkoxy, arylaminocarbonyl-$(C_1-C_7)$-alkylcarbonylamino, $(C_1-C_7)$-alkylaminocarbonyl-$(C_1-C_7)$-alkylcarbonylamino, optionally substituted phenyloxy, heteroaryloxy, amino-$(C_1-C_7)$-alkyl, amino-$(C_2-C_7)$-alkenyl, $(C_1-C_7)$-alkoxycarbonylamino-$(C_1-C_7)$-alkyl, tris-[$(C_1-C_7)$-alkyl]silyl, bis-[$(C_1-C_7)$-alkyl]arylsilyl, bis-[$(C_1-C_7)$-alkyl]-$(C_1-C_7)$-alkylsilyl, R² and R³ with the atoms to which they are attached form a fully saturated, partially saturated or fully unsaturated 5- to 7-membered ring which is optionally interrupted by heteroatoms and optionally substituted further, R³ and R⁴ with the atoms to which they are attached form a fully saturated, partially saturated or fully unsaturated 5- to 7-membered ring which is optionally interrupted by heteroatoms and optionally substituted further, R⁵ represents hydrogen, hydroxyl, $(C_1-C_7)$-alkyl, $(C_3-C_7)$-cycloalkyl, halogen, $(C_2-C_7)$-alkenyl-$(C_1-C_7)$-alkyl, $(C_2-C_7)$-alkynyl-$(C_1-C_7)$-alkyl, $(C_1-C_7)$-haloalkyl, $(C_1-C_7)$-alkoxy-$(C_1-C_7)$-alkyl, $(C_2-C_7)$-alkynyl, $(C_2-C_7)$-alkenyl, $(C_3-C_7)$-cycloalkyl-$(C_1-C_7)$-alkyl, cyano-$(C_1-C_7)$-alkyl, nitro-$(C_1-C_7)$-alkyl, aryl-$(C_1-C_7)$-alkyl, heteroaryl-$(C_1-C_7)$-alkyl, optionally substituted phenyl, $(C_1-C_7)$-alkylamino, $(C_1-C_7)$-alkylamino-$(C_1-C_7)$-alkyl, bis-[$(C_1-C_7)$-alkyl]amino-$(C_1-C_7)$-alkyl, aminocarbonyl-$(C_1-C_7)$-alkyl, $(C_1-C_7)$-alkylaminocarbonyl-$(C_1-C_7)$-alkyl, bis-[$(C_1-C_7)$-alkyl]aminocarbonyl-$(C_1-C_7)$-alkyl, $(C_1-C_7)$-alkoxycarbonyl-$(C_1-C_7)$-alkyl, hydroxycarbonyl-$(C_1-C_7)$-alkyl, $(C_1-C_7)$-alkylcarbonyl, $(C_3-C_7)$-cycloalkylcarbonyl, $(C_1-C_7)$-haloalkylcarbonyl, $(C_1-C_7)$-alkoxycarbonyl, $(C_1-C_7)$-alkylsulphonyl, arylsulphonyl, $(C_3-C_7)$-cycloalkylsulphonyl, aryl-$(C_1-C_7)$-alkylsulphonyl, $(C_2-C_7)$-alkenylsulphonyl, heteroarylsulphonyl, $(C_2-C_7)$-alkynylsulphonyl, $(C_1-C_7)$-alkylsulphinyl, arylsulphinyl, $(C_3-C_7)$-cycloalkylsulphinyl, $(C_2-C_7)$-alkenylsulphinyl, $(C_2-C_7)$-alkynylsulphinyl, arylcarbonyl, heteroarylcarbonyl, $(C_1-C_7)$-alkoxycarbonyl-$(C_1-C_7)$-alkyl, cyano-$(C_1-C_7)$-alkylaminocarbonyl, $(C_2-C_7)$-alkynylaminocarbonyl, heterocyclylcarbonyl, hetaroaryl-$(C_1-C_7)$-alkylaminocarbonyl, $(C_2-C_7)$-alkenyloxycarbonyl, $(C_3-C_7)$-cycloalkyl-$(C_1-C_7)$-alkoxycarbonyl, $(C_3-C_7)$-cycloalkyl-$(C_1-C_7)$-alkoxycarbonylcarbonyl, $(C_1-C_7)$-alkoxycarbonyl, $(C_3-C_7)$-cycloalkyl-$(C_1-C_7)$-alkylaminocarbonyl, aryl-$(C_1-C_7)$-alkylaminocarbonyl or a negative charge, R⁶ represents hydrogen, hydroxy, nitro, halogen, amino, $(C_1-C_7)$-alkyl, $(C_3-C_7)$-cycloalkyl, $(C_1-C_7)$-alkylcarbonyl, arylcarbonyl, $(C_1-C_7)$-alkylaminocarbonyl, bis-$(C_1-C_7)$-alkylaminocarbonyl, $(C_3-C_7)$-cycloalkylaminocarbonyl, $(C_4-C_7)$-cycloalkenylaminocarbonyl, $(C_3-C_7)$-cycloalkyl-[$(C_1-C_7)$-alkyl]aminocarbonyl, $(C_r-C_7)$-alkyl-[$(C_1-C_7)$-alkyl]aminocarbonyl, $(C_3-C_7)$-cycloalkyl-$(C_1-C_7)$-alkylaminocarbonyl, $(C_3-C_7)$-cycloalkyl-$(C_1-C_7)$-alkyl[$(C_1-C_7)$-alkyl]aminocarbonyl, $(C_1-C_7)$-alkyl[$(C_2-C_7)$-alkynyl]aminocarbonyl, $(C_1-C_7)$-alkynylaminocarbonyl, arylaminocarbonyl, heteroarylaminocarbonyl, $(C_2-C_7)$-alkenylaminocarbonyl, cyano-$(C_1-C_7)$-alkylaminocarbonyl, aryl-$(C_1-C_7)$-alkylaminocarbonyl, aryl[$(C_1-C_7)$-alkyl]aminocarbonyl, heteroaryl[$(C_1-C_7)$-alkyl]aminocarbonyl, heterocyclyl-N-carbonyl, $(C_1-C_7)$-alkoxycarbonylheterocyclyl-N-carbonyl, $(C_1-C_7)$-alkoxycarbonyl-$(C_1-C_7)$-alkylaminocarbonyl, hydroxycarbonylheterocyclyl-N-carbonyl, hydroxycarbonyl-$(C_1-C_7)$-alkylaminocarbonyl, $(C_3-C_7)$-cycloalkoxycarbonylheterocyclyl-N-carbonyl, $(C_3-C_7)$-cycloalkoxycarbonyl-($C_1$-$C_7$)-alkylaminocarbonyl, ($C_1$-$C_7$)-alkylaminocarbonyl-($C_1$-$C_7$)-alkylaminocarbonyl, aminocarbonyl-($C_1$-$C_7$)-alkylaminocarbonyl, ($C_3$-$C_7$)-cycloalkylaminocarbonyl-($C_1$-$C_7$)-alkylaminocarbonyl, bis-($C_1$-$C_7$)-alkylamino-($C_1$-$C_7$)-alkylaminocarbonyl, bis-($C_1$-$C_7$)-alkylaminocarbonyl-($C_1$-$C_7$)-alkylaminocarbonyl, ($C_1$-$C_7$)-alkylaminocarbonyl-($C_1$-$C_7$)-alkylaminocarbonyl, heterocyclyl-N-carbonyl-($C_1$-$C_7$)-alkylaminocarbonyl, ($C_3$-$C_7$)-cycloalkyl-N-heterocyclyl-N-carbonyl, ($C_1$-$C_7$)-alkoxy[($C_1$-$C_7$)-alkyl]aminocarbonyl, ($C_1$-$C_7$)-alkoxycarbonylamino, hydroxycarbonyl, ($C_1$-$C_7$)-alkoxycarbonyl, ($C_1$-$C_7$)-cycloalkoxycarbonyl, ($C_1$-$C_7$)-cycloalkyl-($C_1$-$C_7$)-alkoxycarbonyl, ($C_1$-$C_7$)-alkoxy-($C_1$-$C_7$)-alkoxycarbonyl, ($C_1$-$C_7$)-alkoxycarbonyl-($C_1$-$C_7$)-alkoxycarbonyl, ($C_2$-$C_7$)-alkenyloxycarbonyl, ($C_2$-$C_7$)-alkynyloxycarbonyl, hydroxycarbonyl-($C_1$-$C_7$)-alkoxycarbonyl, ($C_1$-$C_7$)-haloalkoxycarbonyl, aryl[($C_1$-$C_7$)-alkyl]aminocarbonylamino, arylaminocarbonylamino, ($C_1$-$C_7$)-alkylaminocarbonylamino, heteroarylaminocarbonylamino, ($C_1$-$C_7$)-alkoxy, ($C_1$-$C_7$)-alkylamino-($C_1$-$C_7$)-alkoxy, ($C_1$-$C_7$)-alkylcarbonyloxy, arylcarbonyloxy, ($C_2$-$C_7$)-alkenyl-($C_1$-$C_7$)-alkyl, ($C_2$-$C_7$)-alkynyl-($C_1$-$C_7$)-alkyl, ($C_1$-$C_7$)-haloalkyl, ($C_1$-$C_7$)-alkoxy-($C_1$-$C_7$)-alkyl, ($C_2$-$C_7$)-alkynyl, ($C_2$-$C_7$)-alkenyl, optionally substituted phenyl, heteroaryl, ($C_1$-$C_7$)-alkoxycarbonyl-($C_1$-$C_7$)-alkyl, ($C_1$-$C_7$)-alkylamino, bis-($C_1$-$C_7$)-alkylamino, ($C_3$-$C_7$)-cycloalkylamino, aryl-($C_1$-$C_7$)-alkylamino, $R^7$ represents hydrogen, halogen, amino, ($C_1$-$C_7$)-alkyl, ($C_1$-$C_7$)-haloalkyl, ($C_3$-$C_7$)-cycloalkyl, ($C_1$-$C_7$)-alkylcarbonyl, arylcarbonyl, heteroarylcarbonyl, ($C_3$-$C_7$)-cycloalkylcarbonyl, ($C_1$-$C_7$)-alkoxycarbonyl, hydroxycarbonyl, optionally substituted phenyl, heteroaryl, arylcarbonyl-($C_1$-$C_7$)-alkoxycarbonyl, ($C_1$-$C_7$)-alkylcarbonyl-($C_1$-$C_7$)-alkoxycarbonyl, ($C_3$-$C_7$)-cycloalkyl-($C_1$-$C_7$)-alkoxycarbonyl, heteroaryl-($C_1$-$C_7$)-alkoxycarbonyl, heteroarylheteroaryl($C_1$-$C_7$)-alkyl-($C_1$-$C_7$)-alkoxycarbonyl, heteroaryl($C_1$-$C_7$)-alkyl-($C_1$-$C_7$)-alkoxycarbonyl, aryl-($C_1$-$C_7$)-alkoxycarbonyl, ($C_1$-$C_7$)-alkylcarbonyloxy, arylaminocarbonyl, ($C_1$-$C_7$)-alkylaminocarbonyl, bis-($C_1$-$C_7$)-alkylaminocarbonyl, ($C_3$-$C_7$)-cycloalkylaminocarbonyl, heterocyclyl-N-carbonyl, aryl-($C_1$-$C_7$)-alkylaminocarbonyl, cyano-($C_1$-$C_7$)-alkylaminocarbonyl, ($C_2$-$C_7$)-alkenylaminocarbonyl, bis-[($C_1$-$C_7$)-alkoxycarbonyl]-($C_2$-$C_7$)-alkenylamino, bis-cyano-($C_1$-$C_7$)-alkenylamino, ($C_1$-$C_7$)-alkoxycarbonyl(cyano)-($C_2$-$C_7$)-alkenylamino, ($C_1$-$C_7$)-alkylamino, arylamino, ($C_3$-$C_7$)-cycloalkylamino, aryl[($C_1$-$C_7$)-alkyl]amino, bis-($C_1$-$C_7$)-alkylamino, $R^8$ represents hydrogen, ($C_1$-$C_7$)-alkyl, ($C_1$-$C_7$)-haloalkyl, ($C_3$-$C_7$)-cycloalkyl, halogen, $R^9$ represents hydrogen, ($C_1$-$C_7$)-alkyl, ($C_1$-$C_7$)-haloalkyl, ($C_3$-$C_7$)-cycloalkyl, halogen, $R^{10}$, $R^{11}$ independently of one another represent hydrogen, halogen, ($C_1$-$C_7$)-alkyl, ($C_3$-$C_7$)-cycloalkyl, ($C_1$-$C_7$)-haloalkyl, aryl-($C_1$-$C_7$)-alkyl, heteroaryl-($C_1$-$C_7$)-alkyl, ($C_1$-$C_7$)-alkylcarbonyl, aryl-($C_1$-$C_7$)-alkylcarbonyl, ($C_3$-$C_7$)-cycloalkylcarbonyl, ($C_3$-$C_7$)-cycloalkyl-($C_1$-$C_7$)-alkylcarbonyl, arylcarbonyl, heteroarylcarbonyl, arylaminocarbonyl, ($C_1$-$C_7$)-alkylaminocarbonyl, ($C_2$-$C_7$)-alkynyl, ($C_2$-$C_7$)-alkenyl, ($C_2$-$C_7$)-haloalkenyl, $R^{12}$ represents hydroxyl, ($C_1$-$C_7$)-alkoxy, ($C_2$-$C_7$)-alkenyloxy, aryl-($C_1$-$C_7$)-alkoxy, ($C_1$-$C_7$)-alkylamino, arylamino, heteroarylamino, heteroarylcarbonylamino, arylcarbonylamino, $R^{13}$ represents hydrogen, ($C_1$-$C_7$)-alkoxy, ($C_2$-$C_7$)-alkenyloxy, optionally substituted phenyl, heteroaryl, heteroarylamino, arylamino, bis-($C_1$-$C_7$)-alkylamino-($C_1$-$C_7$)-alkylamino, ($C_1$-$C_7$)-alkylamino, $R^{14}$, $R^{15}$ independently of one another represent hydrogen, ($C_1$-$C_7$)-alkyl, ($C_3$-$C_7$)-cycloalkyl, ($C_1$-$C_7$)-haloalkyl, ($C_1$-$C_7$)-alkylcarbonyl, ($C_3$-$C_7$)-cycloalkylcarbonyl, ($C_3$-$C_7$)-cycloalkyl-($C_1$-$C_7$)-alkylcarbonyl, arylcarbonyl, heteroarylcarbonyl, ($C_1$-$C_7$)-alkoxycarbonyl, hydroxycarbonyl, ($C_1$-$C_7$)-alkoxy, aryl-($C_1$-$C_7$)-alkyl, heteroaryl-($C_1$-$C_7$)-alkyl, ($C_1$-$C_7$)-alkylaminocarbonyl, ($C_2$-$C_7$)-alkenylaminocarbonyl, ($C_2$-$C_7$)-alkynyl-($C_1$-$C_7$)-alkylaminocarbonyl, cyano-($C_1$-$C_7$)-alkylaminocarbonyl, ($C_3$-$C_7$)-cycloalkylaminocarbonyl, $R^{16}$, $R^{17}$, $R^{18}$, $R^{19}$ independently of one another represent hydrogen, halogen, nitro, amino, cyano, thiocyanato, isothiocyanato, hydroxy, hydrothio, ($C_1$-$C_7$)-alkyl, ($C_3$-$C_7$)-cycloalkyl, ($C_1$-$C_7$)-alkoxy, ($C_1$-$C_7$)-haloalkyl, ($C_1$-$C_7$)-haloalkylthio, ($C_1$-$C_7$)-alkylthio, ($C_1$-$C_7$)-haloalkoxy, ($C_1$-$C_7$)-alkylamino, heteroaryl-($C_1$-$C_7$)-alkylamino, aryl-($C_1$-$C_7$)-alkylamino, ($C_3$-$C_7$)-cycloalkylamino, ($C_1$-$C_7$)-alkylcarbonylamino, bis-[($C_1$-$C_7$)-alkyl]amino-($C_1$-$C_7$)-alkylcarbonylamino, aryl-($C_1$-$C_7$)-alkylcarbonylamino, ($C_3$-$C_7$)-cycloalkylcarbonylamino, ($C_3$-$C_7$)-cycloalkyl-($C_1$-$C_7$)-alkylcarbonylamino ($C_1$-$C_7$)-alkyl-N-heterocyclyl-N, ($C_1$-$C_7$)-alkyl-N-heterobicyclyl-N, bis-($C_1$-$C_7$)-alkylamino-($C_1$-$C_7$)-alkylamino, hydroxycarbonyl, ($C_1$-$C_7$)-alkoxycarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, arylsulphonylamino, ($C_1$-$C_7$)-alkylsulphonylamino, ($C_3$-$C_7$)-cycloalkylsulphonylamino, ($C_1$-$C_7$)-alkoxycarbonylamino, ($C_1$-$C_7$)-alkoxycarbonyl-($C_1$-$C_7$)-alkylamino, ($C_3$-$C_7$)-cycloalkoxycarbonylamino, ($C_3$-$C_7$)-cycloalkyl-($C_1$-$C_7$)-alkoxycarbonylamino, aryl-($C_1$-$C_7$)-alkoxycarbonylamino, ($C_1$-$C_7$)-alkylaminocarbonylamino, bis-[($C_1$-$C_7$)-alkyl]aminocarbonylamino, ($C_3$-$C_7$)-cycloalkylaminocarbonylamino, arylaminocarbonylamino, aryl-($C_1$-$C_7$)-alkylaminocarbonylamino, arylaminocarbonyl-($C_1$-$C_7$)-alkylcarbonylamino, heteroarylaminocarbonylamino, aryl-($C_1$-$C_7$)-alkyliminoamino, heterocyclyl-N-carbonyl, ($C_1$-$C_7$)-alkoxycarbonylheterocyclyl-N-carbonyl, ($C_1$-$C_7$)-alkoxycarbonyl-($C_1$-$C_7$)-alkylaminocarbonyl, hydroxycarbonylheterocyclyl-N-carbonyl, hydroxycarbonyl-($C_1$-$C_7$)-alkylaminocarbonyl, ($C_3$-$C_7$)-cycloalkoxycarbonylheterocyclyl-N-carbonyl, ($C_3$-$C_7$)-cycloalkoxycarbonyl-($C_1$-$C_7$)-alkylaminocarbonyl, ($C_1$-$C_7$)-alkylaminocarbonyl-($C_1$-$C_7$)-alkylaminocarbonyl, aminocarbonyl-($C_1$-$C_7$)-alkylaminocarbonyl, ($C_3$-$C_7$)-cycloalkylaminocarbonyl-($C_1$-$C_7$)-alkylaminocarbonyl, bis-($C_1$-$C_7$)-alkylamino-($C_1$-$C_7$)-alkylaminocarbonyl, bis-($C_1$-$C_7$)-alkylaminocarbonyl-($C_1$-$C_7$)-alkylaminocarbonyl, ($C_1$-$C_7$)-alkylaminocarbonyl-($C_1$-$C_7$)-alkylaminocarbonyl, heterocyclyl-N-carbonyl-($C_1$-$C_7$)-alkylaminocarbonyl, ($C_3$-$C_7$)-cycloalkyl-N-heterocyclyl-N-carbonyl, ($C_1$-$C_7$)-alkoxy[($C_1$-$C_7$)-alkyl]aminocarbonyl, $R^{20}$, $R^{21}$, $R^{22}$, $R^{23}$ independently of one another represent hydrogen, ($C_1$-$C_7$)-alkyl, ($C_3$-$C_7$)-cycloalkyl, ($C_1$-$C_7$)-haloalkyl, and $R^{24}$, $R^{25}$, $R^{26}$, $R^{27}$ independently of one another represent hydrogen, halogen, nitro, ($C_1$-$C_7$)-alkyl, ($C_3$-$C_7$)-cycloalkyl, ($C_1$-$C_7$)-alkoxy, ($C_1$-$C_7$)-haloalkyl, ($C_1$-$C_7$)-haloalkylthio, ($C_1$-$C_7$)-alkylthio, ($C_1$-$C_7$)-haloalkoxy, ($C_1$-$C_7$)-alkylamino, heteroaryl-($C_1$-$C_7$)-alkylamino, aryl-($C_1$-

$C_7$)-alkylamino, ($C_3$-$C_7$)-cycloalkylamino, hydroxycarbonyl, ($C_1$-$C_7$)-alkoxycarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, optionally substituted phenyl, heteroaryl, ($C_3$-$C_7$)-cycloalkoxycarbonyl, ($C_3$-$C_7$)-cycloalkyl-($C_1$-$C_7$)-alkoxycarbonyl, ($C_2$-$C_7$)-alkenyloxycarbonyl, ($C_2$-$C_7$)-alkenylaminocarbonyl, ($C_2$-$C_7$)-alkynyloxycarbonyl, ($C_2$-$C_7$)-alkynylaminocarbonyl, ($C_2$-$C_7$)-alkenyl, ($C_2$-$C_7$)-alkynyl, aminosulphonyl, ($C_1$-$C_7$)-alkylsulphonylamino, ($C_3$-$C_7$)-cycloalkylsulphonylamino, arylsulphonylamino, hetarylsulphonylamino, sulphonyl-($C_1$-$C_7$)-haloalkylamino, amino-($C_1$-$C_7$)-alkylsulphonyl, amino-($C_1$-$C_7$)-haloalkylsulphonyl, ($C_1$-$C_7$)-alkylsulphonyl, ($C_3$-$C_7$)-cycloalkylsulphonyl, arylsulphonyl, ($C_1$-$C_7$)-alkylsulphinyl, ($C_3$-$C_7$)-cycloalkylsulphinyl, arylsulphinyl, ($C_3$-$C_7$)-cycloalkoxy.

Very particular preference is given to the inventive use of compounds of the general formula (I) or salts thereof, in which Q represents

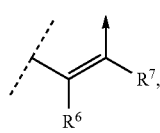
Q-1

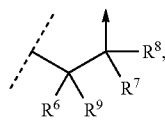
Q-2

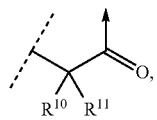
Q-3

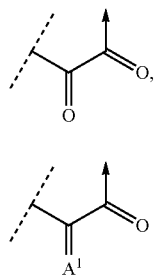
Q-4

Q-5

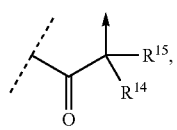
Q-6

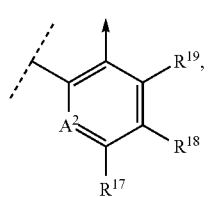
Q-7

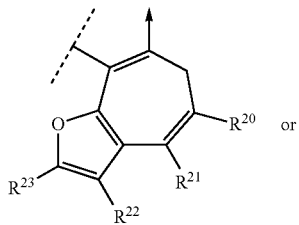
Q-8 or

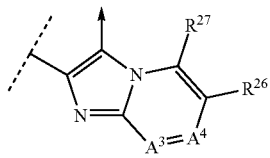
Q-9 where $R^6$ to $R^{27}$ each have the meaning according to the definitions below and where the arrow represents a bond to the group N—$R^5$, W represents oxygen, $A^1$ represents N—$R^{12}$ or the grouping CH$R^{13}$, where $R^{12}$ and $R^{13}$ in the groupings N—$R^{12}$ and CH$R^{13}$ each have the meaning according to the definition below, $A^2$ represents N (nitrogen) or the grouping C—$R^{16}$, where $R^{16}$ in the grouping C—$R^{16}$ in each case has the meaning according to the definition below, $A^3$ represents N (nitrogen) or the grouping C—$R^{24}$, where $R^{24}$ in the grouping C—$R^{24}$ in each case has the meaning according to the definition below, $A^4$ represents N (nitrogen) or the grouping C—$R^{25}$, where $R^{25}$ in the grouping C—$R^{25}$ in each case has the meaning according to the definition below, $R^1, R^2, R^3, R^4$ are each independently hydrogen, nitro, amino, hydroxyl, fluorine, chlorine, bromine, iodine, cyano, thiocyanato, isothiocyanato, ($C_1$-$C_6$)-alkyl, ($C_3$-$C_6$)-cycloalkyl, ($C_2$-$C_6$)-alkenyl, ($C_2$-$C_6$)-alkynyl, optionally substituted phenyl, aryl-($C_1$-$C_6$)-alkyl, aryl-($C_2$-$C_6$)-alkenyl, aryl-($C_2$-$C_6$)-alkynyl, heteroaryl, ($C_3$-$C_6$)-cycloalkyl-($C_1$-$C_6$)-alkyl, ($C_3$-$C_6$)-cycloalkyl-($C_2$-$C_6$)-alkenyl, ($C_3$-$C_6$)-cycloalkyl-($C_2$-$C_6$)-alkynyl, heteroaryl-($C_1$-$C_6$)-alkyl, heteroaryl-($C_2$-$C_6$)-alkenyl, heteroaryl-($C_2$-$C_6$)-alkynyl, ($C_5$-$C_6$)-cycloalkenyl, ($C_1$-$C_6$)-alkoxy[($C_1$-$C_6$)-alkyl]phosphoryl, ($C_1$-$C_6$)-alkylthio[($C_1$-$C_6$)-alkyl]phosphoryl, ($C_1$-$C_6$)-alkylamino[($C_1$-$C_6$)-alkyl]phosphoryl, bis-[($C_1$-$C_6$)-alkyl]amino[($C_1$-$C_6$)-alkyl]phosphoryl, bis-[($C_1$-$C_6$)-alkoxy]phosphoryl, ($C_1$-$C_6$)-haloalkyl, ($C_3$-$C_6$)-halocycloalkyl, ($C_2$-$C_6$)-haloalkenyl, ($C_3$-$C_6$)-halocycloalkenyl, ($C_1$-$C_6$)-haloalkyl-($C_2$-$C_6$)-alkynyl, hydroxy-($C_1$-$C_6$)-haloalkyl-($C_2$-$C_6$)-alkynyl, hydroxy-($C_1$-$C_6$)-alkyl-($C_2$-$C_6$)-alkynyl, ($C_1$-$C_6$)-alkoxy-($C_1$-$C_6$)-alkyl-($C_2$-$C_6$)-alkynyl, tris-[($C_1$-$C_6$)-alkyl]silyl-($C_1$-$C_6$)-alkynyl, bis-[($C_1$-$C_6$)-alkyl]arylsilyl-($C_2$-$C_6$)-alkynyl, bis-aryl-[($C_1$-$C_6$)-alkyl]silyl-($C_1$-$C_6$)-alkynyl, ($C_1$-$C_6$)-alkoxy-($C_1$-$C_6$)-alkyl, ($C_1$-$C_6$)-alkoxy, ($C_1$-$C_6$)-haloalkoxy, ($C_3$-$C_6$)-cycloalkyloxy, ($C_2$-$C_6$)-alkenyloxy-($C_1$-$C_6$)-alkyl, heteroaryl-($C_1$-$C_6$)-alkoxy, aryl-($C_1$-$C_6$)-alkoxy, ($C_1$-$C_6$)-alkoxycarbonyl, aryl-($C_1$-$C_6$)-alkoxycarbonyl, ($C_3$-$C_6$)-cycloalkoxycarbonyl, ($C_3$-$C_6$)-cycloalkyl-($C_1$-$C_6$)-alkoxycarbonyl, ($C_1$-$C_6$)-haloalkoxycarbonyl, hydroxycarbonyl, aminocarbonyl, ($C_1$-$C_6$)-alkylaminocarbonyl, ($C_3$-$C_6$)-cycloalkylaminocarbonyl, ($C_3$-$C_6$)-cycloalkyl-($C_1$-$C_6$)-alkylaminocarbonyl, ($C_1$-$C_6$)-alkylamino, ($C_2$-$C_6$)-alkenylamino, ($C_2$-$C_6$)-alkynylamino, hydrothio, ($C_1$-$C_6$)-alkylthio, ($C_1$-$C_6$)- haloalkylthio, bis-($C_1$-$C_6$)-alkylamino, ($C_3$-$C_6$)-cycloalkylamino, ($C_1$-$C_6$)-alkylcarbonylamino, ($C_3$-$C_6$)-cycloalkylcarbonylamino, ($C_1$-$C_6$)-haloalkylcarbonylamino, ($C_1$-$C_6$)-alkoxycarbonylamino, ($C_1$-$C_6$)-alkoxycarbonyl-($C_1$-$C_6$)-alkylamino, ($C_3$-$C_6$)-cycloalkoxycarbonylamino, ($C_3$-$C_6$)-cycloalkyl-($C_1$-$C_6$)-alkoxycarbonylamino, aryl-($C_1$-$C_6$)-alkoxycarbonylamino, ($C_1$-$C_6$)-alkylaminocarbonylamino, bis-[($C_1$-$C_6$)-alkyl]aminocarbonylamino, ($C_3$-$C_6$)-cycloalkylaminocarbonylamino, arylaminocarbonylamino, aryl-($C_1$-$C_6$)-alkylaminocarbonylamino, arylaminocarbonyl-($C_1$-$C_6$)-alkylcarbonylamino, heteroarylaminocarbonylamino, aryl-($C_1$-$C_6$)-alkyliminoamino, ($C_1$-$C_6$)-alkylsulphonylamino, ($C_3$-$C_6$)-cycloalkylsulphonylamino, arylsulphonylamino, hetarylsulphonylamino, sulphonyl-($C_1$-$C_6$)-haloalkylamino, amino-($C_1$-$C_6$)-alkylsulphonyl, amino-($C_1$-$C_6$)-haloalkylsulphonyl, ($C_1$-$C_6$)-alkylsulphonyl, ($C_3$-$C_6$)-cycloalkylsulphonyl, arylsulphonyl, ($C_1$-$C_6$)-alkylsulphinyl, ($C_3$-$C_6$)-cycloalkylsulphinyl, arylsulphinyl, N,S-di-($C_1$-$C_6$)-alkylsulphonimidoyl, S—($C_1$-$C_6$)-alkylsulphonimidoyl, ($C_1$-$C_6$)-alkylsulphonylaminocarbonyl, ($C_3$-$C_6$)-cycloalkylsulphonylaminocarbonyl, ($C_3$-$C_6$)-cycloalkylaminosulphonyl, ($C_3$-$C_6$)-cycloalkyl-($C_1$-$C_6$)-alkoxy, ($C_2$-$C_6$)-alkynyl-($C_1$-$C_6$)-alkoxy, ($C_2$-$C_6$)-alkenyl-($C_1$-$C_6$)-alkoxy, ($C_2$-$C_6$)-alkenyloxy-($C_1$-$C_6$)-alkoxy, ($C_1$-$C_6$)-alkoxy-($C_1$-$C_6$)-alkoxy, ($C_1$-$C_6$)-alkylamino-($C_1$-$C_6$)-alkoxy, bis-($C_1$-$C_6$)-alkylamino-($C_1$-$C_6$)-alkoxy, ($C_3$-$C_6$)-cycloalkylamino-($C_1$-$C_6$)-alkoxy, heterocyclyl-N—($C_1$-$C_6$)-alkoxy, arylaminocarbonyl-($C_1$-$C_6$)-alkylcarbonylamino, ($C_1$-$C_6$)-alkylaminocarbonyl-($C_1$-$C_6$)-alkylcarbonylamino, optionally substituted phenyloxy, heteroaryloxy, amino-($C_1$-$C_6$)-alkyl, amino-($C_2$-$C_6$)-alkenyl, ($C_1$-$C_6$)-alkoxycarbonylamino-($C_1$-$C_6$)-alkyl, tris-[($C_1$-$C_6$)-alkyl]silyl, bis-[($C_1$-$C_6$)-alkyl]arylsilyl, bis-[($C_1$-$C_6$)-alkyl]-($C_1$-$C_6$)-alkylsilyl, $R^2$ and $R^3$ with the atoms to which they are attached form a fully saturated, partially saturated or fully unsaturated 5- to 7-membered ring which is optionally interrupted by heteroatoms and optionally substituted further, $R^3$ and $R^4$ with the atoms to which they are attached form a fully saturated, partially saturated or fully unsaturated 5- to 6-membered ring which is optionally interrupted by heteroatoms and optionally substituted further, $R^5$ represents hydrogen, hydroxy, ($C_1$-$C_6$)-alkyl, ($C_3$-$C_6$)-cycloalkyl, fluorine, chlorine, bromine, iodine, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-haloalkyl, ($C_1$-$C_6$)-alkoxy-($C_1$-$C_6$)-alkyl, ($C_2$-$C_6$)-alkynyl, ($C_2$-$C_6$)-alkenyl, ($C_3$-$C_6$)-cycloalkyl-($C_1$-$C_6$)-alkyl, cyano-($C_1$-$C_6$)-alkyl, nitro-($C_1$-$C_6$)-alkyl, aryl-($C_1$-$C_6$)-alkyl, heteroaryl-($C_1$-$C_6$)-alkyl, optionally substituted phenyl, ($C_1$-$C_6$)-alkylamino, ($C_1$-$C_6$)-alkylamino-($C_1$-$C_6$)-alkyl, bis-[($C_1$-$C_6$)-alkyl]amino-($C_1$-$C_6$)-alkyl, aminocarbonyl-($C_1$-$C_6$)-alkyl, ($C_1$-$C_6$)-alkylaminocarbonyl-($C_1$-$C_6$)-alkyl, bis-[($C_1$-$C_6$)-alkyl]aminocarbonyl-($C_1$-$C_6$)-alkyl, ($C_1$-$C_6$)-alkoxycarbonyl-($C_1$-$C_6$)-alkyl, hydroxycarbonyl-($C_1$-$C_6$)-alkyl, ($C_1$-$C_6$)-alkylcarbonyl, ($C_3$-$C_6$)-cycloalkylcarbonyl, ($C_1$-$C_6$)-haloalkylcarbonyl, ($C_1$-$C_6$)-alkoxycarbonyl, ($C_1$-$C_6$)-alkylsulphonyl, arylsulphonyl, ($C_3$-$C_6$)-cycloalkylsulphonyl, aryl-($C_1$-$C_6$)-alkylsulphonyl, ($C_2$-$C_6$)-alkenylsulphonyl, heteroarylsulphonyl, ($C_2$-$C_6$)-alkynylsulphonyl, ($C_1$-$C_6$)-alkylsulphinyl, arylsulphinyl, ($C_3$-$C_6$)-cycloalkylsulphinyl, ($C_2$-$C_6$)-alkenylsulphinyl, ($C_2$-$C_6$)-alkynylsulphinyl, arylcarbonyl, heteroarylcarbonyl, ($C_1$-$C_6$)-alkoxycarbonyl-($C_1$-$C_6$)-alkyl, cyano-($C_1$-$C_6$)-alkylaminocarbonyl, ($C_2$-$C_6$)-alkynylaminocarbonyl, heterocyclylcarbonyl, hetaroaryl-($C_1$-$C_6$)-alkylaminocarbonyl, ($C_2$-$C_6$)-alkenyloxycarbonyl, ($C_3$-$C_6$)-cycloalkyl-($C_1$-$C_6$)-alkoxycarbonyl, ($C_3$-$C_6$)-cycloalkyl-($C_1$-$C_6$)-alkoxycarbonylcarbonyl, ($C_1$-$C_6$)-alkoxycarbonylcarbonyl, ($C_3$-$C_6$)-cycloalkyl-($C_1$-$C_6$)-alkylaminocarbonyl, aryl-($C_1$-$C_6$)-alkylaminocarbonyl or a negative charge, $R^6$ represents hydrogen, hydroxy, nitro, fluorine, chlorine, bromine, iodine, amino, ($C_1$-$C_6$)-alkyl, ($C_3$-$C_6$)-cycloalkyl, ($C_1$-$C_6$)-alkylcarbonyl, arylcarbonyl, ($C_1$-$C_6$)-alkylaminocarbonyl, bis-($C_1$-$C_6$)-alkylaminocarbonyl, ($C_3$-$C_6$)-cycloalkylaminocarbonyl, ($C_4$-$C_6$)-cycloalkenylaminocarbonyl, ($C_3$-$C_6$)-cycloalkyl-[($C_1$-$C_6$)-alkyl]aminocarbonyl, ($C_1$-$C_6$)-alkyl-[($C_1$-$C_6$)-alkyl]aminocarbonyl, ($C_3$-$C_6$)-cycloalkyl-($C_1$-$C_6$)-alkylaminocarbonyl, ($C_3$-$C_6$)-cycloalkyl-($C_1$-$C_6$)-alkyl[($C_1$-$C_6$)-alkyl]aminocarbonyl, ($C_1$-$C_6$)-alkyl[($C_2$-$C_6$)-alkynyl]aminocarbonyl, ($C_1$-$C_6$)-alkynylaminocarbonyl, arylaminocarbonyl, heteroarylaminocarbonyl, ($C_2$-$C_6$)-alkenylaminocarbonyl, cyano-($C_1$-$C_6$)-alkylaminocarbonyl, aryl-($C_1$-$C_6$)-alkylaminocarbonyl, aryl[($C_1$-$C_6$)-alkyl]aminocarbonyl, heteroaryl[($C_1$-$C_6$)-alkyl]aminocarbonyl, heterocyclyl-N-carbonyl, ($C_1$-$C_6$)-alkoxycarbonylheterocyclyl-N-carbonyl, ($C_1$-$C_6$)-alkoxycarbonyl-($C_1$-$C_6$)-alkylaminocarbonyl, hydroxycarbonylheterocyclyl-N-carbonyl, hydroxycarbonyl-($C_1$-$C_6$)-alkylaminocarbonyl, ($C_3$-$C_6$)-cycloalkoxycarbonylheterocyclyl-N-carbonyl, ($C_3$-$C_6$)-cycloalkoxycarbonyl-($C_1$-$C_6$)-alkylaminocarbonyl, ($C_1$-$C_6$)-alkylaminocarbonyl-($C_1$-$C_6$)-alkylaminocarbonyl, aminocarbonyl-($C_1$-$C_6$)-alkylaminocarbonyl, ($C_3$-$C_6$)-cycloalkylaminocarbonyl-($C_1$-$C_6$)-alkylaminocarbonyl, bis-($C_1$-$C_6$)-alkylamino-($C_1$-$C_6$)-alkylaminocarbonyl, bis-($C_1$-$C_6$)-alkylaminocarbonyl-($C_1$-$C_6$)-alkylaminocarbonyl, ($C_1$-$C_6$)-alkylaminocarbonyl-($C_1$-$C_6$)-alkylaminocarbonyl, heterocyclyl-N-carbonyl-($C_1$-$C_6$)-alkylaminocarbonyl, ($C_3$-$C_6$)-cycloalkyl-N-heterocyclyl-N-carbonyl, ($C_1$-$C_6$)-alkoxy[($C_1$-$C_6$)-alkyl]aminocarbonyl, ($C_1$-$C_6$)-alkoxycarbonylamino, hydroxycarbonyl, ($C_1$-$C_6$)-alkoxycarbonyl, ($C_1$-$C_6$)-cycloalkoxycarbonyl, ($C_1$-$C_6$)-cycloalkyl-($C_1$-$C_6$)-alkoxycarbonyl, ($C_1$-$C_6$)-alkoxy-($C_1$-$C_6$)-alkoxycarbonyl, ($C_1$-$C_6$)-alkoxycarbonyl-($C_1$-$C_6$)-alkoxycarbonyl, ($C_2$-$C_6$)-alkenyloxycarbonyl, ($C_2$-$C_6$)-alkynyloxycarbonyl, hydroxycarbonyl-($C_1$-$C_6$)-alkoxycarbonyl, ($C_1$-$C_6$)-haloalkoxycarbonyl, aryl[($C_1$-$C_6$)-alkyl]aminocarbonylamino, arylaminocarbonylamino, ($C_1$-$C_6$)-alkylaminocarbonylamino, heteroarylaminocarbonylamino, ($C_1$-$C_6$)-alkoxy, ($C_1$-$C_6$)-alkylamino-($C_1$-$C_6$)-alkoxy, ($C_1$-$C_6$)-alkylcarbonyloxy, arylcarbonyloxy, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-haloalkyl, ($C_1$-$C_6$)-alkoxy-($C_1$-$C_6$)-alkyl, ($C_2$-$C_6$)-alkynyl, ($C_2$-$C_6$)-alkenyl, optionally substituted phenyl, heteroaryl, ($C_1$-$C_6$)-alkoxycarbonyl-($C_1$-$C_6$)-alkyl, ($C_1$-$C_6$)-alkylamino, bis-($C_1$-$C_6$)-alkylamino, ($C_3$-$C_6$)-cycloalkylamino, aryl-($C_1$-$C_6$)-alkylamino, $R^7$ represents hydrogen, fluorine, chlorine, bromine, iodine, amino, ($C_1$-$C_6$)-alkyl, ($C_1$-$C_6$)-haloalkyl, ($C_3$-$C_6$)-cycloalkyl, ($C_1$-$C_6$)-alkylcarbonyl, arylcarbonyl, heteroarylcarbonyl, ($C_3$-$C_6$)-cycloalkylcarbonyl, ($C_1$-$C_6$)-alkoxycarbonyl, hydroxycarbonyl, optionally substituted phenyl, heteroaryl, arylcarbonyl-($C_1$-$C_6$)-alkoxycarbonyl, ($C_1$-$C_6$)-alkylcarbonyl-($C_1$-$C_6$)-alkoxycarbonyl, ($C_3$-$C_6$)-cycloalkyl-($C_1$-$C_6$)-alkoxycarbonyl, heteroaryl-($C_1$-$C_6$)-alkoxycarbonyl, heteroarylheteroaryl($C_1$-$C_6$)-alkyl-($C_1$-$C_6$)-alkoxycarbonyl, heteroaryl($C_1$-$C_6$)-alkyl-($C_1$-$C_6$)-alkoxycarbonyl, aryl-($C_1$-$C_6$)-alkoxycarbonyl, ($C_1$-$C_6$)-alkylcarbonyloxy, arylaminocarbonyl, ($C_1$-$C_6$)-alkylaminocarbonyl, bis-($C_1$-$C_6$)-alkylaminocarbonyl, ($C_3$-$C_6$)-cycloalkylaminocarbonyl, heterocyclyl-N-carbonyl, aryl-($C_1$-$C_6$)-alkylaminocarbonyl, cyano-($C_1$-$C_6$)-alkylaminocarbonyl, ($C_2$-$C_6$)-alkenylaminocarbonyl, bis-[($C_1$-$C_6$)-alkoxycarbonyl]-($C_2$-$C_6$)-alkenylamino, bis-cyano-($C_1$-$C_6$)-alkenylamino, ($C_1$-$C_6$)-alkoxycarbonyl(cyano)-($C_2$-$C_6$)-alkenylamino, ($C_1$-$C_6$)-alkylamino, arylamino, ($C_3$-$C_6$)-cycloalkylamino, aryl[($C_1$-$C_6$)-alkyl]amino, bis-($C_1$-$C_6$)-alkylamino, $R^8$ represents hydrogen, ($C_1$-$C_6$)-alkyl, ($C_1$-$C_6$)-haloalkyl, ($C_3$-$C_6$)-cycloalkyl, fluorine, chlorine, bromine, iodine, $R^9$ represents hydrogen, ($C_1$-$C_6$)-alkyl, ($C_1$-$C_6$)-haloalkyl, ($C_3$-$C_6$)-cycloalkyl, fluorine, chlorine, bromine, iodine, $R^{10}$, $R^{11}$ independently of one another represent hydrogen, fluorine, chlorine, bromine, iodine, ($C_1$-$C_6$)-alkyl, ($C_3$-$C_6$)-cycloalkyl, ($C_1$-$C_6$)-haloalkyl, aryl-($C_1$-$C_6$)-alkyl, heteroaryl-($C_1$-$C_6$)-alkyl, ($C_1$-$C_6$)-alkylcarbonyl, aryl-($C_1$-$C_6$)-alkylcarbonyl, ($C_3$-$C_6$)-cycloalkylcarbonyl, ($C_3$-$C_6$)-cycloalkyl-($C_1$-$C_6$)-alkylcarbonyl, arylcarbonyl, heteroarylcarbonyl, arylaminocarbonyl, ($C_1$-$C_6$)-alkylaminocarbonyl, ($C_2$-$C_6$)-alkynyl, ($C_2$-$C_6$)-alkenyl, ($C_2$-$C_6$)-haloalkenyl, $R^{12}$ represents hydroxyl, ($C_1$-$C_6$)-alkoxy, ($C_2$-$C_6$)-alkenyloxy, aryl-($C_1$-$C_6$)-alkoxy, ($C_1$-$C_6$)-alkylamino, arylamino, heteroarylamino, heteroarylcarbonylamino, arylcarbonylamino, $R^{13}$ represents hydrogen, ($C_1$-$C_6$)-alkoxy, ($C_2$-$C_6$)-alkenyloxy, optionally substituted phenyl, heteroaryl, heteroarylamino, arylamino, bis-($C_1$-$C_6$)-alkylamino-($C_1$-$C_6$)-alkylamino, ($C_1$-$C_6$)-alkylamino, $R^{14}$, $R^{15}$ independently of one another represent hydrogen, ($C_1$-$C_6$)-alkyl, ($C_3$-$C_6$)-cycloalkyl, ($C_1$-$C_6$)-haloalkyl, ($C_1$-$C_6$)-alkylcarbonyl, ($C_3$-$C_6$)-cycloalkylcarbonyl, ($C_3$-$C_6$)-cycloalkyl-($C_1$-$C_6$)-alkylcarbonyl, arylcarbonyl, heteroarylcarbonyl, ($C_1$-$C_6$)-alkoxycarbonyl, hydroxycarbonyl, ($C_1$-$C_6$)-alkoxy, aryl-($C_1$-$C_6$)-alkyl, heteroaryl-($C_1$-$C_6$)-alkyl, ($C_1$-$C_6$)-alkylaminocarbonyl, ($C_2$-$C_6$)-alkenylaminocarbonyl, ($C_2$-$C_6$)-alkynyl-($C_1$-$C_6$)-alkylaminocarbonyl, cyano-($C_1$-$C_6$)-alkylaminocarbonyl, ($C_3$-$C_6$)-cycloalkylaminocarbonyl, $R^{16}$, $R^{17}$, $R^{18}$, $R^{19}$ independently of one another represent hydrogen, fluorine, chlorine, bromine, iodine, nitro, amino, cyano, thiocyanato, isothiocyanato, hydroxy, hydrothio, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkylthio, ($C_1$-$C_6$)-alkylthio, ($C_1$-$C_6$)-haloalkoxy, ($C_1$-$C_6$)-alkylamino, heteroaryl-($C_1$-$C_6$)-alkylamino, aryl-($C_1$-$C_6$)-alkylamino, ($C_3$-$C_6$)-cycloalkylamino, ($C_1$-$C_6$)-alkylcarbonylamino, bis-[($C_1$-$C_6$)-alkyl]amino-($C_1$-$C_6$)-alkylcarbonylamino, aryl-($C_1$-$C_6$)-alkylcarbonylamino, ($C_3$-$C_6$)-cycloalkylcarbonylamino, ($C_3$-$C_6$)-cycloalkyl-($C_1$-$C_6$)-alkylcarbonylamino ($C_1$-$C_6$)-alkyl-N-heterocyclyl-N, ($C_1$-$C_6$)-alkyl-N-heterobicyclyl-N, bis-($C_1$-$C_6$)-alkylamino-($C_1$-$C_6$)-alkylamino, hydroxycarbonyl, ($C_1$-$C_6$)-alkoxycarbonyl, ($C_1$-$C_6$)-alkylaminocarbonyl, ($C_3$-$C_6$)-cycloalkylaminocarbonyl, aryl-($C_1$-$C_6$)-alkylaminocarbonyl, arylsulphonylamino, ($C_1$-$C_6$)-alkylsulphonylamino, ($C_3$-$C_6$)-cycloalkylsulphonylamino, ($C_1$-$C_6$)-alkoxycarbonylamino, ($C_1$-$C_6$)-alkoxycarbonyl-($C_1$-$C_6$)-alkylamino, ($C_3$-$C_6$)-cycloalkoxycarbonylamino, ($C_3$-$C_6$)-cycloalkyl-($C_1$-$C_6$)-alkoxycarbonylamino, aryl-($C_1$-$C_6$)-alkoxycarbonylamino, ($C_1$-$C_6$)-alkylaminocarbonylamino, bis-[($C_1$-$C_6$)-alkyl]aminocarbonylamino, ($C_3$-$C_6$)-cycloalkylaminocarbonylamino, arylaminocarbonylamino, aryl-($C_1$-$C_6$)-alkylaminocarbonylamino, arylaminocarbonyl-($C_1$-$C_6$)-alkylcarbonylamino, heteroarylaminocarbonyl-($C_1$-$C_6$)-alkylamino, heteroarylamino, aryl-($C_1$-$C_6$)-alkyliminoamino, heterocyclyl-N-carbonyl, ($C_1$-$C_6$)-alkoxycarbonylheterocyclyl-N-carbonyl, ($C_1$-$C_6$)-alkoxycarbonyl-($C_1$-$C_6$)-alkylaminocarbonyl, hydroxycarbonylheterocyclyl-N-carbonyl, hydroxycarbonyl-($C_1$-$C_6$)-alkylaminocarbonyl, ($C_3$-$C_6$)-cycloalkoxycarbonylheterocyclyl-N-carbonyl, ($C_3$-$C_6$)-cycloalkoxycarbonyl-($C_1$-$C_6$)-alkylaminocarbonyl, ($C_1$-$C_6$)-alkylaminocarbonyl-($C_1$-$C_6$)-alkylaminocarbonyl, aminocarbonyl-($C_1$-$C_6$)-alkylaminocarbonyl, ($C_3$-$C_6$)-cycloalkylaminocarbonyl-($C_1$-$C_6$)-alkylaminocarbonyl, bis-($C_1$-$C_6$)-alkylamino-($C_1$-$C_6$)-alkylaminocarbonyl, bis-($C_1$-$C_6$)-alkylaminocarbonyl-($C_1$-$C_6$)-alkylaminocarbonyl, ($C_1$-$C_6$)-alkylaminocarbonyl-($C_1$-$C_6$)-alkylaminocarbonyl, heterocyclyl-N-carbonyl-($C_1$-$C_6$)-alkylaminocarbonyl, ($C_3$-$C_6$)-cycloalkyl-N-heterocyclyl-N-carbonyl, ($C_1$-$C_6$)-alkoxy[($C_1$-$C_6$)-alkyl]aminocarbonyl, $R^{20}$, $R^{21}$, $R^{22}$, $R^{23}$ independently of one another represent hydrogen, ($C_1$-$C_6$)-alkyl, ($C_3$-$C_6$)-cycloalkyl, ($C_1$-$C_6$)-haloalkyl, $R^{24}$, $R^{25}$, $R^{26}$, $R^{27}$ independently of one another represent hydrogen, fluorine, chlorine, bromine, iodine, nitro, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkylthio, ($C_1$-$C_6$)-alkylthio, ($C_1$-$C_6$)-haloalkoxy, ($C_1$-$C_6$)-alkylamino, heteroaryl-($C_1$-$C_6$)-alkylamino, aryl-($C_1$-$C_6$)-alkylamino, ($C_3$-$C_6$)-cycloalkylamino, hydroxycarbonyl, ($C_1$-$C_6$)-alkoxycarbonyl, ($C_1$-$C_6$)-alkylaminocarbonyl, ($C_3$-$C_6$)-cycloalkylaminocarbonyl, aryl-($C_1$-$C_6$)-alkylaminocarbonyl, optionally substituted phenyl, heteroaryl, ($C_3$-$C_6$)-cycloalkoxycarbonyl, ($C_3$-$C_6$)-cycloalkyl-($C_1$-$C_6$)-alkoxycarbonyl, ($C_2$-$C_6$)-alkenyloxycarbonyl, ($C_2$-$C_6$)-alkenylaminocarbonyl, ($C_2$-$C_6$)-alkynyloxycarbonyl, ($C_2$-$C_6$)-alkynylaminocarbonyl, ($C_2$-$C_6$)-alkenyl, ($C_2$-$C_6$)-alkynyl, aminosulphonyl, ($C_1$-$C_6$)-alkylsulphonylamino, ($C_3$-$C_6$)-cycloalkylsulphonylamino, arylsulphonylamino, hetarylsulphonylamino, sulphonyl-($C_1$-$C_6$)-haloalkylamino, amino-($C_1$-$C_6$)-alkylsulphonyl, amino-($C_1$-$C_6$)-haloalkylsulphonyl, ($C_1$-$C_6$)-alkylsulphonyl, ($C_3$-$C_6$)-cycloalkylsulphonyl, arylsulphonyl, ($C_1$-$C_6$)-alkylsulphinyl, ($C_3$-$C_6$)-cycloalkylsulphinyl, arylsulphinyl, ($C_3$-$C_6$)-cycloalkoxy, wherewith further very particular preference mention may be made of compounds of the formula (I) in which Q-1 represents one of the groups Q-1.1 to Q-1.98 mentioned below

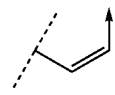

Q-1.1

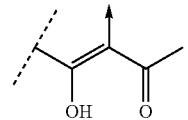

Q-1.2

-continued
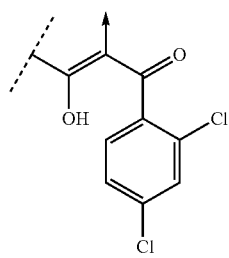
Q-1.3
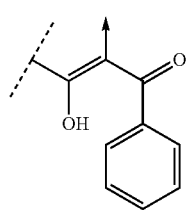
Q-1.4
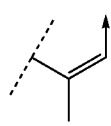
Q-1.5
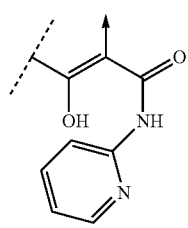
Q-1.6
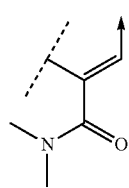
Q-1.7
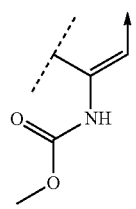
Q-1.8
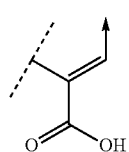
Q-1.9
-continued
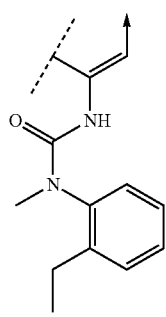
Q-1.10
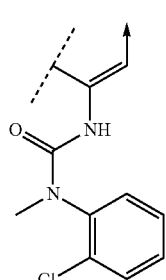
Q-1.11
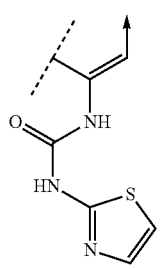
Q-1.12
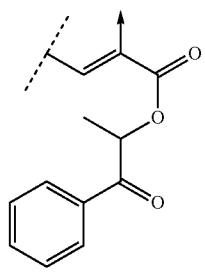
Q-1.13
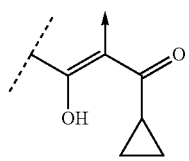
Q-1.14
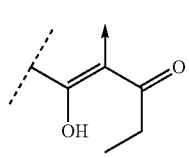
Q-1.15

-continued
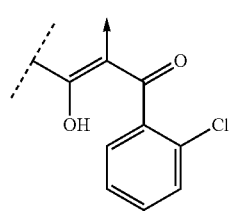
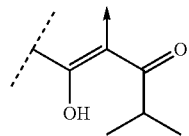
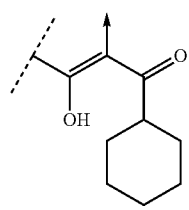
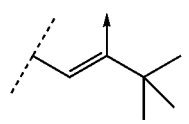
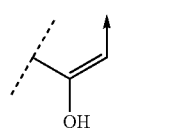
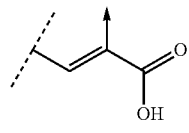
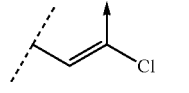
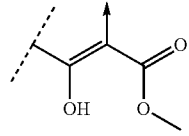
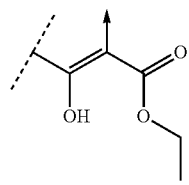
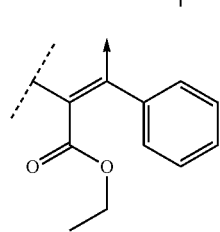
-continued
Q-1.16
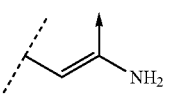
Q-1.17
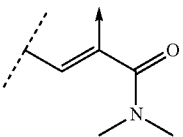
Q-1.18
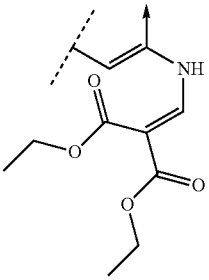
Q-1.19
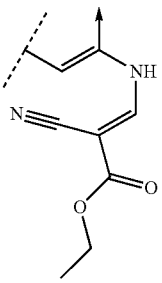
Q-1.20
Q-1.21
Q-1.22
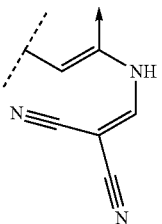
Q-1.23
Q-1.24
Q-1.25
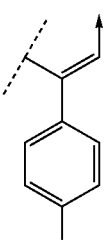
Q-1.26
Q-1.27
Q-1.28
Q-1.29
Q-1.30
Q-1.31
Q-1.32
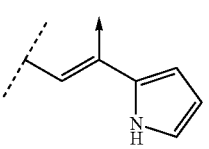

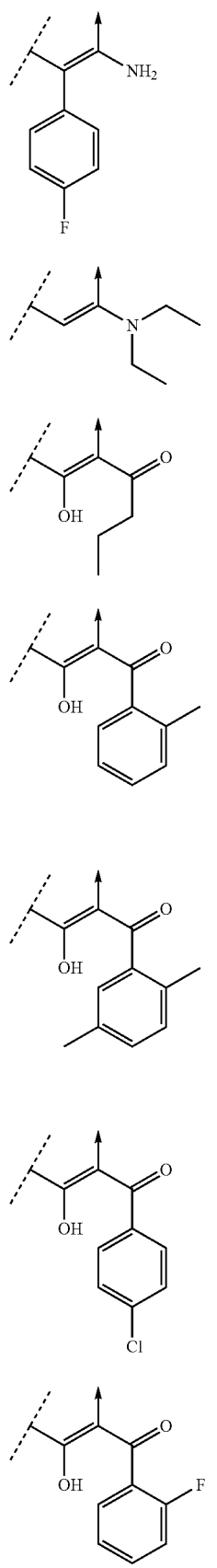
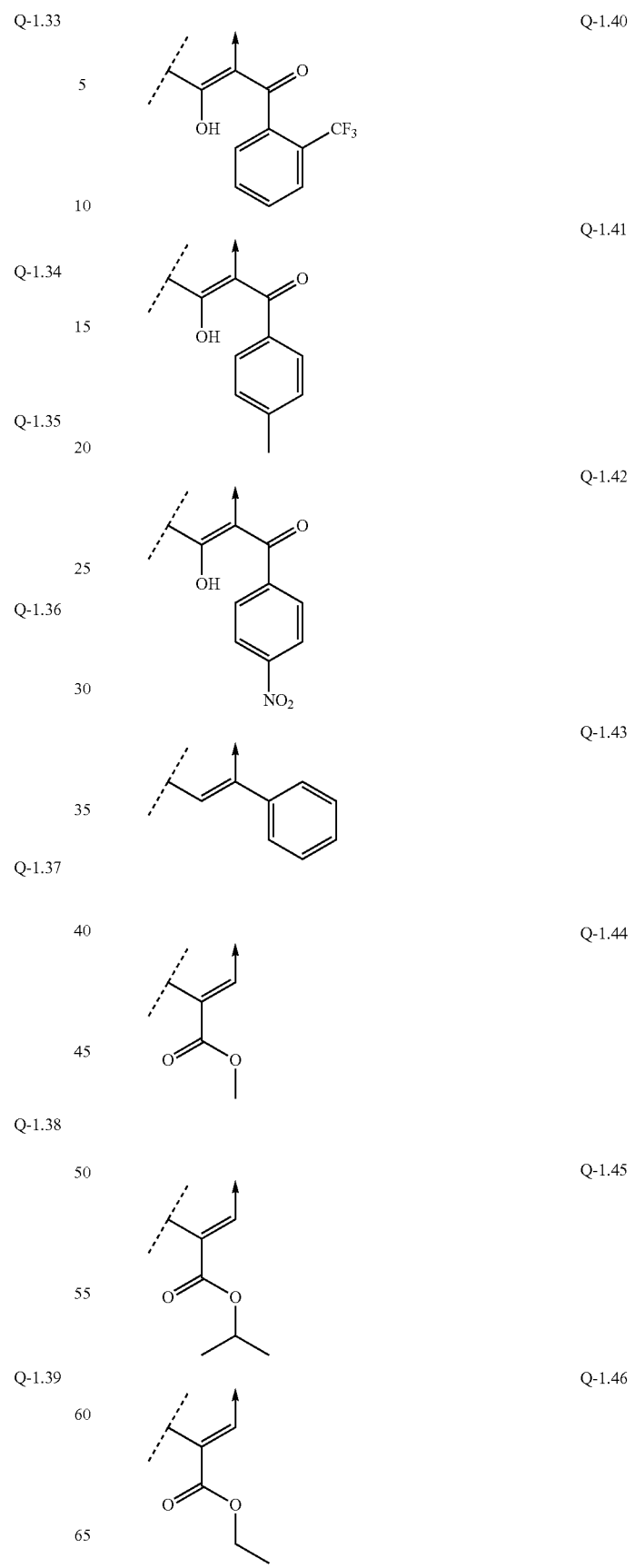

Q-1.47 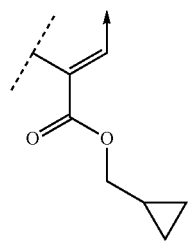
Q-1.48 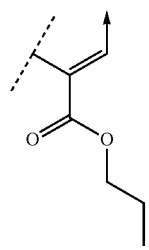
Q-1.49 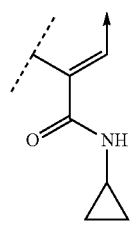
Q-1.50 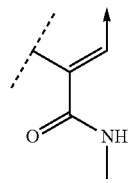
Q-1.51 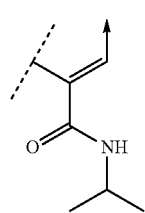
Q-1.52 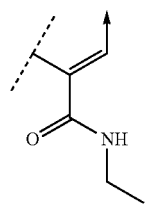
Q-1.53 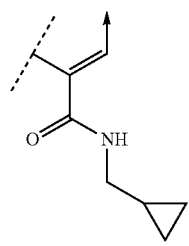
Q-1.54 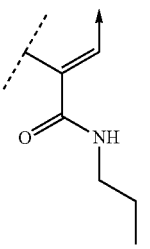
Q-1.55 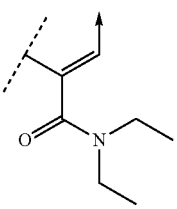
Q-1.56 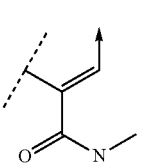
Q-1.57 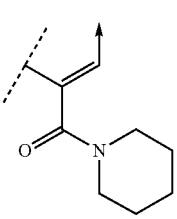
Q-1.58 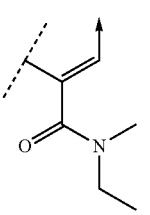
Q-1.59 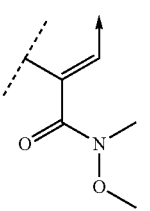
Q-1.60 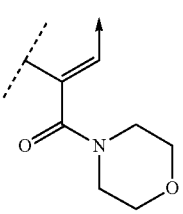

Q-1.61
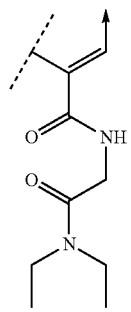
Q-1.62
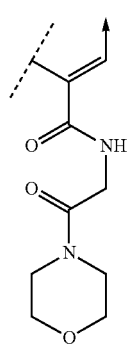
Q-1.63
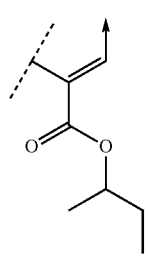
Q-1.64
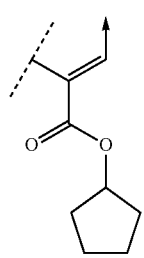
Q-1.65
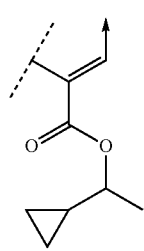
Q-1.66
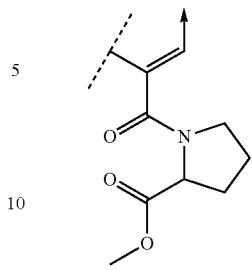
Q-1.67
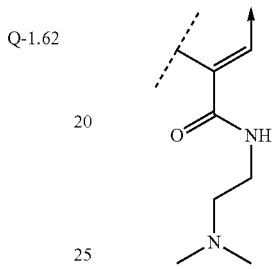
Q-1.68
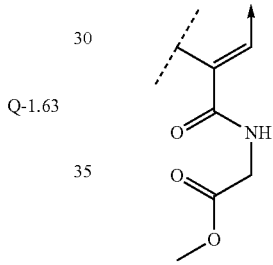
Q-1.69
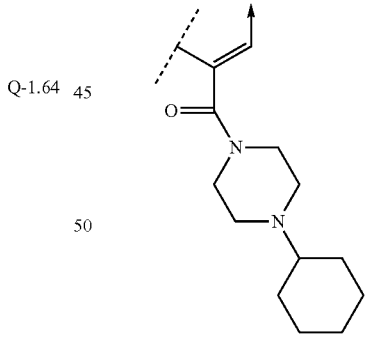
Q-1.70
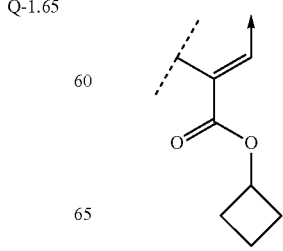

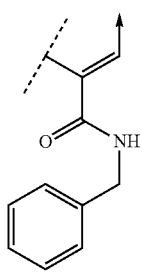 Q-1.66
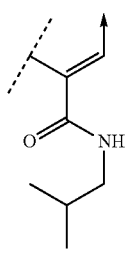 Q-1.67
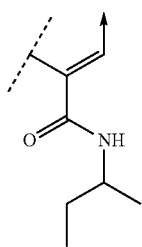 Q-1.68
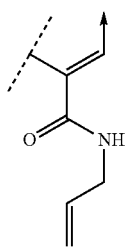 Q-1.69
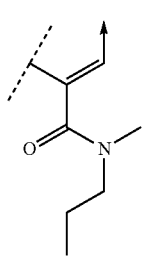 Q-1.70
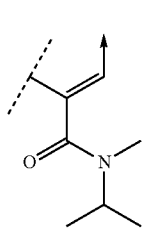 Q-1.71
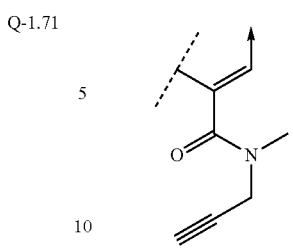 Q-1.77
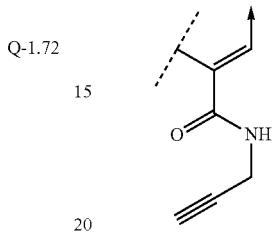 Q-1.78
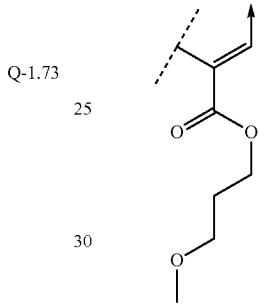 Q-1.79
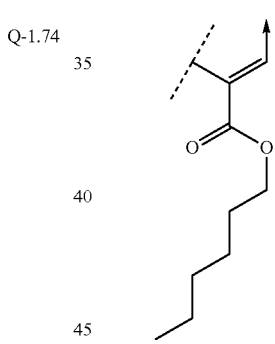 Q-1.80
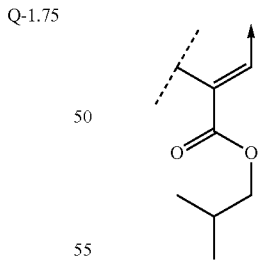 Q-1.81
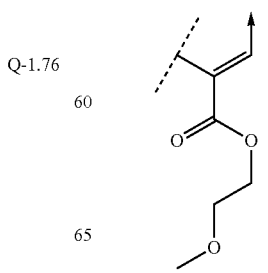 Q-1.82

Q-1.83 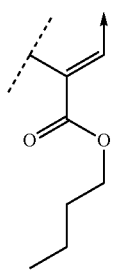
Q-1.84 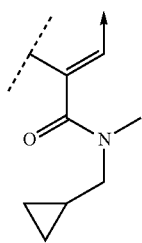
Q-1.85 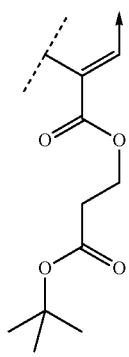
Q-1.86 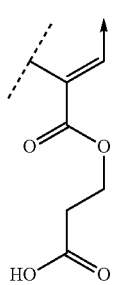
Q-1.87 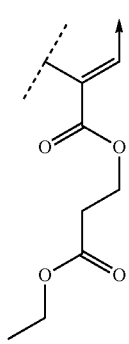
Q-1.88 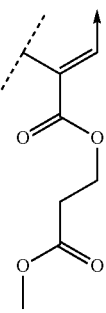
Q-1.89 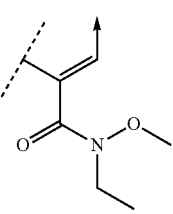
Q-1.90 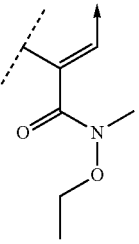
Q-1.91 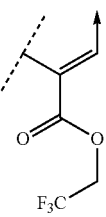
Q-1.92 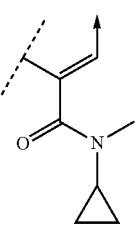
Q-1.93 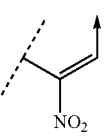
Q-1.94 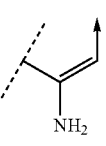

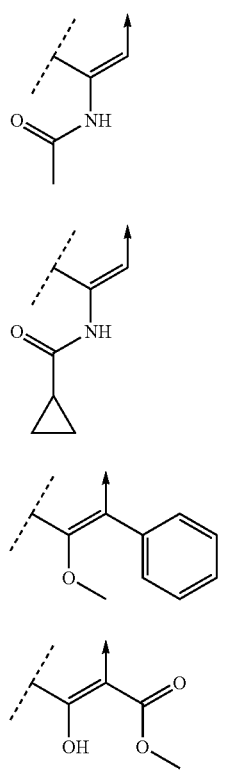
Q-1.95
Q-1.96
Q-1.97
Q-1.98
Q-2 represents one of the groups Q-2.1 to Q-2.44 mentioned below
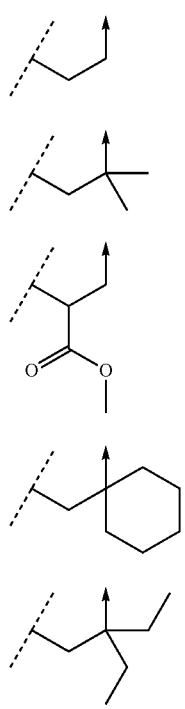
Q-2.1
Q-2.2
Q-2.3
Q-2.4
Q-2.5
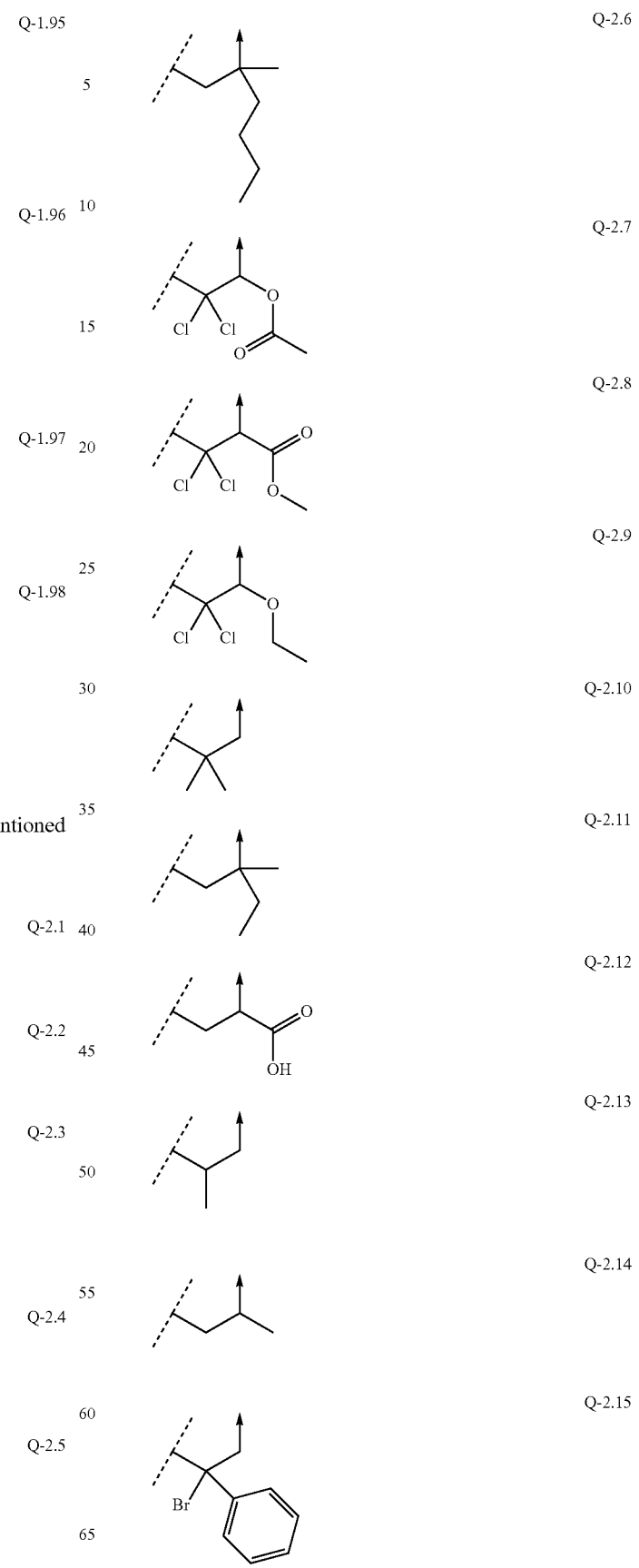
Q-2.6
Q-2.7
Q-2.8
Q-2.9
Q-2.10
Q-2.11
Q-2.12
Q-2.13
Q-2.14
Q-2.15

Q-2.16 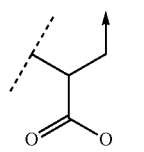
Q-2.17 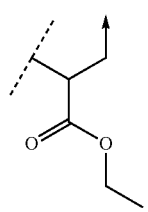
Q-2.18 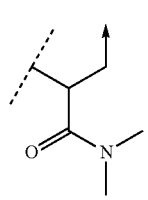
Q-2.19 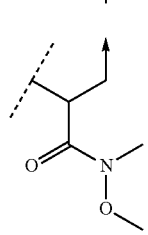
Q-2.20 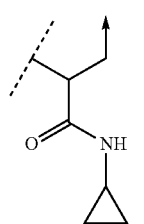
Q-2.21 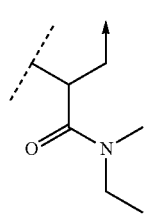
Q-2.22 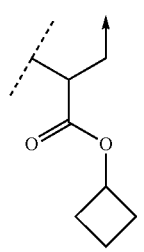
Q-2.23 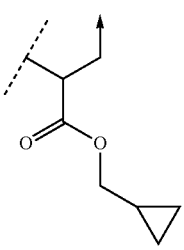
Q-2.24 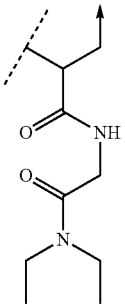
Q-2.25 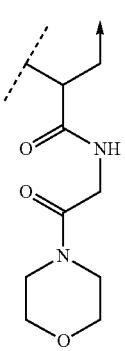
Q-2.26 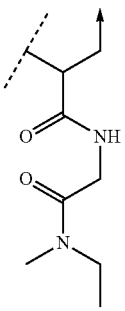
Q-2.27

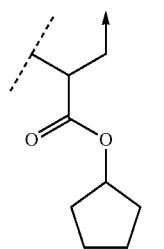
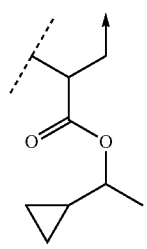
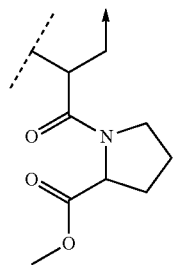
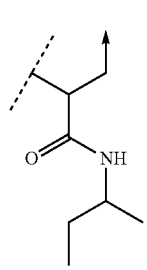
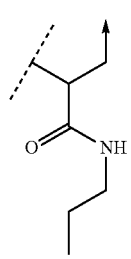
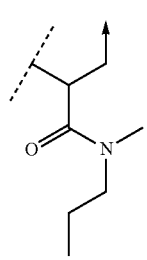
Q-2.28
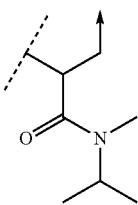
Q-2.29
Q-2.30
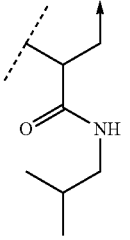
Q-2.31
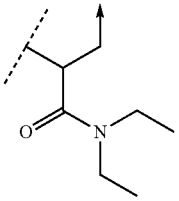
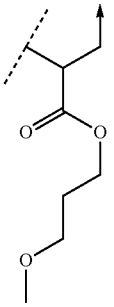
Q-2.32
Q-2.33
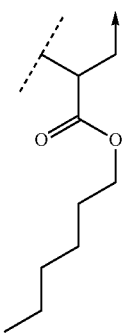
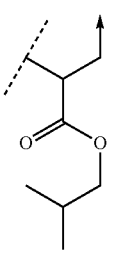
Q-2.34
Q-2.35
Q-2.36
Q-2.37
Q-2.38
Q-2.39

Q-2.40
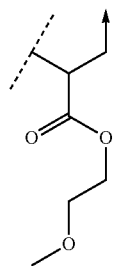
Q-2.41
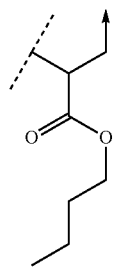
Q-2.42
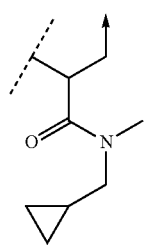
Q-2.43
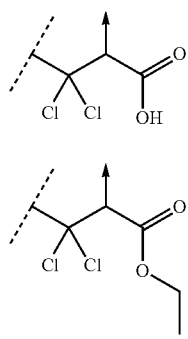
Q-2.44
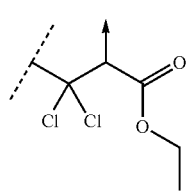
Q-3 represents one of the groups Q-3.1 to Q-3.20 mentioned below
Q-3.1
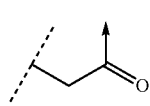
Q-3.2
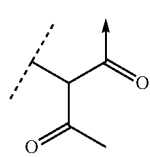
Q-3.3
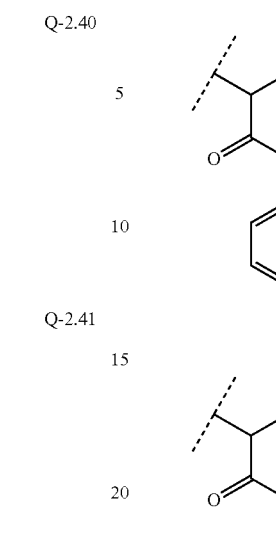
Q-3.4
Q-3.5
Q-3.6
Q-3.7
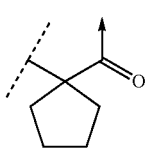
Q-3.8
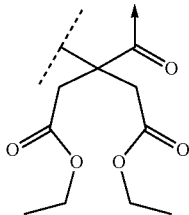

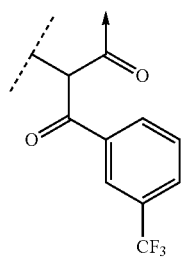
Q-3.9
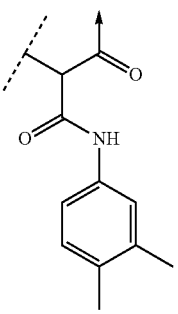
Q-3.14
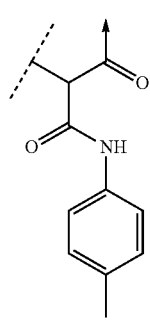
Q-3.10
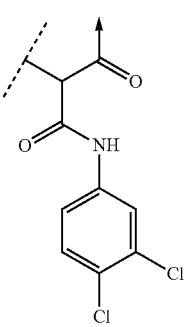
Q-3.15
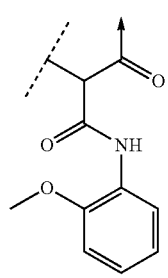
Q-3.11
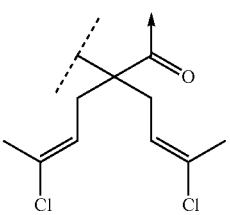
Q-3.16
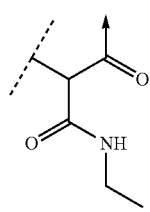
Q-3.12
Q-3.17
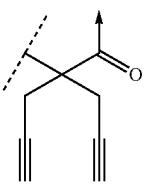
Q-3.18
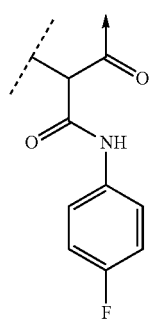
Q-3.13
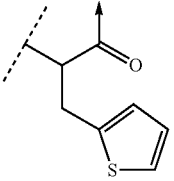
Q-3.19
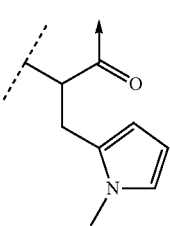
Q-3.20

Q-5 represents one of the groups Q-5.1 to Q-5.78 mentioned below
Q-5.1
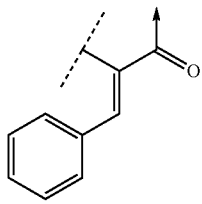
Q-5.2
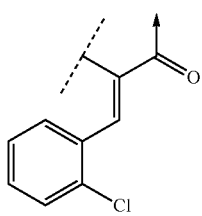
Q-5.3
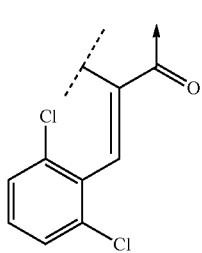
Q-5.4
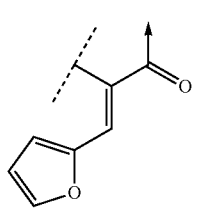
Q-5.5
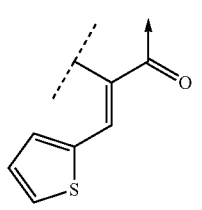
Q-5.6
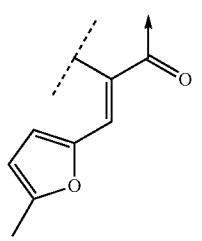
Q-5.7
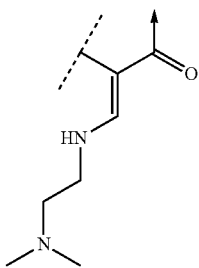
Q-5.8
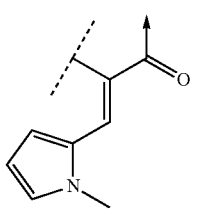
Q-5.9
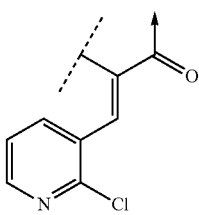
Q-5.10
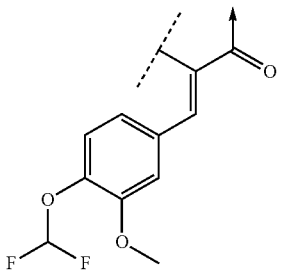
Q-5.11
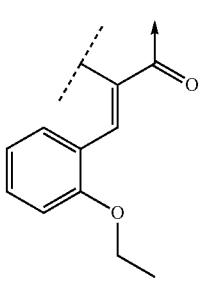
Q-5.12
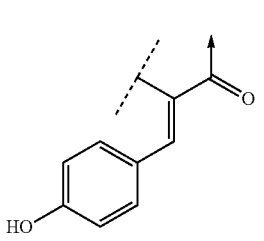

Q-5.13 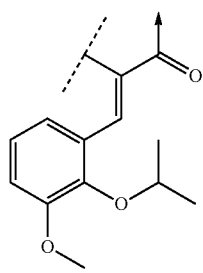
Q-5.14 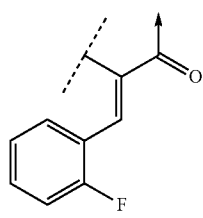
Q-5.15 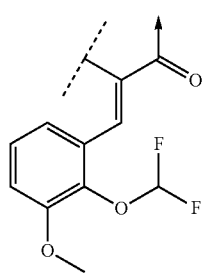
Q-5.16 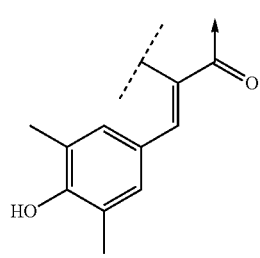
Q-5.17 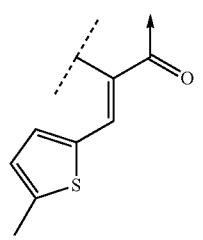
Q-5.18 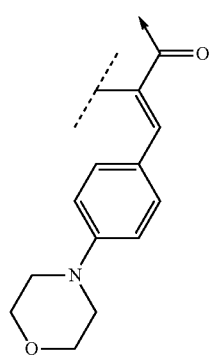
Q-5.19 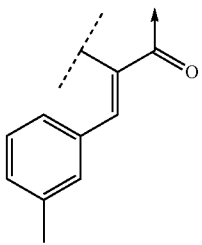
Q-5.20 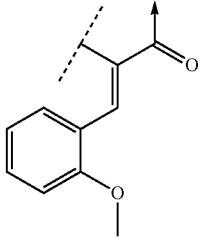
Q-5.21 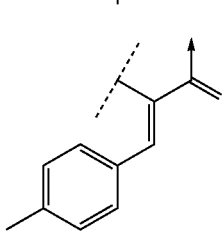
Q-5.22 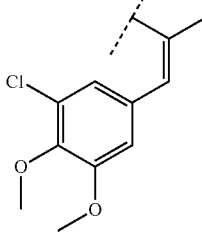
Q-5.23 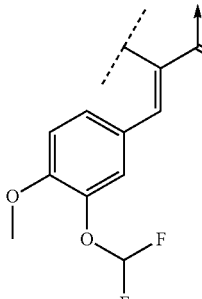
Q-5.24 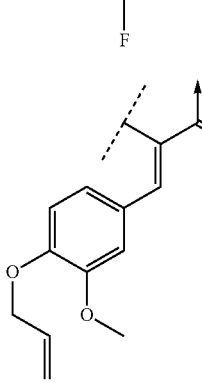

-continued
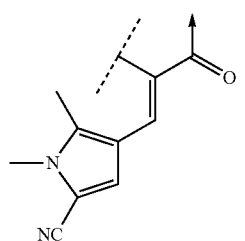
Q-5.25
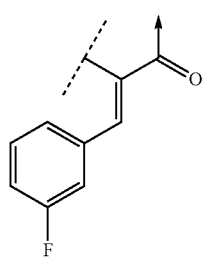
Q-5.26
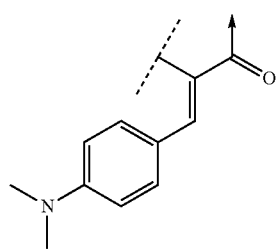
Q-5.27
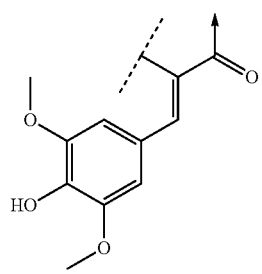
Q-5.28
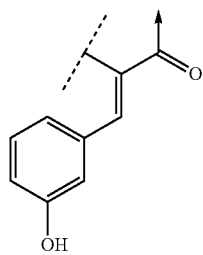
Q-5.29
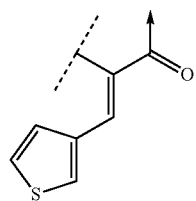
Q-5.30
-continued
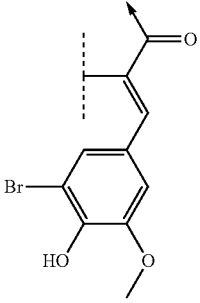
Q-5.31
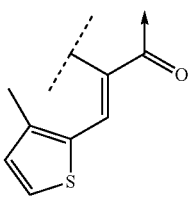
Q-5.32
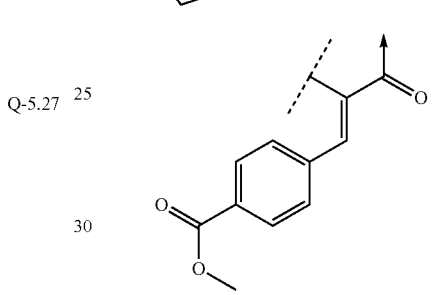
Q-5.33
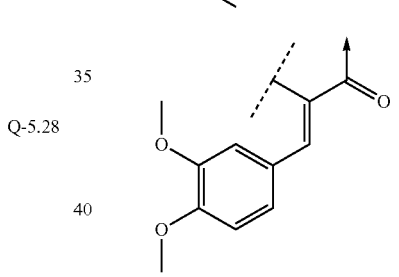
Q-5.34
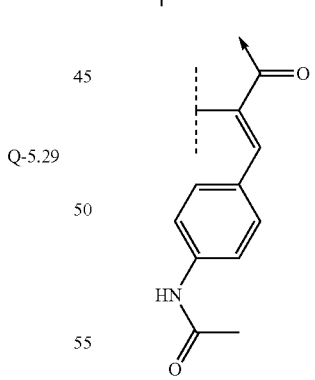
Q-5.35
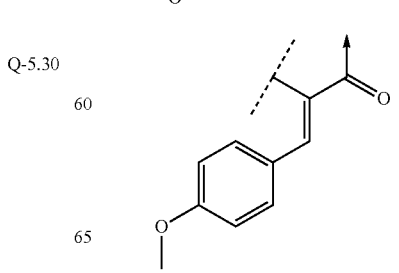
Q-5.36

-continued
Q-5.37
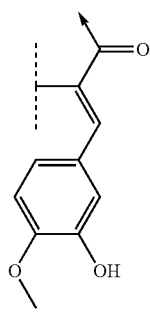
Q-5.38
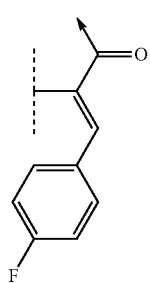
Q-5.39
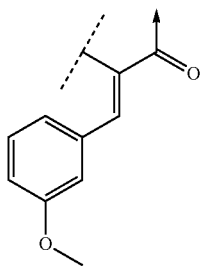
Q-5.40
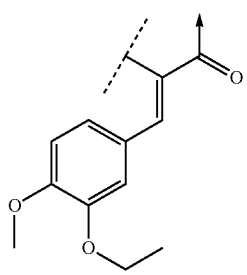
Q-5.41
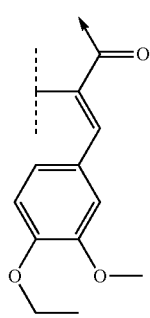
-continued
Q-5.42
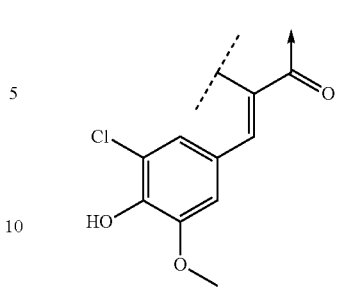
Q-5.43
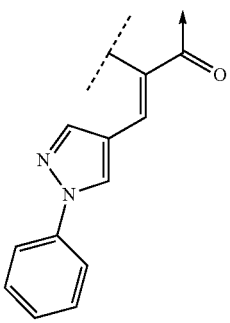
Q-5.44
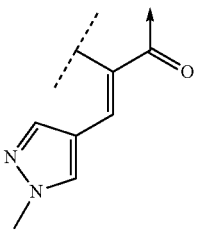
Q-5.45
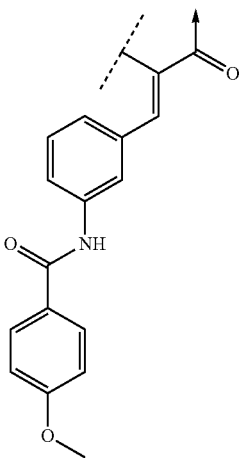
Q-5.46
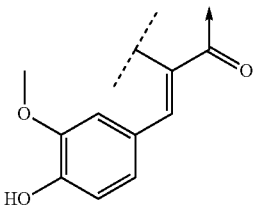

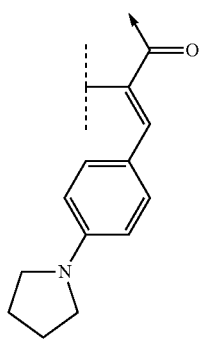
Q-5.47
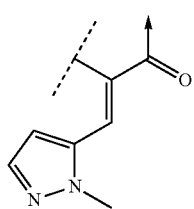
Q-5.48
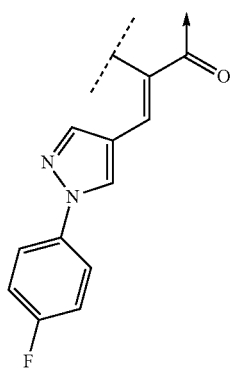
Q-5.49
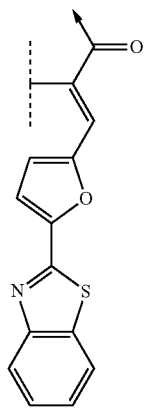
Q-5.50
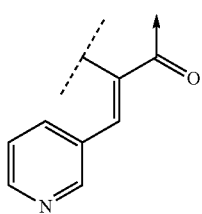
Q-5.51
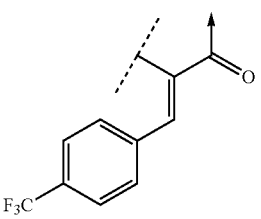
Q-5.52
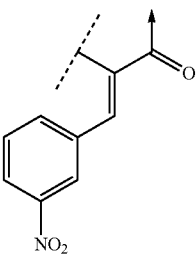
Q-5.53
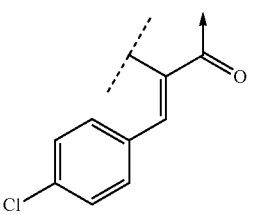
Q-5.54
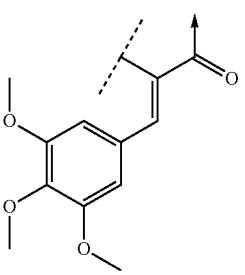
Q-5.55
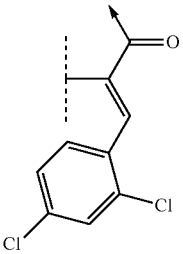
Q-5.56
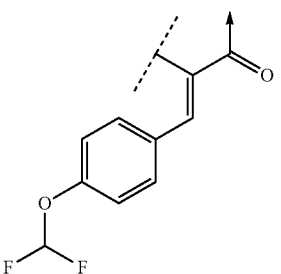
Q-5.57

-continued
Q-5.58
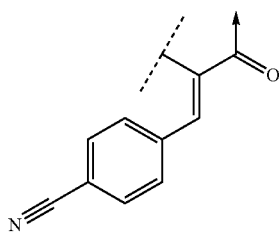
Q-5.59
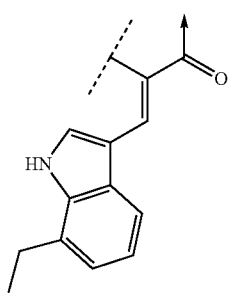
Q-5.60
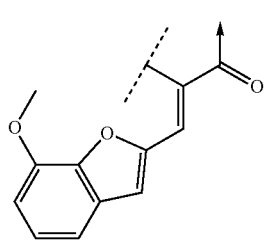
Q-5.61
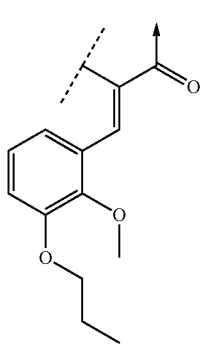
Q-5.62
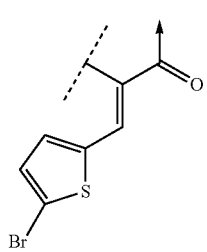
Q-5.63
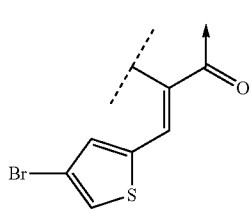
-continued
Q-5.64
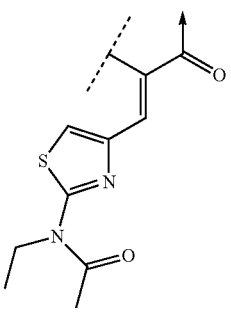
Q-5.65
Q-5.66
Q-5.67
Q-5.68

Q-5.69 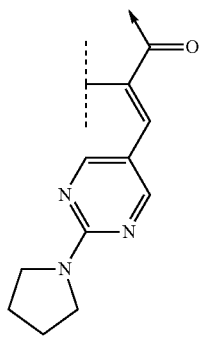
Q-5.70 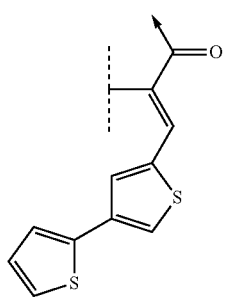
Q-5.71 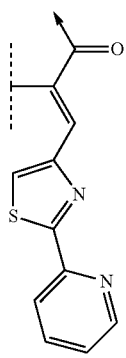
Q-5.72 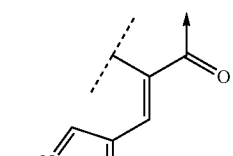
Q-5.73 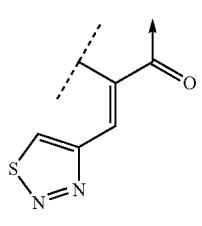
Q-5.74 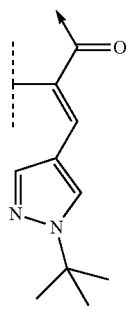
Q-5.75 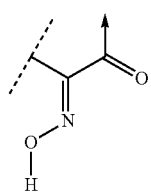
Q-5.76 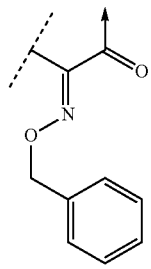
Q-5.77 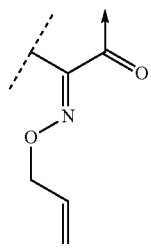
Q-5.78 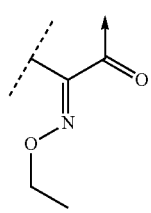
Q-6 represents one of the groups Q-6.1 to Q-6.13 mentioned below
Q-6.1 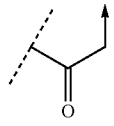

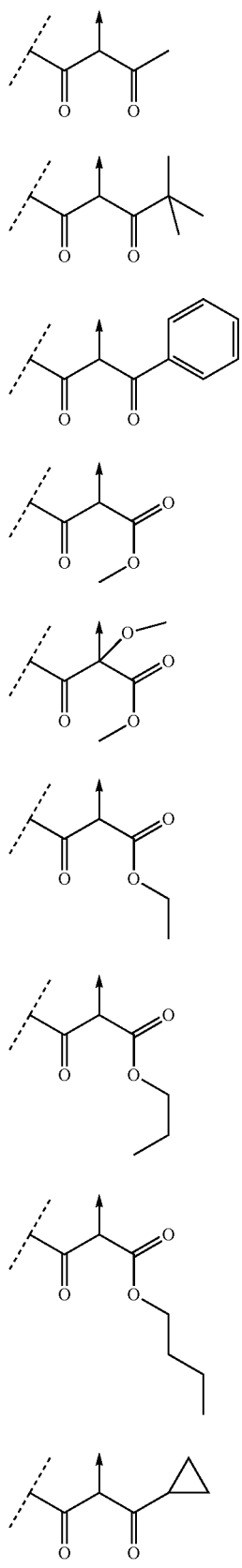
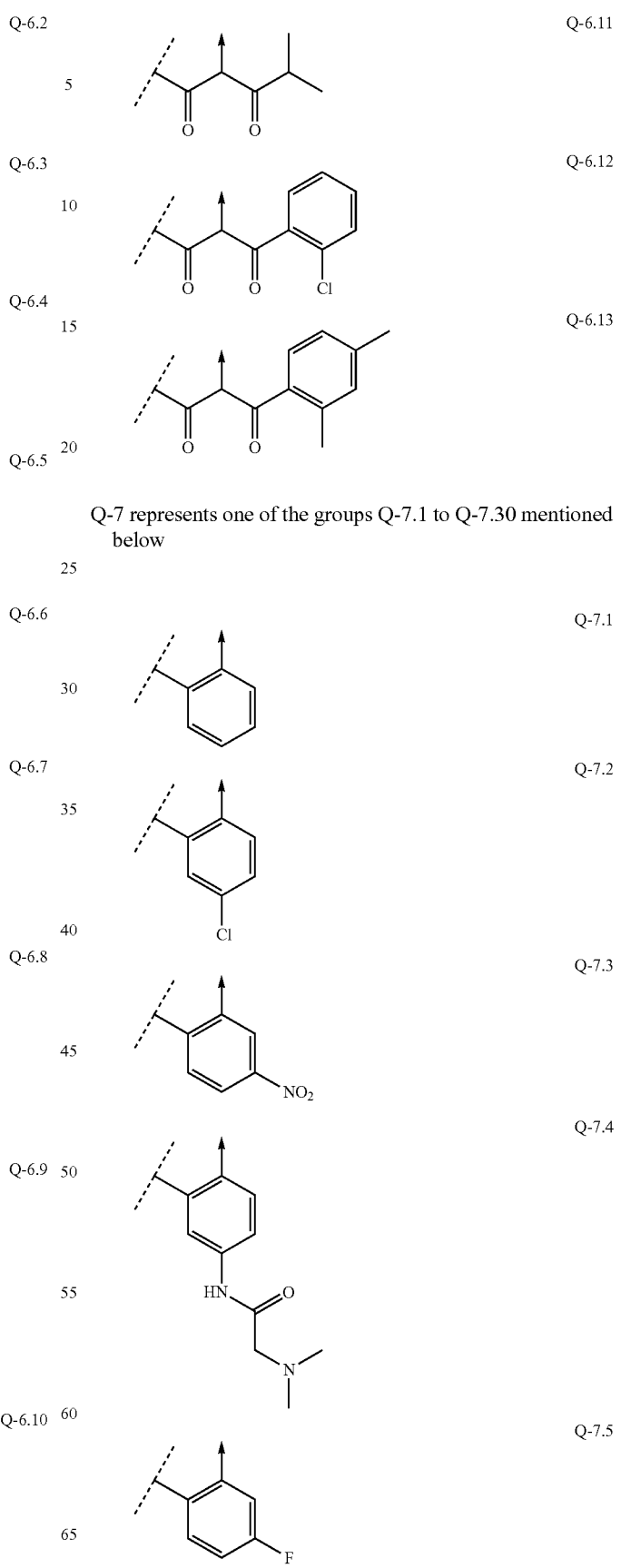
Q-7 represents one of the groups Q-7.1 to Q-7.30 mentioned below

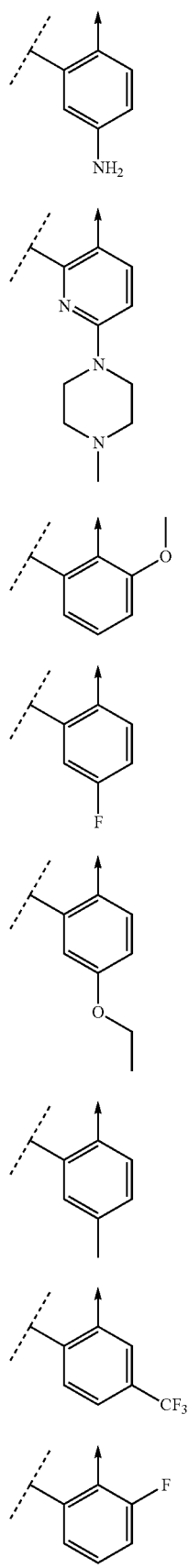
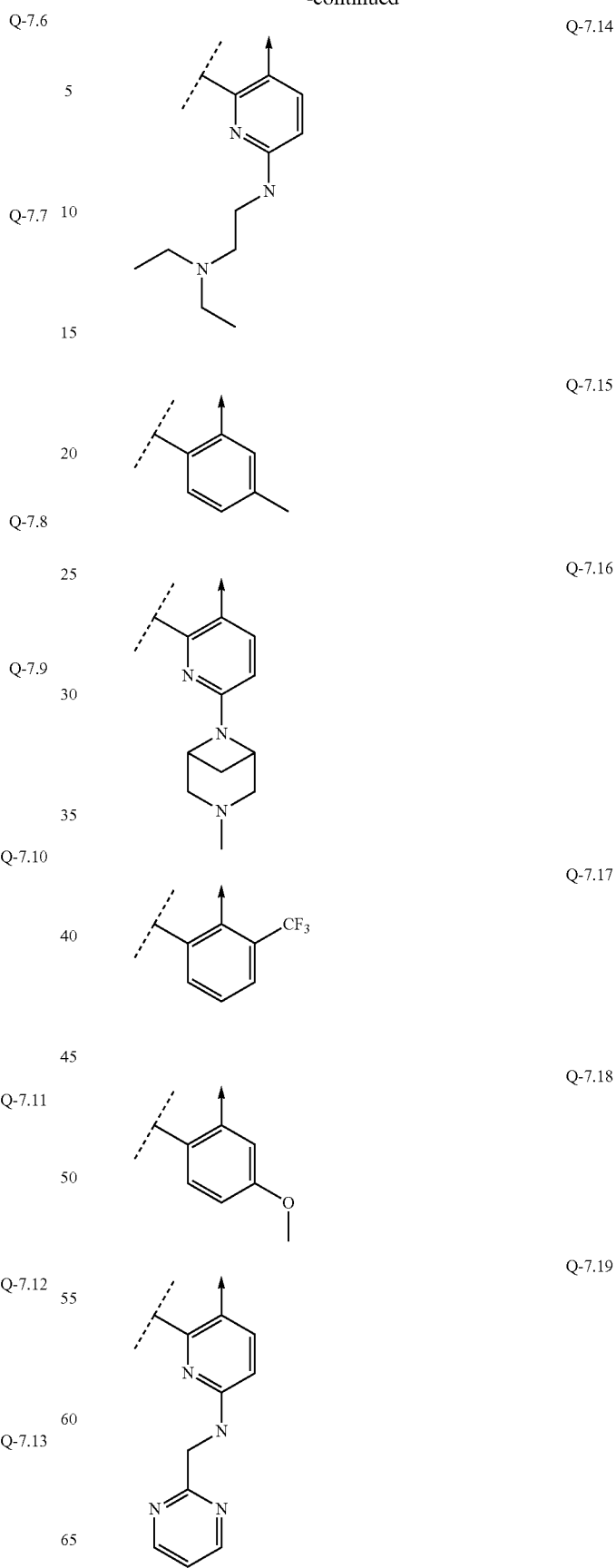

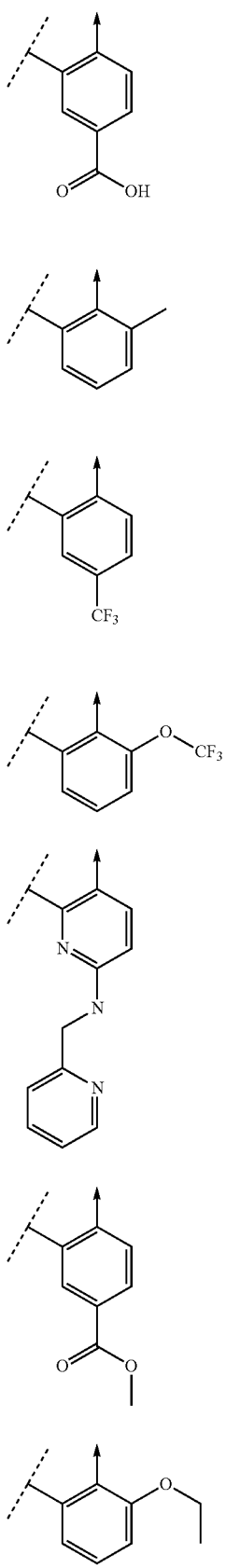
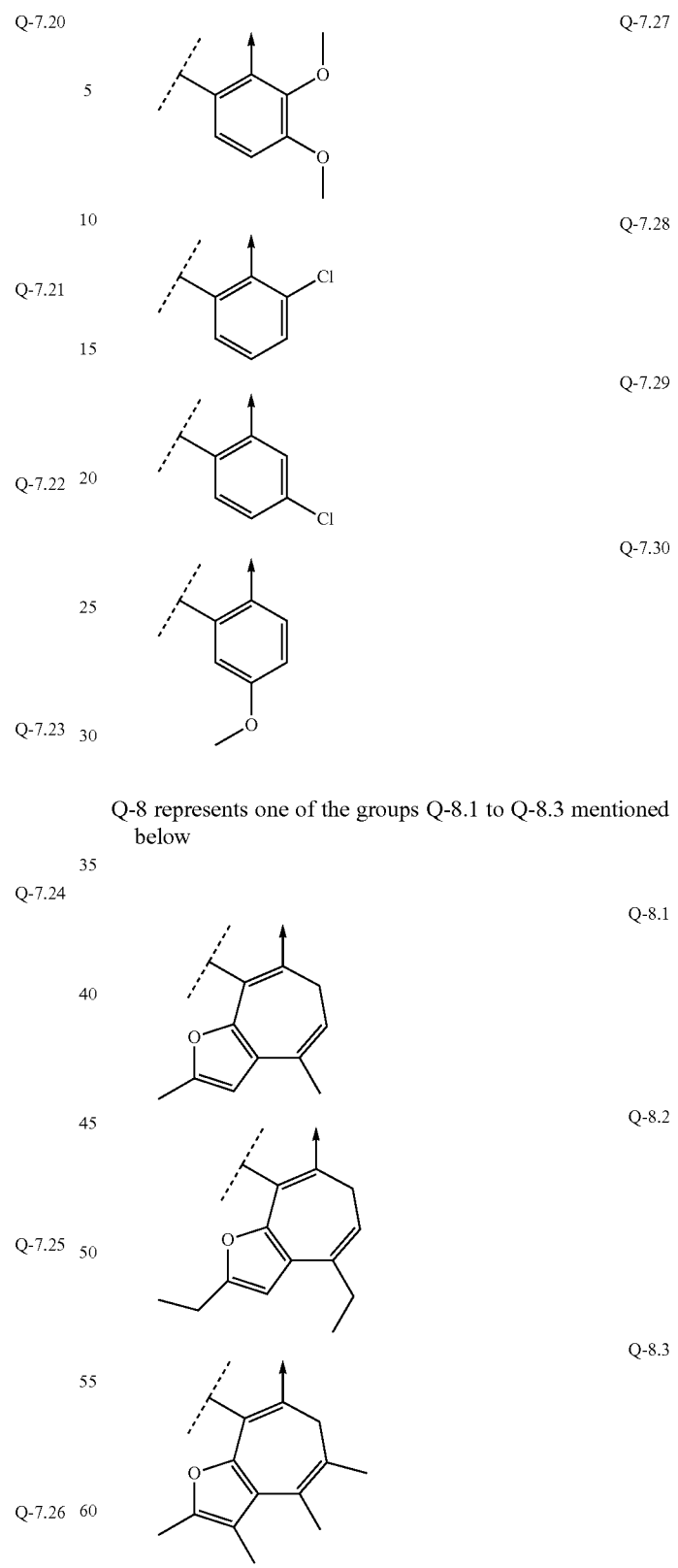
Q-8 represents one of the groups Q-8.1 to Q-8.3 mentioned below
and
Q-9 represents one of the groups Q-9.1 to Q-9.15 mentioned below Q-9.1 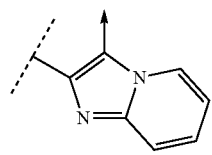
Q-9.2 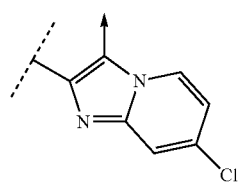
Q-9.3 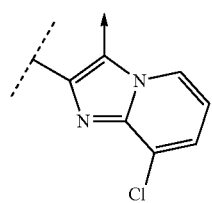
Q-9.4 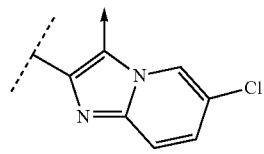
Q-9.5 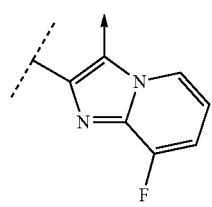
Q-9.6 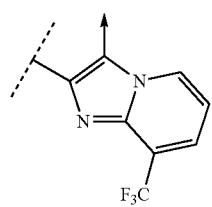
Q-9.7 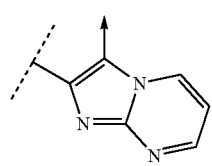
Q-9.8 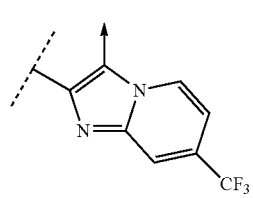
Q-9.9 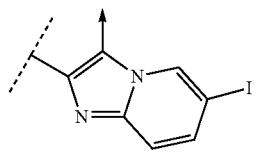
Q-9.10 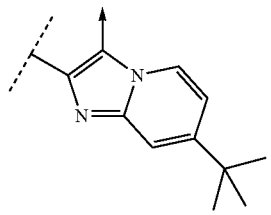
Q-9.11 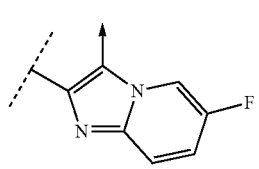
Q-9.12 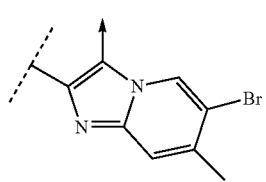
Q-9.13 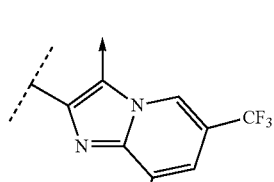
Q-9.14 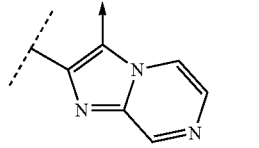
Q-9.15 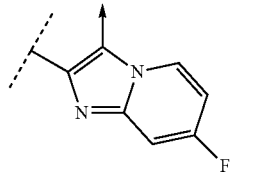
Particular aforementioned substituted isoquinolinones of the general formula (I) are likewise not yet known in the prior art. Thus, a further part of the invention is that of substituted isoquinolinones of the formula (I), or salts thereof, in which

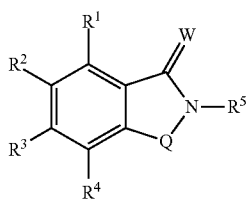

Q represents

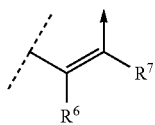

where $R^6$ and $R^7$ each have the meaning according to the definitions below and where the arrow represents a bond to the group $N-R^5$, W represents oxygen or sulphur, preferably oxygen, $R^1$, $R^2$, $R^3$ independently of one another represent hydrogen, nitro, amino, hydroxy, halogen, cyano, ($C_1$-$C_7$)-alkyl, ($C_3$-$C_7$)-cycloalkyl, ($C_1$-$C_7$)-haloalkyl, ($C_1$-$C_7$)-haloalkoxy, ($C_1$-$C_7$)-alkoxy, hydrothio, ($C_1$-$C_7$)-haloalkylthio, ($C_1$-$C_7$)-alkylthio, $R^4$ represents phenyl or phenyl which is mono- or polysubstituted independently of one another by halogen, nitro, cyano, amino, hydroxy, hydrothio, thiocyanato, ($C_1$-$C_7$)-alkyl, ($C_2$-$C_7$)-alkenyl, ($C_2$-$C_7$)-alkynyl, aryl-($C_1$-$C_7$)-alkyl, aryl-($C_2$-$C_7$)-alkenyl, aryl-($C_2$-$C_7$)-alkynyl, heteroaryl, phenyl which is optionally substituted further, ($C_3$-$C_7$)-cycloalkyl-($C_1$-$C_7$)-alkyl, ($C_3$-$C_7$)-cycloalkyl-($C_2$-$C_7$)-alkenyl, ($C_3$-$C_7$)-cycloalkyl-($C_2$-$C_7$)-alkynyl, heteroaryl-($C_1$-$C_7$)-alkyl, heteroaryl-($C_2$-$C_7$)-alkenyl, heteroaryl-($C_2$-$C_7$)-alkynyl, ($C_1$-$C_7$)-alkoxy, ($C_3$-$C_7$)-cycloalkoxy, ($C_1$-$C_7$)-alkylcarbonyloxy, ($C_1$-$C_7$)-haloalkylcarbonyloxy, ($C_3$-$C_7$)-cycloalkylcarbonyloxy, arylcarbonyloxy, ($C_1$-$C_7$)-alkylamino, bis-($C_1$-$C_7$)-alkylamino, ($C_1$-$C_7$)-alkylcarbonylamino, ($C_3$-$C_7$)-cycloalkylcarbonylamino, bis-($C_1$-$C_7$)-alkylcarbonylamino, ($C_1$-$C_7$)-haloalkyl, ($C_1$-$C_7$)-haloalkoxy, ($C_1$-$C_7$)-haloalkylthio, ($C_1$-$C_7$)-alkylthio, ($C_3$-$C_7$)-halocycloalkyl, ($C_3$-$C_7$)-cycloalkyl, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, represents thiophen or thiophen which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents pyrrole or pyrrole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents pyrazole or pyrazole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents furan or furan which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents isoxazole or isoxazole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents thiazole or thiazole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents imidazole or imidazole which is substituted by halogen, hydroxy, hydrothio, nitro, amino, cyano, ($C_1$-

$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents isothiazole or isothiazole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents oxazole or oxazole which is substituted by halogen, hydroxy, hydrothio, nitro, amino, cyano, ($C_1$-$C_7$)-alkyl, ($C_1$-$C_7$)-haloalkyl, ($C_1$-$C_7$)-alkoxy, ($C_1$-$C_7$)-haloalkoxy, ($C_1$-$C_7$)-alkylthio, ($C_1$-$C_7$)-haloalkylthio, ($C_3$-$C_7$)-cycloalkyl, ($C_1$-$C_7$)-alkylamino, bis-($C_1$-$C_7$)-alkylamino, hydroxycarbonyl, ($C_1$-$C_7$)-alkoxycarbonyl, ($C_1$-$C_7$)-cycloalkoxycarbonyl, ($C_2$-$C_7$)-alkenyloxycarbonyl, ($C_3$-$C_7$)-cycloalkyl-($C_1$-$C_7$)-alkoxycarbonyl, aminocarbonyl, ($C_1$-$C_7$)-alkylaminocarbonyl, ($C_3$-$C_7$)-cycloalkylaminocarbonyl, aryl-($C_1$-$C_7$)-alkylaminocarbonyl, ($C_2$-$C_7$)-alkenylaminocarbonyl, ($C_2$-$C_7$)-alkynylaminocarbonyl, optionally substituted phenyl, heteroaryl, represents aryl-($C_2$-$C_7$)-alkenyl, ($C_2$-$C_7$)-alkynyl, aryl-($C_2$-$C_7$)-alkynyl, ($C_1$-$C_7$)-alkyl-($C_1$-$C_7$)-alkynyl, ($C_3$-$C_7$)-cycloalkyl-($C_1$-$C_7$)-alkynyl, ($C_3$-$C_7$)-halocycloalkyl-($C_1$-$C_7$)-alkynyl, heteroaryl-($C_2$-$C_7$)-alkynyl, ($C_1$-$C_7$)-haloalkyl-($C_2$-$C_7$)-alkynyl, hydroxy-($C_1$-$C_7$)-haloalkyl-($C_2$-$C_7$)-alkynyl, hydroxy-($C_1$-$C_7$)-alkyl-($C_2$-$C_7$)-alkynyl, ($C_1$-$C_7$)-alkoxy-($C_1$-$C_7$)-alkyl-($C_2$-$C_7$)-alkynyl, tris-[($C_1$-$C_7$)-alkyl]silyl-($C_1$-$C_7$)-alkynyl, bis-[($C_1$-$C_7$)-alkyl]arylsilyl-($C_2$-$C_7$)-alkynyl, bis-aryl-[($C_1$-$C_7$)-alkyl]silyl-($C_1$-$C_7$)-alkynyl, $R^5$ represents hydrogen, hydroxy, ($C_1$-$C_7$)-alkyl, ($C_3$-$C_7$)-cycloalkyl, halogen, ($C_2$-$C_7$)-alkenyl-($C_1$-$C_7$)-alkyl, ($C_2$-$C_7$)-alkynyl-($C_1$-$C_7$)-alkyl, ($C_1$-$C_7$)-haloalkyl, ($C_1$-$C_7$)-alkoxy-($C_1$-$C_7$)-alkyl, ($C_2$-$C_7$)-alkynyl, ($C_2$-$C_7$)-alkenyl, ($C_3$-$C_7$)-cycloalkyl-($C_1$-$C_7$)-alkyl, cyano-($C_1$-$C_7$)-alkyl, nitro-($C_1$-$C_7$)-alkyl, aryl-($C_1$-$C_7$)-alkyl, heteroaryl-($C_1$-$C_7$)-alkyl, aryl, ($C_1$-$C_7$)-alkylamino, ($C_1$-$C_7$)-alkylamino-($C_1$-$C_7$)-alkyl, bis-[($C_1$-$C_7$)-alkyl]amino-($C_1$-$C_7$)-alkyl, aminocarbonyl-($C_1$-$C_7$)-alkyl, ($C_1$-$C_7$)-alkylaminocarbonyl-($C_1$-$C_7$)-alkyl, bis-[($C_1$-$C_7$)-alkyl]aminocarbonyl-($C_1$-$C_7$)-alkyl, ($C_1$-$C_7$)-alkoxycarbonyl-($C_1$-$C_7$)-alkyl, hydroxycarbonyl-($C_1$-$C_7$)-alkyl, ($C_1$-$C_7$)-alkylcarbonyl, ($C_3$-$C_7$)-cycloalkylcarbonyl, ($C_1$-$C_7$)-haloalkylcarbonyl, ($C_1$-$C_7$)-alkoxycarbonyl, ($C_1$-$C_7$)-alkylsulphonyl, arylsulphonyl, ($C_3$-$C_7$)-cycloalkylsulphonyl, aryl-($C_1$-$C_7$)-alkylsulphonyl, ($C_2$-$C_7$)-alkenylsulphonyl, heteroarylsulphonyl, ($C_2$-$C_7$)-alkynylsulphonyl, ($C_1$-$C_7$)-alkylsulphinyl, arylsulphinyl, ($C_3$-$C_7$)-cycloalkylsulphinyl, ($C_2$-$C_7$)-alkenylsulphinyl, ($C_2$-$C_7$)-alkynylsulphinyl, arylcarbonyl, heteroarylcarbonyl, ($C_1$-$C_7$)-alkoxycarbonyl-($C_1$-$C_7$)-alkyl, cyano-($C_1$-$C_7$)-alkylaminocarbonyl, ($C_2$-$C_7$)-alkynylaminocarbonyl, heterocyclylcarbonyl, hetaroaryl-($C_1$-$C_7$)-alkylaminocarbonyl, ($C_2$-$C_7$)-alkenyloxycarbonyl, ($C_3$-$C_7$)-cycloalkyl-($C_1$-$C_7$)-alkoxycarbonyl, ($C_3$-$C_7$)-cycloalkyl-($C_1$-$C_7$)-alkoxycarbonylcarbonyl, ($C_1$-$C_7$)-alkoxycarbonylcarbonyl, ($C_3$-$C_7$)-cycloalkyl-($C_1$-$C_7$)-alkylaminocarbonyl, aryl-($C_1$-$C_7$)-alkylaminocarbonyl or a negative charge, $R^6$ represents hydrogen, hydroxy, nitro, halogen, amino, ($C_1$-$C_7$)-alkyl, ($C_3$-$C_7$)-cycloalkyl, ($C_1$-$C_7$)-alkylcarbonyl, arylcarbonyl, ($C_1$-$C_7$)-alkylaminocarbonyl, bis-($C_1$-$C_7$)-alkylaminocarbonyl, ($C_3$-$C_7$)-cycloalkylaminocarbonyl, ($C_4$-$C_7$)-cycloalkenylaminocarbonyl, ($C_3$-$C_7$)-cycloalkyl-[($C_1$-$C_7$)-alkyl]aminocarbonyl, ($C_1$-$C_7$)-alkyl-[($C_1$-$C_7$)-alkyl]aminocarbonyl, ($C_3$-$C_7$)-cycloalkyl-($C_1$-$C_7$)-alkylaminocarbonyl, ($C_3$-$C_7$)-cycloalkyl-($C_1$-$C_7$)-alkyl[($C_1$-$C_7$)-alkyl]aminocarbonyl, ($C_1$-$C_7$)-alkyl[($C_2$-$C_7$)-alkynyl]aminocarbonyl, ($C_1$-$C_7$)-alkynylaminocarbonyl, arylaminocarbonyl, heteroarylaminocarbonyl, ($C_2$-$C_7$)-alkenylaminocarbonyl, cyano-($C_1$-$C_7$)-alkylaminocarbonyl, aryl-($C_1$-$C_7$)-alkylaminocarbonyl, aryl[($C_1$-$C_7$)-alkyl]aminocarbonyl, heteroaryl[($C_1$-$C_7$)-alkyl]aminocarbonyl, heterocyclyl-N-carbonyl, ($C_1$-$C_7$)-alkoxycarbonylheterocyclyl-N-carbonyl, ($C_1$-$C_7$)-alkoxycarbonyl-($C_1$-$C_7$)-alkylaminocarbonyl, hydroxycarbonylheterocyclyl-N-carbonyl, hydroxycarbonyl-($C_1$-$C_7$)-alkylaminocarbonyl, ($C_3$-$C_7$)-cycloalkoxycarbonylheterocyclyl-N-carbonyl, ($C_3$-$C_7$)-cycloalkoxycarbonyl-($C_1$-$C_7$)-alkylaminocarbonyl, ($C_1$-$C_7$)-alkylaminocarbonyl-($C_1$-$C_7$)-alkylaminocarbonyl, aminocarbonyl-($C_1$-$C_7$)-alkylaminocarbonyl, ($C_3$-$C_7$)-cycloalkylaminocarbonyl-($C_1$-$C_7$)-alkylaminocarbonyl, bis-($C_1$-$C_7$)-alkylamino-($C_1$-$C_7$)-alkylaminocarbonyl, bis-($C_1$-$C_7$)-alkylaminocarbonyl-($C_1$-$C_7$)-alkylaminocarbonyl, ($C_1$-$C_7$)-alkylaminocarbonyl-($C_1$-$C_7$)-alkylaminocarbonyl, heterocyclyl-N-carbonyl-($C_1$-$C_7$)-alkylaminocarbonyl, ($C_3$-$C_7$)-cycloalkyl-N-heterocyclyl-N-carbonyl, ($C_1$-$C_7$)-alkoxy[($C_1$-$C_7$)-alkyl]aminocarbonyl, ($C_1$-$C_7$)-alkoxycarbonylamino, hydroxycarbonyl, ($C_1$-$C_7$)-alkoxycarbonyl, ($C_1$-$C_7$)-cycloalkoxycarbonyl, ($C_1$-$C_7$)-cycloalkyl-($C_1$-$C_7$)-alkoxycarbonyl, ($C_1$-$C_7$)-alkoxy-($C_1$-$C_7$)-alkoxycarbonyl, ($C_1$-$C_7$)-alkoxycarbonyl-($C_1$-$C_7$)-alkoxycarbonyl, ($C_2$-$C_7$)-alkenyloxycarbonyl, ($C_2$-$C_7$)-alkynyloxycarbonyl, hydroxycarbonyl-($C_1$-$C_7$)-alkoxycarbonyl, ($C_1$-$C_7$)-haloalkoxycarbonyl, aryl[($C_1$-$C_7$)-alkyl]aminocarbonylamino, arylaminocarbonylamino, ($C_1$-$C_7$)-alkylaminocarbonylamino, heteroarylaminocarbonylamino, ($C_1$-$C_7$)-alkoxy, ($C_1$-$C_7$)-alkylamino-($C_1$-$C_7$)-alkoxy, ($C_1$-$C_7$)-alkylcarbonyloxy, arylcarbonyloxy, ($C_2$-$C_7$)-alkenyl-($C_1$-$C_7$)-alkyl, ($C_2$-$C_7$)-alkynyl-($C_1$-$C_7$)-alkyl, ($C_1$-$C_7$)-haloalkyl, ($C_1$-$C_7$)-alkoxy-($C_1$-$C_7$)-alkyl, ($C_2$-$C_7$)-alkynyl, ($C_2$-$C_7$)-alkenyl, aryl, heteroaryl, ($C_1$-$C_7$)-alkoxycarbonyl-($C_1$-$C_7$)-alkyl, ($C_1$-$C_7$)-alkylamino, bis-($C_1$-$C_7$)-alkylamino, ($C_3$-$C_7$)-cycloalkylamino, aryl-($C_1$-$C_7$)-alkylamino, and $R^7$ represents hydrogen, halogen, amino, ($C_1$-$C_7$)-alkyl, ($C_1$-$C_7$)-haloalkyl, ($C_3$-$C_7$)-cycloalkyl, ($C_1$-$C_7$)-alkylcarbonyl, arylcarbonyl, heteroarylcarbonyl, ($C_3$-$C_7$)-cycloalkylcarbonyl, ($C_1$-$C_7$)-alkoxycarbonyl, hydroxycarbonyl, aryl, heteroaryl, arylcarbonyl-($C_1$-$C_7$)-alkoxycarbonyl, ($C_1$-$C_7$)-alkylcarbonyl-($C_1$-$C_7$)-alkoxycarbonyl, ($C_3$-$C_7$)-cycloalkyl-($C_1$-$C_7$)-alkoxycarbonyl, heteroaryl-($C_1$-$C_7$)-alkoxycarbonyl, heteroarylheteroaryl($C_1$-$C_7$)-alkyl-($C_1$-$C_7$)-alkoxycarbonyl, heteroaryl($C_1$-$C_7$)-alkyl-($C_1$-$C_7$)-alkoxycarbonyl, aryl-($C_1$-$C_7$)-alkoxycarbonyl, ($C_1$-$C_7$)- alkylcarbonyloxy, arylaminocarbonyl, $(C_1-C_7)$-alkylaminocarbonyl, bis-$(C_1-C_7)$-alkylaminocarbonyl, $(C_3-C_7)$-cycloalkylaminocarbonyl, heterocyclyl-N-carbonyl, aryl-$(C_1-C_7)$-alkylaminocarbonyl, cyano-$(C_1-C_7)$-alkylaminocarbonyl, $(C_2-C_7)$-alkenylaminocarbonyl, bis-[$(C_1-C_7)$-alkoxycarbonyl]-$(C_2-C_7)$-alkenylamino, bis-cyano-$(C_1-C_7)$-alkenylamino, $(C_1-C_7)$-alkoxycarbonyl(cyano)-$(C_2-C_7)$-alkenylamino, $(C_1-C_7)$-alkylamino, arylamino, $(C_3-C_7)$-cycloalkylamino, aryl[$(C_1-C_7)$-alkyl]amino, bis-$(C_1-C_7)$-alkylamino.

The invention furthermore preferably provides compounds of the general formula (I) or salts thereof in which
Q represents

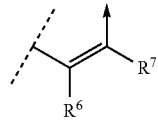

Q-1 where $R^6$ and $R^7$ each have the meaning according to the definitions below and where the arrow represents a bond to the group N—$R^5$, W represents oxygen, $R^1$, $R^2$, $R^3$ independently of one another represent hydrogen, nitro, amino, hydroxy, fluorine, chlorine, bromine, iodine, cyano, $(C_1-C_6)$-alkyl, $(C_3-C_6)$-cycloalkyl, $(C_1-C_6)$-haloalkyl, $(C_1-C_6)$-haloalkoxy, $(C_1-C_6)$-alkoxy, hydrothio, $(C_1-C_6)$-haloalkylthio, $(C_1-C_6)$-alkylthio, $R^4$ represents phenyl or phenyl which is mono- or polysubstituted independently of one another by fluorine, chlorine, bromine, iodine, nitro, cyano, amino, hydroxy, hydrothio, thiocyanato, $(C_1-C_6)$-alkyl, $(C_2-C_6)$-alkenyl, $(C_2-C_6)$-alkynyl, aryl-$(C_1-C_6)$-alkyl, aryl-$(C_2-C_6)$-alkenyl, aryl-$(C_2-C_6)$-alkynyl, heteroaryl, phenyl which is optionally substituted further, $(C_3-C_6)$-cycloalkyl-$(C_1-C_6)$-alkyl, $(C_3-C_6)$-cycloalkyl-$(C_2-C_6)$-alkenyl, $(C_3-C_6)$-cycloalkyl-$(C_2-C_6)$-alkynyl, heteroaryl-$(C_1-C_6)$-alkyl, heteroaryl-$(C_2-C_6)$-alkenyl, heteroaryl-$(C_2-C_6)$-alkynyl, $(C_1-C_6)$-alkoxy, $(C_3-C_6)$-cycloalkoxy, $(C_1-C_6)$-alkylcarbonyloxy, $(C_1-C_6)$-haloalkylcarbonyloxy, $(C_3-C_6)$-cycloalkylcarbonyloxy, arylcarbonyloxy, $(C_1-C_6)$-alkylamino, bis-$(C_1-C_6)$-alkylamino, $(C_1-C_6)$-alkylcarbonylamino, $(C_3-C_6)$-cycloalkylcarbonylamino, bis-$(C_1-C_6)$-alkylcarbonylamino, $(C_1-C_6)$-haloalkyl, $(C_1-C_6)$-haloalkoxy, $(C_1-C_6)$-haloalkylthio, $(C_1-C_6)$-alkylthio, $(C_3-C_6)$-halocycloalkyl, $(C_3-C_6)$-cycloalkyl, hydroxycarbonyl, $(C_1-C_6)$-alkoxycarbonyl, $(C_1-C_6)$-cycloalkoxycarbonyl, $(C_2-C_6)$-alkenyloxycarbonyl, $(C_3-C_6)$-cycloalkyl-$(C_1-C_6)$-alkoxycarbonyl, aminocarbonyl, $(C_1-C_6)$-alkylaminocarbonyl, $(C_3-C_6)$-cycloalkylaminocarbonyl, aryl-$(C_1-C_6)$-alkylaminocarbonyl, $(C_2-C_6)$-alkenylaminocarbonyl, $(C_2-C_6)$-alkynylaminocarbonyl, represents thiophen or thiophen which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, $(C_1-C_6)$-alkyl, $(C_1-C_6)$-haloalkyl, $(C_1-C_6)$-alkoxy, $(C_1-C_6)$-haloalkoxy, heteroaryl, phenyl which is optionally substituted further, represents pyrrole or pyrrole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents pyrazole or pyrazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents furan or furan which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents isoxazole or isoxazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy;

represents thiazole or thiazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents imidazole or imidazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents isothiazole or isothiazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents oxazole or oxazole which is substituted by fluorine, chlorine, bromine, iodine, amino, nitro, cyano, hydroxycarbonyl, $(C_1-C_6)$-alkoxycarbonyl, aminocarbonyl, $(C_1-C_6)$-alkylaminocarbonyl, $(C_3-C_6)$-cycloalkylaminocarbonyl, $(C_3-C_6)$-cycloalkyl, heteroaryl, phenyl which is optionally substituted further, $(C_1-C_6)$-alkyl, $(C_1-C_6)$-haloalkyl, $(C_1-C_6)$-alkoxy, $(C_1-C_6)$-haloalkoxy, represents aryl-$(C_2-C_6)$-alkenyl, $(C_2-C_6)$-alkynyl, aryl-$(C_2-C_6)$-alkynyl, $(C_1-C_6)$-alkyl-$(C_1-C_6)$-alkynyl, $(C_3-C_6)$-cycloalkyl-$(C_1-C_6)$-alkynyl, $(C_3-C_6)$-halocycloalkyl-$(C_1-C_6)$-alkynyl, heteroaryl-$(C_2-C_6)$-alkynyl, $(C_1-C_6)$-haloalkyl-$(C_2-C_6)$-alkynyl, hydroxy-$(C_1-C_6)$-haloalkyl-$(C_2-C_6)$-alkynyl, hydroxy-$(C_1-C_6)$-alkyl-$(C_2-C_6)$-alkynyl, $(C_1-C_6)$-alkoxy-$(C_1-C_6)$-alkyl-$(C_2-C_6)$- alkynyl, tris-[($C_1$-$C_6$)-alkyl]silyl-($C_1$-$C_6$)-alkynyl, bis-[($C_1$-$C_6$)-alkyl]arylsilyl-($C_2$-$C_6$)-alkynyl, bis-aryl-[($C_1$-$C_6$)-alkyl]silyl-($C_1$-$C_6$)-alkynyl, $R^5$ represents hydrogen, hydroxy, ($C_1$-$C_6$)-alkyl, ($C_3$-$C_6$)-cycloalkyl, halogen, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-haloalkyl, ($C_1$-$C_6$)-alkoxy-($C_1$-$C_6$)-alkyl, ($C_2$-$C_6$)-alkynyl, ($C_2$-$C_6$)-alkenyl, ($C_3$-$C_6$)-cycloalkyl-($C_1$-$C_6$)-alkyl, cyano-($C_1$-$C_6$)-alkyl, nitro-($C_1$-$C_6$)-alkyl, aryl-($C_1$-$C_6$)-alkyl, heteroaryl-($C_1$-$C_6$)-alkyl, aryl, ($C_1$-$C_6$)-alkylamino, ($C_1$-$C_6$)-alkylamino-($C_1$-$C_6$)-alkyl, bis-[($C_1$-$C_6$)-alkyl]amino-($C_1$-$C_6$)-alkyl, aminocarbonyl-($C_1$-$C_6$)-alkyl, ($C_1$-$C_6$)-alkylaminocarbonyl-($C_1$-$C_6$)-alkyl, bis-[($C_1$-$C_6$)-alkyl]aminocarbonyl-($C_1$-$C_6$)-alkyl, ($C_1$-$C_6$)-alkoxycarbonyl-($C_1$-$C_6$)-alkyl, hydroxycarbonyl-($C_1$-$C_6$)-alkyl, ($C_1$-$C_6$)-alkylcarbonyl, ($C_3$-$C_6$)-cycloalkylcarbonyl, ($C_1$-$C_6$)-haloalkylcarbonyl, ($C_1$-$C_6$)-alkoxycarbonyl, ($C_1$-$C_6$)-alkylsulphonyl, arylsulphonyl, ($C_3$-$C_6$)-cycloalkylsulphonyl, aryl-($C_1$-$C_6$)-alkylsulphonyl, ($C_2$-$C_6$)-alkenylsulphonyl, heteroarylsulphonyl, ($C_2$-$C_6$)-alkynylsulphonyl, ($C_1$-$C_6$)-alkylsulphinyl, arylsulphinyl, ($C_3$-$C_6$)-cycloalkylsulphinyl, ($C_2$-$C_6$)-alkenylsulphinyl, ($C_2$-$C_6$)-alkynylsulphinyl, arylcarbonyl, heteroarylcarbonyl, ($C_1$-$C_6$)-alkoxycarbonyl-($C_1$-$C_6$)-alkyl, cyano-($C_1$-$C_6$)-alkylaminocarbonyl, ($C_2$-$C_6$)-alkynylaminocarbonyl, heterocyclylcarbonyl, hetaroaryl-($C_1$-$C_6$)-alkylaminocarbonyl, ($C_2$-$C_6$)-alkenyloxycarbonyl, ($C_3$-$C_6$)-cycloalkyl-($C_1$-$C_6$)-alkoxycarbonyl, ($C_3$-$C_6$)-cycloalkyl-($C_1$-$C_6$)-alkoxycarbonylcarbonyl, ($C_1$-$C_6$)-alkoxycarbonylcarbonyl, ($C_3$-$C_6$)-cycloalkyl-($C_1$-$C_6$)-alkylaminocarbonyl, aryl-($C_1$-$C_6$)-alkylaminocarbonyl or a negative charge, $R^6$ represents hydrogen, hydroxy, nitro, halogen, amino, ($C_1$-$C_6$)-alkyl, ($C_3$-$C_6$)-cycloalkyl, ($C_1$-$C_6$)-alkylcarbonyl, arylcarbonyl, ($C_1$-$C_6$)-alkylaminocarbonyl, bis-($C_1$-$C_6$)-alkylaminocarbonyl, ($C_3$-$C_6$)-cycloalkylaminocarbonyl, ($C_4$-$C_6$)-cycloalkenylaminocarbonyl, ($C_3$-$C_6$)-cycloalkyl-[($C_1$-$C_6$)-alkyl]aminocarbonyl, ($C_1$-$C_6$)-alkyl-[($C_1$-$C_6$)-alkyl]aminocarbonyl, ($C_3$-$C_6$)-cycloalkyl-($C_1$-$C_6$)-alkylaminocarbonyl, ($C_3$-$C_6$)-cycloalkyl-($C_1$-$C_6$)-alkyl[($C_1$-$C_6$)-alkyl]aminocarbonyl, ($C_1$-$C_6$)-alkyl[($C_2$-$C_6$)-alkynyl]aminocarbonyl, ($C_1$-$C_6$)-alkynylaminocarbonyl, arylaminocarbonyl, heteroarylaminocarbonyl, ($C_2$-$C_6$)-alkenylaminocarbonyl, cyano-($C_1$-$C_6$)-alkylaminocarbonyl, aryl-($C_1$-$C_6$)-alkylaminocarbonyl, aryl[($C_1$-$C_6$)-alkyl]aminocarbonyl, heteroaryl[($C_1$-$C_6$)-alkyl]aminocarbonyl, heterocyclyl-N-carbonyl, ($C_1$-$C_6$)-alkoxycarbonylheterocyclyl-N-carbonyl, ($C_1$-$C_6$)-alkoxycarbonyl-($C_1$-$C_6$)-alkylaminocarbonyl, hydroxycarbonylheterocyclyl-N-carbonyl, hydroxycarbonyl-($C_1$-$C_6$)-alkylaminocarbonyl, ($C_3$-$C_6$)-cycloalkoxycarbonylheterocyclyl-N-carbonyl, ($C_3$-$C_6$)-cycloalkoxycarbonyl-($C_1$-$C_6$)-alkylaminocarbonyl, ($C_1$-$C_6$)-alkylaminocarbonyl-($C_1$-$C_6$)-alkylaminocarbonyl, aminocarbonyl-($C_1$-$C_6$)-alkylaminocarbonyl, ($C_3$-$C_6$)-cycloalkylaminocarbonyl-($C_1$-$C_6$)-alkylaminocarbonyl, bis-($C_1$-$C_6$)-alkylamino-($C_1$-$C_6$)-alkylaminocarbonyl, bis-($C_1$-$C_6$)-alkylaminocarbonyl-($C_1$-$C_6$)-alkylaminocarbonyl, ($C_1$-$C_6$)-alkylaminocarbonyl-($C_1$-$C_6$)-alkylaminocarbonyl, heterocyclyl-N-carbonyl-($C_1$-$C_6$)-alkylaminocarbonyl, ($C_3$-$C_6$)-cycloalkyl-N-heterocyclyl-N-carbonyl, ($C_1$-$C_6$)-alkoxy[($C_1$-$C_6$)-alkyl]aminocarbonyl, ($C_1$-$C_6$)-alkoxycarbonylamino, hydroxycarbonyl, ($C_1$-$C_6$)-alkoxycarbonyl, ($C_1$-$C_6$)-cycloalkoxycarbonyl, ($C_1$-$C_6$)-cycloalkyl-($C_1$-$C_6$)-alkoxycarbonyl, ($C_1$-$C_6$)-alkoxy-($C_1$-$C_6$)-alkoxycarbonyl, ($C_1$-$C_6$)-alkoxycarbonyl-($C_1$-$C_6$)-alkoxycarbonyl, ($C_2$-$C_6$)-alkenyloxycarbonyl, ($C_2$-$C_6$)-($C_2$-$C_6$)-alkynyloxycarbonyl, hydroxycarbonyl-($C_1$-$C_6$)-alkoxycarbonyl, ($C_1$-$C_6$)-haloalkoxycarbonyl, aryl[($C_1$-$C_6$)-alkyl]aminocarbonylamino, arylaminocarbonylamino, ($C_1$-$C_6$)-alkylaminocarbonylamino, heteroarylaminocarbonylamino, ($C_1$-$C_6$)-alkoxy, ($C_1$-$C_6$)-alkylamino-($C_1$-$C_6$)-alkoxy, ($C_1$-$C_6$)-alkylcarbonyloxy, arylcarbonyloxy, ($C_2$-$C_6$)-alkenyl-($C_1$-$C_6$)-alkyl, ($C_2$-$C_6$)-alkynyl-($C_1$-$C_6$)-alkyl, ($C_1$-$C_6$)-haloalkyl, ($C_1$-$C_6$)-alkoxy-($C_1$-$C_6$)-alkyl, ($C_2$-$C_6$)-alkynyl, ($C_2$-$C_6$)-alkenyl, aryl, heteroaryl, ($C_1$-$C_6$)-alkoxycarbonyl-($C_1$-$C_6$)-alkyl, ($C_1$-$C_6$)-alkylamino, bis-($C_1$-$C_6$)-alkylamino, ($C_3$-$C_6$)-cycloalkylamino, aryl-($C_1$-$C_6$)-alkylamino, and $R^7$ represents hydrogen, halogen, amino, ($C_1$-$C_6$)-alkyl, ($C_1$-$C_6$)-haloalkyl, ($C_3$-$C_6$)-cycloalkyl, ($C_1$-$C_6$)-alkylcarbonyl, arylcarbonyl, heteroarylcarbonyl, ($C_3$-$C_6$)-cycloalkylcarbonyl, ($C_1$-$C_6$)-alkoxycarbonyl, hydroxycarbonyl, aryl, heteroaryl, arylcarbonyl-($C_1$-$C_6$)-alkoxycarbonyl, ($C_1$-$C_6$)-alkylcarbonyl-($C_1$-$C_6$)-alkoxycarbonyl, ($C_3$-$C_6$)-cycloalkyl-($C_1$-$C_6$)-alkoxycarbonyl, heteroaryl-($C_1$-$C_6$)-alkoxycarbonyl, heteroarylheteroaryl($C_1$-$C_6$)-alkyl-($C_1$-$C_6$)-alkoxycarbonyl, heteroaryl($C_1$-$C_6$)-alkyl-($C_1$-$C_6$)-alkoxycarbonyl, aryl-($C_1$-$C_6$)-alkoxycarbonyl, ($C_1$-$C_6$)-alkylcarbonyloxy, arylaminocarbonyl, ($C_1$-$C_6$)-alkylaminocarbonyl, bis-($C_1$-$C_6$)-alkylaminocarbonyl, ($C_3$-$C_6$)-cycloalkylaminocarbonyl, heterocyclyl-N-carbonyl, aryl-($C_1$-$C_6$)-alkylaminocarbonyl, cyano-($C_1$-$C_6$)-alkylaminocarbonyl, ($C_2$-$C_6$)-alkenylaminocarbonyl, bis-[($C_1$-$C_6$)-alkoxycarbonyl]-($C_2$-$C_6$)-alkenylamino, bis-cyano-($C_1$-$C_6$)-alkenylamino, ($C_1$-$C_6$)-alkoxycarbonyl (cyano)-($C_2$-$C_6$)-alkenylamino, ($C_1$-$C_6$)-alkylamino, arylamino, ($C_3$-$C_6$)-cycloalkylamino, aryl[($C_1$-$C_6$)-alkyl]amino, bis-($C_1$-$C_6$)-alkylamino.

The definitions of radicals stated above in general terms or in areas of preference apply both to the end products of the formula (I) and correspondingly to the starting materials or intermediates required in each case for preparation thereof. These radical definitions can be combined with one another as desired, i.e. including combinations between the given preferred ranges.

With regard to the compounds according to the invention, the terms used above and further below will be elucidated. These are familiar to the person skilled in the art and especially have the definitions elucidated hereinafter:

"Alkoxy" is an alkyl radical bonded via an oxygen atom, alkenyloxy is an alkenyl radical bonded via an oxygen atom, alkynyloxy is an alkynyl radical bonded via an oxygen atom, cycloalkyloxy is a cycloalkyl radical bonded via an oxygen atom, and cycloalkenyloxy is a cycloalkenyl radical bonded via an oxygen atom.

The term "aryl" means an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl".

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated, partially saturated or heteroaromatic and may be unsubstituted or substituted, where the point of attachment is located at a ring atom. If the heterocyclyl radical or the heterocyclic ring is optionally substituted, it can be fused to other carbocyclic or heterocyclic rings. Optionally substituted heterocyclyl also includes polycyclic systems, such as, for example, 8-aza-bicyclo[3.2.1]octanyl or 1-aza-bicyclo[2.2.1]heptyl. In the case of optionally substituted heterocyclyl, spirocyclic systems are also included, for example 1-oxa-5-azaspiro[2.3]hexyl. Unless defined differently, the heterocyclic ring contains preferably 3 to 9 ring atoms and especially 3 to 6 ring atoms, and one or more, preferably 1 to 4 and especially 1, 2 or 3 heteroatoms in the heterocyclic ring, preferably from the group of N, O and S, although no two oxygen atoms should be directly adjacent, for example, with one heteroatom from the group of N, O and S, 1- or 2- or 3-pyrrolidinyl, 3,4-dihydro-2H-pyrrol-2- or 3-yl, 2,3-dihydro-1H-pyrrol-1- or 2- or 3- or 4- or 5-yl; 2,5-dihydro-1H-pyrrol-1- or 2- or 3-yl, 1- or 2- or 3- or 4-piperidinyl; 2,3,4,5-tetrahydropyridin-2- or 3- or 4- or 5-yl or 6-yl; 1,2,3,6-tetrahydropyridin-1- or 2- or 3- or 4- or 5- or 6-yl; 1,2,3,4-tetrahydropyridin-1- or 2- or 3- or 4- or 5- or 6-yl; 1,4-dihydropyridin-1- or 2- or 3- or 4-yl; 2,3-dihydropyridin-2- or 3- or 4- or 5- or 6-yl; 2,5-dihydropyridin-2- or 3- or 4- or 5- or 6-yl, 1- or 2- or 3- or 4-azepanyl; 2,3,4,5-tetrahydro-1H-azepin-1- or 2- or 3- or 4- or 5- or 6- or 7-yl; 2,3,4,7-tetrahydro-1H-azepin-1- or 2- or 3- or 4- or 5- or 6- or 7-yl; 2,3,6,7-tetrahydro-1H-azepin-1- or 2- or 3- or 4-yl; 3,4,5,6-tetrahydro-2H-azepin-2- or 3- or 4- or 5- or 6- or 7-yl; 4,5-dihydro-1H-azepin-1- or 2- or 3- or 4-yl; 2,5-dihydro-1H-azepin-1- or -2- or 3- or 4- or 5- or 6- or 7-yl; 2,7-dihydro-1H-azepin-1- or -2- or 3- or 4-yl; 2,3-dihydro-1H-azepin-1- or -2- or 3- or 4- or 5- or 6- or 7-yl; 3,4-dihydro-2H-azepin-2- or 3- or 4- or 5- or 6- or 7-yl; 3,6-dihydro-2H-azepin-2- or 3- or 4- or 5- or 6- or 7-yl; 5,6-dihydro-2H-azepin-2- or 3- or 4- or 5- or 6- or 7-yl; 4,5-dihydro-3H-azepin-2- or 3- or 4- or 5- or 6- or 7-yl; 1H-azepin-1- or -2- or 3- or 4- or 5- or 6- or 7-yl; 2H-azepin-2- or 3- or 4- or 5- or 6- or 7-yl; 3H-azepin-2- or 3- or 4- or 5- or 6- or 7-yl; 4H-azepin-2- or 3- or 4- or 5- or 6- or 7-yl, 2- or 3-oxolanyl (=2- or 3-tetrahydrofuranyl); 2,3-dihydrofuran-2- or 3- or 4- or 5-yl; 2,5-dihydrofuran-2- or 3-yl, 2- or 3- or 4-oxanyl (=2- or 3- or 4-tetrahydropyranyl); 3,4-dihydro-2H-pyran-2- or 3- or 4- or 5- or 6-yl; 3,6-dihydro-2H-pyran-2- or 3- or 4- or 5- or 6-yl; 2H-pyran-2- or 3- or 4- or 5- or 6-yl; 4H-pyran-2- or 3- or 4-yl, 2- or 3- or 4-oxepanyl; 2,3,4,5-tetrahydrooxepin-2- or 3- or 4- or 5- or 6- or 7-yl; 2,3,4,7-tetrahydrooxepin-2- or 3- or 4- or 5- or 6- or 7-yl; 2,3,6,7-tetrahydrooxepin-2- or 3- or 4-yl; 2,3-dihydrooxepin-2- or 3- or 4- or 5- or 6- or 7-yl; 4,5-dihydrooxepin-2- or 3- or 4-yl; 2,5-dihydrooxepin-2- or 3- or 4- or 5- or 6- or 7-yl; oxepin-2- or 3- or 4- or 5- or 6- or 7-yl; 2- or 3-tetrahydrothiophenyl; 2,3-dihydrothiophen-2- or 3- or 4- or 5-yl; 2,5-dihydrothiophen-2- or 3-yl; tetrahydro-2H-thiopyran-2- or 3- or 4-yl; 3,4-dihydro-2H-thiopyran-2- or 3- or 4- or 5- or 6-yl; 3,6-dihydro-2H-thiopyran-2- or 3- or 4- or 5- or 6-yl; 2H-thiopyran-2- or 3- or 4- or 5- or 6-yl; 4H-thiopyran-2- or 3- or 4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 2- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyridazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl;

2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5- dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 4- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of "heterocyclyl" are a partly or fully hydrogenated heterocyclic radical having 3 heteroatoms from the group of N, O and S, for example 1, 4,2-dioxazolidin-2- or 3- or 5-yl; 1,4,2-dioxazol-3- or 5-yl; 1,4,2-dioxazinan-2- or -3- or 5- or 6-yl; 5,6-dihydro-1,4,2-dioxazin-3- or 5- or 6-yl; 1,4,2-dioxazin-3- or 5- or 6-yl; 1,4,2-dioxazepan-2- or 3- or 5- or 6- or 7-yl; 6,7-dihydro-5H-1,4,2-dioxazepin-3- or 5- or 6- or 7-yl; 2,3-dihydro-7H-1,4,2-dioxazepin-2- or 3- or 5- or 6- or 7-yl; 2,3-dihydro-5H-1,4,2-dioxazepin-2- or 3- or 5- or 6- or 7-yl; 5H-1,4,2-dioxazepin-3- or 5- or 6- or 7-yl; 7H-1,4,2-dioxazepin-3- or 5- or 6- or 7-yl.

When a base structure is substituted "by one or more radicals" from a list of radicals (=group) or a generically defined group of radicals, this in each case includes simultaneous substitution by a plurality of identical and/or structurally different radicals.

In the case of a partly or fully saturated nitrogen heterocycle, this may be joined to the remainder of the molecule either via carbon or via the nitrogen.

Suitable substituents for a substituted heterocyclic radical are the substituents specified later on below, and additionally also oxo and thioxo. The oxo group as a substituent on a ring carbon atom is then, for example, a carbonyl group in the heterocyclic ring. As a result, lactones and lactams are preferably also included. The oxo group may also be present on the ring heteroatoms, which can exist in various oxidation states, for example on N and S, in which case they form, for example, the divalent groups N(O), S(O) (also SO for short) and S(O)2 (also SO2 for short) in the heterocyclic ring. In the case of —N(O)— and —S(O)— groups, in each case both enantiomers are included.

According to the invention, the expression "heteroaryl" represents heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl; 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl; 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups according to the invention may also be substituted by one or more identical or different radicals. When two adjacent carbon atoms are part of a further aromatic ring, the systems are fused heteroaromatic systems, such as benzofused or polyannulated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means, for example, fluorine, chlorine, bromine or iodine. If the term is used for a radical, "halogen" means, for example, a fluorine, chlorine, bromine or iodine atom.

According to the invention, "alkyl" means a straight-chain or branched open-chain, saturated hydrocarbyl radical which is optionally mono- or polysubstituted. Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

"Haloalkyl", "-alkenyl" and "-alkynyl" mean alkyl, alkenyl and alkynyl, respectively, partially or fully substituted by identical or different halogen atoms, for example monohaloalkyl such as, for example, $CH_2CH_2Cl$, $CH_2CH_2Br$, $CHClCH_3$, $CH_2Cl$, $CH_2F$; perhaloalkyl such as, for example, $CCl_3$, $CClF_2$, $CFCl_2$, $CF_2CClF_2$, $CF_2CClFCF_3$; polyhaloalkyl such as, for example, $CH_2CHFCl$, $CF_2CClFH$, $CF_2CBrFH$, $CH_2CF_3$; here, the term perhaloalkyl also includes the term perfluoroalkyl.

"Fluoroalkyl", mentioned as an example of halogen-substituted alkyl, means a straight-chain or branched open-chain, saturated and fluorine-substituted hydrocarbon radical, where at least one fluorine atom is located at one of the possible positions.

"Perfluoralkyl", mentioned as an example of perhalogenated alkyl, means a straight-chain or branched open-chain, saturated and fully fluorine-substituted hydrocarbon radical, for example $CF_3$, $CF_2CF_3$, $CF_2CF_2CF_3$.

"Partly fluorinated alkyl", mentioned as an example of partly halogenated alkyl, means a straight-chain or branched, saturated hydrocarbon which is mono- or polysubstituted by fluorine, where the fluorine atoms in question may be present as substituents on one or more different carbon atoms of the straight-chain or branched hydrocarbon chain, for example $CHFCH_3$, $CH_2CH_2F$, $CH_2CH_2CF_3$, $CHF_2$, $CH_2F$, $CHFCF_2CF_3$.

"Partly fluorinated haloalkyl" means a straight-chain or branched, saturated hydrocarbon which is substituted by different halogen atoms with at least one fluorine atom, where any other halogen atoms optionally present are selected from the group of fluorine, chlorine or bromine, iodine. The halogen atoms in question may be present as substituents on one or more different carbon atoms of the straight-chain or branched hydrocarbyl chain. Partly fluorinated haloalkyl also includes full substitution of the straight or branched chain by halogen including at least one fluorine atom.

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "$(C_1-C_4)$-alkyl" mentioned here by way of example is a brief notation for alkyl having one to 4 carbon atoms according to the range stated for carbon atoms, i.e. comprises the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, for the hydrocarbyl radicals such as alkyl, alkenyl and alkynyl radicals, including in composite radicals, preference is given to the lower carbon skeletons, for example having 1 to 6 carbon atoms, or having 2 to 6 carbon atoms in the case of unsaturated groups. Alkyl radicals, including in composite radicals such as alkoxy, haloalkyl, etc., are, for example, methyl, ethyl, n-propyl or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

Alkenyl especially also includes straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl is, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

Alkynyl especially also includes straight-chain or branched open-chain hydrocarbon radicals having more than one triple bond, or else having one or more triple bonds and one or more double bonds, for example 1,3-butatrienyl or 3-penten-1-yn-1-yl. $(C_2-C_6)$-alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), bicyclo[2.2.2]octan-2-yl, adamantan-1-yl and adamantan-2-yl. The term "$(C_3-C_7)$-cycloalkyl" is a brief notation for cycloalkyl having three to 7 carbon atoms corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

"Cycloalkenyl" means a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "alkylidene", for example including in the form of $(C_1-C_{10})$-alkylidene, means the radical of a straight-chain or branched open-chain hydrocarbyl radical bonded via a double bond. Possible bonding sites for alkylidene are naturally only positions on the base structure where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$. Cycloalkylidene is a carbocyclic radical bonded via a double bond.

According to the invention, "arylsulphonyl" represents optionally substituted phenylsulphonyl or optionally substituted polycyclic arylsulphonyl, here especially optionally substituted naphthylsulphonyl, for example substituted by halogen, cyano, nitro, alkyl, haloalkyl, haloalkoxy, amino, alkylamino, alkylcarbonylamino, dialkylamino or alkoxy groups.

According to the invention, "cycloalkylsulphonyl"—alone or as a constituent of a chemical group—represents optionally substituted cycloalkylsulphonyl, preferably having 3 to 6 carbon atoms, for example cyclopropylsulphonyl, cyclobutylsulphonyl, cyclopentylsulphonyl or cyclohexylsulphonyl.

According to the invention, "alkylsulphonyl"—alone or as a constituent of a chemical group—represents straight-chain or branched alkylsulphonyl, preferably having 1 to 8 or having 1 to 6 carbon atoms, for example methylsulphonyl, ethylsulphonyl, n-propylsulphonyl, isopropylsulphonyl, n-butylsulphonyl, isobutylsulphonyl, sec-butylsulphonyl and tert-butylsulphonyl.

According to the invention, "alkylthio"—alone or as part of a chemical group—represents straight-chain or branched S-alkyl, preferably having 1 to 8, particularly preferably having 1 to 6 carbon atoms, for example methylthio, ethylthio, n-propylthio, isopropylthio, n-butylthio, isobutylthio, sec-butylthio and tert-butylthio. Alkenylthio is an alkenyl radical bonded via a sulphur atom, alkynylthio is an alkynyl radical bonded via a sulphur atom, cycloalkylthio is a cycloalkyl radical bonded via a sulphur atom, and cycloalkenylthio is a cycloalkenyl radical bonded via a sulphur atom.

According to the nature and the bonding of the substituents, the compounds of the general formula (I) may be present as stereoisomers. The formula (I) embraces all possible stereoisomers defined by their specific spatial form, such as enantiomers, diastereomers, Z and E isomers. If, for example, one or more alkenyl groups are present, there may be diastereomers (Z and E isomers). If, for example, one or more asymmetric carbon atoms are present, there may be enantiomers and diastereomers. Stereoisomers can be obtained from the mixtures obtained in the preparation by customary separation methods. The chromatographic separation can be effected either on the analytical scale to find the enantiomeric excess or the diastereomeric excess, or on the preparative scale to prepare test specimens for biological testing. It is equally possible to selectively prepare stereoisomers by using stereoselective reactions using optically active starting materials and/or auxiliaries. The invention thus also relates to all stereoisomers which are embraced by the general formula (I) but are not shown in their specific stereomeric form, and to mixtures thereof.

Synthesis of substituted isoquinolinones, isoquinolinediones, isoquinolinetriones and dihydroisoquinolinones and analogues thereof.

Substituted isoquinolinones can be prepared by known processes (cf. ChemMedChem 2008, 3, 914; J. Pharmacol. Exp. Ther. 2003, 305, 943; Farmaco 2003, 58, 851; Tetrahedron 2009, 65, 4751; Heterocycles 2009, 78, 2979; Tetrahedron Lett. 2009, 50, 6476; WO2010039079; WO2002090334; WO2004031171; WO2004009556; WO2004024694; Tetrahedron 2007, 63, 9437; J. Heterocyclic Chem. 2006, 43, 1195; Chem. Heterocycl. Comp. 2005, 41, 1102; Tetrahedron Lett. 2005, 46, 8439; J. Org. Chem. 2001, 66, 8685). The fused subclasses of the phenanthridinones and azaphenanthridinones are accessible via synthesis routes described in the literature (cf. Tetrahedron 2010, 66, 5008; Tetrahedron 2009, 65, 10009; J. Med. Chem. 2003, 46, 3138; Bioorg. Med. Chem. 2006, 14, 1378; Nucl. Med. Biol. 2005, 32, 437; Tetrahedron 2006, 62, 5862; Tetrahedron Lett. 2008, 49, 4467; WO200244183), and the fused subclasses of the pyrido-, pyrimido- and pyrazinoimidazoisoquinolinones can also be prepared via known synthesis routes (cf. J. Heterocycl. Chem. 1987, 24, 549; J. Comb. Chem. 2007, 9, 982; Bioorg. Med. Chem. 2009, 17, 7537). Substituted dihydroisoquinolinones can likewise be prepared by processes known from the literature (cf. ChemMedChem 2008, 3, 914; Anti-Cancer Drug Des. 1991, 7, 107; Bioorg. Med. Chem. Lett. 2007, 17, 453; Synthesis 2009, 2809, WO2010017048; WO99/11649). The synthesis of substituted isoquinolinetriones and -diones also takes place using the preparation processes described in the literature (cf. J. Chem. Soc. Chem. Commun. 2002, 2306; J. Med. Chem. 2006, 49, 1613; WO2004111010; Synth. Commun. 1998, 28, 3195; U.S. Pat. No. 7,713,994). Various preparation routes known from the literature for constructing the isoquinolinone, isoquinolinedione, isoquinolinetrione and dihydroisoquinolinone core structures have been used and in some cases optimized. Selected detailed synthesis examples are detailed in the next section. The synthesis routes used and examined proceed from commercially available or easily preparable synthesis building blocks.

In the synthesis of substituted isoquinolinones starting with substituted isoquinolines, the isoquinoline in question is initially converted with meta-chloroperoxybenzoic acid (MCPBA) into a suitable aprotic solvent, for example dichloromethane (DCM), into the corresponding isoquinoline N-oxide, which is then converted with acetic anhydride (Ac$_2$O) at elevated temperature into the desired substituted isoquinolinone (I)a (Scheme 1). 2-Chloroisoquinolines, optionally with further substitution, can be converted by heating in acetic acid into the corresponding substituted isoquinolinones (I)a. Alternatively, 2-methylbenzoic esters, optionally with further substitution, can be reacted with N,N-dimethylformamide dimethyl acetal (DMF-DMA) in N,N-dimethylformamide (DMF) to give enamine intermediates which, on moist silica gel, form corresponding coumarine derivatives, and from which the isoquinolinones (I)a according to the invention can be obtained by reaction with ammonia. Synthetic access to substituted isoquinolinones is also available by side-chain bromination of 2-methylbenzoic esters, optionally with further substitution, using elemental bromine and a suitable free-radical initiator in a suitable aprotic solvent, followed by substitution of the bromine atom introduced with the aid of ammonium cyanide, since the cyanomethylbenzoic esters obtained, optionally with further substitution, can be converted by reaction with diisobutylaluminium hydride (DIBAL-H) in a suitable polar aprotic solvent, for example dichloromethane or acetonitrile (MeCN), into the corresponding isoquinolinones (I)a according to the invention (Scheme 1).

Scheme 1

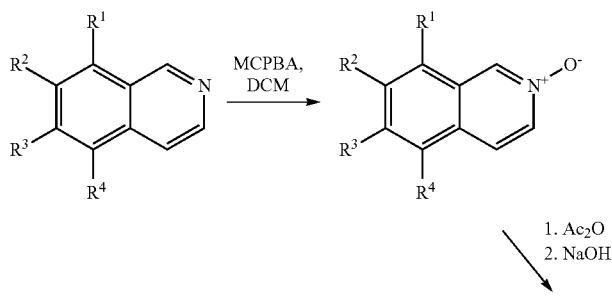

1. Ac$_2$O
2. NaOH

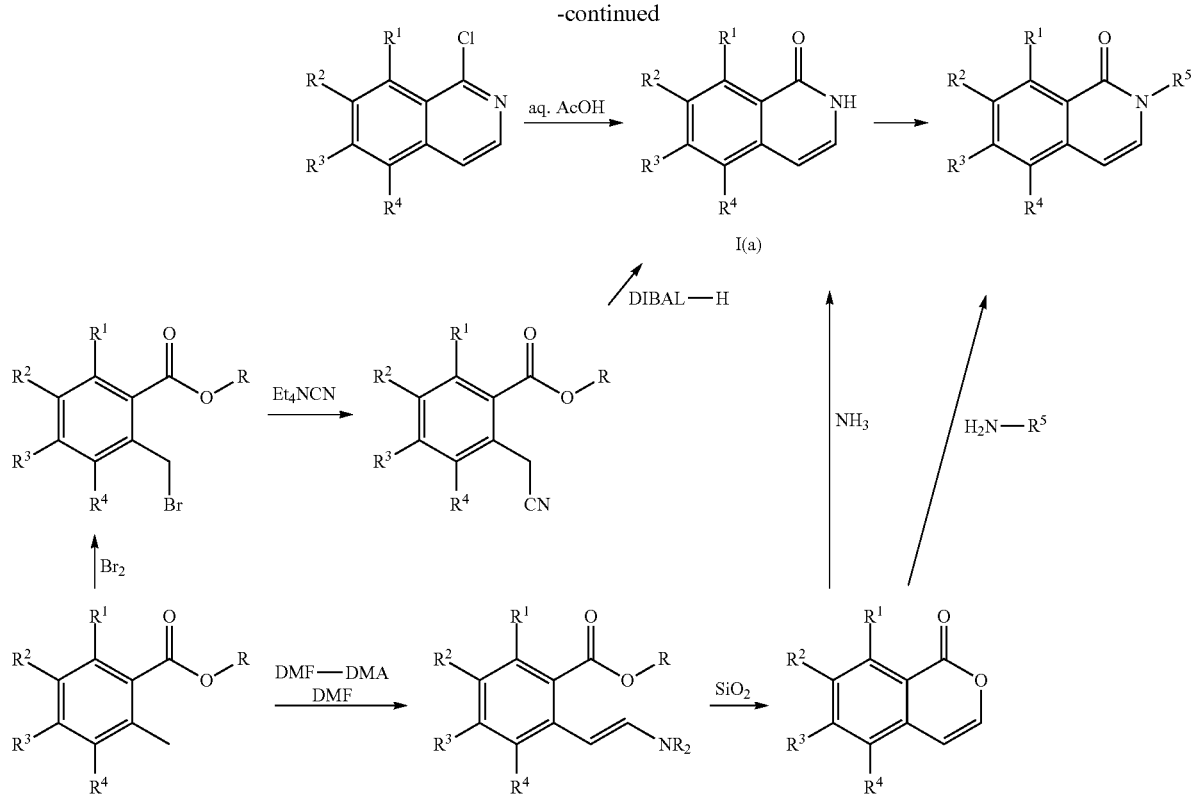

I(a)

Optionally substituted aryl-1,2-dicarboxylic acids can be converted with mercury acetate and then subsequently with elemental iodine and an esterification with the aid of a suitable alcohol (for example methanol or ethanol) and concentrated sulphuric acid into the corresponding 2-iodobenzoic esters, optionally with further substitution. By Sonogashira coupling with suitable terminal alkynes (for example arylalkynes, heteroarylalkynes, alkylsilylalkynes or alkylalkynes), copper(I) chloride and bis-(triphenylphosphine)palladium dichloride as catalyst in a suitable solvent (for example triethylamine or a mixture of triethylamine and tetrahydrofuran), the 2-iodobenzoic esters, optionally with further substitution, can be converted into the corresponding alkyne derivatives. By reacting the 2-alkynylbenzoic esters in question, optionally with further substitution, with mercury sulphate and concentrated sulphuric acid in acetone, cyclization to the corresponding coumarine derivatives can be effected; the latter can be converted by subsequent reaction with ammonia into the substituted isoquinolinones I(b) according to the invention (Scheme 2).

Scheme 2

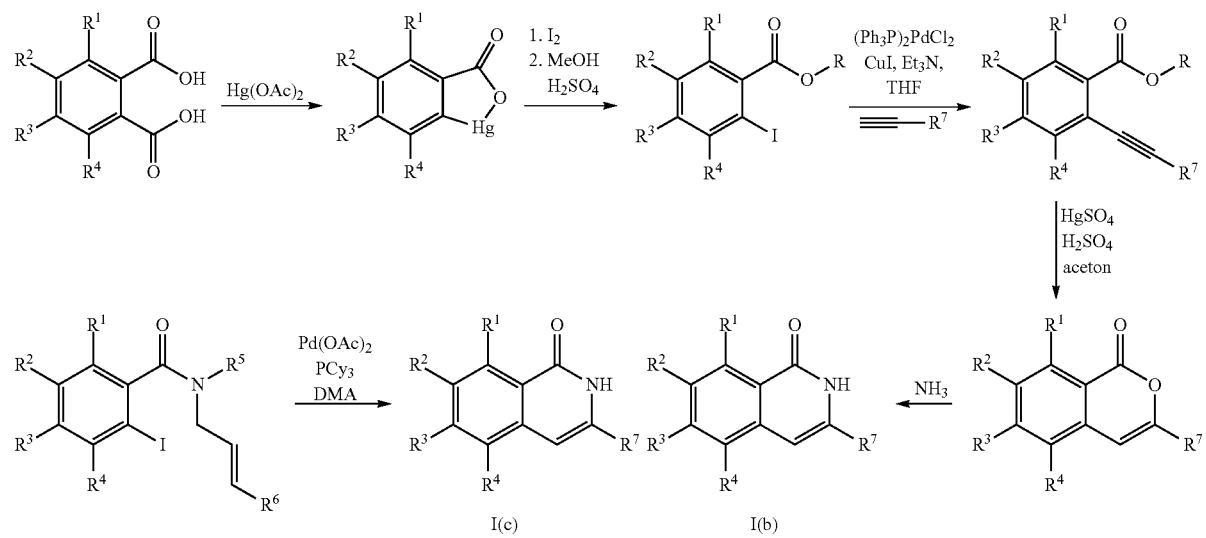

I(c)  I(b)

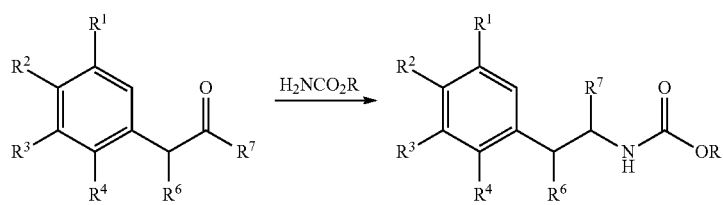

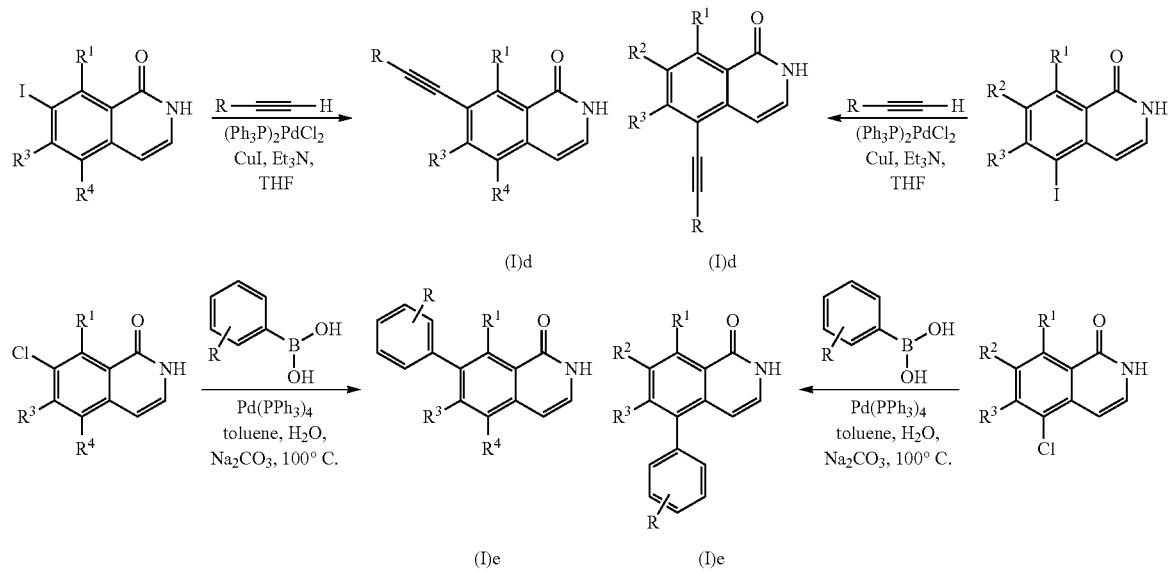

Scheme 3.

By cyclization of 2-iodobenzamides, optionally with further substitution, which cyclization is possible with palladium acetate (Pd(OAc)$_2$), tricyclohexylphosphine (PCy$_3$) in a suitable polar aprotic solvent (for example dimethylacetamide) at elevated temperature, it is likewise possible to obtain substituted isoquinolinones I(c). The reaction of optionally substituted phenylacetaldehydes or benzylketones with ethylurethane leads to the formation of carbamate intermediates which can be converted by further reaction at high temperatures into the substituted isoquinolinones I(c) according to the invention (Scheme 2). Isoquinolinones (I)a-c having chlorine, bromine or iodine substitutents at positions $R^1$, $R^2$, $R^3$ or $R^4$ can be substituted further with the aid of transition metal-catalyzed reactions. Selected examples for this type of reactions are shown in Scheme 3. The substituents R in Scheme 3 are not defined in more detail as these are illustrative reactions. The possible and preferred substituents at the groups introduced result from the definitions mentioned above for the substituents $R^1$, $R^2$, $R^3$ or $R^4$. By Sonogashira coupling using copper(I) chloride and bis-(triphenylphosphine)palladium dichloride in a suitable solvent (for example triethylamine (Et$_3$N) or a mixture of triethylamine and tetrahydrofuran), it is possible to introduce, for example, alkynyl, arylalkynyl, heteroarylalkynyl, alkylsilylalkynyl or alkylalkynyl groups and to form the target molecules (I)d. Via Suzuki coupling with tetrakis-(triphenylphosphine)palladium in a suitable solvent system (such as toluene and water), it is possible to prepare, for example, aryl-, alkenyl-, cycloalkyl- or heteroaryl-substituted isoquinolinones (I)e according to the invention.

Substituted isoquinolinones can be converted by reaction with hydrogen in the presence of a catalyst of the palladium on carbon system in a suitable solvent (for example acetic acid or methanol) into the corresponding dihydroisoquinolinones according to the invention. Further synthetic access to dihydroisoquinolinones is provided by rearrangement of mesylated indanone oximes. Starting with commercially available or easily preparable optionally substituted indanones, mesylated indanone oximes are accessible in good yields by reaction with hydroxylamine and sodium acetate in a suitable polar protic solvent (for example methanol) and subsequent reaction with methanesulphonyl chloride (MsCl) and triethylamine in a suitable aprotic solvent (for example dichloromethane). These synthesis building blocks can then be converted in a Beckmann rearrangement, which is facilitated by certain Lewis acids (for example boron trifluoride (BF$_3$), titanium tetrachloride, zirconium tetrachloride) and suitable additives (for example 2,3-dimethylpropionitrile, methanesulphonyl chloride, cyclopentyl methyl ether) in an aprotic solvent, for example dichloroethane (DCE), into the optionally substituted dihydroisoquinolinones I(f) according to the invention (Scheme 4). Optionally substituted dihydrocinnamic acids can be converted with the aid of diphenylphosphoryl azide (DPPA) and triethylamine at elevated temperature in a suitable aprotic solvent (for example toluene) and subsequent reaction of the resulting crude product with boron trifluoride/etherate complex into the dihydroisoquinolinones I(f) according to the invention.

Further synthetic access to optionally substituted dihydroisoquinolinones I(f) is provided by the reaction of optionally substituted phenethylamines with a suitable alkyl chloroformate and triethylamine in a suitable aprotic solvent (for example dichloromethane) and subsequent condensation using suitable condensing agents, for example polyphospho-

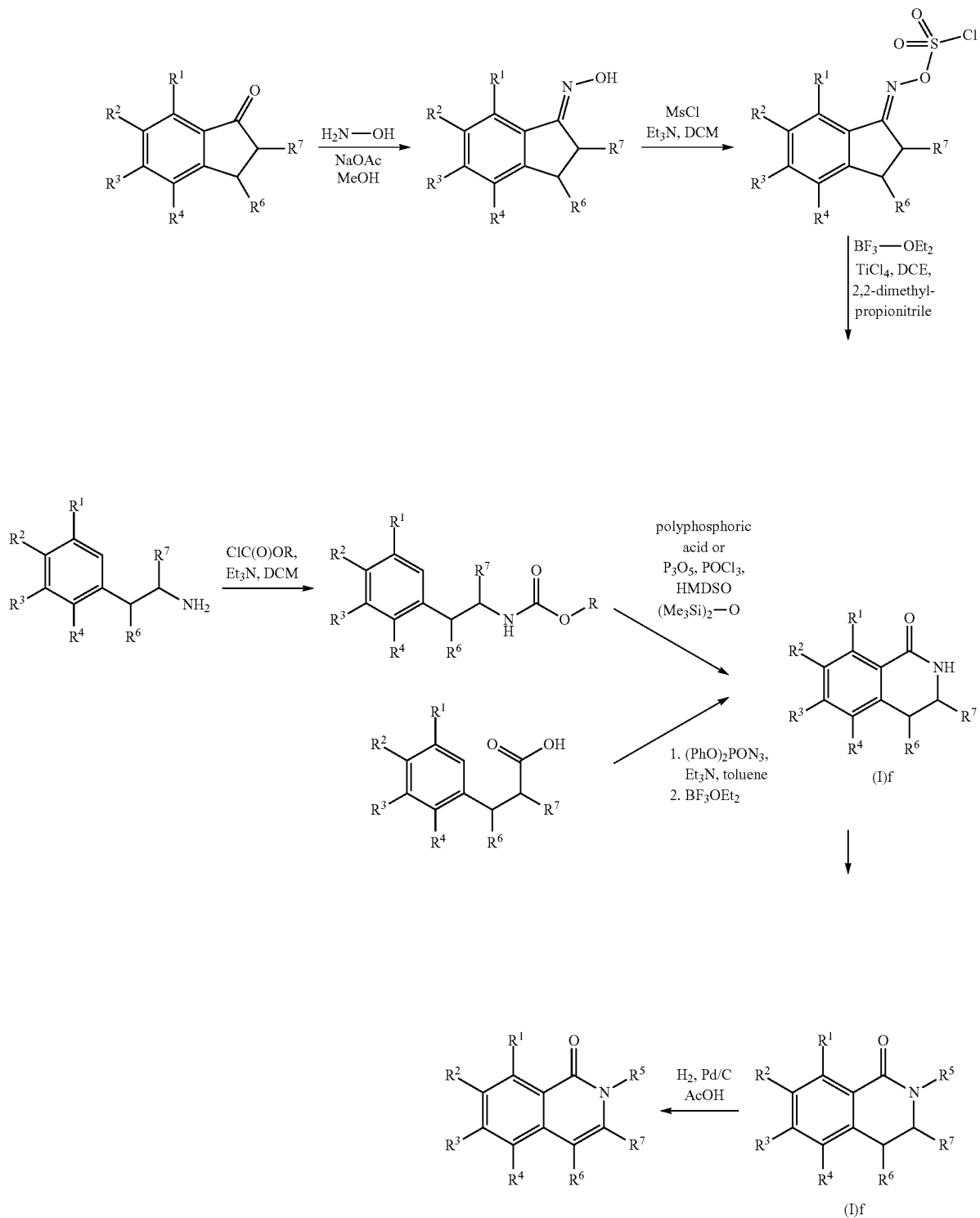

Scheme 4.

ric acid, phosphoryl chloride, phosphorus pentoxide or hexamethyldisiloxane (HMDSO) (Scheme 4).

Scheme 5.

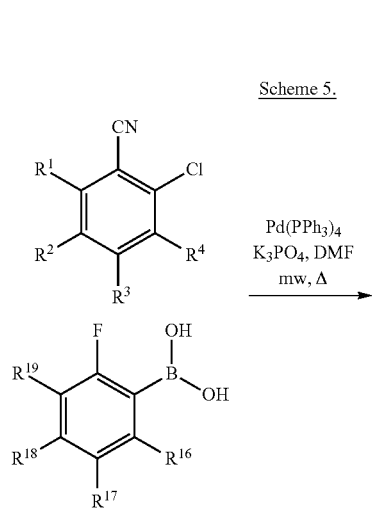

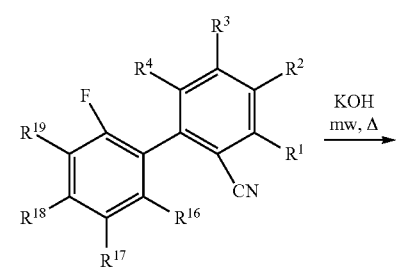

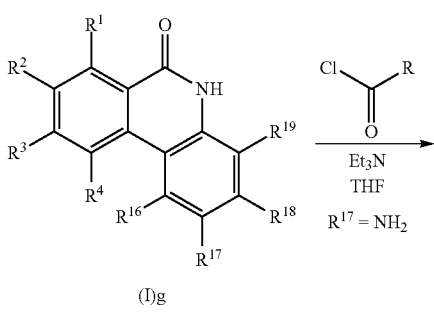

(I)g

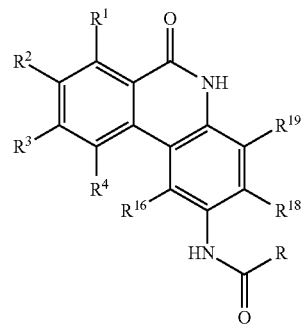

Optionally substituted condensed isoquinolinones of the phenanthridin-6(5H)-one type can be prepared via a two-step reaction starting with 2-chlorobenzonitriles and 2-fluorophenylboronic acids. Via Suzuki coupling of 2-chlorobenzonitriles, optionally with further substitution, with 2-fluorophenylboronic acids, optionally with further substitution, with tetrakis-(triphenylphosphine)palladium with addition of a suitable bases (for example potassium phosphate) in a suitable solvent system (such as dimethylformamide) under microwave conditions, it is possible to prepare bisaryl intermediates which, using potassium hydroxide in a suitable solvent (for example tert-butanol) under microwave conditions, can be converted into the phenanthridin-6(5H)-ones (I)g according to the invention, optionally with further substitution (Scheme 5). Substituted fused isoquinolinones of the azaphenanthridinone type can be prepared via a similar synthesis sequence described below using the preparation of aminoazaphenanthridinones I(h) as an example. Here, in the first step there is a Suzuki coupling of 2-alkylamidophenylboronic acids, optionally with further substitution, with 2,6-dichloro-3-nitropyridine using tetrakis-(triphenylphosphine) palladium with addition of a suitable base (for example potassium carbonate) in a suitable solvent system (such as toluene/ethanol) at elevated temperature. In the next step, the chlorine atom in the pyridine moiety of the intermediate formed can be substituted by a suitable amine with the aid of diisopropylethylamine (DIPEA) in a suitable polar aprotic solvent (for example tetrahydrofuran) at elevated temperature. The nitro group still present is then reduced either with hydrogen in the presence of a catalyst of the palladium on carbon system in a suitable solvent (for example methanol or acetic acid) or using tin(II) chloride in a suitable solvent. The desired aminoazaphenanthridinones I(h) according to the invention can be obtained by final cyclization of the resulting arylated bisaminopyridine with the aid of lithium diisopropylamide (LDA) in a suitable polar aprotic solvent, for example tetrahydrofuran (THF), at low temperatures (for example at −70° C.) (Scheme 6).

Scheme 6.

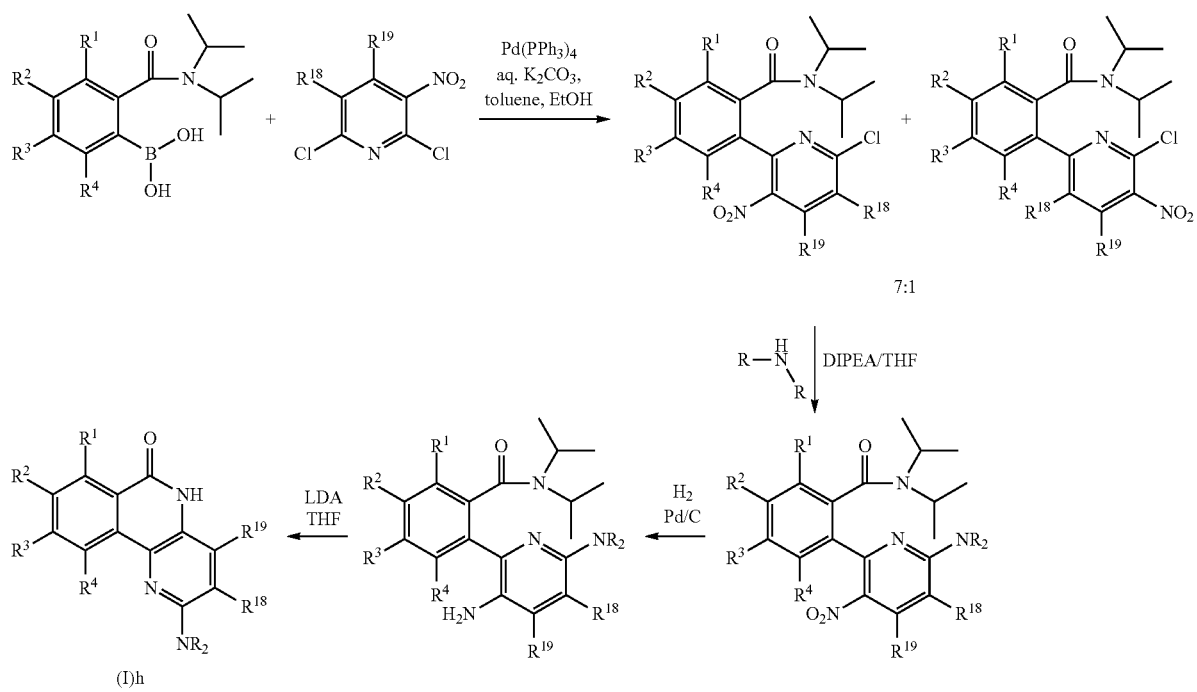

(I)h

Fused isoquinolinones I(i) of the imidazoisoquinolinone type, optionally with further substitution, can be prepared via a multicomponent reaction of a suitable alkyl 2-formylbenzoate, optionally with further substitution, with tert-butylisonitrile and a suitable heteroaromatic amine, optionally with further substitution, with addition of p-toluenesulphonic acid (TsOH) in a suitable polar protic solvent (for example methanol) and subsequent trifluoroacetic acid-(TFA-) mediated condensation (Scheme 7). Suitable heteroaromatic amines are, in addition to aminopyridines, optionally with further substitution, also, for example, corresponding aminopyrimidines and aminopyrazines.

Scheme 7

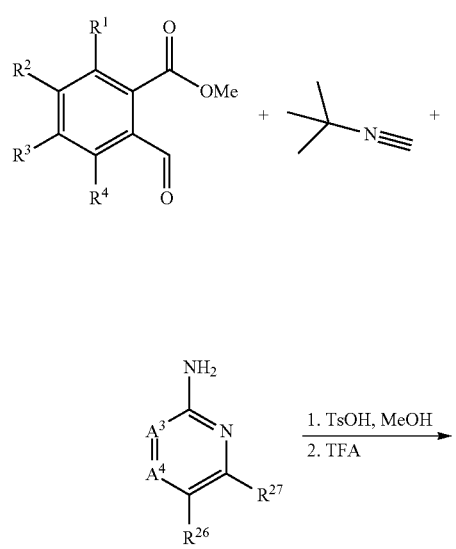

-continued

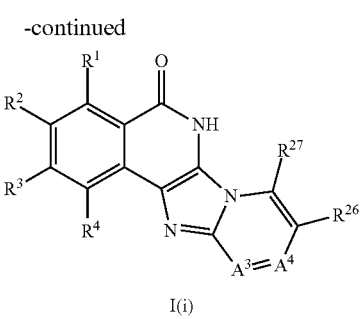

I(i)

Polycyclic isoquinolinones of the 6,7-dihydro-8H-furo[2', 3':3,4]cyclohepta[1,2-c]isoquinolin-8-one type, optionally with further substitution, can be prepared from suitable 2-formylbenzoic acids, optionally with further substitution. By reaction of a corresponding alkyl 2-formylbenzoate with a furan, optionally with further substitution, in the presence of perchloric acid in a suitable polar aprotic solvent (for example dioxane), a bisfuryl adduct intermediate is formed which, by coupling with a suitable amine (mediated, for example, by dicyclohexylcarbodiimide=DCC or isobutyl chloroformate) in a suitable polar aprotic solvent (for example dichloromethan=DCM) is converted into an amide intermediate, which, by acid-mediated condensation (for example with the aid of p-toluenesulphonic acid or p-toluenesulphonic acid bound to macroporous polystyrene) in a suitable aprotic solvent (for example dichloroethane, benzene or toluene) at elevated temperature forms the desired 6,7-dihydro-8H-furo[2',3':3,4]cyclohepta[1,2-c]isoquinolin-8-ones I(k) according to the invention, optionally with further substitution (Scheme 8).

Scheme 8

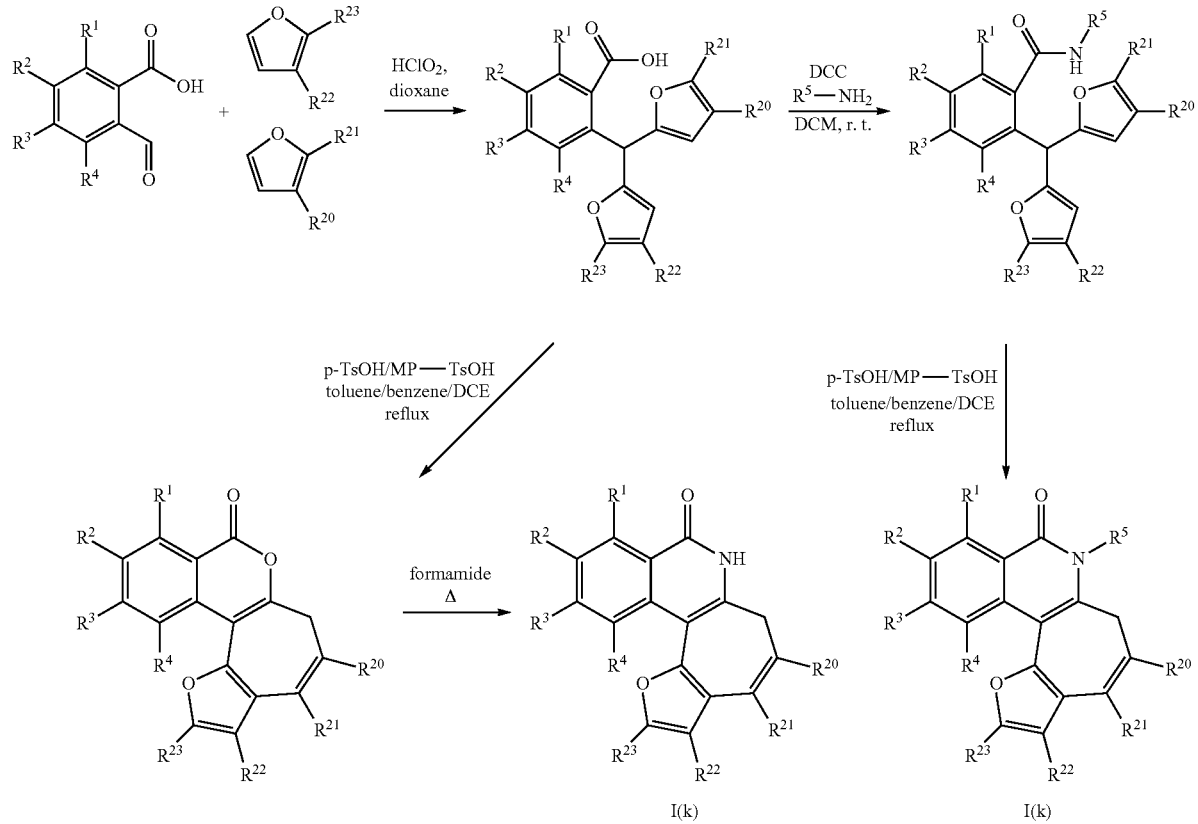

Alternatively, the bisfuryl intermediate can be converted by acid-mediated condensation (for example with the aid of p-toluenesulphonic acid=p-TsOH or p-toluenesulphonic acid bound to macroporous polystyrene=MP-TsOH) in a suitable aprotic solvent (for example dichloroethane, benzene or toluene) at elevated temperature into a corresponding furo[2',3':3,4]cyclohepta[1,2-c]isochromen-8(6H)-one. By reaction with formamide at elevated temperature, the corresponding 6,7-dihydro-8H-furo[2',3':3,4]cyclohepta[1,2-c]isoquinolin-8-one I(k) according to the invention, optionally with further substitution, is then formed (Scheme 8). Isoquinolinetriones, optionally with further substitution, can be prepared via two different synthesis routes which also allow access to optionally substituted isoquinolinediones I(l) and 3-acyl-4-hydroxyisoquinolin-1(2H)-ones I(q). Benzamides, optionally with further substitution, can be converted with chloroacetyl chloride in a suitable aprotic solvent (for example toluene) and subsequent reaction with potassium xanthogenate in a polar aprotic solvent (for example acetonitrile or toluene) into intermediates which, by reaction with tert-butyl peroxide in a suitable solvent (for example 1,2-dichlorobenzene) at elevated temperature, form the desired isoquinolinediones I(l) according to the invention, optionally with further substitution. From these isoquinolinediones, the corresponding isoquinolinetriones I(m) according to the invention, optionally with further substitution, can then be obtained by oxidation with a suitable oxidizing agent (for example selenium dioxide) in a suitable solvent (for example dixoane) at elevated temperature.

Scheme 9

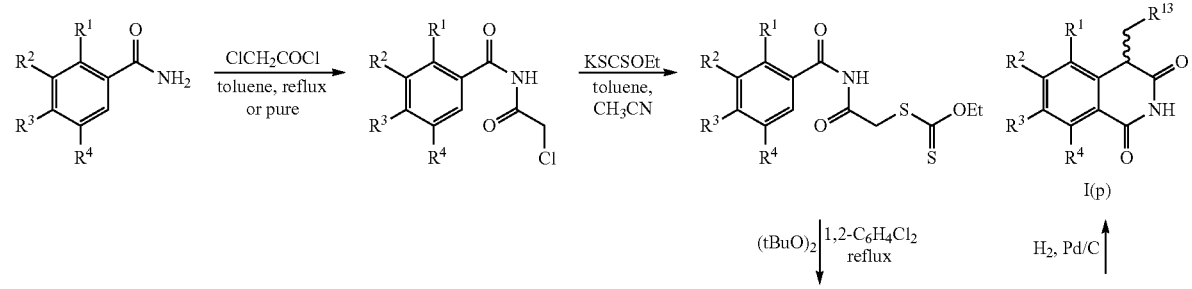

-continued

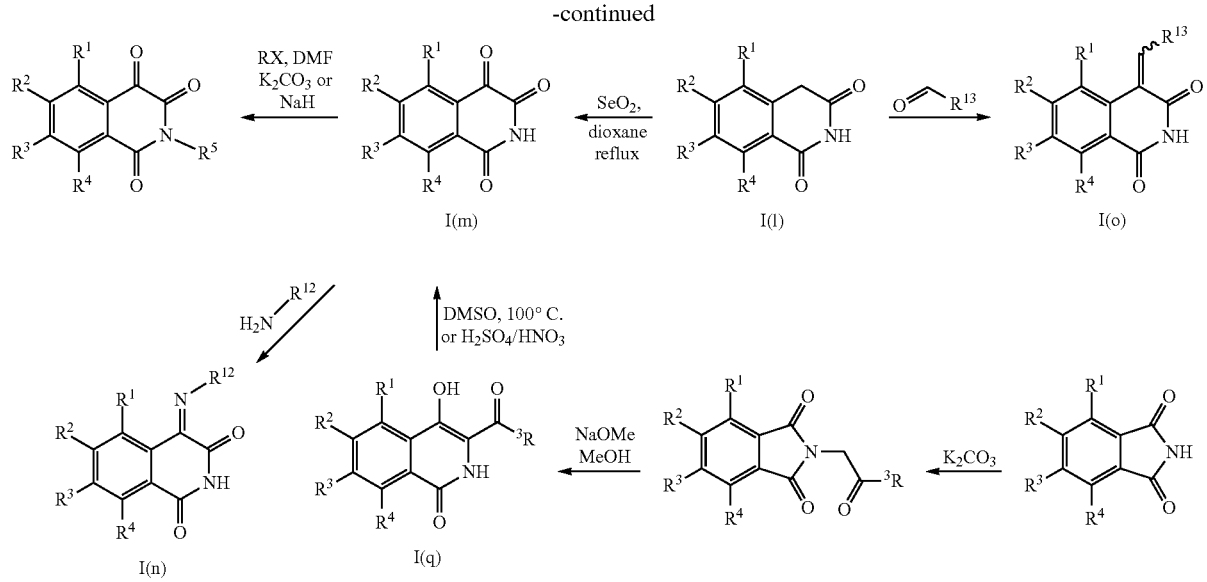

Reaction of the isoquinolinetriones in question with a suitable amine component with further substitution (for example with hydroxylamine optionally with further O-substitution) in a suitable solvent may provide the compounds I(n) according to the invention, optionally with further substitution (for example an isoquinoline-1,3,4(2H)-trione 4-O-alkyl oxime, optionally with further substitution, or related compounds). The isoquinolinediones I(l) can also be converted with an aldehyde, optionally with further substitution, into the corresponding isoquinolinediones I(o) according to the invention, with further substitution at the 4 position (for example 4-arylideneisoquinoline-1,3(2H,4H)-diones, 4-alkylideneisoquinoline-1,3(2H,4H)-diones or 4-heteroarylideneisoquinoline-1,3(2H,4H)-diones, optionally with further substitution), which, using hydrogen in the presence of a catalyst of the system palladium on carbon in a suitable solvent, can be hydrogenated to give the substituted isoquinolinediones I(p) according to the invention. Alternative access to the isoquinolinetriones I(m) according to the invention, optionally with further substitution, is provided by the reaction of phthalimides, optionally with further substitution, with a suitable 2-halomethyl ketone with further substitution in the presence of potassium carbonate and a suitable polar aprotic solvent (for example acetonitrile). Further reaction with sodium methoxide in methanol leads to the formation of 3-acyl-4-hydroxy-isoquinolin-1(2H)-ones I(q) which, in dimethyl sulphoxide at elevated temperature or in a suitable mixture of sulphuric acid and nitric acid, can be converted into the isoquinolinetriones I(m) according to the invention, optionally with further substitution.

SYNTHESIS EXAMPLES FOR COMPOUNDS OF THE GENERAL FORMULA (I)

Selected detailed synthesis examples for the inventive compounds of the general formula (I) are given below. The substance numbers mentioned correspond to the numbers listed in tables 1 to 9. The $^1$H NMR, $^{13}$C NMR and $^{19}$F NMR spectroscopy data which are reported for the chemical examples described in the paragraphs which follow (400 MHz for $^1$H NMR and 150 MHz for $^{13}$C NMR and 375 MHz for $^{19}$F NMR, solvent: CDCl$_3$, CD$_3$OD or d$_6$-DMSO, internal standard: tetramethylsilane δ=0.00 ppm), were obtained on a Bruker instrument, and the signals listed have the meanings given below: br=broad; s=singlet, d=doublet, t=triplet, dd=doublet of doublets, ddd=doublet of a doublet of doublets, m=multiplet, q=quartet, quint=quintet, sext=sextet, sept=septet, dq=doublet of quartets, dt=doublet of triplets. In the case of diastereomer mixtures, either the significant signals for each of the two diastereomers or the characteristic signal of the main diastereomer is/are reported. The abbreviations used for chemical groups are defined as follows: Me=CH$_3$, Et=CH$_2$CH$_3$, t-Hex =C(CH$_3$)$_2$CH(CH$_3$)$_2$, t-Bu=C(CH$_3$)$_3$, n-Bu=unbranched butyl, n-Pr=unbranched propyl, c-Hex=cyclohexyl.

No. I.1-117:
3-Acetyl-7-bromo-4-hydroxyisoquinolin-1(2H)-one

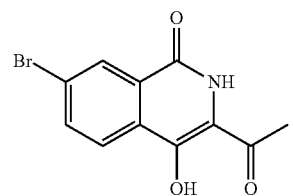 [SMILES: CC(=O)c1[nH]c(=O)c2cc(Br)ccc2c1O]

A mixture of 5-bromoisobenzofuran-1,3-dione (16.21 g, 17.4 mmol) and formamide (42.5 ml, 48.2 g) was stirred at 120° C. for 3 h and, after cooling to room temperature, added to ice water. The resulting colourless solid was filtered off and concentrated under reduced pressure. This gave 5-bromophthalimide in the form of a colourless solid (12.26 g, 76% of theory). $^1$H-NMR (400 MHz, d$^6$-DMSO δ, ppm) 11.45 (br. s, 1H), 8.01 (dd, 1H), 7.99 (d, 1H), 7.75 (d, 1H). 5-Bromophthalimide (1.76 g, 7.8 mmol) was dissolved in abs. ethanol (75 ml), the mixture was heated to 60° C. and an aqueous solution of potassium hydroxide (4 ml, 10.5 mmol) was added dropwise. After 30 min of stirring at 60° C., the reaction mixture was cooled quickly with the aid of an ice bath, and the resulting precipitated colourless solid was filtered off with suction, washed with cold ethanol and dried under reduced pressure.

In this manner, potassium 5-bromophthalimidate (1.04 g, 50% of theory) were obtained in the form of a colourless solid. $^1$H-NMR (400 MHz, d$^6$-DMSO δ, ppm) 7.59 (dd, 1H), 7.45 (d, 1H), 7.29 (d, 1H). A reaction mixture of potassium 5-bromophthalimidate (1030 mg, 3.9 mmol), 1-chloroacetone (361 mg, 3.9 mmol) in abs. N,N-dimethylformamide (10 ml) was stirred at room temperature and an atmosphere of nitrogen for 2 h, and water was then added. The resulting colourless solid was filtered off and concentrated under reduced pressure. This gave 5-bromo-2-(2-oxopropyl)isoindolyl-1,3-dione (770 mg, 70% of theory) which was used without further purification for the next reaction step. $^1$H-NMR (400 MHz, d$^6$-DMSO δ, ppm) 8.12 (d, 1H), 8.08 (dd, 1H), 7.85 (d, 1H), 4.58 (s, 2H), 2.24 (s, 3H). In a three-neck round-bottom flask which had been dried by heating and fitted with dropping funnel and reflux condenser, sodium (45 mg, 2.0 mmol) was dissolved in abs. methanol (5 ml) under an atmosphere of nitrogen. After the sodium had been dissolved completely, the reaction solution was heated to reflux conditions, and a solution of 5-bromo-2-(2-oxopropyl)isoindolyl-1,3-dione (500 mg, 1.8 mmol) in abs. methanol was then added dropwise. The resulting reaction solution was stirred under reflux for 2 h and then, after cooling to room temperature, adjusted to pH 3 by addition of 1M hydrochloric acid. After a further 30 min of stirring at room temperature, the precipitated solid was filtered off, washed with water and dried under reduced pressure. Subsequent purification of the light-yellow crude material by column chromatography (236 mg, 47% of theory) gave 3-acetyl-7-bromo-4-hydroxyisoquinolin-1(2H)-one and 3-acetyl-6-bromo-4-hydroxyisoquinolin-1(2H)-one as colourless solids. $^1$H-NMR (3-acetyl-7-bromo-4-hydroxyisoquinolin-1(2H)-one) (400 MHz, d$^6$-DMSO δ, ppm) 12.56 (br. s, 1H), 10.68 (br. s, 1H), 8.36 (d, 1H), 8.10 (d, 1H), 8.07 (dd, 1H), 2.63 (s, 3H); $^1$H-NMR (3-acetyl-6-bromo-4-hydroxyisoquinolin-1(2H)-one) (400 MHz, d$^6$-DMSO δ, ppm) 12.56 (br. s, 1H), 10.48 (br. s, 1H), 8.28 (d, 1H), 8.18 (d, 1H), 7.95 (dd, 1H), 2.62 (s, 3H).

No. I.1-212: Methyl N-[(1-oxo-1,2-dihydroisoquinolin-4-yl)carbonyl]glycinate

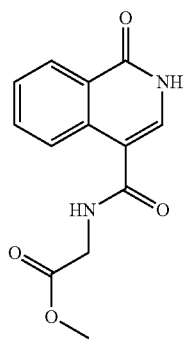 [SMILES: COC(=O)CNC(=O)c1c[nH]c(=O)c2ccccc12]

6.00 g (29.53 mmol) of methyl 1-oxo-1,2-dihydroisoquinoline-4-carboxylate were dissolved in 20 ml of methanol, and 20 ml of 6 N aqueous sodium hydroxide solution were added. The solution was heated at 80° C. for 3 h, cooled to room temperature and, with ice bath cooling, adjusted to pH=3 using concentrated hydrochloric acid. The resulting precipitate was filtered off through a Büchner funnel and washed with cold methanol. The filter cake was air-dried. This gave 5.65 g (99% of theory) of the desired 1-oxo-1,2-dihydroisoquinoline-4-carboxylic acid. $^1$H-NMR (400 MHz, d$^6$-DMSO δ, ppm) 12.69 (br. s, 1H), 11.78 (br. s, 1H), 8.83 (d, 1H), 8.02 (d, 1H), 7.79 (t, 1H), 7.56 (t, 1H). Under an atmosphere of inert nitrogen gas, 0.200 g (1.057 mmol) of 1-oxo-1,2-dihydroisoquinoline-4-carboxylic acid were dissolved in 5 ml of dichloromethane and, with 0.093 ml (1.269 mmol) of thionyl chloride and a drop of N,N-dimethylformamide, heated at the boil for 1 h. The solvent was then removed under reduced pressure and the residue was, under an atmosphere of inert nitrogen gas, dissolved in 5 ml of dichloromethane. To this solution, a solution of 0.245 mg (2.750 mmol) of 2-methoxy-2-oxoethanaminium chloride and 0.383 ml (2.750 mmol) of triethylamine in 5 ml of dichloromethane was added dropwise over a period of 10 min. The suspension was stirred overnight, and 5% strength sodium bicarbonate solution was then added. The solution was extracted with ethyl acetate, the phases were separated, the organic phase was dried over magnesium sulphate and the solvent was removed under reduced pressure. The crude product was purified by chromatography (ethyl acetate:n-heptane 2:1). This gave 120 mg (40% of theory) of the desired methyl N-[(1-oxo-1,2-dihydroisoquinolin-4-yl)carbonyl]glycinate. $^1$H-NMR (400 MHz, d$^6$-DMSO δ, ppm) 11.62 (br. s, 1H), 8.81 (t, 1H), 8.24-8.21 (m, 2H), 7.73 (t, 1H), 7.55-7.52 (m, 2H), 3.99 (d, 2H), 3.68 (s, 3H).

No. I.1-247: 5-[4-(Methylsulphanyl)phenyl]isoquinolin-1(2H)-one

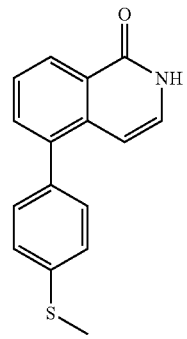 [SMILES: CSc1ccc(-c2cccc3c(=O)[nH]ccc23)cc1]

5.45 g (26.19 mmol) of 5-bromoisoquinoline were dissolved in 250 ml of dichloromethane, and 6.78 g (27.50 mmol) of 3-chloroperoxybenzoic acid monohydrate were added a little at a time over a period of 20 min. The suspension was stirred at room temperature for 2 h. The solution was extracted with saturated sodium bicarbonate solution. The phases were separated, the organic phase was stirred with solid sodium sulphite and the solution was filtered off. The organic phase was dried over magnesium sulphate and the solvent was removed under reduced pressure. This gave 4.94 g (84% of theory) of the desired 5-bromoisoquinoline 2-oxide. $^1$H-NMR (400 MHz, d$^6$-DMSO δ, ppm) 9.02 (s, 1H), 8.26 (d, 1H), 7.99-7.90 (m, 3H), 7.58 (t, 1H). 5.87 g (26.19 mmol) of 5-bromoisoquinoline 2-oxide were then suspended in 50 ml of acetic anhydride and heated at the boil for 3 h. After cooling, the solvent was removed under reduced pressure, the residue was dissolved in 80 ml of 10% strength aqueous sodium hydroxide solution and the mixture was stirred at a temperature of 60° C. for 1 h. The cold suspension was adjusted to pH=6 using 5% strength citric acid solution and the crystals were filtered off with suction and washed with water. The crystals were dried in a vacuum drying cabinet. The crystals were triturated first with ethyl acetate/ethanol and then with acetonitrile. The crystals were then recrystallized from methanol. This gave 4.27 g (72% of theory) of the desired 5-bromoisoquinolin-1(2H)-one. ¹H-NMR (400 MHz, CDCl₃ δ, ppm) 11.55 (br. s, 1H), 8.20 (d, 1H), 8.02 (d, 1H), 7.39 (t, 1H), 7.33 (d, 1H), 6.57 (d, 1H). Under an atmosphere of inert nitrogen gas, 0.20 g (0.89 mmol) of 5-bromoisoquinolin-1(2H)-one, 0.18 g (1.07 mmol) of [4-(methylsulphanyl)phenyl]boronic acid, 0.04 g (0.06 mmol) of bis(triphenylphosphine)palladium dichloride and 0.370 g (2.678 mmol) of potassium carbonate were then suspended in 1.37 ml of 1,2-dimethoxyethane, 0.22 ml of ethanol and 0.27 ml of water in a microwave tube. This reaction vessel was closed with a cap and stirred in a Biotage Initiator sixty© microwave at 175° C. (pressure at most 13 bar) for 45 min. After cooling, the mixture was diluted with water and extracted with dichloromethane. The phases were separated, the organic phase was dried over sodium sulphate and the solvent was removed under reduced pressure. The crude product was suspended in acetonitrile in an ultrasonic bath, and the crystal slurry was filtered off with suction. This gave 91 mg (37% of theory) of the desired 5-[4-(methylsulphanyl)phenyl]isoquinolin-1(2H)-one. ¹H-NMR (400 MHz, d⁶-DMSO δ, ppm) 11.32 (br. s, 1H), 8.22 (d, 1H), 7.61 (d, 1H), 7.54 (t, 1H), 7.39-7.35 (m, 4H), 7.12 (t, 1H), 6.35 (d, 1H), 2.53 (s, 3H).

No. I.1-252: Under an atmosphere of inert nitrogen gas, 7-(4-chloro-2-fluorophenyl)isoquinolin-1(2H)-one

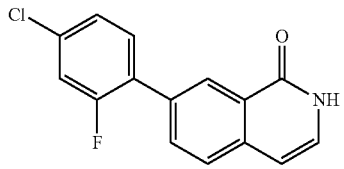 [SMILES: O=c1[nH]ccc2ccc(-c3ccc(Cl)cc3F)cc12]

0.20 g (0.893 mmol) of 7-bromoisoquinolin-1(2H)-one, 0.19 g (1.071 mmol) of [4-(methylsulphanyl)phenyl]boronic acid, 0.044 g (0.062 mmol) of bis(triphenylphosphine)palladium dichloride and 0.370 g (2.678 mmol) of potassium carbonate were suspended in 1.37 ml of 1,2-dimethoxyethane, 0.22 ml of ethanol and 0.27 ml of water in a microwave tube. This was closed with a cap and stirred in a Biotage Initiator Sixty® microwave at 175° C. (pressure at most 13 bar) for 45 min. After cooling, the mixture was diluted with water and extracted with dichloromethane. The phases were separated, the organic phase was dried over sodium sulphate and the solvent was removed under reduced pressure. The crude product was suspended in acetonitrile in an ultrasonic bath, and the crystal slurry was filtered off with suction. This gave 103 mg (40%) of the desired 7-(4-chloro-2-fluorophenyl)isoquinolin-1(2H)-one. 1H-NMR (400 MHz, d⁶-DMSO δ, ppm) 8.33 (d, 1H), 7.88 (d, 1H), 7.77 (d, 1H), 7.66 (t, 1H), 7.58 (d, 1H), 7.43 (d, 1H), 7.23 (d, 1H), 6.60 (d, 1H).

No. I.2-1:
7-Methoxy-3,4-dihydroisoquinolin-1(2H)-one

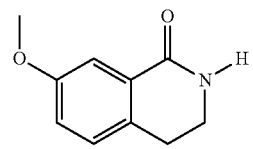

Under argon, hydroxylamine hydrochloride (514 mg, 7.40 mmol) and sodium acetate (607 mg, 7.4 mmol) were initially charged in abs. methanol (15 ml), and after 5 minutes of stirring at room temperature, a solution of 6-methoxy-1-indanone (1000 mg, 6.17 mmol) in abs. methanol (10 ml) was added. The resulting reaction mixture was stirred at room temperature for 3 h. After removal of the solvent under reduced pressure, the residue was taken up in dichloromethane, and water was added. The aqueous phase was extracted repeatedly with dichloromethane and the combined organic phases were dried over magnesium sulphate, filtered and concentrated under reduced pressure. Without further purification, the resulting 6-methoxyindan-1-one oxime (1000 mg, 5.64 mmol) was dissolved in dichloromethane (15 ml), triethylamine (1.02 ml, 7.34 mmol) was added and the mixture was stirred under argon at room temperature for 20 min. After cooling to 0° C., methanesulphonyl chloride (840 mg, 7.34 mmol) was added. The reaction mixture obtained in this manner was stirred at room temperature for 4 h, and water was then added. After repeat extraction of the aqueous phase with dichloromethane, the combined organic phases were dried over magnesium sulphate, filtered and concentrated under reduced pressure. Without any further purification, the 6-methoxyindan-1-one methanesulphonyloxime (1000 mg, 3.92 mmol) that remained was dissolved in dichloroethane (3 ml) under argon, and boron trifluoride etherate complex (0.50 ml, 3.95 mmol), methanesulphonyl chloride (0.50 ml, 6.46 mmol) and titanium tetrachloride (0.50 ml, 4.56 mmol) were added, in each case dropwise. Under argon, the resulting reaction solution was stirred at room temperature for 6 h and then cooled to 0° C., and water and saturated sodium bicarbonate solution were added carefully. After repeated thorough extraction of the aqueous phase with dichloromethane, the combined organic phases were dried over magnesium sulphate, filtered and concentrated under reduced pressure. Purification of the residue that remained by column chromatography (gradient ethyl acetate/n-heptane) gave 7-methoxy-3,4-dihydroisoquinolin-1(2H)-one (380 mg, 55% of theory) in the form of a colourless solid. ¹H-NMR (400 MHz, CDCl₃

δ, ppm) 7.59 (d, 1H), 7.12 (d, 1H), 7.00 (dd, 1H), 6.30 (br. s, 1H, NH), 3.83 (s, 3H), 3.54 (m, 2H), 2.93 (m, 2H).

No. I.2-43: N-Cyclopropyl-1-oxo-1,2,3,4-tetrahydroisoquinoline-4-carboxamide

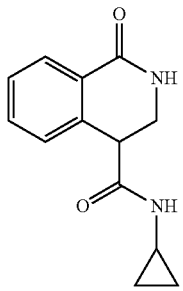 [SMILES: O=C1NCC(C(=O)NC2CC2)c2ccccc21]

2.50 g (12.30 mmol) of methyl 1-oxo-1,2-dihydroisoquinoline-4-carboxylate and 1.30 g of 10% strength palladium on carbon were suspended in an autoclave, and the mixture was hydrogenated at 70° C. and 20 bar of hydrogen for 4 h. The autoclave was vented, after which the catalyst was filtered off and the solvent was removed under reduced pressure, and the crude product was purified by chromatography (ethyl acetate: n-heptane 2:1). This gave 2.28 g (88%) of the desired methyl 1-oxo-1,2,3,4-tetrahydroisoquinoline-4-carboxylate. $^1$H-NMR (400 MHz, CDCl$_3$ δ, ppm) 8.10 (d, 1H), 7.52 (t, 1H), 7.44 (t, 1H), 7.31 (d, 1H), 6.17 (br. s, 1H), 3.98 (dt, 1H), 3.88 (m, 1H), 3.29 (dd, 1H), 3.71 (s, 3H). 2.28 g (11.11 mmol) of methyl 1-oxo-1,2,3,4-tetrahydroisoquinoline-4-carboxylate were dissolved in 20 ml of tetrahydrofuran, and 20 ml of 1 N aqueous sodium hydroxide solution were added. The solution was stirred at room temperature for 8 h, the solvent was removed under reduced pressure and the residue was dissolved in ethyl acetate and 1 N hydrochloric acid. The phases were separated, the organic phase was dried over magnesium sulphate and the solvent was removed under reduced pressure. In this manner, 2.12 g (94% of theory) of the desired 1-oxo-1,2-dihydroisoquinoline-4-carboxylic acid were obtained. $^1$H-NMR (400 MHz, d$^6$-DMSO δ, ppm) 12.65 (br. s, 1H), 7.94 (d, 1H), 7.83 (d, 1H), 7.51 (t, 1H), 7.41-7.35 (m, 2H), 3.89 (t, 1H), 3.68-3.54 (m, 2H). 0.200 g (1.046 mmol) of 1-oxo-1,2-dihydroisoquinoline-4-carboxylic acid were dissolved in 10 ml of acetonitrile, and 0.109 ml (1.569 mmol) of cyclopropylamine, 0.170 g (1.255 mmol) of 1-hydroxy-1H-benzotriazole and 0.221 g (1.151 mmol) of 1-(3-dimethylaminopropyl)-3-ethylcarbodiimide hydrochloride were added. The solution was stirred at room temperature for 8 h, diluted with ethyl acetate and the organic phase was extracted initially with saturated sodium bicarbonate solution and then with 1 N hydrochloric acid.

The phases were separated, the organic phase was dried over magnesium sulphate and the solvent was removed under reduced pressure. The crude product was purified by chromatography (ethyl acetate: n-heptane 2:1), giving 0.050 g (18% of theory) of the desired N-cyclopropyl-1-oxo-1,2,3,4-tetrahydroisoquinoline-4-carboxamide. $^1$H-NMR (400 MHz, d$^6$-DMSO δ, ppm) 8.20 (d, 1H), 7.88-7.83 (m, 2H), 7.49 (t, 1H), 7.38 (t, 1H), 7.18 (d, 1H), 3.72 (t, 1H), 3.56-3.40 (m, 2H), 2.68 (m, 1H), 0.67-0.62 (m, 2H), 0.44-0.39 (m, 2H).

No. I.2-58: 5-({4-[(Trifluoromethyl)sulphanyl]benzyl}oxy)-3,4-dihydroisoquinolin-1(2H)-one

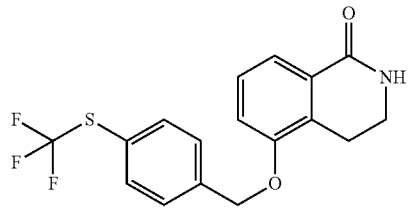 [SMILES: O=C1NCCc2c(OCc3ccc(SC(F)(F)F)cc3)cccc21]

166 mg (1.017 mmol) of 5-hydroxy-3,4-dihydroisoquinolin-1(2H)-one, 289 mg (1.068 mmol) of 1-(bromomethyl)-4-[(trifluoromethyl)sulphanyl]benzene and 365 mg (2.645 mmol) were suspended in 3 ml of ethanol and stirred under reflux for 6 h. After cooling, the insoluble constituents were filtered off and the solvent was removed under reduced pressure. The residue was dissolved in chloroform and water. The phases were separated, the organic phase was dried over sodium sulphate and the solvent was removed under reduced pressure. The crude product was purified by chromatography (ethyl acetate:n-heptane 2:1). This gave 200 mg (54% of theory) of the desired 5-({4-[(trifluoromethyl)sulphanyl]benzyl}oxy)-3,4-dihydroisoquinolin-1(2H)-one. $^1$H-NMR (400 MHz, d$^6$-DMSO δ, ppm) 7.89 (br. s, 1H), 7.52-7.44 (m, 4H), 7.28 (t, 1H), 7.22 (d, 1H), 5.16 (s, 2H), 3.33 (dt, 2H), 2.84 (t, 2H).

No. I.3-13: 6-Chloroisoquinoline-1,3(2H,4H)-dione

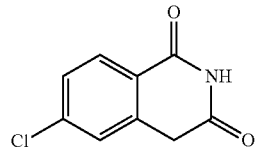 [SMILES: O=C1Cc2cc(Cl)ccc2C(=O)N1]

Under argon, a mixture of 4-chlorobenzamide (2.50 g, 16.0 mmol) and chloroacetaldehyde (5.12 ml, 64.3 mmol) in abs. toluene was stirred at a temperature of 105° C. for 4 h, and after cooling to room temperature, water was added. The precipitated crude product was filtered off, washed with diethyl ether and dried. This gave 3.58 g (96% of theory) of the desired 4-chloro-N-(2-chloroacetyl)benzamide. $^1$H-NMR (400 MHz, d$^6$-DMSO δ, ppm) 11.47 (br. s, 1H), 7.94 (d, 2H), 7.61 (d, 2H), 4.76 (s, 2H). 4-Chloro-N-(2-chloroacetyl)benzamide (3.20 g, 13.8 mml) and potassium ethyl xanthogenate (2.43 g, 15.2 mmol) were combined in abs. acetonitrile (25 ml), and the resulting reaction mixture was stirred at room temperature for 2 h. The solid formed was filtered off, washed thoroughly with water and diisopropyl ether and dried under reduced pressure, giving 3.99 g (91% of theory) of the desired S-{2-[(4-chlorobenzoyl)amino]-2-oxoethyl}O-ethyl dithiocarbonate. $^1$H-NMR (400 MHz, d$^6$-DMSO δ, ppm) 11.46 (br. s, 1H, NH), 7.95 (d, 2H), 7.62 (d, 2H), 4.61 (q, 2H), 4.51 (s, 2H), 1.34 (t, 3H). Under nitrogen, S-{2-[(4-chlorobenzoyl)amino]-2-oxoethyl}O-ethyl dithiocarbonate (1.27 g, 4.0 mmol) was dissolved in 1,2-dichlorobenzene (8 ml), and the solution was heated at 180° C. for 15 minutes. A solution of di-tert-butyl peroxide (0.74 ml, 4.0 mmol) in 1,2-dichlorobenzene (6 ml) was then slowly added dropwise, and the resulting reaction solution was stirred under reflux conditions for 6 h. After cooling to room temperature, the precipitated solid was filtered off, washed with hexane and dried thoroughly under reduced pressure. The desired 6-chloroisoquinoline-1,3(2H,4H)-dione (439 mg, 56% of theory) was obtained in the form of a slightly brownish solid. $^1$H-NMR (400 MHz, d$^6$-DMSO δ, ppm) 11.35 (br. s, 1H, NH), 8.00 (d, 1H), 7.55-7.49 (m, 2H), 4.03 (s, 2H).

No. I.4-6: 6-Chloroisoquinoline-1,3,4(2H)-trione

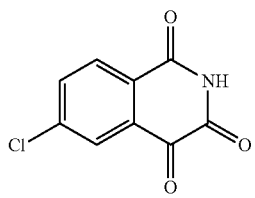 [SMILES: O=C1NC(=O)c2ccc(Cl)cc2C1=O]

Under argon, a mixture of 6-chloroisoquinoline-1,3(2H, 4H)-dione (600 mg g, 3.0 mmol) and selenium dioxide (357 mg, 3.2 mmol) in abs. 1,4-dioxane (20 ml) was stirred at a temperature of 100° C. for 3 h. After cooling to room temperature, the reaction mixture was concentrated under reduced pressure. Purification of the residue that remained by column chromatography (gradient ethyl acetate/n-heptane) gave 6-chloroisoquinoline-1,3,4(2H)-trione (169 mg, 22% of theory) in the form of a slightly yellowish solid. $^1$H-NMR (400 MHz, d$^6$-DMSO δ, ppm) 12.02 (br. s, 1H, NH), 8.12 (d, 1H), 8.01-7.95 (m, 2H).

No. I.7-1: 2-(4-Methylpiperazin-1-yl)benzo[c]-1,5-naphthyridin-6(5H)-one

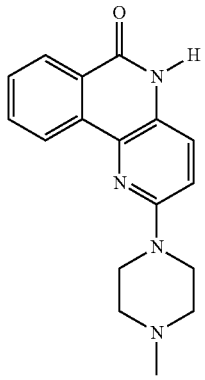 [SMILES: CN1CCN(c2ccc3[nH]c(=O)c4ccccc4c3n2)CC1]

Under argon, 2,5-dichloro-3-nitropyridine (666 mg, 3.18 mmol) was dissolved in toluene (45 ml), and aqueous potassium carbonate solution (2M, 3.47 ml) was added. After 5 minutes of stirring at room temperature, 2-diisopropylaminocarbonylphenylboronic acid (1000 mg, 3.81 mmol) and tetrakis(triphenylphosphine)palladium(0) (110 mg, 0.09 mmol) were added. The resulting reaction mixture was stirred at 80° C. for 13 h and, after cooling to room temperature, concentrated under reduced pressure. After addition of water and ethyl acetate, the aqueous phase was extracted repeatedly with ethyl acetate. The combined organic phases were dried over magnesium sulphate, filtered off and concentrated under reduced pressure. Purification by column chromatography (gradient ethyl acetate/n-heptane) of the residue that remained gave the first synthesis intermediate 2-[6-chloro-3-nitropyridin-2-yl]-N,N-diisopropylbenzamide (560 mg, 49% of theory) in the form of a colourless solid. 2-[6-Chloro-3-nitropyridin-2-yl]-N,N-diisopropylbenzamide (270 mg, 0.75 mmol) was then dissolved in abs. tetrahydrofuran, and 1-methylpiperazine (0.17 ml, 1.49 mmol) and N,N-diisopropylethylamine (0.14 ml, 0.82 mmol) were added. The resulting reaction solution was stirred at 65° C. for 5 h, ethyl acetate and water were added after cooling to room temperature and the aqueous phase was re-extracted repeatedly with ethyl acetate. The combined organic phases were dried over magnesium sulphate, filtered and concentrated under reduced pressure. Without further purification, the resulting 2-[3-(nitro)-6-(4-methylpiperazin-1-yl)pyridin-2-yl]-N,N-diisopropylbenzamide (300 mg, 94% of theory) was dissolved under argon in a high pressure reaction vessel in methanol, and palladium on carbon (Pd content 10%, water-moist, 40 mg) was added. Hydrogen was then introduced, and the mixture was stirred at room temperature and a pressure of 2 bar for two hours. The reaction mixture was then filtered off through Celite, the filter cake was washed with methanol and the filtrate was concentrated under reduced pressure. Without further purification, the resulting 2-[3-amino-6-(4-methylpiperazin-1-yl)pyridin-2-yl]-N,N-diisopropylbenzamide (220 mg, 79% of theory) was dissolved in abs. tetrahydrofuran and, after 5 min of stirring at room temperature, cooled to −65° C. Lithium diisopropylamide (179 mg, 1.67 mmol) was then slowly added a little at a time, and the resulting reaction mixture was stirred at −65° C. for 10 min and then warmed to room temperature over a period of 1 h. After careful addition of water, the aqueous phase was repeatedly extracted thoroughly with ethyl acetate. The combined organic phases were dried over magnesium sulphate, filtered off and concentrated under reduced pressure. Purification of the residue that remained by column chromatography (gradient ethyl acetate/n-heptane) gave 2-(4-methylpiperazin-1-yl)benzo[c]-1,5-naphthyridin-6(5H)-one (90 mg, 52% of theory) in the form of a colourless solid. $^1$H-NMR (400 MHz, CD$_3$OD δ, ppm) 8.78 (d, 1H), 8.39 (s, 1H), 7.89 (dd, 1H), 7.71 (dd, 1H), 7.60 (d, 1H), 7.10 (d, 1H), 3.72 (m, 4H), 3.32 (s, 3H), 2.65 (m, 4H); $^{13}$C-NMR (100 MHz, CD$_3$OD δ, ppm) 163.3, 156.9, 137.2, 134.9, 133.9, 129.9, 128.3, 128.0, 127.4, 125.9, 124.9, 111.5, 55.8, 46.4, 46.2.

No. I.7-10: 2-Ethoxyphenanthridin-6(5H)-one

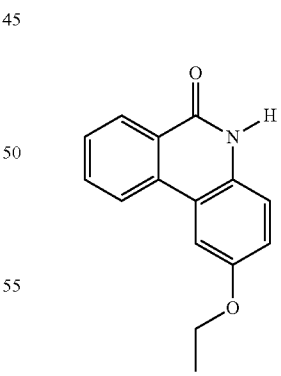

Under argon, 5-ethoxy-2-fluorophenylboronic acid (300 mg, 1.63 mmol), potassium phosphate (433 mg, 2.04 mmol) and tetrakis(triphenylphosphine)palladium(0) (57 mg, 0.05 mmol) were dissolved in abs. N,N-dimethylformamide (8 ml), and the mixture was stirred at room temperature for 5 minutes. 2-Chlorobenzonitrile (112 mg, 0.82 mmol) was then added, and the reaction mixture was stirred at 160° C. for 4 h. After cooling to room temperature, water (>100 ml) was added and the aqueous phase was repeatedly extracted thoroughly with ethyl acetate. The combined organic phases were dried over magnesium sulphate, filtered off and concentrated under reduced pressure. Purification of the residue that remained by column chromatography (gradient ethyl acetate/n-heptane) gave 5'-ethoxy-2'-fluorobiphenyl-2-carbonitrile (150 mg, 76% of theory) in the form of a colourless solid. 5'-Ethoxy-2'-fluorobiphenyl-2-carbonitrile (150 mg, 0.62 mmol) was then dissolved in methanol (5 ml), finely powdered potassium hydroxide (174 mg, 3.10 mmol) was added and the mixture was stirred under reflux conditions for 2 h. After cooling to room temperature, the reaction mixture was concentrated under reduced pressure, water was added and the resulting precipitated solid was filtered off and dried. This gave 2-ethoxyphenanthridin-6(5H)-one (72 mg, 46% of theory) as a colourless solid. $^1$H-NMR (400 MHz, $d_6$-DMSO δ, ppm) 11.58 (br. s, 1H, NH), 8.56 (d, 1H), 8.32 (d, 1H), 7.86 (d, 1H), 7.82 (dd, 1H), 7.64 (dd, 1H), 7.29 (d, 1H), 7.13 (dd, 1H), 4.17 (q, 2H), 1.39 (t, 3H).

No. I.8-9: 2,4-Diethyl-10-methoxy-6,7-dihydro-8H-furo[2',3':3,4]cyclohepta[1,2-c]isoquinolin-8-one

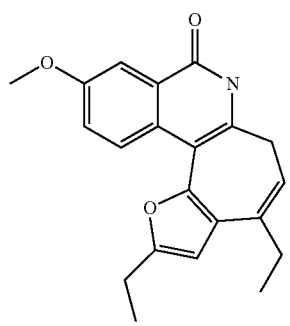 [SMILES: CCC1=CCc2[nH]c(=O)c3cc(OC)ccc3c2-c2oc(CC)cc21]

Under argon, 2-formyl-5-methoxybenzoic acid (10 mmol) and 2-ethylfuran (40 mmol) were dissolved in abs. dioxane (20 ml), and after 10 minutes of stirring at room temperature, conc. perchloric acid (0.3 ml) was added. The resulting reaction mixture was subsequently stirred at 60° C. for 1 h, then poured into water and stirred. Filtration and drying of the resulting precipitate gave 2-[bis(5-ethyl-2-furyl)methyl]-5-methoxybenzoic acid in the form of a colourless solid (60% of theory). 2-[Bis(5-ethyl-2-furyl)methyl]-5-methoxybenzoic acid (10 mmol), dicyclohexylcarbodiimide (2.27 g, 11 mmol) were dissolved in abs. dichloromethane (90 ml) and stirred at room temperature for 10 min. Aqueous ammonia (4 ml) was then added, and the resulting reaction mixture was then stirred at room temperature for 1 h. Filtration, concentration under reduced pressure and subsequent purification by column chromatography (gradient ethyl acetate/n-heptane) of the residue that remained gave 2-[bis(5-ethyl-2-fury))methyl]-5-methoxybenzamide (982 mg, 28% of theory) in the form of a colourless solid. Under argon, abs. 1,2-dichloroethane (10 ml) was added to 2-[bis(5-ethyl-2-furyl)methyl]-5-methoxybenzamide (706 mg, 2 mmol) and p-toluenesulphonic acid bound to macroporous polystyrene resin (2 mmol). The resulting reaction mixture was stirred at a temperature of 100° C. for 1 h, after cooling to room temperature filtered off through Celite and concentrated under reduced pressure. Purification of the residue that remained by column chromatography (gradient ethyl acetate/n-heptane) gave 2,4-diethyl-10-methoxy-6,7-dihydro-8H-furo[2',3':3,4]cyclohepta[1,2-c]isoquinolin-8-one (51 mg, 8% of theory) in the form of a colourless solid. $^1$H-NMR (400 MHz, $d_6$-DMSO δ, ppm) 11.66 (br. s, 1H, NH), 8.31 (d, 1H), 7.68 (d, 1H), 7.38 (dd, 1H), 6.47 (s, 1H), 5.35 (t, 1H), 3.87 (s, 3H), 2.79 (q, 2H), 2.68 (m, 2H), 2.33 (q, 2H), 1.30 (t, 3H), 0.96 (t, 3H).

No. I.9-1: 10-Chloro-1,3-dimethoxypyrido[2',1':2,3]imidazo[4,5-c]isoquinolin-5(6H)-one

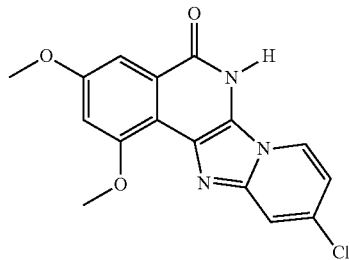 [SMILES: COc1cc(OC)c2c(c1)c(=O)[nH]c1c2nc2cc(Cl)ccn21]

Under argon, methyl 2-formyl-3,5-dimethoxybenzoate (200 mg, 0.89 mmol) and 2-amino-4-chloropyridine (115 mg, 0.89 mmol) were dissolved in methanol (5 ml), after 5 minutes of stirring at room temperature tert-butylisonitrile (89 mg, 1.07 mmol) was added and after a further 10 minutes of stirring at room temperature 4-toluenesulphonic acid monohydrate (8 mg, 0.05 mmol) was added. The resulting reaction mixture was then stirred at room temperature for 6 h and subsequently concentrated under reduced pressure and taken up in 4 ml of trifluoroacetic acid. The mixture obtained in this manner was stirred at 50° C. for 3 h and then concentrated again, ethanol and water were added to the resulting residue and the pH was then adjusted to 8 using saturated sodium bicarbonate solution. Drying and removal of the resulting precipitate by filtration gave 10-chloro-1,3-dimethoxypyrido[2',1':2,3]imidazo[4,5-c]isoquinolin-5(6H)-one in the form of a light-yellow solid (70 mg, 22% of theory). $^1$H-NMR (400 MHz, $d_6$-DMSO δ, ppm) 13.20 (br. s, 1H, NH), 8.83 (d, 1H), 8.02 (s, 1H), 7.49 (m, 1H), 7.39 (d, 1H), 7.15 (s, 1H), 4.10 (s, 3H), 3.96 (s, 3H).

Analogously to the preparation examples given above, and taking into account the general information regarding the preparation of substituted vinyl- and alkynylcyclohexenols and their analogs of the general formula (I), the following compounds are obtained:

Table 1—with base structure I.1 and the radical definitions specified below:

(I.1)

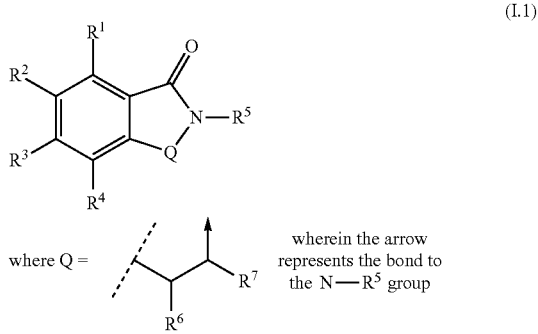

and where the definition in table form below of the radical "Q" corresponds to the definition of the radicals "Q-1.1" to "Q-1.98" mentioned above as being very particularly preferred

| No. | R¹ | R² | R³ | R⁴ | R⁵ | Q |
| --- | --- | --- | --- | --- | --- | --- |
| I.1-1 | H | H | H | H | H | Q-1.1 |
| I.1-2 | CH₃ | H | H | CH₃ | H | Q-1.1 |
| I.1-3 | CH₃ | H | H | H | H | Q-1.1 |
| I.1-4 | H | CH₃ | H | H | H | Q-1.1 |
| I.1-5 | H | H | CH₃ | H | H | Q-1.1 |
| I.1-6 | H | H | H | CH₃ | H | Q-1.1 |
| I.1-7 | H | CH₃ | CH₃ | H | H | Q-1.1 |
| I.1-8 | OCH₃ | H | H | OCH₃ | H | Q-1.1 |
| I.1-9 | OCH₃ | H | H | H | H | Q-1.1 |
| I.1-10 | H | OCH₃ | H | H | H | Q-1.1 |
| I.1-11 | H | H | OCH₃ | H | H | Q-1.1 |
| I.1-12 | H | H | H | OCH₃ | H | Q-1.1 |
| I.1-13 | H | OCH₃ | OCH₃ | H | H | Q-1.1 |
| I.1-14 | NO₂ | H | H | NO₂ | H | Q-1.1 |
| I.1-15 | NO₂ | H | H | H | H | Q-1.1 |
| I.1-16 | H | NO₂ | H | H | H | Q-1.1 |
| I.1-17 | H | H | NO₂ | H | H | Q-1.1 |
| I.1-18 | H | H | H | NO₂ | H | Q-1.1 |
| I.1-19 | H | NO₂ | NO₂ | H | H | Q-1.1 |
| I.1-20 | CF₃ | CF₃ | H | H | H | Q-1.1 |
| I.1-21 | CF₃ | H | H | H | H | Q-1.1 |
| I.1-22 | H | CF₃ | H | H | H | Q-1.1 |
| I.1-23 | H | H | CF₃ | H | H | Q-1.1 |
| I.1-24 | H | H | H | CF₃ | H | Q-1.1 |
| I.1-25 | H | CF₃ | CF₃ | H | H | Q-1.1 |
| I.1-26 | OCF₃ | OCF₃ | H | H | H | Q-1.1 |
| I.1-27 | OCF₃ | H | H | H | H | Q-1.1 |
| I.1-28 | H | OCF₃ | H | H | H | Q-1.1 |
| I.1-29 | H | H | OCF₃ | H | H | Q-1.1 |
| I.1-30 | H | H | H | OCF₃ | H | Q-1.1 |
| I.1-31 | H | OCF₃ | OCF₃ | H | H | Q-1.1 |
| I.1-32 | F | H | H | F | H | Q-1.1 |
| I.1-33 | F | H | H | H | H | Q-1.1 |
| I.1-34 | H | F | H | H | H | Q-1.1 |
| I.1-35 | H | H | F | H | H | Q-1.1 |
| I.1-36 | H | H | H | F | H | Q-1.1 |
| I.1-37 | H | F | F | H | H | Q-1.1 |
| I.1-38 | F | F | H | H | H | Q-1.1 |
| I.1-39 | Cl | H | H | Cl | H | Q-1.1 |
| I.1-40 | Cl | H | H | H | H | Q-1.1 |
| I.1-41 | H | Cl | H | H | H | Q-1.1 |
| I.1-42 | H | H | Cl | H | H | Q-1.1 |
| I.1-43 | H | H | H | Cl | H | Q-1.1 |
| I.1-44 | H | Cl | Cl | H | H | Q-1.1 |
| I.1-45 | Cl | Cl | H | H | H | Q-1.1 |
| I.1-46 | Br | H | H | Br | H | Q-1.1 |
| I.1-47 | Br | H | H | H | H | Q-1.1 |
| I.1-48 | H | Br | H | H | H | Q-1.1 |
| I.1-49 | H | H | Br | H | H | Q-1.1 |
| I.1-50 | H | H | H | Br | H | Q-1.1 |
| I.1-51 | H | Br | Br | H | H | Q-1.1 |
| I.1-52 | Br | Br | H | H | H | Q-1.1 |
| I.1-53 | I | H | H | H | H | Q-1.1 |
| I.1-54 | H | I | H | H | H | Q-1.1 |
| I.1-55 | H | H | I | H | H | Q-1.1 |
| I.1-56 | H | H | H | I | H | Q-1.1 |
| I.1-57 | H | OCF₃ | H | OCF₃ | H | Q-1.1 |
| I.1-58 | H | OCH₃ | H | OCH₃ | H | Q-1.1 |
| I.1-59 | H | CF₃ | H | CF₃ | H | Q-1.1 |
| I.1-60 | H | CH₃ | H | CH₃ | H | Q-1.1 |
| I.1-61 | H | NO₂ | H | NO₂ | H | Q-1.1 |
| I.1-62 | H | F | H | F | H | Q-1.1 |
| I.1-63 | H | Cl | H | Cl | H | Q-1.1 |
| I.1-64 | H | Br | H | Br | H | Q-1.1 |
| I.1-65 | H | I | H | I | H | Q-1.1 |
| I.1-66 | SCF₃ | H | H | H | H | Q-1.1 |
| I.1-67 | H | SCF₃ | H | H | H | Q-1.1 |
| I.1-68 | H | H | SCF₃ | H | H | Q-1.1 |
| I.1-69 | H | H | H | SCF₃ | H | Q-1.1 |
| I.1-70 | SCH₃ | H | H | H | H | Q-1.1 |
| I.1-71 | H | SCH₃ | H | H | H | Q-1.1 |
| I.1-72 | H | H | SCH₃ | H | H | Q-1.1 |
| I.1-73 | H | H | H | SCH₃ | H | Q-1.1 |
| I.1-74 | H | H | H | H | CH₃ | Q-1.1 |
| I.1-75 | H | H | H | H | CH₂CH₃ | Q-1.1 |
| I.1-76 | H | H | H | H | CH(CH₃)₂ | Q-1.1 |
| I.1-77 | H | H | H | H | CH₂CH₂CH₃ | Q-1.1 |
| I.1-78 | H | Cl | H | H | CH₃ | Q-1.1 |
| I.1-79 | H | Cl | H | H | CH₂CH₃ | Q-1.1 |

-continued

| No. | R¹ | R² | R³ | R⁴ | R⁵ | Q |
|---|---|---|---|---|---|---|
| I.1-80 | H | Cl | H | H | CH(CH₃)₂ | Q-1.1 |
| I.1-81 | H | Cl | H | H | CH₂CH₂CH₃ | Q-1.1 |
| I.1-82 | H | F | H | H | CH₃ | Q-1.1 |
| I.1-83 | H | F | H | H | CH₂CH₃ | Q-1.1 |
| I.1-84 | H | F | H | H | CH(CH₃)₂ | Q-1.1 |
| I.1-85 | H | F | H | H | CH₂CH₂CH₃ | Q-1.1 |
| I.1-86 | H | OCH₃ | H | H | CH₃ | Q-1.1 |
| I.1-87 | H | OCH₃ | H | H | CH₂CH₃ | Q-1.1 |
| I.1-88 | H | OCH₃ | H | H | CH(CH₃)₂ | Q-1.1 |
| I.1-89 | H | OCH₃ | H | H | CH₂CH₂CH₃ | Q-1.1 |
| I.1-90 | H | CH₃ | H | H | CH₃ | Q-1.1 |
| I.1-91 | H | CH₃ | H | H | CH₂CH₃ | Q-1.1 |
| I.1-92 | H | CH₃ | H | H | CH(CH₃)₂ | Q-1.1 |
| I.1-93 | H | CH₃ | H | H | CH₂CH₂CH₃ | Q-1.1 |
| I.1-94 | H | H | CH₃ | H | CH₃ | Q-1.1 |
| I.1-95 | H | H | CH₃ | H | CH₂CH₃ | Q-1.1 |
| I.1-96 | H | H | CH₃ | H | CH(CH₃)₂ | Q-1.1 |
| I.1-97 | H | H | CH₃ | H | CH₂CH₂CH₃ | Q-1.1 |
| I.1-98 | H | H | Cl | H | CH₃ | Q-1.1 |
| I.1-99 | H | H | Cl | H | CH₂CH₃ | Q-1.1 |
| I.1-100 | H | CONH₂ | H | H | H | Q-1.19 |
| I.1-101 | H | H | H | H | H | Q-1.20 |
| I.1-102 | H | H | H | H | H | Q-1.21 |
| I.1-103 | CH₃ | H | H | CH₃ | H | Q-1.22 |
| I.1-104 | H | H | H | H | H | Q-1.2 |
| I.1-105 | H | H | H | H | H | Q-1.24 |
| I.1-106 | H | H | H | H | H | Q-1.27 |
| I.1-107 | H | H | H | H | H | Q-1.3 |
| I.1-108 | H | H | H | H | CH₃ | Q-1.3 |
| I.1-109 | H | H | H | H | H | Q-1.26 |
| I.1-110 | H | H | H | H | H | Q-1.28 |
| I.1-111 | H | H | H | H | H | Q-1.29 |
| I.1-112 | H | Cl | H | H | H | Q-1.31 |
| I.1-113 | H | H | H | H | H | Q-1.32 |
| I.1-114 | H | NO₂ | H | H | H | Q-1.33 |
| I.1-115 | H | H | H | H | H | Q-1.4 |
| I.1-116 | H | H | H | H | H | Q-1.5 |
| I.1-117 | H | Br | H | H | H | Q-1.2 |
| I.1-118 | H | H | H | H | CH₃ | Q-1.6 |
| I.1-119 | H | H | H | H | 3-pyridyl-CH₂– | Q-1.7 |
| I.1-120 | H | H | H | H | 2-pyridyl-CH₂– | Q-1.7 |
| I.1-121 | H | H | H | H | 3-pyridyl-CH₂– | Q-1.8 |
| I.1-122 | H | H | H | H | [3-chloro-5-(trifluoromethyl)pyridin-2-yl]-N(CH₃)– | Q-1.9 |
| I.1-123 | H | H | H | H | CH₃ | Q-1.10 |
| I.1-124 | H | H | H | H | CH₃ | Q-1.11 |
| I.1-125 | H | H | H | H | CH₃ | Q-1.12 |
| I.1-126 | H | H | H | H | H | Q-1.13 |
| I.1-127 | H | H | H | H | CH₃ | Q-1.2 |
| I.1-128 | H | H | H | H | CH₃ | Q-1.14 |
| I.1-129 | H | CH₃ | H | H | CH₃ | Q-1.14 |
| I.1-130 | H | Cl | Cl | H | CH₃ | Q-1.14 |
| I.1-131 | H | H | H | H | H | Q-1.15 |
| I.1-132 | H | H | H | H | H | Q-1.16 |

-continued

| No. | R¹ | R² | R³ | R⁴ | R⁵ | Q |
|---|---|---|---|---|---|---|
| I.1-133 | H | H | H | H | CH₃ | Q-1.15 |
| I.1-134 | H | H | H | H | H | Q-1.14 |
| I.1-135 | H | CH₃ | H | H | H | Q-1.2 |
| I.1-136 | H | CH₃ | H | H | H | Q-1.3 |
| I.1-137 | H | CH₃ | H | H | H | Q-1.16 |
| I.1-138 | H | CH₃ | H | H | H | Q-1.15 |
| I.1-139 | H | CH₃ | H | H | H | Q-1.14 |
| I.1-140 | H | Cl | Cl | H | H | Q-1.14 |
| I.1-141 | H | Cl | H | H | H | Q-1.16 |
| I.1-142 | H | Cl | H | H | H | Q-1.3 |
| I.1-143 | H | Cl | H | H | H | Q-1.14 |
| I.1-144 | H | H | H | H | H | Q-1.17 |
| I.1-145 | H | Cl | H | H | H | Q-1.2 |
| I.1-146 | H | Cl | Cl | H | H | Q-1.2 |
| I.1-147 | H | Cl | H | H | H | Q-1.18 |
| I.1-148 | H | Cl | Cl | H | H | Q-1.15 |
| I.1-149 | H | CH₃ | H | H | H | Q-1.18 |
| I.1-150 | H | CH₃ | H | H | CH₃ | Q-1.18 |
| I.1-151 | H | Cl | Cl | H | H | Q-1.18 |
| I.1-152 | H | H | H | H | H | Q-1.18 |
| I.1-153 | H | H | H | H | CH₃ | Q-1.18 |
| I.1-154 | H | Cl | H | H | CH₃ | Q-1.18 |
| I.1-155 | H | Cl | H | H | CH₃ | Q-1.14 |
| I.1-156 | H | H | H | H | CH₃ | Q-1.17 |
| I.1-157 | H | CH₃ | H | H | CH₃ | Q-1.2 |
| I.1-158 | H | CH₃ | H | H | CH₃ | Q-1.15 |
| I.1-159 | H | Cl | H | H | H | Q-1.15 |
| I.1-160 | H | Cl | H | H | H | Q-1.17 |
| I.1-161 | H | Cl | H | H | CH₃ | Q-1.17 |
| I.1-162 | H | Cl | Cl | H | CH₃ | Q-1.4 |
| I.1-163 | H | Cl | Cl | H | H | Q-1.4 |
| I.1-164 | H | Cl | Cl | H | CH₃ | Q-1.18 |
| I.1-165 | H | H | H | 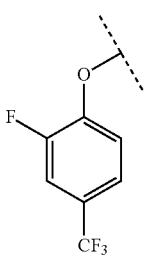 | H | Q-1.1 |
| I.1-166 | H | H | H | H | H | Q-1.97 |
| I.1-167 | H | H | H | H | H | Q-1.23 |
| I.1-168 | H | 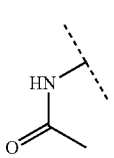 | H | H | H | Q-1.1 |
| I.1-169 | H | NO₂ | H | H | H | Q-1.23 |
| I.1-170 | H | H | H | H | H | Q-1.98 |
| I.1-171 | H | NO₂ | H | H | H | Q-1.25 |
| I.1-172 | H | H | H | H | H | Q-1.30 |
| I.1-173 | H | OCH₃ | OCH₃ | H | H | Q-1.34 |
| I.1-174 | H | H | H | CH₃ | H | Q-1.43 |
| I.1-175 | H | H | H | H | H | Q-1.9 |
| I.1-176 | H | 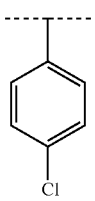 | H | H | H | Q-1.1 |

-continued

| No. | R¹ | R² | R³ | R⁴ | R⁵ | Q |
|---|---|---|---|---|---|---|
| I.1-177 | H | phenyl | H | H | H | Q-1.1 |
| I.1-178 | H | H | H | Br | H | Q-1.1 |
| I.1-179 | H | 4-OCF₃-phenyl | H | H | H | Q-1.1 |
| I.1-180 | H | pyridin-4-yl | H | H | H | Q-1.1 |
| I.1-181 | H | pyridin-3-yl | H | H | H | Q-1.1 |
| I.1-182 | H | 4-OMe-phenyl | H | H | H | Q-1.1 |
| I.1-183 | H | 3-Cl-phenyl | H | H | H | Q-1.1 |
| I.1-184 | H | 2,4-diCl-phenyl | H | H | H | Q-1.1 |
| I.1-185 | H | H | H | phenyl | H | Q-1.1 |
| I.1-186 | H | H | H | pyridin-4-yl | H | Q-1.1 |

-continued
| No. | R¹ | R² | R³ | R⁴ | R⁵ | Q |
|---|---|---|---|---|---|---|
| I.1-187 | H | H | H | 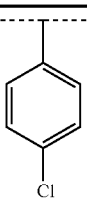 | H | Q-1.1 |
| I.1-188 | H | H | H | 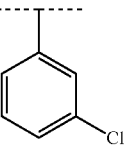 | H | Q-1.1 |
| I.1-189 | H | H | H | 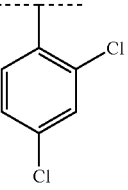 | H | Q-1.1 |
| I.1-190 | H | H | H | 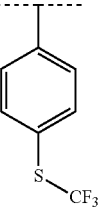 | H | Q-1.1 |
| I.1-191 | H | H | H | H | H | Q-1.45 |
| I.1-192 | H | H | H | H | H | Q-1.49 |
| I.1-193 | H | H | H | H | H | Q-1.55 |
| I.1-194 | H | H | H | H | H | Q-1.57 |
| I.1-195 | H | H | H | H | H | Q-1.58 |
| I.1-196 | H | H | H | H | H | Q-1.56 |
| I.1-197 | H | H | H | H | H | Q-1.50 |
| I.1-198 | H | H | H | H | H | Q-1.59 |
| I.1-199 | H | H | H | H | H | Q-1.60 |
| I.1-200 | H | H | H | H | H | Q-1.61 |
| I.1-201 | H | H | H | H | H | Q-1.62 |
| I.1-202 | H | H | H | H | H | Q-1.46 |
| I.1-203 | H | H | H | H | H | Q-1.48 |
| I.1-204 | H | H | H | H | H | Q-1.47 |
| I.1-205 | H | H | H | H | H | Q-1.63 |
| I.1-206 | H | H | H | H | H | Q-1.64 |
| I.1-207 | H | H | H | H | H | Q-1.65 |
| I.1-208 | H | H | H | H | H | Q-1.66 |
| I.1-209 | H | H | H | H | H | Q-1.67 |
| I.1-210 | H | H | H | H | H | Q-1.69 |
| I.1-211 | H | H | H | H | H | Q-1.54 |
| I.1-212 | H | H | H | H | H | Q-1.68 |
| I.1-213 | H | H | H | H | H | Q-1.70 |
| I.1-214 | H | H | H | H | H | Q-1.71 |
| I.1-215 | H | H | H | H | H | Q-1.72 |
| I.1-216 | H | H | H | H | H | Q-1.73 |
| I.1-217 | H | H | H | H | H | Q-1.52 |
| I.1-218 | H | 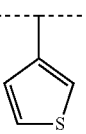 | H | H | H | Q-1.1 |
| I.1-219 | H | H | H | H | H | Q-1.74 |
| I.1-220 | H | H | H | H | H | Q-1.75 |
| I.1-221 | H | H | H | H | H | Q-1.76 |
| I.1-222 | H | H | H | H | H | Q-1.53 |
| I.1-223 | H | H | H | H | H | Q-1.77 |

-continued
| No. | R¹ | R² | R³ | R⁴ | R⁵ | Q |
|---|---|---|---|---|---|---|
| I.1-224 | H | H | H | H | H | Q-1.78 |
| I.1-225 | H | 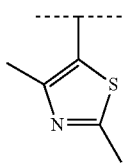 | H | H | H | Q-1.1 |
| I.1-226 | H | H | H | H | H | Q-1.79 |
| I.1-227 | H | H | H | H | H | Q-1.80 |
| I.1-228 | H | 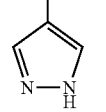 | H | H | H | Q-1.1 |
| I.1-229 | H | H | H | H | H | Q-1.81 |
| I.1-230 | H | 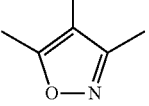 | H | H | H | Q-1.1 |
| I.1-231 | H | H | H | H | H | Q-1.82 |
| I.1-232 | H | H | H | H | H | Q-1.83 |
| I.1-233 | H | H | H | H | H | Q-1.84 |
| I.1-234 | H | H | H | I | H | Q-1.1 |
| I.1-235 | H | H | H | H | H | Q-1.85 |
| I.1-236 | H | H | H | H | H | Q-1.86 |
| I.1-237 | H | H | H | H | H | Q-1.89 |
| I.1-238 | H | H | H | H | H | Q-1.90 |
| I.1-239 | H | H | H | H | H | Q-1.91 |
| I.1-240 | H | H | H | H | H | Q-1.92 |
| I.1-241 | H | H | H | H | H | Q-1.93 |
| I.1-242 | H | H | H | H | H | Q-1.94 |
| I.1-243 | H | H | H | 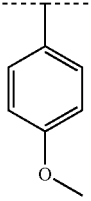 | H | Q-2.1 |
| I.1-244 | H | H | H | 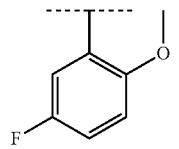 | H | Q-2.1 |
| I.1-245 | H | H | H | 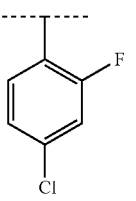 | H | Q-2.1 |

-continued
| No. | R¹ | R² | R³ | R⁴ | R⁵ | Q |
|---|---|---|---|---|---|---|
| I.1-246 | H | H | H |  | H | Q-2.1 |
| I.1-247 | H | H | H | 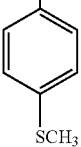 | H | Q-2.1 |
| I.1-248 | H | H | H | 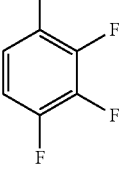 | H | Q-2.1 |
| I.1-249 | H | H | H | 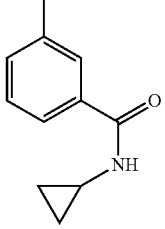 | H | Q-2.1 |
| I.1-250 | H | H | H | 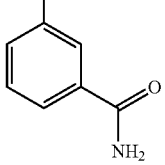 | H | Q-2.1 |
| I.1-251 | H | H | H | 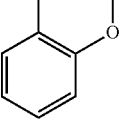 | H | Q-2.1 |
| I.1-252 | H | 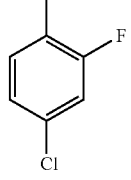 | H | H | H | Q-2.1 |

-continued

| No. | R¹ | R² | R³ | R⁴ | R⁵ | Q |
|---|---|---|---|---|---|---|
| I.1-253 | H | 3-(cyclopropylcarbamoyl)phenyl | H | H | H | Q-2.1 |
| I.1-254 | H | 3-carbamoylphenyl | H | H | H | Q-2.1 |
| I.1-255 | H | 2-methoxyphenyl | H | H | H | Q-2.1 |
| I.1-256 | H | H | H | 3,3,3-trifluoro-2-hydroxy-2-(trifluoromethyl)prop-1-ynyl | H | Q-2.1 |
| I.1-257 | H | 2-chlorophenyl | H | H | H | Q-1.1 |
| I.1-258 | H | H | H | 2-chlorophenyl | H | Q-1.1 |
| I.1-259 | H | 2-fluorophenyl | H | H | H | Q-1.1 |
| I.1-260 | H | H | H | 2-fluorophenyl | H | Q-1.1 |
| I.1-261 | H | 2-bromophenyl | H | H | H | Q-1.1 |

-continued
| No. | R¹ | R² | R³ | R⁴ | R⁵ | Q |
|---|---|---|---|---|---|---|
| I.1-262 | H | H | H | 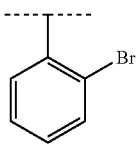 | H | Q-1.1 |
| I.1-263 | H | 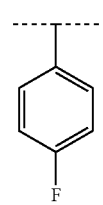 | H | H | H | Q-1.1 |
| I.1-264 | H | H | H | 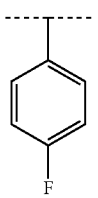 | H | Q-1.1 |
| I.1-265 | H | 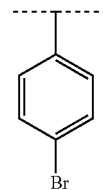 | H | H | H | Q-1.1 |
| I.1-266 | H | H | H | 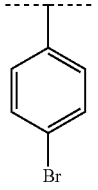 | H | Q-1.1 |
| I.1-267 | H | H | H | 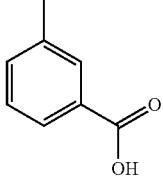 | H | Q-2.1 |
| I.1-268 | H | H | H | 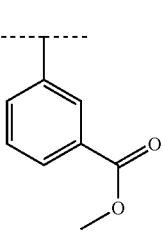 | H | Q-2.1 |

-continued
| No. | R¹ | R² | R³ | R⁴ | R⁵ | Q |
|---|---|---|---|---|---|---|
| I.1-269 | H | H | H | 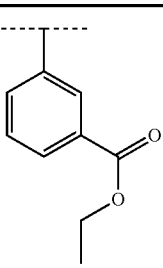 | H | Q-2.1 |
| I.1-270 | H | H | H | 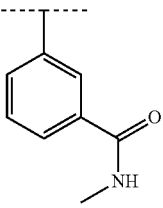 | H | Q-2.1 |
| I.1-271 | H | H | H | 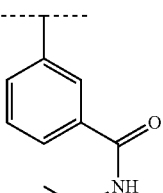 | H | Q-2.1 |
| I.1-272 | H | H | H | 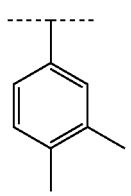 | H | Q-2.1 |
| I.1-273 | H | H | H | 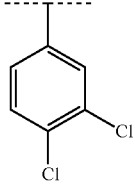 | H | Q-2.1 |
| I.1-274 | H | H | H | 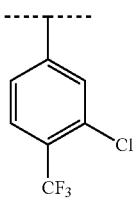 | H | Q-2.1 |
| I.1-275 | H | H | H | 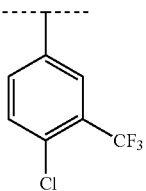 | H | Q-2.1 |

-continued

| No. | R¹ | R² | R³ | R⁴ | R⁵ | Q |
|---|---|---|---|---|---|---|
| I.1-276 | H | H | H | 4-methylphenyl | H | Q-2.1 |
| I.1-277 | H | H | H | 3-methylphenyl | H | Q-2.1 |
| I.1-278 | H | H | H | 3-(trifluoromethyl)phenyl | H | Q-2.1 |
| I.1-279 | H | H | H | 3-methoxyphenyl | H | Q-2.1 |
| I.1-280 | H | H | H | 3-(trifluoromethoxy)phenyl | H | Q-2.1 |
| I.1-281 | H | H | H | 4-(trifluoromethyl)phenyl | H | Q-2.1 |
| I.1-282 | H | H | H | 4-iodophenyl | H | Q-2.1 |
| I.1-283 | H | H | H | 3,3,3-trifluoro-2-(trifluoromethyl)-2-fluoroprop-1-ynyl | H | Q-2.1 |

-continued

| No. | R¹ | R² | R³ | R⁴ | R⁵ | Q |
|---|---|---|---|---|---|---|
| I.1-284 | H | H | H | ethynyl-trimethylsilyl | H | Q-2.1 |
| I.1-285 | H | H | H | thiophen-3-yl | H | Q-1.1 |
| I.1-286 | H | H | H | thiophen-2-yl | H | Q-1.1 |
| I.1-287 | H | H | H | furan-2-yl | H | Q-1.1 |
| I.1-288 | H | H | H | 2,4-dimethylthiazol-5-yl | H | Q-1.1 |
| I.1-289 | H | H | H | 1H-pyrazol-4-yl | H | Q-1.1 |
| I.1-290 | H | H | H | 3,5-dimethylisoxazol-4-yl | H | Q-1.1 |

Table 2—with base structure I.2 and the radical definitions specified below:

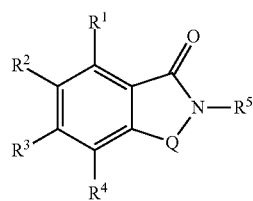
(I.2)

where Q =

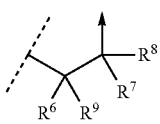

wherein the arrow represents the bond to the N—R⁵ group and where the definition in table form below of the radical "Q" corresponds to the definition of the radicals "Q-2.1" to "Q-2.44" mentioned above as being very particularly preferred

| No. | R¹ | R² | R³ | R⁴ | R⁵ | Q |
|---|---|---|---|---|---|---|
| 1.2-1 | H | H | H | H | H | Q-2.2 |
| 1.2-2 | H | H | OCH₃ | H | H | Q-2.1 |
| 1.2-3 | H | H | H | H | H | Q-2.4 |
| 1.2-4 | H | H | H | H | H | Q-2.1 |
| 1.2-5 | H | OCH₃ | OCH₃ | H | H | Q-2.1 |
| 1.2-6 | H | H | H | H | H | Q-2.5 |
| 1.2-7 | H | CH₃ | CH₃ | H | H | Q-2.2 |
| 1.2-8 | H | H | H | H | H | Q-2.7 |
| 1.2-9 | H | H | H | H | H | Q-2.10 |
| 1.2-10 | H | H | H | H | H | Q-2.11 |
| 1.2-11 | H | H | H | H | H | Q-2.12 |
| 1.2-12 | CH₃ | H | CH₃ | H | H | Q-2.1 |
| 1.2-13 | H | Cl | H | H | H | Q-2.1 |
| 1.2-14 | H | H | F | H | H | Q-2.1 |
| 1.2-15 | H | H | Cl | H | H | Q-2.1 |
| 1.2-16 | H | H | H | H | H | Q-2.43 |
| 1.2-17 | H | H | H | H | H | Q-2.3 |
| 1.2-18 | OCH₃ | H | H | H | H | Q-2.1 |
| 1.2-19 | H | H | H | OCH₃ | H | Q-2.1 |
| 1.2-20 | H | H | H | CH₃ | H | Q-2.1 |
| 1.2-21 | H | CH₃ | H | H | H | Q-2.1 |
| 1.2-22 | H | Br | H | H | H | Q-2.1 |
| 1.2-23 | Cl | H | H | H | H | Q-2.1 |
| 1.2-24 | H | H | CH₃ | H | H | Q-2.1 |
| 1.2-25 | H | 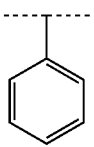 | H | H | H | Q-2.1 |
| 1.2-26 | H | CH₃ | H | CH₃ | H | Q-2.1 |
| 1.2-27 | H | Et | H | H | H | Q-2.1 |
| 1.2-28 | H | F | H | H | H | Q-2.1 |
| 1.2-29 | H | t-Bu | H | H | H | Q-2.1 |
| 1.2-30 | CH₃ | H | H | H | H | Q-2.1 |
| 1.2-31 | H | OCH₃ | H | H | H | Q-2.1 |
| 1.2-32 | H | t-Bu | H | H | H | Q-2.10 |
| 1.2-33 | H | Cl | H | Cl | H | Q-2.1 |
| 1.2-34 | H | H | H | CH₃ | H | Q-2.13 |
| 1.2-35 | H | H | Br | H | H | Q-2.1 |
| 1.2-36 | H | H | H | CH₃ | H | Q-2.10 |
| 1.2-37 | H | H | H | CH₃ | H | Q-2.13 |
| 1.2-38 | H |  | H | H | H | Q-2.1 |
| 1.2-39 | H | H | H | H | H | Q-2.16 |
| 1.2-40 | H | H | H | H | H | Q-2.18 |
| 1.2-41 | H | H | H | H | H | Q-2.17 |
| 1.2-42 | H | H | H | H | H | Q-2.19 |
| 1.2-43 | H | H | H | H | H | Q-2.20 |
| 1.2-44 | H | H | H | H | H | Q-2.21 |
| 1.2-45 | H | H | H | H | H | Q-2.22 |
| 1.2-46 | H | H | H | H | H | Q-2.23 |
| 1.2-47 | H | H | H | H | 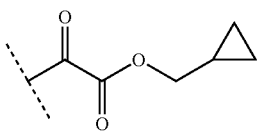 | Q-2.23 |
| 1.2-48 | H | H | H | H | H | Q-2.24 |
| 1.2-49 | H | H | H | 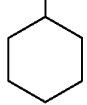 | H | Q-2.1 |

-continued
| No. | R¹ | R² | R³ | R⁴ | R⁵ | Q |
|---|---|---|---|---|---|---|
| 1.2-50 | H | H | H | 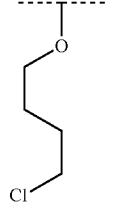 | H | Q-2.1 |
| 1.2-51 | H | H | H | OH | H | Q-2.1 |
| 1.2-52 | H | H | H | SCH₃ | H | Q-2.1 |
| 1.2-53 | H | H | H |  | H | Q-2.1 |
| 1.2-54 | H | H | H |  | H | Q-2.1 |
| 1.2-55 | H | H | H | 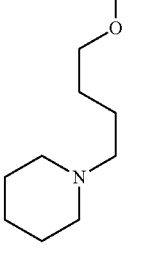 | H | Q-2.1 |
| 1.2-56 | H | H | H | 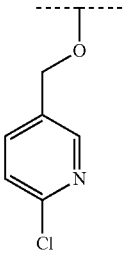 | H | Q-2.1 |
| 1.2-57 | H | H | H | 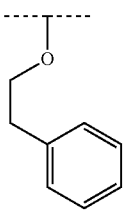 | H | Q-2.1 |

-continued
| No. | R¹ | R² | R³ | R⁴ | R⁵ | Q |
|---|---|---|---|---|---|---|
| 1.2-58 | H | H | H | 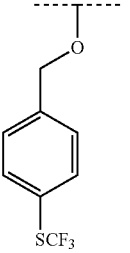 | H | Q-2.1 |
| 1.2-59 | H | H | H | 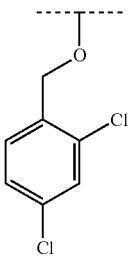 | H | Q-2.1 |
| 1.2-60 | H | H | H | 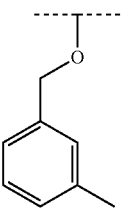 | H | Q-2.1 |
| 1.2-61 | H | H | H | 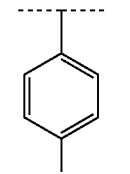 | H | Q-2.1 |
| 1.2-62 | H | H | H | | H | Q-2.1 |
| 1.2-63 | H | CH₃ | H | H | H | Q-2.16 |
| 1.2-64 | H | CH₃ | H | H | H | Q-2.18 |
| 1.2-65 | H | CH₃ | H | H | H | Q-2.17 |
| 1.2-66 | H | CH₃ | H | H | H | Q-2.19 |
| 1.2-67 | H | CH₃ | H | H | H | Q-2.20 |
| 1.2-68 | H | CH₃ | H | H | H | Q-2.21 |
| 1.2-69 | H | CH₃ | H | H | H | Q-2.22 |
| 1.2-70 | H | CH₃ | H | H | H | Q-2.23 |
| 1.2-71 | H | OCH₃ | H | H | H | Q-2.16 |
| 1.2-72 | H | OCH₃ | H | H | H | Q-2.18 |
| 1.2-73 | H | OCH₃ | H | H | H | Q-2.17 |
| 1.2-74 | H | OCH₃ | H | H | H | Q-2.19 |
| 1.2-75 | H | OCH₃ | H | H | H | Q-2.20 |
| 1.2-76 | H | OCH₃ | H | H | H | Q-2.21 |
| 1.2-77 | H | OCH₃ | H | H | H | Q-2.22 |
| 1.2-78 | H | OCH₃ | H | H | H | Q-2.23 |
| 1.2-79 | H | H | H | H | H | Q-2.15 |
| 1.2-80 | H | 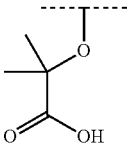 | H | H | H | Q-2.1 |

-continued

| No. | R¹ | R² | R³ | R⁴ | R⁵ | Q |
|---|---|---|---|---|---|---|
| 1.2-81 | H | H | (1,3-dioxolan-2-yl) | H | H | Q-2.1 |
| 1.2-82 | H | H | (2,3-dimethyl-2,5-dihydro-1H-pyrrol-4-yl) | H | H | Q-2.1 |
| 1.2-83 | H | H | (3-{2-[(tert-butoxycarbonyl)amino]ethyl}-2,5-dihydro-1H-pyrrol-4-yl) | H | H | Q-2.1 |
| 1.2-84 | H | H | (3-(2-aminoethyl)-2,5-dihydro-1H-pyrrol-4-yl) | H | H | Q-2.1 |
| 1.2-85 | H | H | (4-(2-aminoethyl)-1H-pyrrol-2-yl) | H | H | Q-2.1 |
| 1.2-86 | H | H | (4,5-dimethyl-1H-pyrrol-2-yl) | H | H | Q-2.1 |

Table 3—with base structure I.3 and the radical definitions specified below:

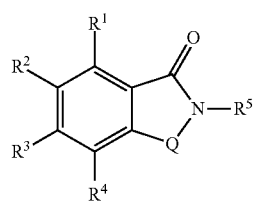

(I.3)

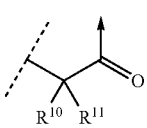

where Q = wherein the arrow represents the bond to the N—R⁵ group and where the definition in table form below of the radical "Q" corresponds to the definition of the radicals "Q-3.1" to "Q-3.20" mentioned above as being very particularly preferred

| No. | R¹ | R² | R³ | R⁴ | R⁵ | Q |
|---|---|---|---|---|---|---|
| 1.3-1 | H | H | H | H | H | Q-3.2 |
| 1.3-2 | H | H | H | H | H | Q-3.3 |
| 1.3-3 | H | H | H | H | H | Q-3.4 |
| 1.3-4 | H | H | H | H | H | Q-3.7 |
| 1.3-5 | H | H | H | H | H | Q-3.8 |
| 1.3-6 | H | H | H | H | H | Q-3.5 |
| 1.3-7 | H | H | H | H | H | Q-3.11 |
| 1.3-8 | H | H | H | H | H | Q-3.10 |
| 1.3-9 | H | OCH₃ | OCH₃ | H | H | Q-3.12 |
| 1.3-10 | H | H | H | H | H | Q-3.5 |
| 1.3-11 | H | H | H | H | H | Q-3.16 |
| 1.3-12 | H | Cl | H | H | H | Q-3.1 |
| 1.3-13 | H | H | Cl | H | H | Q-3.1 |
| 1.3-14 | Cl | H | Cl | H | H | Q-3.1 |
| 1.3-15 | H | H | OCH₃ | H | H | Q-3.1 |
| 1.3-16 | H | H | H | Cl | OH | Q-3.1 |
| 1.3-17 | H | 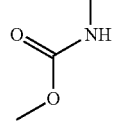 | H | H | H | Q-3.18 |
| 1.3-18 | H | 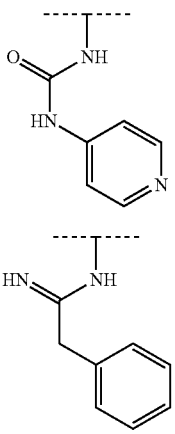 | H | H | H | Q-3.18 |
| 1.3-19 | H | 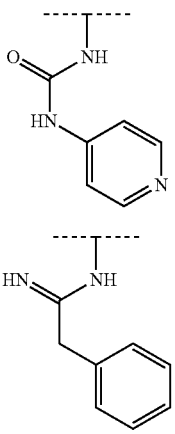 | H | H | H | Q-3.18 |
| 1.3-20 | H | Br | H | H | H | Q-3.18 |
| 1.3-21 | H | NH₂ | H | H | H | Q-3.18 |
| 1.3-22 | H | 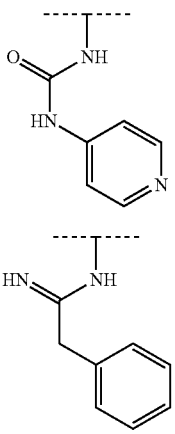 | H | H | H | Q-3.18 |
| 1.3-23 | NH₂ | NH₂ | H | H | H | Q-3.18 |
| 1.3-24 | NO₂ | NH₂ | H | H | H | Q-3.18 |
| 1.3-25 | NO₂ | 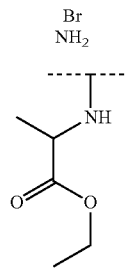 | H | H | H | Q-3.18 |
| 1.3-26 | H | 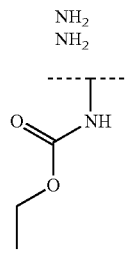 | H | H | H | Q-3.18 |

-continued

| No. | R¹ | R² | R³ | R⁴ | R⁵ | Q |
|---|---|---|---|---|---|---|
| 1.3-27 | H | OH | H | H | H | Q-3.18 |
| 1.3-28 | H | Cl | H | Cl | H | Q-3.1 |
| 1.3-29 | H | H | CH₃ | H | H | Q-3.1 |
| 1.3-30 | H | H | CF₃ | H | H | Q-3.1 |
| 1.3-31 | H | H | OCF₃ | H | H | Q-3.1 |
| 1.3-32 | H | H | F | H | H | Q-3.1 |
| 1.3-33 | H | H | Br | H | H | Q-3.1 |
| 1.3-34 | H | H | H | F | H | Q-3.1 |
| 1.3-35 | H | H | H | Cl | H | Q-3.1 |
| 1.3-36 | H | H | H | OCH₃ | H | Q-3.1 |
| 1.3-37 | H | H | Cl | Cl | H | Q-3.1 |
| 1.3-38 | H | H | H | CH₃ | H | Q-3.1 |
| 1.3-39 | F | H | CF₃ | H | H | Q-3.1 |
| 1.3-40 | H | H | CF₃ | H | H | Q-3.1 |
| 1.3-41 | H | H | H | CF₃ | H | Q-3.1 |
| 1.3-42 | H | Cl | H | H | H | Q-3.19 |
| 1.3-43 | H | H | F | H | H | Q-3.20 |

Table 4—with base structure I.4 and the radical definitions specified below:

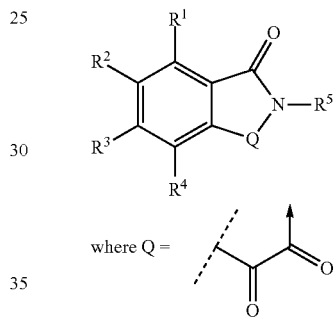

(I.4)

where Q =  wherein the arrow represents the bond to the N—R⁵ group

| No. | R¹ | R² | R³ | R⁴ | R⁵ |
|---|---|---|---|---|---|
| 1.4-1 | H | H | H | H | H |
| 1.4-2 | H | 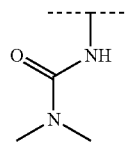 | H | H | H |
| 1.4-3 | H | NO₂ | H | H | H |
| 1.4-4 | H | NH₂ | H | H | H |
| 1.4-5 | H | Cl | H | H | H |
| 1.4-6 | H | H | Cl | H | H |
| 1.4-7 | H | H | OCH₃ | H | H |
| 1.4-8 | H | H | OCF₃ | H | H |
| 1.4-9 | H | H | CH₃ | H | H |
| 1.4-10 | H | H | F | H | H |
| 1.4-11 | H | OCH₃ | H | H | H |
| 1.4-12 | H | OCF₃ | H | H | H |
| 1.4-13 | H | CH₃ | H | H | H |

-continued

| No. | R¹ | R² | R³ | R⁴ | R⁵ |
|---|---|---|---|---|---|
| 1.4-14 | H | H | H | CH₃ | H |
| 1.4-15 | H | H | CF₃ | H | H |
| 1.4-16 | H | H | H | F | H |
| 1.4-17 | H | F | H | H | H |
| 1.4-18 | H | Br | H | H | H |
| 1.4-19 | H | H | H | Cl | H |
| 1.4-20 | H | H | H | Br | H |
| 1.4-21 | H | H | H | OCH₃ | H |
| 1.4-22 | H | H | H | OCF₃ | H |
| 1.4-23 | Cl | H | H | H | H |
| 1.4-24 | Br | H | H | H | H |
| 1.4-25 | OCH₃ | H | H | H | H |
| 1.4-26 | OCF₃ | H | H | H | H |
| 1.4-27 | CF₃ | H | H | H | H |
| 1.4-28 | CH₃ | H | H | H | H |
| 1.4-29 | H | H | H | CF₃ | H |
| 1.4-30 | F | H | H | H | H |
| 1.4-31 | H | OCH₃ | OCH₃ | H | H |
| 1.4-32 | H | Cl | Cl | H | H |
| 1.4-33 | H | CH₃ | CH₃ | H | H |

Table 5—with base structure I.5 and the radical definitions specified below:

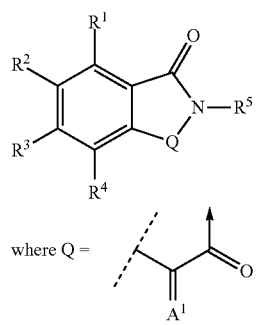

(I.5)

where Q = 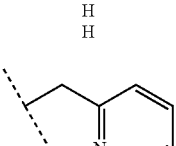 wherein the arrow represents the bond to the N—R⁵ group and where the definition in table form below of the radical "Q" corresponds to the definition of the radicals "Q-5.1" to "Q-5.78" mentioned above as being very particularly preferred

| No. | R¹ | R² | R³ | R⁴ | R⁵ | Q |
|---|---|---|---|---|---|---|
| 1.5-1 | H | H | H | H | H | Q-5.2 |
| 1.5-2 | H | H | H | H | H | Q-5.4 |
| 1.5-3 | H | H | H | H | H | Q-5.5 |
| 1.5-4 | H | H | H | H | (2-pyridylmethyl) | Q-5.6 |
| 1.5-5 | H | H | H | H | (2-pyridyl) | Q-5.7 |
| 1.5-6 | H | H | H | H | (2-pyridylmethyl) | Q-5.8 |
| 1.5-7 | H | H | H | H | (3,4-dimethylphenyl) | Q-5.9 |
| 1.5-8 | H | H | H | H | (3-chlorophenyl) | Q-5.9 |
| 1.5-9 | H | H | H | H | H | Q-5.10 |
| 1.5-10 | H | H | H | H | H | Q-5.11 |
| 1.5-11 | H | H | H | H | H | Q-5.12 |
| 1.5-12 | H | H | H | H | H | Q-5.13 |
| 1.5-13 | H | H | H | H | H | Q-5.15 |
| 1.5-14 | H | H | H | H | H | Q-5.14 |
| 1.5-15 | H | H | H | H | H | Q-5.16 |
| 1.5-16 | H | H | H | H | H | Q-5.5 |
| 1.5-17 | H | H | H | H | H | Q-5.18 |
| 1.5-18 | H | H | H | H | H | Q-5.17 |
| 1.5-19 | H | H | H | H | H | Q-5.19 |
| 1.5-20 | H | H | H | H | H | Q-5.20 |
| 1.5-21 | H | H | H | H | H | Q-5.21 |
| 1.5-22 | H | H | H | H | H | Q-5.22 |
| 1.5-23 | H | H | H | H | H | Q-5.23 |
| 1.5-24 | H | H | H | H | H | Q-5.24 |
| 1.5-25 | H | H | H | H | H | Q-5.25 |
| 1.5-26 | H | H | H | H | H | Q-5.27 |
| 1.5-27 | H | H | H | H | H | Q-5.26 |
| 1.5-28 | H | H | H | H | H | Q-5.29 |
| 1.5-29 | H | H | H | H | H | Q-5.30 |
| 1.5-30 | H | H | H | H | H | Q-5.28 |
| 1.5-31 | H | H | H | H | H | Q-5.31 |
| 1.5-32 | H | H | H | H | H | Q-5.32 |
| 1.5-33 | H | H | H | H | H | Q-5.33 |
| 1.5-34 | H | H | H | H | H | Q-5.34 |
| 1.5-35 | H | H | H | H | H | Q-5.35 |
| 1.5-36 | H | H | H | H | H | Q-5.36 |
| 1.5-37 | H | H | H | H | H | Q-5.37 |
| 1.5-38 | H | H | H | H | H | Q-5.38 |
| 1.5-39 | H | H | H | H | H | Q-5.39 |
| 1.5-40 | H | H | H | H | H | Q-5.40 |
| 1.5-41 | H | H | H | H | H | Q-5.41 |
| 1.5-42 | H | H | H | H | H | Q-5.42 |
| 1.5-43 | H | H | H | H | H | Q-5.43 |
| 1.5-44 | H | H | H | H | H | Q-5.44 |
| 1.5-45 | H | H | H | H | H | Q-5.45 |
| 1.5-46 | H | H | H | H | H | Q-5.46 |
| 1.5-47 | H | H | H | H | H | Q-5.47 |
| 1.5-48 | H | H | H | H | H | Q-5.48 |
| 1.5-49 | H | H | H | H | H | Q-5.49 |
| 1.5-50 | H | H | H | H | H | Q-5.50 |
| 1.5-51 | H | H | H | H | H | Q-5.51 |
| 1.5-52 | H | H | H | H | H | Q-5.52 |
| 1.5-53 | H | H | H | H | H | Q-5.53 |
| 1.5-54 | H | H | H | H | H | Q-5.54 |
| 1.5-55 | H | H | H | H | H | Q-5.55 |
| 1.5-56 | H | H | H | H | H | Q-5.56 |
| 1.5-57 | H | H | H | H | H | Q-5.57 |
| 1.5-58 | H | H | H | H | H | Q-5.58 |
| 1.5-59 | H | H | H | H | H | Q-5.59 |
| 1.5-60 | H | H | H | H | H | Q-5.60 |
| 1.5-61 | H | H | H | H | H | Q-5.61 |
| 1.5-62 | H | H | H | H | H | Q-5.62 |
| 1.5-63 | H | H | H | H | H | Q-5.63 |
| 1.5-64 | H | H | H | H | H | Q-5.64 |
| 1.5-65 | H | H | H | H | H | Q-5.65 |
| 1.5-66 | H | H | H | H | H | Q-5.66 |
| 1.5-67 | H | H | H | H | H | Q-5.67 |

-continued

| No. | R¹ | R² | R³ | R⁴ | R⁵ | Q |
|---|---|---|---|---|---|---|
| I.5-68 | H | H | H | H | H | Q-5.68 |
| I.5-69 | H | H | H | H | H | Q-5.69 |
| I.5-70 | H | H | H | H | H | Q-5.70 |
| I.5-71 | H | H | H | H | H | Q-5.71 |
| I.5-72 | H | H | H | H | H | Q-5.72 |
| I.5-73 | H | H | H | H | H | Q-5.73 |
| I.5-74 | H | H | H | H | H | Q-5.74 |
| I.5-75 | H | H | F | H | H | Q-5.5 |
| I.5-76 | H | H | F | H | H | Q-5.8 |
| I.5-77 | H | H | Cl | H | H | Q-5.75 |
| I.5-78 | H | H | Cl | H | H | Q-5.76 |
| I.5-79 | H | H | Cl | H | H | Q-5.5 |
| I.5-80 | H | H | CF₃ | H | H | Q-5.1 |
| I.5-81 | H | H | CF₃ | H | H | Q-5.5 |
| I.5-82 | H | H | CF₃ | H | H | Q-5.8 |
| I.5-83 | H | H | F | H | H | Q-5.1 |
| I.5-84 | H | H | H | H | H | Q-5.76 |
| I.5-85 | H | Cl | H | Cl | H | Q-5.5 |
| I.5-86 | H | Cl | H | H | H | Q-5.5 |
| I.5-87 | H | H | Br | H | H | Q-5.8 |
| I.5-88 | H | H | Br | H | H | Q-5.77 |

Table 6—with base structure I.6 and the radical definitions specified below:

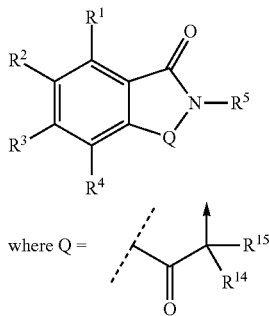

(I.6)

and where the definition in table form below of the radical "Q" corresponds to the definition of the radicals "Q-6.1" to "Q-6.13" mentioned above as being very particularly preferred

| No. | R¹ | R² | R³ | R⁴ | R⁵ | Q |
|---|---|---|---|---|---|---|
| I.6-1 | H | H | H | H | H | Q-6.2 |
| I.6-2 | H | H | H | H | H | Q-6.3 |
| I.6-3 | H | H | H | H | H | Q-6.4 |
| I.6-4 | H | H | H | H | H | Q-6.6 |
| I.6-5 | H | H | H | H | H | Q-6.9 |
| I.6-6 | H | H | H | H | H | Q-6.13 |
| I.6-7 | H | H | H | H | H | Q-6.5 |
| I.6-8 | H | CH₃ | H | H | H | Q-6.2 |
| I.6-9 | H | CH₃ | H | H | H | Q-6.3 |
| I.6-10 | H | CH₃ | H | H | H | Q-6.4 |
| I.6-11 | H | CH₃ | H | H | H | Q-6.6 |
| I.6-12 | H | CH₃ | H | H | H | Q-6.9 |
| I.6-13 | H | CH₃ | H | H | H | Q-6.13 |
| I.6-14 | H | CH₃ | H | H | H | Q-6.5 |
| I.6-15 | H | OCH₃ | H | H | H | Q-6.2 |
| I.6-16 | H | OCH₃ | H | H | H | Q-6.3 |
| I.6-17 | H | OCH₃ | H | H | H | Q-6.4 |
| I.6-18 | H | OCH₃ | H | H | H | Q-6.6 |
| I.6-19 | H | OCH₃ | H | H | H | Q-6.9 |
| I.6-20 | H | OCH₃ | H | H | H | Q-6.13 |
| I.6-21 | H | OCH₃ | H | H | H | Q-6.5 |
| I.6-22 | H | CF₃ | H | H | H | Q-6.2 |
| I.6-23 | H | CF₃ | H | H | H | Q-6.3 |
| I.6-24 | H | CF₃ | H | H | H | Q-6.4 |
| I.6-25 | H | CF₃ | H | H | H | Q-6.6 |
| I.6-26 | H | CF₃ | H | H | H | Q-6.9 |
| I.6-27 | H | CF₃ | H | H | H | Q-6.13 |
| I.6-28 | H | CF₃ | H | H | H | Q-6.5 |
| I.6-29 | H | Cl | H | H | H | Q-6.2 |
| I.6-30 | H | Cl | H | H | H | Q-6.3 |
| I.6-31 | H | Cl | H | H | H | Q-6.4 |
| I.6-32 | H | Cl | H | H | H | Q-6.6 |
| I.6-33 | H | Cl | H | H | H | Q-6.9 |
| I.6-34 | H | Cl | H | H | H | Q-6.13 |
| I.6-35 | H | Cl | H | H | H | Q-6.5 |

Table 7—with base structure I.7 and the radical definitions specified below:

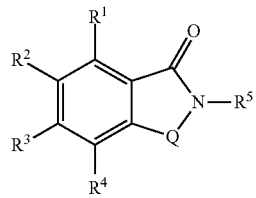

(I.7)

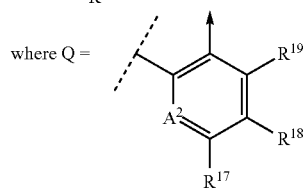

and where the definition in table form below of the radical "Q" corresponds to the definition of the radicals "Q-7.1" to "Q-7.30" mentioned above as being very particularly preferred

| No. | R¹ | R² | R³ | R⁴ | R⁵ | Q |
|---|---|---|---|---|---|---|
| I.7-1 | H | H | H | H | H | Q-7.8 |
| I.7-2 | H | H | H | H | H | Q-7.1 |
| I.7-3 | H | H | H | H | H | Q-7.2 |
| I.7-4 | H | H | H | H | H | Q-7.3 |
| I.7-5 | H | H | H | H | H | Q-7.4 |
| I.7-6 | H | H | H | H | H | Q-7.5 |
| I.7-7 | H | H | H | H | H | Q-7.6 |
| I.7-8 | H | H | H | H | H | Q-7.7 |
| I.7-9 | H | H | H | H | H | Q-7.9 |
| I.7-10 | H | H | H | H | H | Q-7.10 |
| I.7-11 | H | H | H | H | H | Q-7.11 |
| I.7-12 | H | H | H | H | H | Q-7.12 |
| I.7-13 | H | H | H | H | H | Q-7.13 |
| I.7-14 | H | H | H | H | H | Q-7.14 |
| I.7-15 | H | H | H | H | H | Q-7.15 |
| I.7-16 | H | H | H | H | H | Q-7.16 |
| I.7-17 | H | H | H | H | H | Q-7.17 |
| I.7-18 | H | H | H | H | H | Q-7.18 |
| I.7-19 | H | H | H | H | H | Q-7.19 |
| I.7-20 | H | H | H | H | H | Q-7.20 |
| I.7-21 | H | H | H | H | H | Q-7.26 |
| I.7-22 | H | H | H | H | H | Q-7.27 |
| I.7-23 | H | CH₃ | H | H | H | Q-7.1 |
| I.7-24 | H | CH₃ | H | H | H | Q-7.2 |
| I.7-25 | H | CH₃ | H | H | H | Q-7.3 |
| I.7-26 | H | CH₃ | H | H | H | Q-7.4 |
| I.7-27 | H | CH₃ | H | H | H | Q-7.5 |
| I.7-28 | H | CH₃ | H | H | H | Q-7.6 |
| I.7-29 | H | CH₃ | H | H | H | Q-7.7 |

-continued

| No. | $R^1$ | $R^2$ | $R^3$ | $R^4$ | $R^5$ | Q |
|---|---|---|---|---|---|---|
| I.7-30 | H | CH$_3$ | H | H | H | Q-7.9 |
| I.7-31 | H | CH$_3$ | H | H | H | Q-7.10 |
| I.7-32 | H | CH$_3$ | H | H | H | Q-7.11 |
| I.7-33 | H | CH$_3$ | H | H | H | Q-7.12 |
| I.7-34 | H | CH$_3$ | H | H | H | Q-7.13 |
| I.7-35 | H | CH$_3$ | H | H | H | Q-7.14 |
| I.7-36 | H | CH$_3$ | H | H | H | Q-7.15 |
| I.7-37 | H | CH$_3$ | H | H | H | Q-7.16 |
| I.7-39 | H | CH$_3$ | H | H | H | Q-7.17 |
| I.7-40 | H | CH$_3$ | H | H | H | Q-7.18 |
| I.7-41 | H | CH$_3$ | H | H | H | Q-7.19 |
| I.7-42 | H | CH$_3$ | H | H | H | Q-7.20 |
| I.7-43 | H | CH$_3$ | H | H | H | Q-7.21 |
| I.7-44 | H | CH$_3$ | H | H | H | Q-7.22 |
| I.7-45 | H | OCH$_3$ | H | H | H | Q-7.1 |
| I.7-46 | H | OCH$_3$ | H | H | H | Q-7.2 |
| I.7-47 | H | OCH$_3$ | H | H | H | Q-7.3 |
| I.7-48 | H | OCH$_3$ | H | H | H | Q-7.4 |
| I.7-49 | H | OCH$_3$ | H | H | H | Q-7.5 |
| I.7-50 | H | OCH$_3$ | H | H | H | Q-7.6 |
| I.7-51 | H | OCH$_3$ | H | H | H | Q-7.7 |
| I.7-52 | H | OCH$_3$ | H | H | H | Q-7.9 |
| I.7-53 | H | OCH$_3$ | H | H | H | Q-7.10 |
| I.7-54 | H | OCH$_3$ | H | H | H | Q-7.11 |
| I.7-55 | H | OCH$_3$ | H | H | H | Q-7.12 |
| I.7-56 | H | OCH$_3$ | H | H | H | Q-7.13 |
| I.7-57 | H | OCH$_3$ | H | H | H | Q-7.14 |
| I.7-58 | H | OCH$_3$ | H | H | H | Q-7.15 |
| I.7-59 | H | OCH$_3$ | H | H | H | Q-7.16 |
| I.7-60 | H | OCH$_3$ | H | H | H | Q-7.17 |
| I.7-61 | H | OCH$_3$ | H | H | H | Q-7.18 |
| I.7-62 | H | OCH$_3$ | H | H | H | Q-7.19 |
| I.7-63 | H | OCH$_3$ | H | H | H | Q-7.20 |
| I.7-64 | H | OCH$_3$ | H | H | H | Q-7.21 |
| I.7-65 | H | OCH$_3$ | H | H | H | Q-7.22 |
| I.7-66 | H | H | H | H | H | Q-7.21 |
| I.7-67 | H | H | H | H | H | Q-7.22 |
| I.7-68 | H | H | H | H | H | Q-7.23 |
| I.7-69 | H | H | H | H | H | Q-7.24 |
| I.7-70 | H | H | H | H | H | Q-7.25 |
| I.7-71 | H | H | H | H | H | Q-7.26 |

Table 8—with base structure I.8 and the radical definitions specified below:

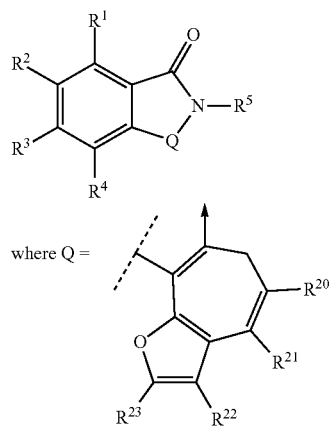

(I.8)

and where the definition in table form below of the radical "Q" corresponds to the definition of the radicals "Q-8.1" to "Q-8.3" mentioned above as being very particularly preferred

| No. | $R^1$ | $R^2$ | $R^3$ | $R^4$ | $R^5$ | Q |
|---|---|---|---|---|---|---|
| I.8-1 | H | H | H | H | H | Q-8.1 |
| I.8-2 | H | Cl | H | H | H | Q-8.2 |
| I.8-3 | H | OCH$_3$ | H | H | H | Q-8.1 |
| I.8-4 | H | Br | H | H | H | Q-8.1 |
| I.8-5 | H | F | H | H | H | Q-8.1 |
| I.8-6 | H | F | H | H | H | Q-8.2 |
| I.8-7 | H | Cl | H | H | H | Q-8.1 |
| I.8-8 | H | Br | H | H | H | Q-8.2 |
| I.8-9 | H | OCH$_3$ | H | H | H | Q-8.2 |
| I.8-10 | H | H | H | H | n-Pr | Q-8.1 |
| I.8-11 | H | H | H | H | CH$_2$CH=CH$_2$ | Q-8.1 |
| I.8-12 | H | H | H | H | H | Q-8.2 |
| I.8-13 | H | H | H | H | H | Q-8.3 |
| I.8-14 | H | H | F | H | H | Q-8.2 |
| I.8-15 | H | H | Cl | H | H | Q-8.2 |
| I.8-16 | H | H | Br | H | H | Q-8.2 |
| I.8-17 | H | H | OCH$_3$ | H | H | Q-8.2 |
| I.8-18 | H | H | F | H | H | Q-8.1 |
| I.8-19 | H | H | Cl | H | H | Q-8.1 |
| I.8-20 | H | H | Br | H | H | Q-8.1 |
| I.8-21 | H | H | OCH$_3$ | H | H | Q-8.1 |
| I.8-22 | H | F | H | H | H | Q-8.3 |
| I.8-23 | H | Cl | H | H | H | Q-8.3 |
| I.8-24 | H | Br | H | H | H | Q-8.3 |
| I.8-28 | H | OCH$_3$ | H | H | H | Q-8.3 |

Table 9—with base structure I.9 and the radical definitions specified below:

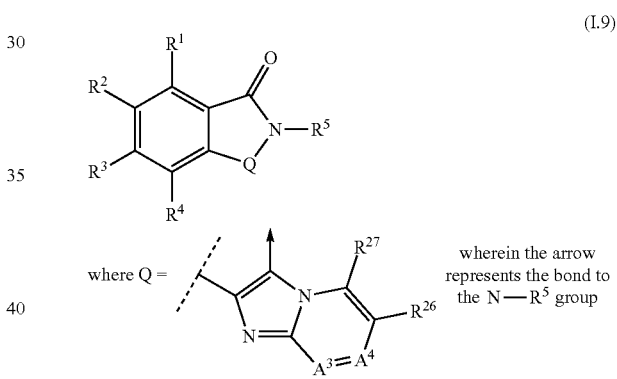

(I.9)

and where the definition in table form below of the radical "Q" corresponds to the definition of the radicals "Q-9.1" to "Q-9.15" mentioned above as being very particularly preferred

| No. | $R^1$ | $R^2$ | $R^3$ | $R^4$ | $R^5$ | Q |
|---|---|---|---|---|---|---|
| I.9-1 | H | H | H | H | H | Q-9.1 |
| I.9-2 | H | OCH$_3$ | H | OCH$_3$ | H | Q-9.1 |
| I.9-3 | H | OCH$_3$ | H | OCH$_3$ | H | Q-9.2 |
| I.9-4 | H | OCH$_3$ | H | OCH$_3$ | H | Q-9.3 |
| I.9-5 | H | OCH$_3$ | H | OCH$_3$ | H | Q-9.4 |
| I.9-6 | H | H | H | H | H | Q-9.5 |
| I.9-7 | H | H | H | H | H | Q-9.2 |
| I.9-8 | H | H | H | H | H | Q-9.6 |
| I.9-9 | H | OCH$_3$ | H | OCH$_3$ | H | Q-9.6 |
| I.9-10 | H | OCH$_3$ | H | OCH$_3$ | H | Q-9.7 |
| I.9-11 | H | OCH$_3$ | H | OCH$_3$ | H | Q-9.8 |
| I.9-12 | H | H | H | H | H | Q-9.8 |
| I.9-13 | H | H | H | H | H | Q-9.9 |
| I.9-14 | H | H | H | H | H | Q-9.10 |
| I.9-15 | H | F | H | H | H | Q-9.4 |
| I.9-16 | H | H | H | H | H | Q-9.11 |
| I.9-17 | H | F | H | H | H | Q-9.11 |
| I.9-18 | H | F | H | H | H | Q-9.1 |

-continued

| No. | R¹ | R² | R³ | R⁴ | R⁵ | Q |
|---|---|---|---|---|---|---|
| I.9-19 | H | OCH₃ | H | H | H | Q-9.4 |
| I.9-20 | H | OCH₃ | H | H | H | Q-9.1 |
| I.9-21 | H | OCH₃ | H | H | H | Q-9.12 |
| I.9-22 | H | OCH₃ | H | H | H | Q-9.11 |
| I.9-23 | H | OCH₃ | H | H | H | Q-9.9 |
| I.9-24 | H | H | H | H | H | Q-9.13 |
| I.9-25 | OCH₃ | OCH₃ | H | H | H | Q-9.3 |
| I.9-26 | H | H | H | H | H | Q-9.14 |
| I.9-27 | H | H | H | H | H | Q-9.3 |
| I.9-28 | OCH₃ | OCH₃ | H | H | H | Q-9.4 |
| I.9-29 | H | H | H | H | H | Q-9.4 |
| I.9-30 | H | H | H | H | H | Q-9.7 |
| I.9-31 | OCH₃ | OCH₃ | H | H | H | Q-9.7 |
| I.9-32 | OCH₃ | OCH₃ | H | H | H | Q-9.1 |
| I.9-33 | H | Cl | H | H | H | Q-9.11 |
| I.9-34 | H | Cl | H | H | H | Q-9.1 |
| I.9-35 | H | Cl | H | H | H | Q-9.7 |
| I.9-36 | H | Cl | H | H | H | Q-9.4 |
| I.9-37 | H | Br | H | H | H | Q-9.11 |
| I.9-38 | H | Br | H | H | H | Q-9.1 |
| I.9-39 | H | Br | H | H | H | Q-9.7 |
| I.9-40 | H | Br | H | H | H | Q-9.4 |

Spectroscopic data of selected table examples:

Example No. I.1-1

$^1$H-NMR (400 MHz, CDCl$_3$ δ, ppm) 11.33 (br. s, 1H), 8.42 (d, 1H), 7.67 (m, 1H), 7.56 (d, 1H), 7.52 (t, 1H), 7.18 (d, 1H), 6.57 (d, 1H).

Example No. I.1-48

$^1$H-NMR (400 MHz, CDCl$_3$ δ, ppm) 10.62 (br. s, 1H), 8.56 (s, 1H), 7.73 (d, 1H), 7.43 (d, 1H), 7.13 (d, 1H), 6.51 (d, 1H).

Example No. I.1-100

$^1$H-NMR (400 MHz, d$_6$-DMSO δ, ppm) 11.17 (br. s, 1H, NH), 8.70 (d, 1H), 8.20 (br. s, 1H, NH), 8.12 (dd, 1H), 7.68 (dd, 1H), 7.42 (br. s, 1H, NH), 6.46 (s, 1H), 1.32 (s, 9H).

Example No. I.1-101

$^1$H-NMR (400 MHz, d$_6$-DMSO δ, ppm) 11.98 (br. s, 1H, NH), 10.68 (br. s, 1H, OH), 8.17 (d, 1H), 8.06 (d, 1H), 7.88 (dd, 1H), 7.74 (dd, 1H), 6.62 (s, 1H).

Example No. I.1-102

$^1$H-NMR (400 MHz, d$_6$-DMSO δ, ppm) 10.89 (br. s, 1H, NH), 10.19 (br. s, 1H, OH), 8.24 (d, 1H), 7.87 (d, 1H), 7.79 (dd, 1H), 7.65 (dd, 1H), 7.40 (s, 1H).

Example No. I.1-103

$^1$H-NMR (400 MHz, d$_6$-DMSO δ, ppm) 12.10 (br. s, 1H, NH), 7.40 (d, 1H), 7.13 (d, 1H), 6.61 (s, 1H), 2.73 (s, 3H), 2.39 (s, 3H).

Example No. I.1-104

$^1$H-NMR (400 MHz, d$_6$-DMSO δ, ppm) 12.86 (br. s, 1H), 10.62 (br. s, 1H), 8.32 (d, 1H), 8.18 (d, 1H), 7.92 (dd, 1H), 7.82 (dd, 1H), 2.63 (s, 3H).

Example No. I.1-105

$^1$H-NMR (400 MHz, d$_6$-DMSO δ, ppm) 10.70 (br. s, 1H, NH), 10.51 (br. s, 1H, OH), 8.30 (d, 1H), 8.11 (d, 1H), 7.92 (dd, 1H), 7.79 (dd, 1H), 4.39 (q, 2H), 1.37 (t, 3H).

Example No. I.1-106

$^1$H-NMR (400 MHz, d$_6$-DMSO δ, ppm) 11.46 (br. s, 1H, NH), 8.20 (d, 1H), 7.75 (m, 2H), 7.55 (dd, 1H), 6.68 (s, 1H), 3.02 (s, 3H), 2.98 (s, 3H).

Example No. I.1-109

$^1$H-NMR (400 MHz, d$_6$-DMSO δ, ppm) 10.60 (br. s, 1H, NH), 7.90 (d, 1H), 7.39 (dd, 1H), 7.20 (d, 1H), 6.98 (dd, 1H), 5.54 (br. s, 2H, NH), 5.44 (s, 1H)

Example No. I.1-110

$^1$H-NMR (400 MHz, d$_6$-DMSO δ, ppm) 11.42 (br. s, 1H, NH), 8.40 (br. s, 1H, NH), 8.10 (d, 1H), 7.67 (m, 3H), 7.39 (dd, 1H), 6.60 (1H, NH), 4.52 (q, 2H), 4.18 (q, 2H), 1.27 (t, 6H).

Example No. I.1-112

$^1$H-NMR (400 MHz, d$_6$-DMSO δ, ppm) 11.71 (br. s, 1H, NH), 8.23 (d, 1H), 7.75 (dd, 1H), 7.55 (m, 2H), 7.51 (d, 1H), 7.47 (m, 2H), 7.19 (s, 1H).

Example No. I.1-113

$^1$H-NMR (400 MHz, d$_6$-DMSO δ, ppm) 11.63 (br. s, 1H, NH), 10.95 (br. s, 1H, NH), 8.08 (d, 1H), 7.70 (dd, 1H), 7.61 (d, 2H), 7.55 (dd, 1H), 7.48 (d, 1H), 7.39 (d, 2H).

Example No. I.1-114

$^1$H-NMR (400 MHz, d$_6$-DMSO δ, ppm) 11.23 (br. s, 1H, NH), 8.75 (d, 1H), 8.07 (dd, 1H), 7.34 (m, 4H), 6.82 (d, 1H), 5.88 (br. s, 2H, NH)

Example No. I.1-116

$^1$H-NMR (400 MHz, CDCl$_3$ δ, ppm) 7.88 (br. s, 1H, NH), 7.83 (d, 1H), 7.62 (d, 1H), 7.57 (dd, 1H), 7.46 (dd, 1H), 5.66 (dd, 1H), 1.98 (d, 3H).

Example No. I.1-127

$^1$H-NMR (400 MHz, d$_6$-DMSO δ, ppm) 13.14 (br. s, 1H, OH), 8.32 (d, 1H), 8.22 (d, 1H), 7.95 (m, 2H), 4.07 (s, 3H), 2.72 (s, 3H).

Example No. I.1-128

$^1$H-NMR (400 MHz, d$_6$-DMSO δ, ppm) 13.44 (br. s, 1H, OH), 8.31 (d, 1H), 8.32 (d, 1H), 7.93 (m, 2H), 4.11 (s, 3H), 3.57 (m, 1H), 1.23 (m, 4H).

Example No. I.1-129

$^1$H-NMR (400 MHz, d$_6$-DMSO δ, ppm) 13.47 (br. s, 1H, OH), 8.13 (d, 1H), 8.10 (s, 1H), 7.73 (d, 1H), 4.09 (s, 3H), 3.55 (m, 1H), 2.58 (s, 2H), 1.22 (m, 2H), 1.20 (m, 2H).

Example No. I.1-130

¹H-NMR (400 MHz, d₆-DMSO δ, ppm) 13.33 (br. s, 1H, OH), 8.44 (s, 1H), 8.39 (s, 1H), 4.11 (s, 3H), 3.52 (m, 1H), 1.27 (m, 2H), 1.23 (m, 2H).

Example No. I.1-133

¹H-NMR (400 MHz, d₆-DMSO δ, ppm) 13.10 (br. s, 1H, OH), 8.31 (d, 1H), 8.23 (d, 1H), 7.94 (m, 2H), 4.07 (s, 3H), 3.28 (q, 2H), 1.19 (t, 3H).

Example No. I.1-148

¹H-NMR (400 MHz, d₆-DMSO δ, ppm) 12.13 (br. s, 1H, OH), 11.96 (br. s, 1H, NH), 8.23 (s, 1H), 8.20 (s, 1H), 2.22 (q, 2H), 0.99 (t, 3H).

Example No. I.1-153

¹H-NMR (400 MHz, d₆-DMSO δ, ppm) 13.26 (br. s, 1H, OH), 8.31 (d, 1H), 8.22 (d, 1H), 7.91 (dd, 1H), 4.07 (s, 3H), 3.83 (m, 1H), 1.98 (m, 2H), 1.83 (m, 2H), 1.42 (m, 4H), 1.23 (m, 2H).

Example No. I.1-155

¹H-NMR (400 MHz, d₆-DMSO δ, ppm) 13.41 (br. s, 1H, OH), 8.31 (d, 1H), 8.24 (d, 1H), 7.93 (dd, 1H), 4.10 (s, 3H), 3.57 (m, 1H), 1.26 (m, 2H), 1.22 (m, 2H).

Example No. I.1-156

¹H-NMR (400 MHz, d₆-DMSO δ, ppm) 13.23 (br. s, 1H, OH), 8.32 (d, 1H), 8.23 (d, 1H), 7.93 (m, 2H), 4.11 (m, 1H), 4.09 (s, 3H), 1.23 (s, 6H).

Example No. I.1-174

¹H-NMR (400 MHz, CDCl₃ δ, ppm) 9.90 (br. s, 1H), 8.29 (d, 1H), 7.72 (d, 2H), 7.53-7.45 (m, 4H), 7.38 (t, 1H), 6.87 (s, 1H), 2.59 (s, 3H).

Example No. I.1-175

¹H-NMR (400 MHz, d⁶-DMSO δ, ppm) 12.68 (br. s, 1H), 11.79 (br. s, 1H), 8.84 (d, 1H), 8.23 (d, 1H), 8.03 (d, 1H), 7.78 (t, 1H), 7.54 (d, 1H).

Example No. I.1-176

¹H-NMR (400 MHz, d₆-DMSO δ, ppm) 11.31 (br. s, 1H), 8.41 (s, 1H), 8.02 (d, 1H), 7.81-7.75 (m, 3H), 7.53 (d, 1H), 7.20 (d, 1H), 6.59 (d, 1H).

Example No. I.1-177

¹H-NMR (400 MHz, d⁶-DMSO δ, ppm) 11.31 (br. s, 1H), 8.41 (s, 1H), 8.02 (d, 1H), 7.77-7.73 (m, 3H), 7.53-7.48 (m, 2H), 7.41 (t, 1H), 7.19 (m, 1H), 6.59 (d, 1H).

Example No. I.1-178

¹H-NMR (400 MHz, d⁶-DMSO δ, ppm) 11.53 (br. s, 1H), 8.23 (s, 1H), 8.02 (d, 1H), 7.40 (t, 1H), 7.32 (d, 1H), 6.65 (d, 1H).

Example No. I.1-179

¹H-NMR (400 MHz, d⁶-DMSO δ, ppm) 11.31 (br. s, 1H), 8.43 (s, 1H), 8.03 (d, 1H), 7.89 (d, 2H), 7.78 (d, 1H), 7.48 (d, 2H), 7.20 (t, 1H), 6.60 (d, 1H).

Example No. I.1-180

¹H-NMR (400 MHz, d⁶-DMSO δ, ppm) 11.39 (br. s, 1H), 8.68 (d, 2H), 8.55 (s, 1H), 8.13 (d, 1H), 7.83-7.79 (m, 3H), 7.23 (t, 1H), 6.61 (d, 1H).

Example No. I.1-181

¹H-NMR (400 MHz, d⁶-DMSO δ, ppm) 11.34 (br. s, 1H), 8.98 (s, 1H), 8.61 (d, 1H), 8.45 (s, 1H), 8.17 (d, 1H), 8.08 (d, 1H), 7.79 (d, 1H), 7.22 (t, 1H), 6.61 (t, 1H).

Example No. I.1-182

¹H-NMR (400 MHz, d⁶-DMSO δ, ppm) 11.23 (br. s, 1H), 8.36 (s, 1H), 7.98 (d, 1H), 7.72-7.68 (m, 3H), 7.16 (t, 1H), 7.05 (d, 2H), 6.56 (d, 1H).

Example No. I.1-183

¹H-NMR (400 MHz, d⁶-DMSO δ, ppm) 11.31 (br. s, 1H), 8.41 (s, 1H), 8.03 (d, 1H), 7.80-7.70 (m, 3H), 7.52 (t, 1H), 7.47 (d, 1H), 7.20 (t, 1H), 6.61 (d, 1H).

Example No. I.1-184

¹H-NMR (400 MHz, d⁶-DMSO δ, ppm) 11.34 (br. s, 1H), 8.19 (s, 1H), 7.76-7.73 (m, 3H), 7.54-7.50 (m, 2H), 7.22 (t, 1H), 6.61 (d, 1H).

Example No. I.1-185

¹H-NMR (400 MHz, d⁶-DMSO δ, ppm) 11.33 (br. s, 1H), 8.23 (d, 1H), 7.62 (d, 1H), 7.58-7.39 (m, 6H), 7.13 (t, 1H), 6.33 (d, 1H).

Example No. I.1-186

¹H-NMR (400 MHz, d⁶-DMSO δ, ppm) 11.38 (br. s, 1H), 8.71 (d, 2H), 8.31 (d, 1H), 7.66 (d, 1H), 7.57 (t, 1H), 6.98 (d, 2H), 7.18 (t, 1H), 6.31 (d, 1H).

Example No. I.1-187

¹H-NMR (400 MHz, d⁶-DMSO δ, ppm) 11.32 (br. s, 1H), 8.25 (d, 1H), 7.63 (d, 1H), 7.60-7.53 (m, 3H), 7.43 (d, 2H), 7.13 (m, 1H), 6.29 (d, 1H).

Example No. I.1-188

¹H-NMR (400 MHz, d⁶-DMSO δ, ppm) 11.32 (br. s, 1H), 8.27 (d, 1H), 7.62 (d, 1H), 7.57-7.50 (m, 4H), 7.48 (s, 1H), 7.17 (t, 1H), 6.29 (d, 1H).

Example No. I.1-189

¹H-NMR (400 MHz, d⁶-DMSO δ, ppm) 11.32 (br. s, 1H), 8.29 (m, 1H), 7.80 (s, 1H), 7.55-7.51 (m, 3H), 7.42 (d, 1H), 7.12 (m, 1H), 5.88 (d, 1H).

Example No. I.1-191

¹H-NMR (400 MHz, CDCl₃ δ, ppm) 9.84 (br. s, 1H), 8.89 (d, 1H), 8.43 (d, 1H), 8.12 (d, 1H), 7.78 (t, 1H), 7.55 (t, 1H), 5.38 (m, 1H), 1.39 (d, 6H).

Example No. I.1-193

¹H-NMR (400 MHz, CDCl₃ δ, ppm) 11.75 (br. s, 1H), 8.45 (d, 1H), 7.73 (t, 1H), 7.57-7.53 (m, 2H), 7.19 (s, 1H), 3.64-3.18 (m, 4H), 1.37-1.00 (m, 6H).

Example No. I.1-194

¹H-NMR (400 MHz, CDCl₃ δ, ppm) 10.97 (br. s, 1H), 8.44 (d, 1H), 7.72 (t, 1H), 7.61 (d, 1H), 7.56 (t, 1H), 7.23 (s, 1H), 3.74 (m, 2H), 3.33 (m, 2H), 1.70-1.45 (m, 1H).

Example No. I.1-195

¹H-NMR (400 MHz, CDCl₃ δ, ppm) 10.94 (br. s, 1H), 8.44 (d, 1H), 7.71 (t, 1H), 7.58-7.53 (m, 2H), 7.21 (s, 1H), 3.65-2.85 (m, 5H), 1.30-1.02 (m, 3H).

Example No. I.1-196

¹H-NMR (400 MHz, CDCl₃ δ, ppm) 10.60 (br. s, 1H), 8.43 (d, 1H), 7.73 (t, 1H), 7.57-7.52 (m, 2H), 7.21 (s, 1H), 3.28-2.85 (m, 3H).

Example No. I.1-197

¹H-NMR (400 MHz, d⁶-DMSO δ, ppm) 8.29-8.21 (m, 3H), 7.72 (t, 1H), 7.53 (t, 1H), 7.48 (d, 1H), 3.60-3.40 (m, 3H).

Example No. I.1-198

¹H-NMR (400 MHz, CDCl₃ δ, ppm) 10.56 (br. s, 1H), 8.43 (d, 1H), 7.79 (d, 1H), 7.73 (t, 1H), 7.55 (t, 1H), 7.42 (s, 1H), 3.57 (s, 1H), 3.40 (s, 3H).

Example No. I.1-199

¹H-NMR (400 MHz, d⁶-DMSO δ, ppm) 11.49 (br. s, 1H), 8.23 (d, 1H), 7.75 (t, 1H), 7.57-7.53 (m, 2H), 7.28 (d, 1H), 3.70-3.38 (m, 8H).

Example No. I.1-200

¹H-NMR (400 MHz, d⁶-DMSO δ, ppm) 11.54 (br. s, 1H), 8.41 (m, 1H), 8.21-8.14 (m, 2H), 7.71 (t, 1H), 7.53-7.49 (m, 2H), 4.02 (d, 2H), 3.90 (m, 2H), 3.32-3.24 (m, 2H), 1.13 (t, 3H), 1.00 (t, 3H).

Example No. I.1-201

¹H-NMR (400 MHz, d⁶-DMSO δ, ppm) 11.50 (br. s, 1H), 8.48 (t, 1H), 8.20 (d, 1H), 8.16 (d, 1H), 7.72 (t, 1H), 7.52-7.49 (m, 2H), 4.08 (d, 2H), 3.75-3.40 (m, 8H).

Example No. I.1-202

¹H-NMR (400 MHz, CDCl₃ δ, ppm) 10.70 (br. s, 1H), 8.91 (d, 1H), 8.44 (d, 1H), 8.20 (d, 1H), 7.79 (t, 1H), 7.56 (t, 1H), 4.39 (q, 2H), 1.41 (t, 3H).

Example No. I.1-203

¹H-NMR (400 MHz, CDCl₃ δ, ppm) 10.15 (br. s, 1H), 8.89 (d, 1H), 8.44 (d, 1H), 8.16 (d, 1H), 7.79 (t, 1H), 7.58 (t, 1H), 4.29 (t, 2H), 1.81 (q, 2H), 1.06 (t, 3H).

Example No. I.1-204

¹H-NMR (400 MHz, CDCl₃ δ, ppm) 9.87 (br. s, 1H), 8.89 (d, 1H), 8.43 (d, 1H), 8.19 (d, 1H), 7.78 (t, 1H), 7.56 (t, 1H), 4.15 (d, 2H), 1.24 (m, 1H), 0.66-0.62 (m, 2H), 0.48-0.45 (m, 2H).

Example No. I.1-205

¹H-NMR (400 MHz, CDCl₃ δ, ppm) 10.70 (br. s, 1H), 8.91 (d, 1H), 8.43 (d, 1H), 8.17 (d, 1H), 7.77 (t, 1H), 7.56 (t, 1H), 5.12 (m, 1H), 1.71-1.65 (m, 2H), 1.33 (d, 3H), 0.98 (t, 3H).

Example No. I.1-206

¹H-NMR (400 MHz, CDCl₃ δ, ppm) 10.03 (br. s, 1H), 8.88 (d, 1H), 8.44 (d, 1H), 8.11 (d, 1H), 7.78 (t, 1H), 7.56 (t, 1H), 5.44 (m, 1H), 2.13-1.93 (m, 2H), 1.90-1.63 (m, 6H).

Example No. I.1-207

¹H-NMR (400 MHz, CDCl₃ δ, ppm) 10.92 (br. s, 1H), 8.92 (d, 1H), 8.46 (d, 1H), 8.22 (d, 1H), 7.79 (t, 1H), 7.56 (t, 1H), 4.59 (m, 1H), 1.43 (d, 3H), 1.13 (m, 1H), 0.65-0.40 (m, 4H).

Example No. I.1-208

¹H-NMR (400 MHz, CDCl₃ δ, ppm) 10.32 (br. s, 1H), 8.43 (d, 1H), 7.91 (d, 1H), 7.74 (t, 1H), 7.56 (t, 1H), 7.30 (s, 1H), 4.73 (m, 1H), 3.82 (s, 3H), 3.56-3.35 (m, 2H), 2.32 (m, 1H), 2.12-1.83 (m, 3H).

Example No. I.1-210

¹H-NMR (400 MHz, d⁶-DMSO δ, ppm) 11.48 (br. s, 1H), 8.22 (d, 1H), 7.74 (t, 1H), 7.55-7.49 (m, 2H), 7.22 (d, 1H), 3.56-3.29 (m, 9H), 2.54-2.38 (m, 8H), 2.24 (m, 1H), 1.76-1.66 (m, 2H), 1.54 (m, 1H), 1.23-0.99 (m, 3H).

Example No. I.1-211

¹H-NMR (400 MHz, d⁶-DMSO δ, ppm) 8.24 (m, 1H), 8.22-8.19 (m, 2H), 7.67 (t, 1H), 7.50 (s, 1H), 7.48 (t, 1H), 3.19 (q, 2H), 1.55-1.49 (m, 2H), 0.89 (t, 3H).

Example No. I.1-212

¹H-NMR (400 MHz, d⁶-DMSO δ, ppm) 11.62 (br. s, 1H), 8.81 (t, 1H), 8.24-8.21 (m, 2H), 7.73 (t, 1H), 7.55-7.52 (m, 2H), 3.99 (d, 2H), 3.68 (s, 3H).

Example No. I.1-213

¹H-NMR (400 MHz, d⁶-DMSO δ, ppm) 8.72 (d, 1H), 8.23 (d, 1H), 8.05 (d, 1H), 7.80 (t, 1H), 7.56 (t, 1H), 5.11 (m, 1H), 2.41-2.32 (m, 2H), 2.21-2.13 (m, 2H)

Example No. I.1-214

¹H-NMR (400 MHz, d⁶-DMSO δ, ppm) 8.87 (t, 1H), 8.26-8.21 (m, 2H), 7.72 (t, 1H), 7.57 (s, 1H), 7.51 (t, 1H), 7.36-7.32 (m, 4H), 7.24 (m, 1H), 4.44 (d, 2H).

Example No. I.1-215

¹H-NMR (400 MHz, d⁶-DMSO δ, ppm) 11.52 (br. s, 1H), 8.33 (t, 1H), 8.21 (d, 1H), 8.18 (d, 1H), 7.72 (t, 1H), 7.51 (t, 1H), 7.43 (d, 1H), 3.06 (t, 2H), 1.81 (m, 1H), 0.89 (d, 6H).

Example No. I.1-216

¹H-NMR (400 MHz, d⁶-DMSO δ, ppm) 11.51 (br. s, 1H), 8.21 (d, 1H), 8.18 (d, 1H), 8.12 (d, 1H), 7.73 (t, 1H), 7.52 (t, 1H), 7.41 (d, 1H), 3.88 (m, 1H), 1.52-1.44 (m, 2H), 1.12 (d, 3H), 0.87 (t, 3H)

Example No. I.1-217

¹H-NMR (400 MHz, d⁶-DMSO δ, ppm) 11.57 (br. s, 1H), 8.33 (t, 1H), 8.22 (d, 2H), 7.72 (t, 1H), 7.53 (t, 1H), 7.43 (d, 1H), 3.25 (q, 2H), 1.12 (t, 3H).

Example No. I.1-218

¹H-NMR (400 MHz, d⁶-DMSO δ, ppm) 11.30 (br. s, 1H), 8.44 (s, 1H), 8.08 (d, 1H), 8.03 (d, 1H), 7.71-7.64 (m, 3H). 7.17 (t, 1H), 6.56 (d, 1H).

Example No. I.1-219

¹H-NMR (400 MHz, d⁶-DMSO δ, ppm) 11.55 (br. s, 1H), 8.51 (t, 1H), 8.22 (d, 2H), 7.73 (t, 1H), 7.53-7.49 (m, 2H), 5.90 (m, 1H), 5.20 (dt, 1H), 5.10 (dt, 1H), 3.88 (m, 2H).

Example No. I.1-220

¹H-NMR (400 MHz, CDCl₃ δ, ppm) 10.42 (br. s, 1H), 8.44 (d, 1H), 7.71 (dd, 1H), 7.63-7.54 (m, 2H), 7.30 (br. s, 1H), 4.36 (t, 2H), 3.14 (s, 3H), 1.89 (m, 2H), 1.26 (t, 3H).

Example No. I.1-221

¹H-NMR (400 MHz, CDCl₃ δ, ppm) 10.33 (br. s, 1H), 8.46 (d, 1H), 7.72 (t, 1H), 7.57-7.53 (m, 2H), 7.17 (m, 1H), 3.10-2.68 (m, 3H), 1.69-1.43 (m, 1H), 1.28-1.00 (m, 6H).

Example No. I.1-222

¹H-NMR (400 MHz, d⁶-DMSO δ, ppm) 11.53 (br. s, 1H), 8.41 (t, 1H), 8.21 (d, 2H), 7.72 (t, 1H), 7.51 (t, 1H), 7.43 (d, 1H), 2.61 (t, 2H), 1.00 (m, 1H), 0.44-0.40 (m, 2H), 0.24-0.15 (m, 2H).

Example No. I.1-223

¹H-NMR (400 MHz, CDCl₃ δ, ppm) 10.11 (br. s, 1H), 8.46 (d, 1H), 7.72 (t, 1H), 7.61-7.53 (m, 2H), 7.29 (br. s, 1H), 4.29 (br. s, 2H), 3.11 (br. s, 3H), 2.31 (t, 1H).

Example No. I.1-224

¹H-NMR (400 MHz, d⁶-DMSO δ, ppm) 11.58 (br. s, 1H), 8.78 (t, 1H), 8.25-8.19 (m, 2H), 7.72 (t, 1H), 7.53-7.47 (m, 2H), 4.02 (t, 2H), 3.12 (t, 1H).

Example No. I.1-225

¹H-NMR (400 MHz, d⁶-DMSO δ, ppm) 11.38 (br. s, 1H), 8.18 (s, 1H), 7.79-7.72 (m, 2H), 7.21 (t, 1H), 6.59 (d, 1H), 2.63 (s, 3H), 2.42 (s, 3H).

Example No. I.1-226

¹H-NMR (400 MHz, d⁶-DMSO δ, ppm) 11.85 (br. s, 1H), 8.72 (d, 1H), 8.24 (d, 1H), 8.03 (d, 1H), 7.80 (t, 1H), 7.56 (t, 1H), 4.28 (t, 2H), 3.45 (t, 2H), 3.25 (s, 3H), 1.97-1.91 (m, 2H).

Example No. I.1-227

¹H-NMR (400 MHz, d⁶-DMSO δ, ppm) 11.84 (br. s, 1H), 8.72 (d, 1H), 8.25 (d, 1H), 8.01 (d, 1H), 7.80 (t, 1H), 7.57 (t, 1H), 4.23 (t, 2H), 1.73-1.67 (m, 2H), 1.42-1.25 (m, 6H), 0.87 (t, 3H)

Example No. I.1-228

¹H-NMR (400 MHz, d⁶-DMSO δ, ppm) 13.01 (br. s, 1H), 11.20 (br. s, 1H), 8.40-8.29 (m, 2H), 8.02 (s, 1H), 7.97 (d, 1H), 7.64 (d, 1H), 7.13 (t, 1H), 6.52 (d, 1H).

Example No. I.1-229

¹H-NMR (400 MHz, d⁶-DMSO δ, ppm) 11.83 (br. s, 1H), 8.72 (d, 1H), 8.25 (d, 1H), 8.03 (d, 1H), 7.81 (t, 1H), 7.57 (t, 1H), 4.03 (d, 2H), 2.03 (m, 1H), 0.98 (d, 6H).

Example No. I.1-230

¹H-NMR (400 MHz, d⁶-DMSO δ, ppm) 11.36 (br. s, 1H), 8.10 (s, 1H), 7.77-7.70 (m, 2H), 7.21 (t, 1H), 6.59 (d, 1H), 2.43 (s, 3H), 2.24 (s, 3H).

Example No. I.1-231

¹H-NMR (400 MHz, d⁶-DMSO δ, ppm) 11.89 (br. s, 1H), 8.72 (d, 1H), 8.25 (d, 1H), 8.02 (s, 1H), 7.80 (t, 1H), 7.58 (t, 1H), 4.38 (t, 2H), 3.66 (t, 2H), 3.29 (s, 3H).

Example No. I.1-232

¹H-NMR (400 MHz, d⁶-DMSO δ, ppm) 11.88 (br. s, 1H), 8.73 (d, 1H), 8.25 (d, 1H), 8.03 (d, 1H), 7.81 (t, 1H), 7.58 (t, 1H), 4.23 (t, 2H), 1.71-1.66 (m, 2H), 1.45-1.37 (m, 2H), 0.93 (t, 3H)

Example No. I.1-233

¹H-NMR (400 MHz, d⁶-DMSO δ, ppm) 11.42 (br. s, 1H), 8.22 (d, 1H), 7.73 (t, 1H), 7.54 (t, 1H), 7.48 (d, 1H), 7.21 (d, 1H), 3.01 (br. s, 3H), 1.15-0.78 (m, 1H), 0.53-0.02 (m, 4H).

Example No. I.1-235

¹H-NMR (400 MHz, d⁶-DMSO δ, ppm) 8.82-8.79 (m, 2H), 8.42 (d, 1H), 8.05 (t, 1H), 7.92 (t, 1H), 4.57 (t, 2H), 2.79 (t, 2H), 1.39 (s, 9H).

Example No. I.1-236

¹H-NMR (400 MHz, d⁶-DMSO δ, ppm) 12.42 (br. s, 1H), 11.89 (br. s, 1H), 8.71 (d, 1H), 8.24 (d, 1H), 7.99 (d, 1H), 7.80 (t, 1H), 7.57 (t, 1H), 4.41 (t, 2H), 2.71 (t, 2H)

Example No. I.1-237

¹H-NMR (400 MHz, d⁶-DMSO δ, ppm) 11.55 (br. s, 1H), 8.22 (d, 1H), 7.72 (t, 1H), 7.57 (d, 1H), 7.53 (t, 1H), 7.38 (d, 1H), 3.70 (q, 2H), 3.54 (s, 3H), 1.19 (t, 3H).

Example No. I.1-238

$^1$H-NMR (400 MHz, d$^6$-DMSO δ, ppm) 11.52 (br. s, 1H), 8.22 (d, 1H), 7.73 (t, 1H), 7.62 (d, 1H), 7.53 (t, 1H), 7.41 (d, 1H), 3.79 (q, 2H), 3.29 (s, 3H), 0.91 (t, 3H)

Example No. I.1-239

$^1$H-NMR (400 MHz, d$^6$-DMSO δ, ppm) 12.00 (br. s, 1H), 8.69 (d, 1H), 8.28 (d, 1H), 8.09 (d, 1H), 7.84 (t, 1H), 7.60 (t, 1H), 4.98 (q, 2H).

Example No. I.1-240

$^1$H-NMR (400 MHz, d$^6$-DMSO δ, ppm) 11.49 (br. s, 1H), 8.22 (d, 1H), 7.71 (t, 1H), 7.53-7.48 (m, 2H), 7.33 (d, 1H), 2.98 (s, 3H), 2.77 (m, 1H), 0.56-0.43 (m, 4H).

Example No. I.1-241

$^1$H-NMR (400 MHz, d$^6$-DMSO δ, ppm) 11.77 (br. s, 1H), 8.58 (d, 1H), 8.46 (d, 1H), 7.66 (t, 1H), 7.44 (d, 1H), 6.97 (d, 1H).

Example No. I.1-242

$^1$H-NMR (400 MHz, d$^6$-DMSO δ, ppm) 11.04 (br. s, 1H), 7.39 (d, 1H), 7.13 (t, 1H), 7.01 (dt, 1H), 6.84 (d, 1H), 6.66 (d, 1H), 5.61 (br. s, 2H).

Example No. I.1-243

$^1$H-NMR (400 MHz, d$^6$-DMSO δ, ppm) 11.28 (br. s, 1H), 8.21 (d, 1H), 7.53 (t, 1H), 7.33 (d, 2H), 7.12 (dt, 1H), 7.07 (d, 2H), 6.38 (d, 1H), 3.82 (s, 3H).

Example No. I.1-244

$^1$H-NMR (400 MHz, d$^6$-DMSO δ, ppm) 11.24 (br. s, 1H), 8.22 (d, 1H), 7.56-7.49 (m, 2H), 7.26 (m, 1H), 7.15 (m, 1H), 7.09-7.04 (m, 2H), 5.99 (d, 1H), 3.65 (s, 3H).

Example No. I.1-245

$^1$H-NMR (400 MHz, d$^6$-DMSO δ, ppm) 11.35 (br. s, 1H), 8.30 (d, 1H), 7.66-7.57 (m, 3H), 7.47-7.43 (m, 2H), 7.14 (t, 1H). 6.08 (d, 1H).

Example No. I.1-246

$^1$H-NMR (400 MHz, d$^6$-DMSO δ, ppm) 11.35 (br. s, 1H), 8.28 (d, 1H), 7.64 (d, 1H), 7.56-7.48 (m, 5H), 7.15 (t, 1H), 6.28 (d, 1H).

Example No. I.1-247

$^1$H-NMR (400 MHz, d$^6$-DMSO δ, ppm) 11.32 (br. s, 1H), 8.22 (d, 1H), 7.61 (d, 1H), 7.54 (t, 1H), 7.39-7.35 (m, 4H), 7.12 (t, 1H), 6.35 (d, 1H), 2.53 (s, 3H).

Example No. I.1-248

$^1$H-NMR (400 MHz, d$^6$-DMSO δ, ppm) 11.38 (br. s, 1H), 8.32 (d, 1H), 7.67 (d, 1H), 7.59 (m, 1H), 7.46 (m, 1H), 7.30 (m, 1H), 7.16 (t, 1H), 6.13 (d, 1H).

Example No. I.1-249

$^1$H-NMR (400 MHz, d$^6$-DMSO δ, ppm) 11.32 (br. s, 1H), 8.49 (m, 1H), 7.89 (d, 1H), 7.87 (s, 1H), 7.66 (d, 1H), 7.61-7.54 (m, 3H), 7.14 (t, 1H), 6.29 (d, 1H), 2.87 (m, 1H), 0.71-0.66 (m, 2H), 0.59-0.54 (m, 2H).

Example No. I.1-250

$^1$H-NMR (400 MHz, d$^6$-DMSO δ, ppm) 8.24 (d, 1H), 8.03 (s, 1H), 7.97-7.89 (m, 2H), 7.66 (d, 1H), 7.15 (t, 1H), 6.31 (d, 1H).

Example No. I.1-251

$^1$H-NMR (400 MHz, d$^6$-DMSO δ, ppm) 11.20 (br. s, 1H, NH), 8.21 (d, 1H), 7.53-7.40 (m, 2H), 7.17-7.13 (m, 2H), 7.08-7.03 (m, 2H), 5.98 (d, 1H), 3.66 (s, 3H).

Example No. I.1-252

$^1$H-NMR (400 MHz, d$^6$-DMSO δ, ppm) 8.33 (d, 1H), 7.88 (d, 1H), 7.77 (d, 1H), 7.66 (t, 1H), 7.58 (d, 1H), 7.43 (d, 1H), 7.23 (d, 1H), 6.60 (d, 1H).

Example No. I.1-253

$^1$H-NMR (400 MHz, d$^6$-DMSO δ, ppm) 8.62 (d, 1H), 8.50 (s, 1H), 8.18 (m, 1H), 8.09 (d, 1H), 7.90 (d, 1H), 7.87-7.75 (m, 2H), 7.59 (t, 1H), 7.19 (t, 1H), 6.61 (d, 1H), 2.86 (m, 1H), 0.74-0.66 (m, 2H), 0.62-0.54 (m, 2H).

Example No. I.1-254

$^1$H-NMR (400 MHz, d$^6$-DMSO δ, ppm) 8.50 (s, 1H), 8.30 (s, 1H), 8.18 (m, 1H), 8.09 (d, 1H), 7.90 (t, 1H), 7.77 (d, 1H), 7.58 (t, 1H), 7.42 (br. s, 2H, NH), 7.21 (d, 1H), 6.61 (d, 1H).

Example No. I.1-255

$^1$H-NMR (400 MHz, d$^6$-DMSO δ, ppm) 8.24 (s, 1H), 8.17 (d, 1H), 7.80 (d, 1H), 7.67-7.64 (m, 1H), 7.37-7.35 (m, 1H), 7.18-7.13 (m, 1H), 7.16 (dd, 1H), 6.55 (d, 1H), 3.79 (s, 3H).

Example No. I.2-1

$^1$H-NMR (400 MHz, d$^6$-DMSO δ, ppm) 7.87 (br. s, 1H, NH), 7.83 (d, 1H), 7.49 (dd, 1H), 7.34 (dd, 1H), 7.26 (d, 1H), 2.87 (s, 2H), 1.20 (s, 6H).

Example No. I.2-2

$^1$H-NMR (400 MHz, d$^6$-DMSO δ, ppm) 11.15 (br. s, 1H, NH), 7.93 (d, 1H), 7.52 (dd, 1H), 6.68 (d, 1H), 3.52 (m, 2H), 2.86 (m, 2H).

Example No. I.2-3

$^1$H-NMR (400 MHz, d$^6$-DMSO δ, ppm) 7.89 (br. s, 1H, NH), 7.81 (d, 1H), 7.48 (dd, 1H), 7.33 (dd, 1H), 7.29 (d, 1H), 2.93 (s, 2H), 1.58 (m, 2H), 1.49 (m, 8H).

Example No. I.2-4

$^1$H-NMR (400 MHz, CDCl$_3$ δ, ppm) 8.08 (d, 1H), 7.48 (m, 1H), 7.35 (m, 1H), 7.20 (d, 1H), 6.37 (br. s, 1H, NH), 3.58 (m, 2H), 3.01 (m, 2H).

Example No. I.2-5

¹H-NMR (400 MHz, CDCl₃ δ, ppm) 7.58 (s, 1H), 6.68 (s, 1H), 6.34 (br. s, 1H, NH), 3.93 (s, 6H), 3.58 (m, 2H), 2.93 (m, 2H).

Example No. I.2-6

¹H-NMR (400 MHz, d⁶-DMSO δ, ppm) 7.88 (br. s, 1H, NH), 7.82 (d, 1H), 7.47 (d, 1H), 7.33 (dd, 1H), 7.28 (d, 1H), 2.86 (s, 2H), 1.46 (q, 4H), 0.81 (t, 6H).

Example No. I.2-7

¹H-NMR (400 MHz, d⁶-DMSO δ, ppm) 7.74 (br. s, 1H, NH), 7.49 (s, 1H), 7.02 (s, 1H), 2.88 (s, 2H), 2.24 (s, 3H), 2.23 (s, 3H), 1.17 (s, 6H).

Example No. I.2-8

¹H-NMR (400 MHz, d⁶-DMSO δ, ppm) 11.12 (br. d, 1H, NH), 7.91 (m, 2H), 7.74 (dd, 1H), 7.62 (d, 1H), 7.36 (s, 1H, NH), 5.18 (d, 1H), 2.55 (s, 3H).

Example No. I.2-9

¹H-NMR (400 MHz, d⁶-DMSO δ, ppm) 9.46 (br. s, 1H, NH), 7.84 (d, 1H), 7.52 (dd, 1H), 7.40 (d, 1H), 7.34 (dd, 1H), 3.16 (d, 1H), 3.14 (d, 1H), 1.27 (s, 6H).

Example No. I.2-10

¹H-NMR (400 MHz, d⁶-DMSO δ, ppm) 7.88 (br. s, 1H, NH), 7.83 (d, 1H), 7.49 (dd, 1H), 7.33 (dd, 1H), 7.29 (d, 1H), 2.93 (d, 1H), 2.89 (d, 1H), 1.49 (m, 2H), 1.15 (s, 3H), 0.85 (t, 3H).

Example No. I.2-11

¹H-NMR (400 MHz, d⁶-DMSO δ, ppm) 12.98 (br. s, 1H, OH), 8.01 (d, 1H, NH), 7.85 (d, 1H), 7.48 (dd, 1H), 7.36 (dd, 1H), 7.31 (d, 1H), 4.23 (m, 1H), 3.20 (dd, 1H), 3.16 (dd, 1H).

Example No. I.2-12

¹H-NMR (400 MHz, CDCl₃ δ, ppm) 6.94 (s, 1H), 6.86 (s, 1H), 5.89 (br. s, 1H, NH), 3.44 (m, 2H), 2.91 (m, 2H), 2.68 (s, 3H), 2.32 (s, 3H).

Example No. I.2-13

¹H-NMR (400 MHz, CDCl₃ δ, ppm) 8.07 (d, 1H), 7.41 (dd, 1H), 7.18 (d, 1H), 6.26 (br. s, 1H, NH), 3.58 (m, 2H), 2.97 (m, 2H).

Example No. I.2-14

¹H-NMR (400 MHz, CDCl₃ δ, ppm) 7.78 (m, 1H), 7.18 (m, 1H), 7.14 (m, 1H), 6.33 (br. s, 1H, NH), 3.58 (m, 2H), 2.98 (m, 2H).

Example No. I.2-15

¹H-NMR (400 MHz, CDCl₃ δ, ppm) 8.00 (d, 1H), 7.32 (dd, 1H), 7.22 (d, 1H), 6.22 (br. s, 1H, NH), 3.58 (m, 2H), 2.99 (m, 2H).

Example No. I.2-16

¹H-NMR (400 MHz, d⁶-DMSO δ, ppm) 9.12 (s, 1H, OH), 7.93 (m, 2H), 7.74 (dd, 1H), 7.63 (dd, 1H), 7.36 (br. d, 1H, NH), 5.17 (d, 1H).

Example No. I.2-17

¹H-NMR (400 MHz, CDCl₃ δ, ppm) 8.10 (d, 1H), 7.51 (t, 1H), 7.43 (t, 1H), 7.31 (d, 1H), 6.19 (br. s, 1H), 3.97 (m, 1H), 3.78 (m, 1H), 3.70 (s, 3H).

Example No. I.2-18

¹H-NMR (400 MHz, CDCl₃ δ, ppm) 7.44-7.36 (m, 2H), 6.89 (d, 1H), 6.71 (d, 1H), 3.91 (s, 3H), 3.49-3.44 (m, 2H), 2.93 (t, 2H).

Example No. I.2-19

¹H-NMR (400 MHz, CDCl₃ δ, ppm) 7.69 (d, 1H), 7.30 (t, 1H), 7.03 (d, 1H), 6.23 (br. s, 1H), 3.86 (s, 3H), 3.53 (dt, 2H), 2.97 (t, 2H).

Example No. I.2-20

¹H-NMR (400 MHz, CDCl₃ δ, ppm) 7.96 (d, 1H), 7.31 (d, 1H), 7.26 (m, 1H), 5.78 (br. s, 1H), 3.55 (dt, 2H), 2.92 (t, 2H), 2.30 (s, 3H).

Example No. I.2-21

¹H-NMR (400 MHz, CDCl₃ δ, ppm) 7.96 (d, 1H), 7.26 (dd, 1H), 7.12 (d, 1H), 5.92 (br. m, 1H), 2.98 (m, 2H), 2.69 (m, 2H), 2.31 (s, 3H).

Example No. I.2-22

¹H-NMR (400 MHz, CDCl₃ δ, ppm) 7.83 (br. s, 1H), 7.32-7.25 (m, 2H), 6.62 (d, 1H), 2.94 (t, 2H), 2.63 (t, 2H).

Example No. I.2-23

¹H-NMR (400 MHz, CDCl₃ δ, ppm) 7.47 (d, 1H), 7.29 (m, 1H), 7.08 (d, 1H), 6.32 (br. m, 1H), 3.48 (m, 2H), 2.91 (m, 2H).

Example No. I.2-24

¹H-NMR (400 MHz, CDCl₃ δ, ppm) 7.93 (d, 1H), 7.17 (d, 1H), 6.61 (br. s, 1H), 3.56 (dt, 2H), 2.95 (t, 2H), 2.48 (s, 3H).

Example No. I.2-26

¹H-NMR (400 MHz, CDCl₃ δ, ppm) 7.78 (s, 1H), 7.13 (s, 2H), 6.20 (br. s, 1H), 3.56-3.49 (m, 2H), 2.88 (t, 2H), 2.31 (s, 3H), 2.27 (s, 3H).

Example No. I.2-27

¹H-NMR (400 MHz, CDCl₃ δ, ppm) 7.90 (s, 1H), 7.31 (d, 1H), 7.13 (d, 1H), 3.56 (dt, 2H), 2.98 (t, 2H), 2.68 (q, 2H), 1.23 (t, 3H).

Example No. I.2-29

¹H-NMR (400 MHz, CDCl₃ δ, ppm) 12.40 (br. s, 1H), 8.09 (s, 1H), 7.50 (d, 1H), 7.15 (d, 1H), 3.56 (dt, 2H), 2.97 (t, 2H), 1.32 (s, 9H).

Example No. I.2-30

¹H-NMR (400 MHz, CDCl₃ δ, ppm) 7.58 (d, 1H), 7.39 (d, 1H), 7.14 (m, 1H), 5.86 (br. m, 1H), 3.53 (m, 2H), 2.95 (m, 2H), 2.32 (s, 3H).

Example No. I.2-32

¹H-NMR (400 MHz, CDCl₃ δ, ppm) 8.11 (s, 1H), 7.52 (d, 1H), 7.26 (d, 1H), 5.89 (br. s, 1H), 3.29 (d, 2H), 1.32 (s, 15H).

Example No. I.2-33

¹H-NMR (400 MHz, CDCl₃ δ, ppm) 8.01 (s, 1H), 7.52 (s, 1H), 5.90 (br. s, 1H), 3.58 (dt, 2H), 3.08 (t, 2H).

Example No. I.2-34

¹H-NMR (400 MHz, CDCl₃ δ, ppm) 7.94 (d, 1H), 7.31 (d, 1H), 7.23 (t, 1H), 6.39 (br. s, 1H), 3.76 (dd, 1H), 3.32-3.28 (m, 2H), 3.32 (s, 3H), 1.29 (d, 2H).

Example No. I.2-39

¹H-NMR (400 MHz, d⁶-DMSO δ, ppm) 12.77 (br. s, 1H), 7.93 (d, 1H), 7.82 (d, 1H), 7.49 (t, 1H), 7.43-7.41 (m, 2H), 3.89 (t, 1H), 3.68-3.53 (m, 2H).

Example No. I.2-40

¹H-NMR (400 MHz, d⁶-DMSO δ, ppm) 7.97 (m, 1H), 7.85 (d, 1H), 7.52 (t, 1H), 7.42 (t, 1H), 7.38 (d, 1H), 4.06 (t, 1H), 3.69-3.58 (m, 5H), 3.34 (s, 3H).

Example No. I.2-41

¹H-NMR (400 MHz, d⁶-DMSO δ, ppm) 8.10 (d, 1H), 7.52 (t, 1H), 7.43 (t, 1H), 7.32 (d, 1H), 5.87 (br. s, 1H), 4.20-4.14 (m, 2H), 3.96 (m, 1H), 3.85 (m, 1H), 3.77 (m, 1H), 1.21 (t, 3H).

Example No. I.2-42

¹H-NMR (400 MHz, d⁶-DMSO δ, ppm) 7.91-7.84 (m, 2H), 7.47 (t, 1H), 7.39 (t, 1H), 7.17 (d, 1H), 4.32 (t, 1H), 3.78 (s, 3H), 3.55-3.49 (m, 2H), 3.18 (s, 3H).

Example No. I.2-43

¹H-NMR (400 MHz, d⁶-DMSO δ, ppm) 8.20 (d, 1H), 7.88-7.83 (m, 2H), 7.49 (t, 1H), 7.38 (t, 1H), 7.18 (d, 1H), 3.72 (t, 1H), 3.56-3.40 (m, 2H), 2.68 (m, 1H), 0.67-0.62 (m, 2H), 0.44-0.39 (m, 2H).

Example No. I.2-44

¹H-NMR (400 MHz, d⁶-DMSO δ, ppm) 7.91 (br. s, 1H), 7.88 (d, 1H), 7.49 (m, 1H), 7.38 (t, 1H), 7.04 (d, 1H), 4.38 (m, 1H), 3.52-3.25 (m, 6H), 1.17 (t, 3H).

Example No. I.2-45

¹H-NMR (400 MHz, d⁶-DMSO δ, ppm) 7.98 (m, 1H), 7.84 (d, 1H), 7.53 (t, 1H), 7.42 (t, 1H), 7.38 (d, 1H), 4.90 (m, 1H), 4.01 (t, 1H), 3.68-3.59 (m, 2H), 2.29-2.18 (m, 2H), 1.99-1.84 (m, 2H), 1.71 (m, 1H), 1.58 (m, 1H).

Example No. I.2-46

¹H-NMR (400 MHz, d⁶-DMSO δ, ppm) 7.98 (m, 1H), 7.85 (d, 1H), 7.52 (t, 1H), 7.41 (t, 1H), 7.39 (d, 1H), 4.07 (t, 1H), 3.92 (d, 2H), 3.68-3.59 (m, 2H), 1.03 (m, 1H), 0.48-0.45 (m, 2H), 0.23-0.19 (m, 2H).

Example No. I.2-47

¹H-NMR (400 MHz, d⁶-DMSO δ, ppm) 8.02 (d, 1H), 7.73 (t, 1H), 7.57-7.54 (m, 2H), 4.70 (d, 1H), 4.39 (m, 1H), 4.13-4.05 (m, 2H), 3.98-3.85 (m, 4H), 1.13 (m, 1H), 1.02 (m, 1H), 0.57-0.53 (m, 2H), 0.19-0.15 (m, 2H).

Example No. I.2-48

¹H-NMR (400 MHz, d⁶-DMSO δ, ppm) 8.39 (br. s, 1H), 7.86 (d, 1H), 7.53 (t, 1H), 7.41 (t, 1H), 7.33 (d, 1H), 4.89 (m, 1H), 3.99 (m, 1H), 3.66-3.58 (m, 2H), 1.18 (d, 3H), 1.13 (d, 3H).

Example No. I.2-50

¹H-NMR (400 MHz, CDCl₃ δ, ppm) 7.69 (d, 1H), 7.28 (t, 1H), 6.99 (d, 1H), 5.87 (br. s, 1H), 4.03 (t, 2H), 3.62 (t, 2H), 3.53 (dt, 2H), 2.98 (t, 2H), 2.02-1.99 (m, 4H), 1.57 (dt, 2H), 0.98 (t, 2H).

Example No. I.2-51

¹H-NMR (400 MHz, CDCl₃ δ, ppm) 7.70 (d, 1H), 7.21 (t, 1H), 6.92 (d, 1H), 5.81 (br. s, 1H), 5.02 (br. s, 1H).

Example No. I.2-52

¹H-NMR (400 MHz, CDCl₃ δ, ppm) 7.81 (d, 1H), 7.31 (t, 1H), 7.16 (d, 1H), 6.08 (br. s, 1H), 3.51 (dt, 2H), 2.94 (t, 2H), 2.64 (s, 3H),

Example No. I.2-53

¹H-NMR (400 MHz, CDCl₃ δ, ppm) 7.68 (t, 1H), 7.30-7.26 (m, 1H), 6.98 (d, 1H), 6.27 (br. s, 1H), 4.05-4.00 (m, 2H), 3.63 (t, 2H), 3.55-3.51 (m, 2H), 3.07 (t, 2H), 2.95 (t, 2H), 2.48-2.37 (m, 3H), 1.99 (t, 2H), 1.86-1.78 (m, 3H), 1.74-1.58 (m, 4H), 1.45 (m, 1H).

Example No. I.2-54

¹H-NMR (400 MHz, d⁶-DMSO δ, ppm) 8.45 (d, 1H), 7.97 (dd, 1H), 7.91 (br. s, 1H), 7.57 (d, 1H), 7.48 (d, 1H), 7.32 (t, 1H), 7.25 (d, 1H), 5.21 (s, 2H), 3.37-3.29 (m, 2H), 2.85 (t, 2H).

Example No. I.2-55

¹H-NMR (400 MHz, d⁶-DMSO δ, ppm) 7.89 (br. s, 1H), 7.42 (d, 1H), 7.28-7.21 (m, 6H), 7.17 (d, 1H), 4.23 (t, 2H), 3.32 (dt, 2H), 3.07 (t, 2H), 2.73 (t, 2H).

Example No. I.2-56

¹H-NMR (400 MHz, d⁶-DMSO δ, ppm) 7.90 (br. s, 1H), 7.47 (d, 1H), 7.28 (t, 1H), 7.23 (d, 1H), 7.05 (s, 2H), 6.96 (s, 1H), 5.07 (s, 2H), 3.33 (dt, 2H), 2.84 (t, 2H), 2.28 (s, 6H).

Example No. I.2-57

¹H-NMR (400 MHz, d⁶-DMSO δ, ppm) 7.89 (br. s, 1H), 7.52-7.44 (m, 4H), 7.28 (t, 1H), 7.22 (d, 1H), 5.16 (s, 2H), 3.33 (dt, 2H), 2.84 (t, 2H).

Example No. I.2-58

¹H-NMR (400 MHz, d⁶-DMSO δ, ppm) 7.92 (br. s, 1H), 7.77 (d, 1H), 7.65 (d, 1H), 7.49 (d, 1H), 7.31 (t, 1H), 7.23 (d, 1H), 5.27 (s, 2H), 3.33 (dt, 2H), 2.88 (t, 2H).

Example No. I.2-59

¹H-NMR (400 MHz, d⁶-DMSO δ, ppm) 7.91 (br. s, 1H), 7.71 (s, 1H), 7.66 (d, 1H), 7.51-7.48 (m, 2H), 7.32 (t, 1H), 7.27 (d, 1H), 5.20 (s, 2H), 3.32 (dt, 2H), 2.84 (t, 2H).

Example No. I.2-60

¹H-NMR (400 MHz, d⁶-DMSO δ, ppm) 7.90 (br. s, 1H), 7.48 (d, 1H), 7.31-7.21 (m, 5H), 7.14 (d, 1H), 5.11 (s, 2H), 3.33 (dt, 2H), 2.85 (t, 2H), 2.31 (s, 3H).

Example No. I.2-83

¹H-NMR (400 MHz, d⁶-DMSO δ, ppm) 11.14 (br. s, 1H, NH), 7.64 (d, 1H), 7.62 (s, 1H), 7.25 (d, 1H), 7.19 (br. s, 1H, NH), 6.96 (br. m, 1H, NH), 3.43 (m, 2H), 3.29 (m, 2H), 3.21 (m, 2H), 2.95 (m, 2H), 1.37 (s, 9H).

Example No. I.2-86

¹H-NMR (400 MHz, d⁶-DMSO δ, ppm) 10.82 (br. s, 1H, NH), 7.92 (s, 1H), 7.63 (br. s, 1H, NH), 7.05 (s, 1H), 3.37 (m, 2H), 2.94 (m, 2H), 2.29 (s, 3H), 2.16 (s, 3H).

Example No. I.3-1

¹H-NMR (400 MHz, d⁶-DMSO δ, ppm) 11.29 (br. s, 1H, NH), 8.12 (d, 1H), 7.88 (d, 1H), 7.71 (dd, 1H), 7.40 (dd, 1H), 5.04 (s, 1H), 2.65 (s, 3H).

Example No. I.3-2

¹H-NMR (400 MHz, d⁶-DMSO δ, ppm) 11.63 (br. s, 1H, NH), 10.94 (br. s, 1H, NH), 8.09 (d, 1H), 7.69 (dd, 1H), 7.61 (m, 3H), 7.47 (dd, 1H), 7.38 (d, 2H), 5.09 (s, 1H).

Example No. I.3-3

¹H-NMR (400 MHz, d⁶-DMSO δ, ppm) 11.60 (br. s, 1H, NH), 8.28 (d, 1H), 8.19 (d, 1H), 7.95 (m, 2H), 7.79 (m, 3H), 7.69 (dd, 1H), 7.65 (dd, 1H), 5.05 (s, 1H).

Example No. I.3-4

¹H-NMR (400 MHz, d⁶-DMSO δ, ppm) 11.31 (br. s, 1H, NH), 8.01 (d, 1H), 7.73 (dd, 1H), 7.56 (d, 1H), 7.48 (dd, 1H), 2.38 (m, 4H), 1.91 (m, 4H).

Example No. I.3-5

¹H-NMR (400 MHz, d⁶-DMSO δ, ppm) 11.50 (br. s, 1H, NH), 8.04 (d, 1H), 7.76 (d, 1H), 7.67 (dd, 1H), 7.48 (dd, 1H), 3.77 (q, 4H), 3.21 (s, 2H), 3.20 (s, 2H), 0.90 (t, 6H).

Example No. I.3-6

¹H-NMR (400 MHz, d⁶-DMSO δ, ppm) 11.63 (br. s, 1H, NH), 10.82 (br. s, 1H, NH), 8.09 (d, 1H), 7.71 (d, 1H), 7.58 (m, 3H), 7.49 (dd, 1H), 7.35 (m, 2H), 7.11 (dd, 1H), 5.10 (s, 1H).

Example No. I.3-7

¹H-NMR (400 MHz, d⁶-DMSO δ, ppm) 11.61 (br. s, 1H, NH), 10.13 (br. s, 1H, NH), 8.08 (d, 1H), 7.80 (d, 1H), 7.72 (dd, 1H), 7.61 (m, 1H), 7.53 (m, 2H), 7.49 (m, 1H), 6.88 (dd, 1H), 5.51 (s, 1H), 3.91 (s, 3H).

Example No. I.3-8

¹H-NMR (400 MHz, d⁶-DMSO δ, ppm) 11.61 (br. s, 1H, NH), 10.73 (br. s, 1H, NH), 8.08 (d, 1H), 7.71 (dd, 1H), 7.53 (dd, 1H), 7.46 (m, 3H), 7.04 (d, 2H), 5.07 (s, 1H), 2.25 (s, 3H).

Example No. I.3-9

¹H-NMR (400 MHz, d⁶-DMSO δ, ppm) 11.33 (br. s, 1H, NH), 8.64 (br. t, 1H, NH), 7.46 (s, 1H), 6.92 (s, 1H), 4.66 (s, 1H), 3.84 (s, 3H), 3.83 (s, 3H), 3.11 (dq, 2H), 1.04 (t, 3H).

Example No. I.3-10

¹H-NMR (400 MHz, d⁶-DMSO δ, ppm) 11.64 (br. s, 1H, NH), 10.77 (s, 1H, NH), 7.58 (m, 2H), 7.54 (s, 1H), 7.41 (d, 1H), 7.35 (m, 2H), 7.29 (d, 1H), 7.12 (m, 1H), 5.01 (s, 1H), 3.84 (s, 3H).

Example No. I.3-11

¹H-NMR (400 MHz, d⁶-DMSO δ, ppm) 11.56 (br. s, 1H, NH), 8.08 (d, 1H), 7.73 (m, 1H), 7.69 (d, 1H), 7.52 (m, 1H), 5.04 (m, 2H), 2.93 (m, 2H), 2.86 (m, 2H), 1.89 (s, 6H).

Example No. I.3-15

¹H-NMR (400 MHz, d⁶-DMSO δ, ppm) 11.84 (br. s, 1H, NH), 8.07 (d, 1H), 7.45 (d, 1H), 7.46 (s, 1H), 3.91 (s, 3H), 3.86 (s, 2H).

Example No. I.3-28

¹H-NMR (400 MHz, d⁶-DMSO δ, ppm) 11.64 (br. s, 1H, NH), 8.02 (s, 1H), 7.97 (s, 1H), 3.90 (s, 2H).

Example No. I.3-29

¹H-NMR (400 MHz, d⁶-DMSO δ, ppm) 11.23 (br. s, 1H, NH), 7.90 (d, 1H), 7.28 (dd, 1H), 7.19 (d, 1H), 3.98 (s, 2H).

Example No. I.3-30

¹H-NMR (400 MHz, d⁶-DMSO δ, ppm) 11.53 (br. s, 1H, NH), 8.26 (m, 1H), 8.20 (m, 1H), 7.81 (m, 1H), 4.13 (s, 2H).

Example No. I.3-31

¹H-NMR (400 MHz, d⁶-DMSO δ, ppm) 11.42 (br. s, 1H, NH), 8.12 (d, 1H), 7.88 (dd, 1H), 7.43 (d, 1H), 4.09 (s, 2H).

Example No. I.3-32

¹H-NMR (400 MHz, d⁶-DMSO δ, ppm) 11.35 (br. s, 1H, NH), 8.08 (d, 1H), 7.30 (m, 2H), 4.08 (s, 2H).

Example No. I.3-33

¹H-NMR (400 MHz, d⁶-DMSO δ, ppm) 11.56 (br. s, 1H, NH), 8.12 (d, 1H), 7.92 (d, 1H), 7.67 (s, 1H), 3.98 (s, 2H).

Example No. I.3-36

¹H-NMR (400 MHz, d⁶-DMSO δ, ppm) 11.33 (br. s, 1H, NH), 7.62 (d, 1H), 7.44 (dd, 1H), 7.30 (d, 1H), 3.87 (s, 3H), 3.74 (s, 2H).

Example No. I.3-38

¹H-NMR (400 MHz, d⁶-DMSO δ, ppm) 11.33 (br. s, 1H, NH), 7.89 (d, 1H), 7.52 (d, 1H), 7.38 (dd, 1H), 3.90 (s, 2H).

Example No. I.3-39

¹H-NMR (400 MHz, d⁶-DMSO δ, ppm) 11.70 (br. s, 1H, NH), 8.10 (m, 2H), 4.04 (s, 2H).

Example No. I.3-42

¹H-NMR (400 MHz, d⁶-DMSO δ, ppm) 11.41 (br. s, 1H, NH), 7.88 (m, 2H), 7.54 (m, 1H), 7.26 (d, 1H), 6.81 (dd, 1H), 6.41 (d, 1H), 4.29 (m, 1H), 3.67 (m, 1H), 3.60 (m, 1H).

Example No. I.4-1

¹H-NMR (400 MHz, d₆-DMSO δ, ppm) 11.97 (br. s, 1H, NH), 8.13 (d, 1H), 8.06 (d, 1H), 7.94 (dd, 1H), 7.88 (dd, 1H).

Example No. I.4-8

¹H-NMR (400 MHz, d₆-DMSO δ, ppm) 12.07 (br. s, 1H, NH), 8.26 (d, 1H), 7.91 (d, 1H), 7.89 (s, 1H).

Example No. I.4-9

¹H-NMR (400 MHz, d₆-DMSO δ, ppm) 11.91 (br. s, 1H, NH), 8.01 (d, 1H), 7.86 (s, 1H), 7.73 (d, 1H), 2.49 (s, 3H).

Example No. I.4-10

¹H-NMR (400 MHz, d₆-DMSO δ, ppm) 11.99 (s, 1H, NH), 8.20 (m, 1H), 7.76 (m, 2H).

Example No. I.4-11

¹H-NMR (400 MHz, d₆-DMSO δ, ppm) 11.99 (s, 1H, NH), 8.03 (d, 1H), 7.54 (s, 1H), 7.42 (d, 1H), 3.96 (s, 3H)

Example No. I.4-14

¹H-NMR (400 MHz, d₆-DMSO δ, ppm) 11.90 (br. s, 1H, NH), 8.06 (d, 1H), 7.81 (dd, 1H), 7.70 (d, 1H), 2.67 (s, 3H).

Example No. I.5-1

¹H-NMR (400 MHz, d₆-DMSO δ, ppm) 11.78 (br. s, 1H, NH), 8.20 (d, 1H), 8.11 (d, 1H), 8.04 (m, 1H), 7.68 (s, 1H), 7.50 (m, 2H), 7.42 (m, 3H), 7.18 (m, 1H).

Example No. I.5-2

¹H-NMR (400 MHz, d₆-DMSO δ, ppm) 11.59 (br. s, 1H, NH), 8.22 (d, 1H), 8.10 (d, 1H), 8.02 (s, 1H), 7.73 (m, 1H), 7.54 (m, 2H), 7.38 (m, 1H), 6.82 (m, 1H).

Example No. I.5-3

¹H-NMR (400 MHz, d₆-DMSO δ, ppm) 11.57 (br. s, 1H, NH), 8.64 (s, 1H), 8.30 (d, 1H), 8.12 (d, 1H), 8.04 (m, 2H), 7.79 (m, 1H), 7.53 (m, 1H), 7.32 (m, 1H).

Example No. I.5-17

¹H-NMR (400 MHz, d₆-DMSO δ, ppm) 11.36 (br. s, 1H, NH), 8.09 (d, 1H), 8.05 (m, 1H), 7.96 (s, 1H), 7.89 (d, 1H), 7.48 (m, 3H), 6.98 (m, 2H), 3.77 (m, 4H), 3.39 (m, 4H).

Example No. I.5-18

¹H-NMR (400 MHz, d₆-DMSO δ, ppm) 11.53 (br. s, 1H, NH), 8.53 (s, 1H), 8.26 (d, 1H), 8.09 (d, 1H), 7.88 (d, 1H), 7.76 (dd, 1H), 7.51 (dd, 1H), 7.06 (d, 1H), 2.58 (s, 3H).

Example No. I.5-25

¹H-NMR (400 MHz, d₆-DMSO δ, ppm) 11.41 (br. s, 1H, NH), 8.19 (d, 1H), 8.12 (s, 1H), 8.08 (d, 1H), 7.86 (s, 1H), 7.73 (dd, 1H), 7.50 (dd, 1H), 3.72 (s, 3H), 2.29 (s, 3H).

Example No. I.5-30

¹H-NMR (400 MHz, d₆-DMSO δ, ppm) 11.54 (br. s, 1H, NH), 9.15 (br. s, 1H, OH), 8.05 (d, 1H), 7.96 (s, 1H), 7.88 (m, 1H), 7.52 (m, 1H), 7.48 (m, 1H), 6.91 (s, 2H), 3.81 (s, 3H), 3.68 (s, 3H).

Example No. I.5-31

¹H-NMR (400 MHz, d₆-DMSO δ, ppm) 11.57 (br. s, 1H, NH), 10.16 (br. s, 1H, OH), 8.08 (d, 1H), 7.92 (s, 1H), 7.74 (m, 1H), 7.51 (m, 2H), 7.33 (s, 1H), 7.18 (s, 1H), 3.88 (s, 3H).

Example No. I.5-32

¹H-NMR (400 MHz, d₆-DMSO δ, ppm) 11.56 (br. s, 1H, NH), 8.32 (s, 1H), 8.23 (d, 1H), 8.11 (d, 1H), 7.93 (d, 1H), 7.78 (dd, 1H), 7.53 (dd, 1H), 7.19 (d, 1H), 2.60 (s, 3H).

Example No. I.5-36

¹H-NMR (400 MHz, d₆-DMSO δ, ppm) 11.57 (br. s, 1H, NH), 8.08 (d, 1H), 8.00 (s, 1H), 7.69 (m, 1H), 7.52 (m, 2H), 7.48 (m, 2H), 7.00 (m, 2H), 3.84 (s, 3H).

Example No. I.5-42

¹H-NMR (400 MHz, d₆-DMSO δ, ppm) 11.48 (br. s, 1H, NH), 10.17 (br. s, 1H, OH), 8.07 (d, 1H), 7.94 (s, 1H), 7.73 (m, 1H), 7.50 (m, 2H), 7.34 (s, 1H), 7.18 (s, 1H), 3.92 (s, 3H).

Example No. I.5-43

¹H-NMR (400 MHz, d₆-DMSO δ, ppm) 11.45 (br. s, 1H, NH), 8.78 (s, 1H), 8.23 (s, 1H), 8.17 (d, 1H), 8.15 (d, 1H), 7.76 (dd, 1H), 7.49 (dd, 1H), 3.95 (s, 3H).

Example No. I.5-52

¹H-NMR (400 MHz, d₆-DMSO δ, ppm) 11.72/11.51 (br. s, 1H, NH), 8.29/8.21 (s, 1H), 8.10 (m, 2H), 7.78 (m, 2H), 7.75

(m, 1H), 7.70 (m, 1H), 7.51 (m, 1H), 7.44 (m, 1H), 3.81 (s, 3H), 3.73 (s, 3H), 3.68 (s, 3H).

Example No. I.5-55

$^1$H-NMR (400 MHz, d$_6$-DMSO δ, ppm) 11.61 (br. s, 1H, NH), 8.08 (m, 1H), 7.72 (m, 1H), 7.51 (m, 2H), 6.89 (s, 1H), 3.81 (s, 3H), 3.73 (s, 3H), 3.68 (s, 3H).

Example No. I.5-62

$^1$H-NMR (400 MHz, d$_6$-DMSO δ, ppm) 11.69 (br. s, 1H, NH), 8.58 (s, 1H), 8.28 (d, 1H), 8.12 (m, 2H), 8.04 (d, 1H), 7.81 (dd, 1H), 7.58 (dd, 1H).

Example No. I.5-63

$^1$H-NMR (400 MHz, d$_6$-DMSO δ, ppm) 11.69 (br. s, 1H, NH), 8.57 (s, 1H), 8.30 (d, 1H), 8.18 (d, 1H), 7.86 (d, 1H), 7.79 (dd, 1H), 7.56 (dd, 1H), 7.47 (d, 1H).

Example No. I.5-65

$^1$H-NMR (400 MHz, d$_6$-DMSO δ, ppm) 11.69 (br. s, 1H, NH), 8.56 (s, 1H), 8.29 (d, 1H), 8.12 (d, 1H), 7.92 (d, 1H), 7.80 (dd, 1H), 7.56 (dd, 1H), 7.38 (d, 1H).

Example No. I.5-75

$^1$H-NMR (400 MHz, d$_6$-DMSO δ, ppm) 11.62 (s, 1H, NH), 8.68 (s, 1H), 8.20 (m, 1H), 8.17 (m, 1H), 8.09 (m, 2H), 7.38 (m, 1H), 7.33 (m, 1H).

Example No. I.5-77

$^1$H-NMR (400 MHz, d$_6$-DMSO δ, ppm) 14.35 (br. s, 1H, OH), 11.81 (s, 1H, NH), 8.94 (s, 1H), 8.18 (d, 1H), 7.79 (d, 1H).

Example No. I.5-78

$^1$H-NMR (400 MHz, d$_6$-DMSO δ, ppm) 11.90 (s, 1H, NH), 8.74 (s, 1H), 8.17 (d, 1H), 7.80 (d, 1H), 7.49 (m, 2H), 7.42 (m, 3H), 5.58 (s, 2H).

Example No. I.5-81

$^1$H-NMR (400 MHz, d$_6$-DMSO δ, ppm) 11.81 (br. s, 1H, NH), 8.82 (s, 1H), 8.66 (s, 1H), 8.29 (d, 1H), 8.15 (d, 1H), 8.09 (d, 1H), 7.83 (d, 1H), 7.34 (m, 1H).

Example No. I.5-83

$^1$H-NMR (400 MHz, d$_6$-DMSO δ, ppm) 11.71/11.48 (br. s, 1H, NH), 8.23/8.19 (s, 1H), 8.14 (m, 1H), 7.78 (m, 1H), 7.49 (m, 3H), 7.41 (m, 2H), 7.34 (m, 1H).

Example No. I.5-84

$^1$H-NMR (400 MHz, d$_6$-DMSO δ, ppm) 11.83 (br. s, 1H, NH), 8.75 (d, 1H), 8.19 (d, 1H), 7.81 (dd, 1H), 7.72 (dd, 1H), 7.49 (m, 2H), 7.41 (m, 2H), 7.39 (m, 1H), 5.54 (s, 2H).

Example No. I.5-86

$^1$H-NMR (400 MHz, d$_6$-DMSO δ, ppm) 11.73 (br. s, 1H, NH), 8.67 (s, 1H), 8.34 (d, 1H), 8.06 (m, 2H), 8.03 (d, 1H), 7.85 (d, 1H), 7.32 (d, 1H).

Example No. I.5-87

$^1$H-NMR (400 MHz, d$_6$-DMSO δ, ppm) 11.73 (br. s, 1H, NH), 8.38 (s, 1H), 8.12 (d, 1H), 7.96 (m, 1H), 7.84 (s, 1H), 7.63 (d, 1H), 7.39 (d, 1H), 6.32 (d, 1H), 3.95 (s, 3H).

Example No. I.6-1

$^1$H-NMR (400 MHz, d$^6$-DMSO δ, ppm) 10.57 (br. d, 1H, NH), 8.31 (d, 1H), 8.19 (d, 1H), 7.91 (m, 2H), 7.82 (dd, 1H), 2.63 (s, 3H).

Example No. I.6-2

$^1$H-NMR (400 MHz, d$^6$-DMSO δ, ppm) 11.12 (br. d, 1H, NH), 8.28 (d, 1H), 8.18 (d, 1H), 7.84 (m, 2H), 7.62 (m, 1H), 1.28 (s, 9H).

Example No. I.6-3

$^1$H-NMR (400 MHz, d$^6$-DMSO δ, ppm) 10.64 (br. d, 1H, NH), 8.30 (d, 1H), 8.12 (d, 1H), 7.88 (m, 4H), 7.76 (dd, 1H), 7.69 (dd, 1H), 7.55 (m, 2H).

Example No. I.6-4

$^1$H-NMR (400 MHz, d$^6$-DMSO δ, ppm) 9.73 (br. s, 1H, NH), 8.16 (d, 1H), 7.99 (m, 2H), 7.88 (d, 1H), 3.72 (s, 3H), 3.27 (s, 3H).

Example No. I.6-5

$^1$H-NMR (400 MHz, d$^6$-DMSO δ, ppm) 10.60 (br. d, 1H, NH), 8.30 (d, 1H), 8.11 (d, 1H), 8.02 (d, 1H), 7.90 (dd, 1H), 7.92 (dd, 1H), 4.34 (t, 2H), 1.75 (m, 2H), 1.45 (m, 2H), 0.95 (t, 3H).

Example No. I.6-6

$^1$H-NMR (400 MHz, d$^6$-DMSO δ, ppm) 11.40 (br. s, 1H, NH), 8.29 (d, 1H), 8.16 (d, 1H), 7.92 (dd, 1H), 7.81 (dd, 1H), 7.42 (d, 1H), 7.35 (s, 1H), 7.17 (s, 1H), 7.12 (d, 1H), 2.35 (s, 3H), 2.32 (s, 3H)

Example No. I.7-1

$^1$H-NMR (400 MHz, CDCl$_3$ δ, ppm) 9.08 (br. s, 1H, NH), 8.52 (d, 1H), 8.27 (d, 1H), 7.79 (m, 2H), 7.59 (m, 1H), 7.21 (dd, 1H), 6.98 (d, 1H), 4.00 (s, 3H).

Example No. I.7-2

$^1$H-NMR (400 MHz, CDCl$_3$ δ, ppm) 9.09 (br. s, 1H, NH), 8.53 (d, 1H), 8.30 (d, 1H), 8.23 (d, 1H), 7.81 (m, 1H), 7.61 (dd, 1H), 7.48 (m, 1H), 7.30 (m, 1H), 7.19 (d, 1H).

Example No. I.7-3

$^1$H-NMR (400 MHz, d$^6$-DMSO δ, ppm) 11.80 (d, 1H), 8.58 (d, 1H), 8.49 (d, 1H), 8.31 (d, 1H), 7.87 (dd, 1H), 7.78 (dd, 1H), 7.53 (d, 1H), 7.36 (d, 1H).

Example No. I.7-4

$^1$H-NMR (400 MHz, CD$_3$OD δ, ppm) 9.26 (d, 1H), 8.58 (d, 1H), 8.44 (d, 1H), 8.35 (dd, 1H), 7.95 (dd, 1H), 7.74 (dd, 1H), 7.49 (d, 1H).

Example No. I.7-5

$^1$H-NMR (400 MHz, d$^6$-DMSO δ, ppm) 11.62 (br. s, 1H, NH), 9.79 (br. s, 1H, NH), 8.66 (d, 1H), 8.31 (d, 1H), 8.29 (d, 1H), 7.87 (dd, 1H), 7.79 (dd, 1H), 7.64 (dd, 1H), 7.29 (d, 1H), 3.10 (s, 2H), 2.30 (s, 6H).

Example No. I.7-6

$^1$H-NMR (400 MHz, CDCl$_3$ δ, ppm) 9.27 (br. s, 1H, NH), 8.52 (m, 1H), 8.19 (m, 2H), 7.80 (m, 1H), 7.61 (dd, 1H), 7.02 (m, 1H), 6.91 (m, 1H).

Example No. I.7-7

$^1$H-NMR (400 MHz, CDCl$_3$ δ, ppm) 11.33 (br. s, 1H, NH), 8.29 (d, 1H), 8.21 (d, 1H), 7.81 (dd, 1H), 7.59 (dd, 1H), 7.48 (d, 1H), 7.10 (d, 1H), 6.81 (dd, 1H), 5.02 (br. s, 2H, NH).

Example No. I.7-8

$^1$H-NMR (400 MHz, CD$_3$OD δ, ppm) 8.74 (d, 1H), 8.37 (d, 1H), 7.84 (dd, 1H), 7.67 (dd, 1H), 7.58 (d, 1H), 7.05 (d, 1H), 3.68 (m, 4H), 2.62 (m, 4H), 2.38 (s, 3H).

Example No. I.7-9

$^1$H-NMR (400 MHz, CDCl$_3$ δ, ppm) 11.73 (br. s, 1H, NH), 8.52 (d, 1H), 8.31 (d, 1H), 8.28 (d, 1H), 7.83 (dd, 1H), 7.68 (dd, 1H), 7.37 (m, 2H).

Example No. I.7-11

$^1$H-NMR (400 MHz, d$^6$-DMSO δ, ppm) 11.58 (br. s, 1H, NH), 8.48 (d, 1H), 8.31 (d, 1H), 8.19 (s, 1H), 7.82 (m, 1H), 7.61 (dd, 1H), 7.30 (m, 1H), 7.27 (d, 1H), 2.41 (s, 3H).

Example No. I.7-12

$^1$H-NMR (400 MHz, d$^6$-DMSO δ, ppm) 11.91 (br. s, 1H, NH), 8.59 (d, 1H), 8.57 (d, 1H), 8.32 (d, 1H), 7.89 (dd, 1H), 7.71 (d, 1H), 7.68 (s, 1H), 7.54 (d, 1H).

Example No. I.7-13

$^1$H-NMR (400 MHz, d$^6$-DMSO δ, ppm) 11.60 (br. s, 1H, NH), 8.51 (d, 1H), 8.35 (d, 1H), 8.22 (d, 1H), 7.87 (dd, 1H), 7.69 (dd, 1H), 7.40 (m, 1H), 7.24 (m, 1H).

Example No. I.7-14

$^1$H-NMR (400 MHz, CD$_3$OD δ, ppm) 8.77 (d, 1H), 8.36 (d, 1H), 7.82 (dd, 1H), 7.64 (dd, 1H), 7.43 (d, 1H), 6.70 (d, 1H), 3.63 (m, 2H), 2.80 (m, 2H), 2.71 (q, 4H), 1.12 (t, 6H).

Example No. I.7-15

$^1$H-NMR (400 MHz, CDCl$_3$ δ, ppm) 9.81 (br. s, 1H, NH), 8.53 (d, 1H), 8.23 (d, 1H), 7.78 (dd, 1H), 7.58 (dd, 1H), 7.10 (d, 1H), 7.07 (s, 1H), 2.49 (s, 3H).

Example No. I.7-16

$^1$H-NMR (400 MHz, CDCl$_3$ δ, ppm) 10.68 (br. s, 1H, NH), 8.77 (d, 1H), 8.51 (d, 1H), 7.81 (dd, 1H), 7.64 (dd, 1H), 7.51 (d, 1H), 6.59 (dd, 1H), 4.83 (s, 1H), 3.72 (d, 1H), 3.60 (s, 1H), 3.48 (m, 1H), 3.08 (d, 1H), 2.79 (d, 1H), 2.44 (s, 3H), 2.07 (d, 1H), 1.93 (d, 1H).

Example No. I.7-17

$^1$H-NMR (400 MHz, CDCl$_3$ δ, ppm) 11.28 (br. s, 1H, NH), 8.79 (d, 1H), 8.61 (d, 1H), 8.36 (dd, 1H), 7.90 (m, 2H), 7.72 (dd, 1H), 7.47 (dd, 1H).

Example No. I.7-18

$^1$H-NMR (400 MHz, CDCl$_3$ δ, ppm) 11.58 (br. s, 1H, NH), 8.37 (d, 1H), 8.24 (m, 2H), 7.78 (dd, 1H), 7.53 (dd, 1H), 6.88 (m, 2H), 3.82 (s, 3H).

Example No. I.7-19

$^1$H-NMR (400 MHz, CDCl$_3$ δ, ppm) 9.51 (br. s, 1H, NH), 9.01 (br. t, 1H, NH), 8.78 (d, 2H), 8.44 (d, 1H), 7.83 (dd, 1H), 7.64 (dd, 1H), 7.38 (d, 1H), 7.23 (t, 1H), 7.20 (d, 1H), 6.80 (dd, 1H), 5.00 (s, 2H).

Example No. I.7-20

$^1$H-NMR (400 MHz, d$^6$-DMSO δ, ppm) 11.71 (br. s, 1H, NH), 8.74 (s, 1H), 8.39 (d, 1H), 8.28 (d, 1H), 7.94 (d, 1H), 7.82 (dd, 1H), 7.49 (dd, 1H), 7.20 (d, 1H).

Example No. I.7-21

$^1$H-NMR (400 MHz, CDCl$_3$ δ, ppm) 9.10 (br. s, 1H, NH), 8.53 (d, 1H), 8.25 (d, 1H), 7.78 (m, 2H), 7.59 (m, 1H), 7.20 (dd, 1H), 6.94 (d, 1H), 4.21 (q, 2H), 1.54 (t, 3H).

Example No. I.7-22

$^1$H-NMR (400 MHz, CDCl$_3$ δ, ppm) 9.01 (br. s, 1H, NH), 8.48 (d, 1H), 8.16 (d, 1H), 7.88 (d, 1H), 7.74 (dd, 1H), 7.53 (dd, 1H), 6.90 (d, 1H), 3.99 (s, 3H), 3.98 (s, 3H).

Example No. I.7-67

$^1$H-NMR (400 MHz, d$^6$-DMSO δ, ppm) 12.02 (br. s, 1H, NH), 8.71 (s, 1H), 8.68 (d, 1H), 8.31 (d, 1H), 7.88 (m, 1H), 7.81 (d, 1H), 7.71 (dd, 1H), 7.51 (d, 1H).

Example No. I.8-1

$^1$H-NMR (400 MHz, d$_6$-DMSO δ, ppm) 11.66 (br. s, 1H, NH), 8.38 (d, 1H), 8.26 (d, 1H), 7.75 (dd, 1H), 7.51 (dd, 1H), 6.47 (s, 1H), 5.35 (t, 1H), 2.91 (m, 2H), 2.45 (s, 3H), 1.97 (s, 3H).

Example No. I.8-2

$^1$H-NMR (400 MHz, d$_6$-DMSO δ, ppm) 11.89 (br. s, 1H, NH), 8.37 (d, 1H), 8.18 (d, 1H), 7.82 (dd, 1H), 6.49 (s, 1H), 5.34 (t, 1H), 2.91 (m, 2H), 2.79 (q, 2H), 2.34 (q, 2H), 1.31 (t, 3H), 0.97 (t, 3H).

Example No. I.8-3

$^1$H-NMR (400 MHz, d$_6$-DMSO δ, ppm) 11.64 (br. s, 1H, NH), 8.32 (d, 1H), 7.68 (d, 1H), 7.38 (dd, 1H), 6.46 (s, 1H), 5.35 (t, 1H), 3.90 (s, 3H), 2.88 (m, 2H), 2.44 (s, 3H), 1.92 (s, 3H).

Example No. I.8-4

¹H-NMR (400 MHz, d₆-DMSO δ, ppm) 11.87 (br. s, 1H, NH), 8.31 (m, 2H), 7.91 (dd, 1H), 6.48 (s, 1H), 5.35 (t, 1H), 2.90 (m, 2H), 2.45 (s, 3H), 1.97 (s, 3H).

Example No. I.8-5

¹H-NMR (400 MHz, d₆-DMSO δ, ppm) 11.82 (br. s, 1H, NH), 8.44 (m, 1H), 7.90 (m, 1H), 7.64 (m, 1H), 6.48 (s, 1H), 5.36 (t, 1H), 2.90 (m, 2H), 2.45 (s, 3H), 1.97 (s, 3H).

Example No. I.8-6

¹H-NMR (400 MHz, d₆-DMSO δ, ppm) 11.83 (br. s, 1H, NH), 8.42 (m, 1H), 7.90 (m, 1H), 7.67 (m, 1H), 6.49 (s, 1H), 5.34 (t, 1H), 2.92 (m, 2H), 2.78 (q, 2H), 2.36 (q, 2H), 1.30 (t, 3H), 0.98 (t, 3H).

Example No. I.8-7

¹H-NMR (400 MHz, d₆-DMSO δ, ppm) 11.87 (br. s, 1H, NH), 8.38 (d, 1H), 8.18 (d, 1H), 7.80 (dd, 1H), 6.48 (s, 1H), 5.35 (t, 1H), 2.91 (m, 2H), 2.45 (s, 3H), 1.97 (s, 3H).

Example No. I.8-8

¹H-NMR (400 MHz, d₆-DMSO δ, ppm) 11.89 (br. s, 1H, NH), 8.33 (d, 1H), 8.29 (d, 1H), 7.91 (dd, 1H), 6.49 (s, 1H), 5.34 (t, 1H), 2.92 (m, 2H), 2.81 (q, 2H), 2.36 (q, 2H), 1.30 (t, 3H), 0.98 (t, 3H).

Example No. I.8-10

¹H-NMR (400 MHz, d₆-DMSO δ, ppm) 8.34 (d, 1H), 8.29 (d, 1H), 7.75 (dd, 1H), 7.52 (dd, 1H), 6.53 (s, 1H), 5.54 (t, 1H), 3.90 (t, 2H), 2.64 (m, 2H), 2.48 (s, 3H), 2.01 (s, 3H), 1.71 (m, 2H), 1.00 (t, 3H).

Example No. I.8-11

¹H-NMR (400 MHz, d₆-DMSO δ, ppm) 8.38 (d, 1H), 8.29 (d, 1H), 7.77 (dd, 1H), 7.53 (dd, 1H), 6.53 (s, 1H), 6.08 (m, 1H), 5.46 (m, 1H), 5.22 (m, 1H), 5.03 (m, 1H), 3.91 (s, 2H), 2.49 (s, 3H), 2.00 (s, 3H).

Example No. I.8-12

¹H-NMR (400 MHz, d₆-DMSO δ, ppm) 11.71 (br. s, 1H, NH), 8.35 (d, 1H), 8.26 (d, 1H), 7.77 (dd, 1H), 7.49 (dd, 1H), 6.53 (s, 1H), 5.35 (m, 1H), 2.82 (q, 2H), 2.70 (q, 2H), 1.33 (t, 3H), 0.98 (t, 3H).

Example No. I.9-1

¹H-NMR (400 MHz, d₆-DMSO δ, ppm) 12.91 (br. s, 1H, NH), 8.66 (d, 1H), 8.36 (d, 1H), 8.28 (d, 1H), 7.89 (d, 1H), 7.68 (d, 1H), 7.59 (dd, 1H), 7.30 (d, 1H), 7.04 (dd, 1H).

Example No. I.9-2

¹H-NMR (400 MHz, d₆-DMSO δ, ppm) 12.86 (br. s, 1H, NH), 8.98 (d, 1H), 8.06 (d, 1H), 7.74 (dd, 1H), 7.66 (dd, 1H), 7.43 (s, 1H), 7.23 (s, 1H), 4.16 (s, 3H), 3.98 (s, 3H).

Example No. I.9-3

¹H-NMR (400 MHz, d₆-DMSO δ, ppm) 12.96 (br. s, 1H, NH), 8.82 (d, 1H), 8.02 (s, 1H), 7.51 (d, 1H), 7.40 (s, 1H), 7.16 (s, 1H), 4.12 (s, 3H), 3.96 (s, 3H).

Example No. I.9-4

¹H-NMR (400 MHz, d₆-DMSO δ, ppm) 12.94 (br. s, 1H, NH), 8.67 (d, 1H), 7.51 (d, 1H), 7.46 (s, 1H), 7.08 (s, 1H), 7.01 (dd, 1H), 4.06 (s, 3H), 3.93 (s, 3H).

Example No. I.9-5

¹H-NMR (400 MHz, d₆-DMSO δ, ppm) 12.92 (br. s, 1H, NH), 8.99 (s, 1H), 7.99 (d, 1H), 7.88 (d, 1H), 7.38 (s, 1H), 7.13 (s, 1H), 4.11 (s, 3H), 3.94 (s, 3H).

Example No. I.9-6

¹H-NMR (400 MHz, d₆-DMSO δ, ppm) 12.93 (br. s, 1H, NH), 8.51 (d, 1H), 8.33 (d, 1H), 8.31 (m, 1H), 7.86 (m, 1H), 7.60 (dd, 1H), 7.19 (m, 1H), 6.98 (m, 1H).

Example No. I.9-7

¹H-NMR (400 MHz, d₆-DMSO δ, ppm) 12.91 (br. s, 1H, NH), 8.68 (d, 1H), 8.34 (d, 1H), 8.28 (m, 1H), 7.88 (m, 2H), 7.61 (dd, 1H), 7.12 (dd, 1H).

Example No. I.9-8

¹H-NMR (400 MHz, d₆-DMSO δ, ppm) 12.91 (br. s, 1H, NH), 8.89 (d, 1H), 8.37 (d, 1H), 8.21 (m, 1H), 7.88 (d, 1H), 7.81 (dd, 1H), 7.64 (m, 2H).

Example No. I.9-9

¹H-NMR (400 MHz, d₆-DMSO δ, ppm) 10.19 (br. s, 1H, NH), 8.53 (d, 1H), 8.18 (d, 1H), 7.77 (dd, 1H), 6.93 (s, 1H), 6.81 (s, 1H), 3.93 (s, 3H), 3.88 (s, 3H).

Example No. I.9-10

¹H-NMR (400 MHz, d₆-DMSO δ, ppm) 12.88 (br. s, 1H, NH), 9.01 (d, 1H), 8.50 (d, 1H), 7.64 (dd, 1H), 7.21 (s, 1H), 6.89 (s, 1H), 4.11 (s, 3H), 3.92 (s, 3H).

Example No. I.9-11

¹H-NMR (400 MHz, d₆-DMSO δ, ppm) 12.92 (br. s, 1H, NH), 8.75 (d, 1H), 8.16 (s, 1H), 7.45 (s, 1H), 7.21 (m, 1H), 7.04 (d, 1H), 4.01 (s, 3H), 3.92 (s, 3H).

Example No. I.9-12

¹H-NMR (400 MHz, d₆-DMSO δ, ppm) 12.84 (br. s, 1H, NH), 8.62 (d, 1H), 8.35 (d, 1H), 8.32 (d, 1H), 7.88 (s, 1H), 7.79 (dd, 1H), 7.54 (dd, 1H), 7.11 (d, 1H).

Example No. I.9-13

¹H-NMR (400 MHz, d₆-DMSO δ, ppm) 12.73 (br. s, 1H, NH), 9.00 (m, 1H), 8.33 (m, 1H), 8.27 (m, 1H), 7.88 (dd, 1H), 7.59 (dd, 1H), 7.51 (m, 1H), 7.43 (m, 1H).

Example No. I.9-14

$^1$H-NMR (400 MHz, d$_6$-DMSO δ, ppm) 12.77 (br. s, 1H, NH), 8.59 (d, 1H), 8.32 (d, 1H), 8.25 (d, 1H), 7.86 (dd, 1H), 7.58 (dd, 1H), 7.48 (s, 1H), 7.17 (m, 1H), 1.35 (s, 9H).

Example No. I.9-15

$^1$H-NMR (400 MHz, d$_6$-DMSO δ, ppm) 12.87 (br. s, 1H, NH), 8.83 (s, 1H), 8.38 (m, 1H), 7.89 (m, 1H), 7.71 (d, 1H), 7.42 (dd, 1H), 7.32 (m, 1H).

Example No. I.9-16

$^1$H-NMR (400 MHz, d$_6$-DMSO δ, ppm) 12.79 (br. s, 1H, NH), 8.78 (m, 1H), 8.33 (d, 1H), 8.28 (d, 1H), 7.88 (dd, 1H), 7.75 (m, 1H), 7.61 (dd, 1H), 7.39 (m, 1H).

Example No. I.9-17

$^1$H-NMR (400 MHz, d$_6$-DMSO δ, ppm) 12.91 (br. s, 1H, NH), 8.67 (m, 1H), 8.38 (m, 1H), 7.91 (m, 1H), 7.77 (d, 1H), 7.41 (m, 2H).

Example No. I.9-18

$^1$H-NMR (400 MHz, d$_6$-DMSO δ, ppm) 12.96 (br. s, 1H, NH), 8.67 (d, 1H), 8.39 (m, 1H), 7.90 (m, 1H), 7.68 (d, 1H), 7.42 (m, 1H), 7.31 (m, 1H), 7.06 (m, 1H).

Example No. I.9-19

$^1$H-NMR (400 MHz, d$_6$-DMSO δ, ppm) 12.72 (br. s, 1H, NH), 8.81 (s, 1H), 8.19 (d, 1H), 7.78 (d, 1H), 7.68 (d, 1H), 7.50 (dd, 1H), 7.28 (m, 1H), 3.91 (s, 3H).

Example No. I.9-20

$^1$H-NMR (400 MHz, d$_6$-DMSO δ, ppm) 12.93 (br. s, 1H, NH), 8.48 (d, 1H), 8.11 (d, 1H), 7.79 (d, 1H), 7.48 (d, 1H), 7.30 (dd, 1H), 7.09 (m, 1H), 6.83 (dd, 1H), 3.87 (s, 3H).

Example No. I.9-21

$^1$H-NMR (400 MHz, d$_6$-DMSO δ, ppm) 12.74 (br. s, 1H, NH), 8.77 (s, 1H), 8.11 (d, 1H), 7.77 (d, 1H), 7.53 (s, 1H), 7.34 (dd, 1H), 3.88 (s, 3H), 2.41 (s, 3H).

Example No. I.9-22

$^1$H-NMR (400 MHz, d$_6$-DMSO δ, ppm) 12.91 (br. s, 1H, NH), 8.59 (m, 1H), 8.11 (d, 1H), 7.79 (d, 1H), 7.58 (m, 1H), 7.33 (dd, 1H), 7.18 (m, 1H), 3.88 (s, 3H).

Example No. I.9-23

$^1$H-NMR (400 MHz, d$_6$-DMSO δ, ppm) 12.85 (br. s, 1H, NH), 9.02 (s, 1H), 8.20 (d, 1H), 7.78 (d, 1H), 7.53 (m, 3H), 3.92 (s, 3H).

Example No. I.9-26

$^1$H-NMR (400 MHz, d$_6$-DMSO δ, ppm) 13.01 (br. s, 1H, NH), 9.12 (s, 1H), 8.61 (d, 1H), 8.36 (d, 1H), 8.32 (m, 1H), 7.92 (m, 2H), 7.68 (m, 1H).

Example No. I.9-27

$^1$H-NMR (400 MHz, d$_6$-DMSO δ, ppm) 12.97 (br. s, 1H, NH), 6.65 (d, 1H), 8.40 (d, 1H), 8.36 (d, 1H), 7.91 (dd, 1H), 7.64 (d, 1H), 7.50 (d, 1H), 7.04 (t, 1H).

Example No. I.9-30

$^1$H-NMR (400 MHz, d$_6$-DMSO δ, ppm) 12.92 (br. s, 1H, NH), 9.01 (d, 1H), 8.58 (d, 1H), 8.36 (d, 1H), 8.31 (d, 1H), 7.92 (dd, 1H), 7.64 (dd, 1H), 7.17 (dd, 1H).

Example No. I.9-31

$^1$H-NMR (400 MHz, d$_6$-DMSO δ, ppm) 12.51 (br. s, 1H, NH), 8.97 (d, 1H), 8.51 (m, 1H), 8.08 (m, 1H), 7.69 (m, 1H), 7.12 (m, 1H), 3.92 (s, 3H), 3.90 (s, 3H).

Example No. I.9-32

$^1$H-NMR (400 MHz, d$_6$-DMSO δ, ppm) 12.49 (br. s, 1H, NH), 8.61 (d, 1H), 8.02 (m, 1H), 7.78 (m, 1H), 7.61 (d, 1H), 7.24 (m, 1H), 6.99 (m, 1H), 3.92 (s, 3H), 3.82 (s, 3H).

The present invention accordingly provides for the use of at least one compound selected from the group consisting of optionally substituted isoquinolinones, isoquinolinediones, isoquinolinetriones and dihydroisoquinolinones of the general formula (I) or their respective salts, and of any mixtures of these optionally substituted isoquinolinones, isoquinolinediones, isoquinolinetriones and dihydroisoquinolinones of the general formula (I) according to the invention or their respective salts with agrochemically active compounds corresponding to the definition below, for increasing the resistance of plants to abiotic stress factors, preferably to cold stress or drought stress, particularly preferably to drought stress, and for enhancing plant growth and/or for increasing plant yield.

The present invention further provides a spray solution for treatment of plants, comprising an amount, effective for enhancement of the resistance of plants to abiotic stress factors, of at least one compound selected from the group consisting of optionally substituted isoquinolinones, isoquinolinediones, isoquinolinetriones and dihydroisoquinolinones of the general formula (I) or their respective salts. The abiotic stress conditions which can be relativized may include, for example, heat, drought, cold and aridity stress (stress caused by aridity and/or lack of water), osmotic stress, waterlogging, elevated soil salinity, elevated exposure to minerals, ozone conditions, strong light conditions, limited availability of nitrogen nutrients, limited availability of phosphorus nutrients.

In one embodiment, it is possible, for example, that the compounds envisaged in accordance with the invention, i.e. the appropriate optionally substituted isoquinolinones, isoquinolinediones, isoquinolinetriones and dihydroisoquinolinones of the general formula (I), are applied by spray application to appropriate plants or plant parts to be treated. The compounds of the general formula (I) or salts thereof are used as envisaged in accordance with the invention preferably with a dosage between 0.00005 and 3 kg/ha, more preferably between 0.0001 and 2 kg/ha, especially preferably between 0.0005 and 1 kg/ha, specifically preferably between 0.001 and 0.25 kg/ha. If, in the context of the present invention, abscisic acid is used simultaneously with substituted isoquinolinones, isoquinolinediones, isoquinolinetriones and dihydroisoquinolinones of the general formula (I), for example in the context of a combined preparation or formulation, the addition of abscisic acid is preferably carried out in a dosage from 0.0001 to 3 kg/ha, particularly preferably from 0.001 to 2 kg/ha, very particularly preferably from 0.005 to 1 kg/ha, especially preferably from 0.006 to 0.25 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon and tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibres, better fibre quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought and aridity, and also oxygen deficiency as a result of waterlogging, improved tolerance to elevated salt contents in soil and water, enhanced tolerance to ozone stress, improved compatibility with respect to herbicides and other plant treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the inventive use of one or more compounds of the general formula (I) exhibits the advantages described in spray application to plants and plant parts. Combinations of the corresponding substituted isoquinolinones, isoquinolinediones, isoquinolinetriones and dihydroisoquinolinones of the general formula (I) or their respective salts with substances including insecticides, attractants, acaricides, fungicides, nematicides, herbicides, growth regulators, safeners, substances which influence plant maturity, and bactericides can likewise be employed in the control of plant disorders in the context of the present invention. In addition, the combined use of corresponding substituted isoquinolinones, isoquinolinediones, isoquinolinetriones and dihydroisoquinolinones of the general formula (I) or their respective salts with genetically modified cultivars with a view to increased tolerance to abiotic stress is likewise possible.

As is known, the various advantages for plants, which have been mentioned further above, can be combined in part, and generally applicable terms can be used to describe them. Such terms are, for example, the following names: phytotonic effect, resistance to stress factors, less plant stress, plant health, healthy plants, plant fitness, plant wellness, plant concept, vigour effect, stress shield, protective shield, crop health, crop health properties, crop health products, crop health management, crop health therapy, plant health, plant health properties, plant health products, plant health management, plant health therapy, greening effect or regreening effect, freshness, or other terms with which a person skilled in the art is quite familiar.

In the context of the present invention, a good effect on resistance to abiotic stress is understood to mean, without limitation, at least an emergence improved by generally 3%, especially more than 5%, more preferably more than 10%,
at least a yield enhanced by generally 3%, especially more than 5%, more preferably more than 10%,
at least a root development improved by generally 3%, especially more than 5%, more preferably more than 10%,
at least a shoot size rising by generally 3%, especially more than 5%, more preferably more than 10%,
at least a leaf area increased by generally 3%, especially more than 5%, more preferably more than 10%,
at least a photosynthesis performance improved by generally 3%, especially more than 5%, more preferably more than 10%, and/or
at least a flower development improved by generally 3%, especially more than 5%, more preferably more than 10%, it being possible for the effects to manifest themselves individually or else in any combination of two or more effects.

The present invention further provides a spray solution for treatment of plants, comprising an amount, effective for enhancement of the resistance of plants to abiotic stress factors, of at least one compound selected from the group of the substituted isoquinolinones, isoquinolinediones, isoquinolinetriones and dihydroisoquinolinones of the general formula (I). The spray solution may comprise other customary constituents, such as solvents, formulation aids, especially water. Further constituents may include active agrochemical compounds described below.

The present invention further provides for the use of corresponding spray solutions for increasing the resistance of plants to abiotic stress factors. The remarks which follow apply both to the use according to the invention of the compounds of the general formula (I) per se and to the corresponding spray solutions.

In accordance with the invention, it has additionally been found that the application, to plants or in their environment, of the compounds of the general formula (I) in combination with at least one fertilizer as defined below is possible.

Fertilizers which can be used in accordance with the invention together with the compounds of the general formula (I) elucidated in detail above are generally organic and inorganic nitrogen-containing compounds, for example ureas, urea/formaldehyde condensation products, amino acids, ammonium salts and ammonium nitrates, potassium salts (preferably chlorides, sulphates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonia nitrate sulphate (general formula $(NH_4)_2SO_4 \; NH_4NO_3$), ammonium phosphate and ammonium sulphate. These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulphur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain other salts such as monoammonium phosphate (MAP), diammonium phosphate (DAP), potassium sulphate, potassium chloride, magnesium sulphate. Suitable amounts for the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail further below.

The fertilizers can be employed for example in the form of powders, granules, prills or compactates. However, the fertilizers can also be employed in liquid form, dissolved in an aqueous medium. In this case, dilute aqueous ammonia may also be employed as nitrogen fertilizer. Further possible ingredients for fertilizers are described, for example, in Ullmann's Encyclopedia of Industrial Chemistry, 5th edition, 1987, volume A 10, pages 363 to 401, DE-A 41 28 828, DE-A 19 05 834 and DE-A 196 31 764. The general composition of the fertilizers which, within the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is usually in the ppm range, preferably in the range from 1 to 1000 ppm.

In the context of the present invention, the fertilizer and the compounds of the general formula (I) may be administered simultaneously. However, it is also possible first to apply the fertilizer and then a compound of the formula (I), or first to apply a compound of the general formula (I) and then the fertilizer. In the case of nonsynchronous application of a compound of the general formula (I) and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the inventive compound of the formula (I) and the fertilizer are applied within a time frame of less than 1 hour, preferably less than 30 minutes, more preferably less than 15 minutes.

Preference is given to the use of compounds of the general formula (I) on plants from the group of the useful plants, ornamentals, turfgrass types, commonly used trees which are used as ornamentals in the public and domestic sectors, and forestry trees. Forestry trees include trees for the production of timber, cellulose, paper and products made from parts of the trees. The term "useful plants" as used here refers to crop plants which are employed as plants for obtaining foods, animal feeds, fuels or for industrial purposes.

The useful plants include, for example, the following types of plants: triticale, durum wheat, turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruits, for example oranges, lemons, grapefruits and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugar cane, tea, pepper, grapevines, hops, bananas, latex plants and ornamentals, for example flowers, shrubs, deciduous trees and coniferous trees, such as conifers. This enumeration has no limitation.

The following plants are considered to be particularly suitable target crops for applying the method according to the invention: oats, rye, triticale, durum, cotton, aubergine, turf, pome fruit, stone fruit, soft fruit, maize, wheat, barley, cucumber, tobacco, vines, rice, cereals, pears, pepper, beans, soybeans, oilseed rape, tomato, bell pepper, melons, cabbage, potatoes and apples.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus: A. hippocastanum, A. pariflora, A. carnea*; from the tree species *Platanus: P. aceriflora, P. occidentalis, P. racemosa*; from the tree species *Picea: P. abies*; from the tree species *Pinus: P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus: E. grandis, E. globulus, E. camadentis, E. nitens, E. obliqua, E. regnans, E. pilularus*.

Particularly preferred trees which can be improved by the method according to the invention include: from the tree species *Pinus: P. radiate, P. ponderosa, P. contorta, P. sylvestre, P. strobes*; from the tree species *Eucalyptus: E. grandis, E. globulus and E. camadentis*.

Particularly preferred trees which can be improved by the method according to the invention include: horse chestnut, Platanaceae, linden tree and maple tree.

The present invention can also be applied to any turfgrasses, including cool-season turfgrasses and warm-season turfgrasses. Examples of cold-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.);

fescues (*Festuca* spp.), such as red fescue (*Festuca rubra* L. spp. rubra), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), *zoysia* grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore *paspalum* (*Paspalum vaginatum* Swartz) and sideoats grama (*Bouteloua curtipendula* (Michx. Torr.). Cool-season turfgrasses are generally preferred for the use in accordance with the invention. Particular preference is given to bluegrass, bentgrass and redtop, fescues and ryegrasses. Bentgrass is especially preferred.

More preferably, plants of the plant cultivars which are commercially available or are in use are treated in accordance with the invention. Plant cultivars are to be understood as meaning plants having new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable and non-protectable by plant breeders' rights.

The treatment method according to the invention can thus also be used for the treatment of genetically modified organisms (GMOs), for example plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Plants and plant cultivars which are preferably treated according to the invention include all plants which have genetic material which imparts particularly advantageous, useful traits to these plants (whether obtained by breeding and/or biotechnological means).

Plants and plant cultivars which may also be treated according to the invention are those plants which are resistant to one or more abiotic stress factors. The abiotic stress conditions may include, for example, drought, cold and hot conditions, stress owing to dry conditions, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant cultivars which can likewise be treated in accordance with the invention are those plants which are characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may also be treated according to the invention are hybrid plants that already express the characteristics of heterosis, or hybrid vigour, which results in generally higher yield, vigour, health and resistance towards biotic and abiotic stress factors. Such plants are typically made by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (for example in maize) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species (WO 92/005251, WO 95/009910, WO 98/27806, WO 05/002324, WO 06/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 91/002069).

Plants or plant cultivars (obtained by plant biotechnology methods such as genetic engineering) which can likewise be treated in accordance with the invention are herbicide-tolerant plants, i.e. plants which have been made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *Eleusine* EPSPS (WO 01/66704). It can also be a mutated EPSPS, as described, for example, in EP-A 0837944, WO 00/066746, WO 00/066747 or WO 02/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described, for example, in WO 02/036782, WO 03/092360, WO 05/012515 and WO 07/024,782. Glyphosate-tolerant plants can also be obtained by selecting plants containing naturally occurring mutations of the above-mentioned genes as described, for example, in WO 01/024615 or WO 03/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally occurring resistant HPPD enzyme, or a gene encoding a mutated HPPD enzyme according to WO 96/038567, WO 99/024585 and WO 99/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 99/034008 and WO 2002/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 96/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described, for example in WO 2007/024782.

Further plants tolerant to ALS inhibitors, in particular to imidazolinones, sulphonylureas and/or sulphamoylcarbonyltriazolinones, can be obtained by induced mutagenesis, by selection in cell cultures in the presence of the herbicide or by mutation breeding, as described, for example, for soybeans in U.S. Pat. No. 5,084,082, for rice in WO 97/41218, for sugarbeet in U.S. Pat. No. 5,773,702 and WO 99/057965, for lettuce in U.S. Pat. No. 5,198,599 or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second, other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising portions from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of the target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress tolerance plants include:
a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5;
b. plants which contain a stress tolerance-enhancing transgene capable of reducing the expression and/or the activity of the PARG-encoding genes of the plants or plant cells, as described, for example, in WO 2004/090140;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002, 433.

Plants or plant cultivars (obtained by plant biotechnology methods such as genetic engineering) which may also be treated according to the invention show altered quantity, quality and/or storage stability in the harvested product and/or altered properties of specific components of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 95/004826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 95/26407, WO 96/34968, WO 98/20145, WO 99/12950, WO 99/66050, WO 99/53072, U.S. Pat. No. 6,734,341, WO 2000/11192, WO 98/22604, WO 98/32326, WO 2001/98509, WO 2001/98509, WO 2005/002359, U.S. Pat. No. 5,824,790, U.S. Pat. No. 6,013,861, WO 94/004693, WO 94/009144, WO 94/11520, WO 95/35026 and WO 97/20936.
2) Transgenic plants which synthesize non starch carbohydrate polymers or which synthesize non starch carbohydrate polymers with altered properties in comparison to wild type plants without genetic modification. Examples are plants producing polyfructose, especially of the inulin and levan type, as described in EP 0663956, WO 96/001904, WO 96/021023, WO 98/039460 and WO 99/024593, plants producing alpha-1,4-glucans, as described in WO 95/031553, US 2002/031826, U.S. Pat. No. 6,284,479, U.S. Pat. No. 5,712,107, WO 97/047806, WO 97/047807, WO 97/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.
3) Transgenic plants which produce hyaluronan, as for example described in WO 06/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes, as described in WO 98/000549;
b) plants, such as cotton plants, which contain an altered form of rsw2 or rsw3 homologous nucleic acids, as described in WO 2004/053219;
c) plants, such as cotton plants, with an increased expression of sucrose phosphate synthase, as described in WO 2001/017333;
d) plants, such as cotton plants, with an increased expression of sucrose synthase, as described in WO 02/45485;
e) plants, such as cotton plants, wherein the timing of the plasmodesmatal gating at the basis of the fibre cell is altered, for example through downregulation of fibre-selective β-1,3-glucanase as described in WO 2005/017157;
f) plants, such as cotton plants, which have fibres with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;
b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated according to the invention are plants containing transformation events, or a combination of transformation events, and that are listed for example in the databases of various national or regional regulatory agencies.

Particularly useful transgenic plants which may be treated according to the invention are plants, for example, which comprise one or more genes which encode one or more toxins and are the transgenic plants available under the following trade names: YIELD GARD@ (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soybean varieties which are available under the following trade names: Roundup Ready® (tolerance to glyphosates, for example maize, cotton, soybeans), Liberty Link® (tolerance to phosphinothricin, for example oilseed rape), IMI® (tolerance to imidazolinone) and SOS@ (tolerance to sulphonylurea, for example maize). Herbicide-resistant plants (plants bred in a conventional manner for herbicide tolerance) which may be mentioned include the cultivars sold under the name Clearfield® (for example maize).

The compounds of the formula (I) to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural substances impregnated with active compound, synthetic substances impregnated with active compound, fertilizers, and also microencapsulations in polymeric substances. In the context of the present invention, it is especially preferred when the compounds of the general formula (I) are used in the form of a spray formulation.

The present invention therefore additionally also relates to a spray formulation for enhancing the resistance of plants to abiotic stress. A spray formulation is described in detail hereinafter:

The formulations for spray application are produced in a known manner, for example by mixing the compounds of the general formula (I) for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable facilities or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical compounds. Preference is given to using alkyl naphthalenesulphonates, such as diisopropyl or diisobutyl naphthalenesulphonates.

Useful dispersants and/or emulsifiers which may be present in the formulations usable in accordance with the invention are all nonionic, anionic and cationic dispersants conventionally used for the formulation of active agrochemical compounds. Usable with preference are nonionic or anionic dispersants or mixtures of nonionic or anionic dispersants. Suitable nonionic dispersants are especially ethylene oxide/propylene oxide block polymers, alkylphenol polyglycol ethers and tristyrylphenol polyglycol ether, and the phosphated or sulphated derivatives thereof. Suitable anionic dispersants are especially lignosulphonates, polyacrylic salts and arylsulphonate/formaldehyde condensates.

Antifoams which may be present in the formulations usable in accordance with the invention are all foam-inhibiting substances conventionally used for the formulation of active agrochemical compounds. Silicone antifoams and magnesium stearate can preferably be used.

Suitable preservatives which may be present in the formulations which can be used in accordance with the invention are all substances usable for such purposes in agrochemical compositions. Dichlorophene and benzyl alcohol hemiformal may be mentioned by way of example.

Suitable secondary thickeners which may be present in the formulations which can be used in accordance with the invention are all substances usable for such purposes in agrochemical compositions. Cellulose derivatives, acrylic acid derivatives, xanthan, modified clays and finely divided silica are preferred.

Suitable stickers which may be present in the formulations which can be used in accordance with the invention include all customary binders usable in seed-dressing products. Polyvinylpyrrolidone, polyvinyl acetate, polyvinyl alcohol and tylose may be mentioned as being preferred. Suitable gibberellins which can be present in the formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, pp. 401-412).

Other possible additives are perfumes, mineral or vegetable oils which are optionally modified, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations contain generally between 0.01 and 98% by weight, preferably between 0.5 and 90%, of the compound of the general formula (I).

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

In addition, the described positive effect of the compounds of the formula (I) on the plants' own defences can be supported by an additional treatment with active insecticidal, fungicidal or bactericidal compounds.

Preferred times for the application of compounds of the general formula (I) for enhancing resistance to abiotic stress are treatments of the soil, stems and/or leaves with the approved application rates.

The active compounds of the formula (I) may generally additionally be present in their commercial formulations and in the use forms prepared from these formulations in mixtures with other active compounds, such as insecticides, attractants, sterilants, acaricides, nematicides, fungicides, bactericides, growth-regulating substances, substances which influence plant maturity, safeners or herbicides. Particularly favourable mixing partners are, for example, the active compounds of the different classes, specified below in groups, without any preference resulting from the sequence thereof:

Fungicides:

F1) nucleic acid synthesis inhibitors, for example benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid;

F2) mitosis and cell division inhibitors, for example benomyl, carbendazim, diethofencarb, fuberidazole, fluopicolid, pencycuron, thiabendazole, thiophanate-methyl, zoxamide and chloro-7-(4-methylpiperidin-1-yl)-6-(2,4,6-trifluorophenyl)[1,2,4]triazolo[1,5-a]pyrimidine;

F3) respiratory chain complex I/II inhibitors, for example diflumetorim, bixafen, boscalid, carboxin, diflumethorim, fenfuram, fluopyram, flutolanil, furametpyr, mepronil, oxycarboxin, penflufen, penthiopyrad, thifluzamid, N-[2-(1,3-dimethylbutyl)phenyl]-5-fluoro-1,3-dimethyl-1H-pyrazole-4-carboxamide, isopyrazam, sedaxan, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and corresponding salts;

F4) respiratory chain complex III inhibitors, for example amisulbrom, azoxystrobin, cyazofamid, dimoxystrobin, enestrobin, famoxadon, fenamidon, fluoxastrobin, kresoxim-methyl, metominostrobin, orysastrobin, pyraclostrobin, pyribencarb, picoxystrobin, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(ethoxyimino)-N-methyl-2-(2-{[({(1E)-1-[3-(trifluoromethyl)phenyl]ethylidene}amino)oxy]methyl}phenylethanamide and corresponding salts, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyhethylidene]amino}oxy) methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, 2-methyl {2-[({cyclopropyl[(4-methoxyphenyl)imino]methyl}sulphanyl)methyl]phenyl}-3-methoxyacrylate, N-(3-ethyl-3,5,5-trimethylcyclohexyl)-3-(formylamino)-2-hydroxybenzamide and corresponding salts;

F5) decouplers, for example dinocap, fluazinam;

F6) ATP production inhibitors, for example fentin acetate, fentin chloride, fentin hydroxide, silthiofam F7) amino acid and protein biosynthesis inhibitors, for example andoprim, blasticidin-S, cyprodinil, kasugamycin, kasugamycin hydrochloride hydrate, mepanipyrim, pyrimethanil F8) signal transduction inhibitors, for example fenpiclonil, fludioxonil, quinoxyfen F9) lipid and membrane synthesis inhibitors, for example chlozolinate, iprodione, procymidone, vinclozolin, ampropylfos, potassium-ampropylfos, edifenphos, iprobenfos (IBP), isoprothiolane, pyrazophos, tolclofos-methyl, biphenyl, iodocarb, propamocarb, propamocarb hydrochloride F10) ergosterol biosynthesis inhibitors, for example fenhexamid, azaconazole, bitertanol, bromuconazole, diclobutrazole, difenoconazole, diniconazole, diniconazole-M, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, spiroxamine, tebuconazole, triadimefon, triadimenol, triticonazole, uniconazole, voriconazole, imazalil, imazalil sulphate, oxpoconazole, fenarimol, flurprimidol, nuarimol, pyrifenox, triforin, pefurazoate, prochloraz, triflumizole, viniconazole, aldimorph, dodemorph, dodemorph acetate, fenpropimorph, tridemorph, fenpropidin, naftifin, pyributicarb, terbinafin, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]2,2-dimethylpropyl}-1H-imidazole-1-carbothioate;

F11) cell wall synthesis inhibitors, for example benthiavalicarb, bialaphos, dimethomorph, flumorph, iprovalicarb, polyoxins, polyoxorim, validamycin A F12) melanine biosynthesis inhibitors, for example capropamide, diclocymet, fenoxanil, phthalide, pyroquilon, tricyclazole F13) resistance induction, for example acibenzolar-S-methyl, probenazole, tiadinil F14) multisite, for example captafol, captan, chlorothalonil, copper salts such as: copper hydroxide, copper naphthenate, copper oxychloride, copper sulphate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram F15) unknown mechanism, for example amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolide, fluoroimide, fosatyl-AI, hexachlorobenzene, 8-hydroxyquinoline sulphate, iprodione, irumamycin, isotianil, methasulfocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl) phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyl)imino]methyl]thio]methyl]-.alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulphonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-ylmethyl-2,4-dichloronicotinamide, 2-butoxy-6-iodo-3-propylbenzopyranon-4-one, N-{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene] amino]oxy]methyl]alpha-(methoxyimino)-N-methyl-alphaE-benzacetamide, N-{2-[3-chloro-5-(trifluoromethyl) pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy) methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

I1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

I2) GABA-gated chloride channel antagonists, for example organochlorines, e.g. chlordane and endosulfan (alpha-); or fiproles (phenylpyrazoles), e.g. ethiprole, fipronil, pyrafluprole and pyriprole.

I3) Sodium channel modulators/voltage-gated sodium channel blockers, for example pyrethroids, e.g. acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or _DDT; or methoxychlor.

I4) Nicotinergic acetylcholine receptor agonists, for example neonicotinoids, e.g. acetamiprid, clothianidin, dinotefuran, imidacloprid, nitenpyram, thiacloprid, thiamethoxam; or nicotine.

I5) Allosteric acetylcholine receptor modulators (agonists) for example spinosyns, e.g. spinetoram and spinosad.

I6) Chloride channel activators, for example avermectins/milbemycins, e.g. abamectin, emamectin, emamectin benzoate, lepimectin and milbemectin.

I7) Juvenile hormone analogs, e.g. hydroprene, kinoprene, methoprene; or fenoxycarb; pyriproxyfen.

I8) Active compounds with unknown or non-specific mechanisms of action, for example fumigants, for example methyl bromide and other alkyl halides; or chloropicrin; sulphuryl fluoride; borax; tartar emetic.

I9) Selective antifeedants, e.g. pymetrozine; or flonicamid.

I10) Mite growth inhibitors, e.g. clofentezine, diflovidazin, hexythiazox, etoxazole.

I11) Microbial disruptors of the insect gut membrane, for example *Bacillus thuringiensis* subspecies *israelensis, Bacil-*

*lus sphaericus, Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.

I12) Oxidative phosphorylation inhibitors, ATP disruptors, for example diafenthiuron; or organotin compounds, e.g. azocyclotin, cyhexatin, fenbutatin oxide; or propargite; tetradifon.

I13) Oxidative phosphorylation decouplers through interruption of the H proton gradient, for example chlorfenapyr and DNOC.

I14) Nicotinergic acetylcholine receptor antagonists, for example bensultap, cartap (-hydrochloride), thiocyclam, and thiosultap (-sodium).

I15) Chitin biosynthesis inhibitors, type 0, for example benzoylureas, e.g. bistrifluron, chlorfluazuron, diflubenzuron, flucycloxuron, flufenoxuron, hexaflumuron, lufenuron, novaluron, noviflumuron, teflubenzuron and triflumuron.

I16) Chitin biosynthesis inhibitors, type 1, for example buprofezin.

I17) Moulting disruptors, for example cyromazine.

I18) Ecdysone agonists/disruptors, for example diacylhydrazines, for example chromafenozide, halofenozide, methoxyfenozide and tebufenozide.

I19) Octopaminergic agonists, for example amitraz.

I20) Complex III electron transport inhibitors, for example hydramethylnone; acequinocyl; fluacrypyrim.

I21) Complex I electron transport inhibitors, for example from the group of the METI acaricides, e.g. fenazaquin, fenpyroximate, pyrimidifen, pyridaben, tebufenpyrad, tolfenpyrad; or rotenone (Derris).

I22) Voltage-gated sodium channel blockers, e.g. indoxacarb; metaflumizone.

I23) Inhibitors of acetyl-CoA carboxylase, for example tetronic acid derivatives, e.g. spirodiclofen and spiromesifen; or tetramic acid derivatives, e.g. spirotetramat.

I24) Complex IV electron transport inhibitors, for example phosphines, e.g. aluminium phosphide, calcium phosphide, phosphine, zinc phosphide; or cyanide.

I25) Complex II electron transport inhibitors, for example cyenopyrafen.

I26) Ryanodine receptor effectors such as, for example, diamides, e.g. flubendiamide, chlorantraniliprole (Rynaxypyr), cyantraniliprole (Cyazypyr) and 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677), methyl 2-[2-({[1-(3-chloropyridin-2-yl)-3-{([4-(trifluoromethyl)-1H-1,2,3-triazol-1-yl]methyl}-1H-pyrazol-5-yl]carbonyl}amino)-5-iodo-3-methylbenzoyl]-1-methylhydrazinecarboxylate (known from WO2010131770).

Further active compounds having an unknown mechanism of action, such as, for example, azadirachtin, amidoflumet, benzoximate, bifenazate, chinomethionat, cryolite, cyflumetofen, dicofol, 5-chloro-2-[(3,4,4-trifluorobut-3-en-1-yl)sulphonyl]-1,3-thiazole, flufenerim, pyridalyl and pyrifluquinazon; furthermore preparations based on *Bacillus firmus* (1-1582, BioNeem, Votivo) and the following known active compounds 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-ylmethyl)(2-fluoroethyl)amino}furan-2(5H)-one (known from WO 2007/115644), 4-{[(6-chloropyrid-3-ylmethyl)(2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP0539588), 4-{[(6-chloropyrid-3-yl)methyl](methyl)amino}furan-2(5H)-one (known from EP0539588), [1-(6-chloropyridin-3-yl)ethyl](methyl)oxido-$\lambda^4$-sulphanylidenecyanamide (known from WO 2007/149134) and its diastereomers {[(1R)-1-(6-chloropyridin-3-yl)ethyl](methyl)oxido-lambda$^6$-sulphanylidene}cyanamide and {[(1S)-1-(6-chloropyridin-3-yl)ethyl]methyl)oxido-lambda$^6$-sulphanylidene}cyanamide (likewise known from WO 2007/149134) and sulfoxaflor (likewise known from WO 2007/149134), 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methylcyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407), N-[1-(2,3-dimethylphenyl)-2-(3,5-dimethylphenyl)ethyl]-4,5-dihydro-1,3-thiazole-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280/282), 2-ethyl-7-methoxy-3-methyl-6-[(2,2,3,3-tetrafluoro-2,3-dihydro-1,4-benzodioxin-6-yl)oxy]quinolin-4-yl methyl carbonate (known from JP2008110953), 2-ethyl-7-methoxy-3-methyl-6-[(2,2,3,3-tetrafluoro-2,3-dihydro-1,4-benzodioxin-6-yl)oxy]quinolin-4-yl acetate (known from JP2008110953), PF1364 (Chemical Abstracts No 1204776-60-2, known from JP2010018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2- oxo-2-[(2,2,2-trifluoroethyl)amino]ethyl}benzamide (known from WO2005/085216).

Safeners are preferably selected from the group consisting of:

S1) Compounds of the formula (S1)

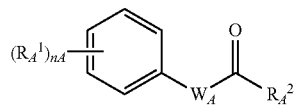

(S1)

where the symbols and indices have the following meanings:
$n_A$ is a natural number from 0 to 5, preferably 0 to 3;
$R_A^1$ is halogen, $(C_1-C_4)$-alkyl, $(C_1-C_4)$-alkoxy, nitro or $(C_1-C_4)$-haloalkyl;

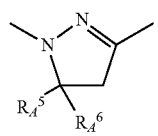

($W_A^1$)

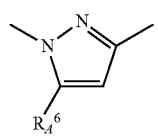

($W_A^2$)

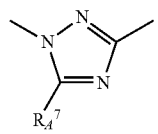

($W_A^3$)

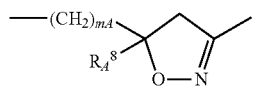

($W_A^4$)

$W_A$ is an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of ($W_A^1$) to ($W_A^4$);
$m_A$ is 0 or 1;
$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1-C_4)$alkyl, $(C_1-C_4)$alkoxy or optionally substituted phenyl, preferably a radical of the formula $OR_A^3$, $NHR_A^4$ or $N(CH_3)_2$, especially of the formula $OR_A^3$;
$R_A^3$ is hydrogen or an unsubstituted or substituted aliphatic hydrocarbyl radical, preferably having a total of 1 to 18 carbon atoms;
$R_A^4$ is hydrogen, $(C_1-C_6)$-alkyl, $(C_1-C_6)$-alkoxy or substituted or unsubstituted phenyl;
$R_A^5$ is H, $(C_1-C_8)$-alkyl, $(C_1-C_8)$-haloalkyl, $(C_1-C_4)$-alkoxy-$(C_1-C_8)$-alkyl, cyano or $COOR_A^9$ in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;
$R_A^6$, $R_A^7$, $R_A^8$ are the same or different and are each hydrogen, $(C_1-C_8)$-alkyl, $(C_1-C_8)$-haloalkyl, $(C_3-C_{12})$-cycloalkyl or substituted or unsubstituted phenyl;
preferably:
a) compounds of the dichlorophenylpyrazoline-3-carboxylic acid ($S1^a$ type, preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;
b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;
c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;
d) compounds of the triazolecarboxylic acid type ($S1^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;
e) compounds of the 5-benzyl- or 5-phenyl-2-isoxazoline-3-carboxylic acid type or of the 5,5-diphenyl-2-isoxazoline-3-carboxylic acid type ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

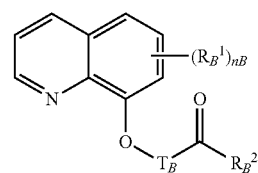

(S2)

where the symbols and indices have the following meanings:
$R_B^1$ is halogen, $(C_1-C_4)$-alkyl, $(C_1-C_4)$-alkoxy, nitro or $(C_1-C_4)$-haloalkyl;
$n_B$ is a natural number from 0 to 5, preferably 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B{}^3$ is hydrogen or an unsubstituted or substituted aliphatic hydrocarbyl radical preferably having a total of 1 to 18 carbon atoms;

$R_B{}^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$alkyl radicals or by $[(C_1-C_3)$-alkoxy]carbonyl;

preferably:

a) compounds of the 8-quinolinoxyacetic acid type (S2$^a$), preferably 1-methylhexyl (5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminium, iron, ammonium, quaternary ammonium, sulphonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy) malonate, methyl ethyl (5-chloro-8-quinolinoxy)malonate and related compounds, as described in EP-A-0 582 198.

S3) Compounds of the formula (S3)

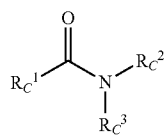

(S3)

where the symbols and indices have the following meanings:

$R_C{}^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C{}^2$, $R_C{}^3$ are the same or different and are each hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C{}^2$ and $R_C{}^3$ together form a substituted or unsubstituted heterocyclic ring, preferably an oxazolidine, thiazolidine, piperidine, morpholine, hexahydropyrimidine or benzoxazine ring; preferably: active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulphonamides of the formula (S4) and salts thereof,

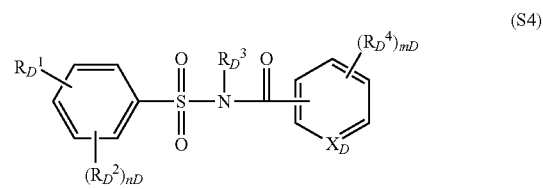

(S4)

where the symbols and indices have the following meanings:

$X_D$ is CH or N;

$R_D{}^1$ is CO—NR$_D{}^5$R$_D{}^6$ or NHCO—R$_D{}^7$;

$R_D{}^2$ is halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulphonyl, $(C_1-C_4)$-alkoxycarbonyl or $(C_1-C_4)$-alkylcarbonyl;

$R_D{}^3$ is hydrogen, $(C_1-C_4)$-alkyl, $(C_2-C_4)$-alkenyl or $(C_2-C_4)$-alkynyl;

$R_D{}^4$ is halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulphinyl, $(C_1-C_4)$-alkylsulphonyl, $(C_1-C_4)$-alkoxycarbonyl or $(C_1-C_4)$-alkylcarbonyl;

$R_D{}^5$ is hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group of nitrogen, oxygen and sulphur, where the seven latter radicals are substituted by $v_D$ substituents from the group of halogen, $(C_1-C_6)$-alkoxy, $(C_1-C_6)$-haloalkoxy, $(C_1-C_2)$-alkylsulphinyl, $(C_1-C_2)$-alkylsulphonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D{}^6$ is hydrogen, $(C_1-C_6)$-alkyl, $(C_2-C_6)$-alkenyl or $(C_2-C_6)$-alkynyl, where the three latter radicals are substituted by $v_D$ radicals from the group of halogen, hydroxyl, $(C_1-C_4)$-alkyl, $(C_1-C_4)$-alkoxy and $(C_1-C_4)$-alkylthio, or $R_D{}^5$ and $R_D{}^6$, together with the nitrogen atom bearing them, form a pyrrolidinyl or piperidinyl radical;

$R_D{}^7$ is hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ is 0, 1 or 2;

$m_D$ is 1 or 2;

$v_D$ is 0, 1, 2 or 3;

among these, preference is given to compounds of the N-acylsulphonamide type, for example of the formula (S4$^a$) below, which are known, for example, from WO-A-97/45016

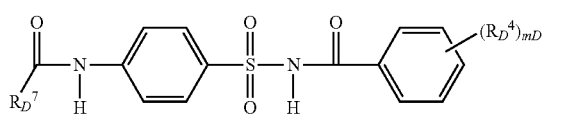

(S4$^a$)

in which
R$_D^7$ is (C$_1$-C$_6$)-alkyl, (C$_3$-C$_6$)-cycloalkyl, where the 2 latter radicals are substituted by v$_D$ substituents from the group of halogen, (C$_1$-C$_4$)-alkoxy, (C$_1$-C$_6$)-haloalkoxy and (C$_1$-C$_4$)-alkylthio and, in the case of cyclic radicals, also (C$_1$-C$_4$)-alkyl and (C$_1$-C$_4$)-haloalkyl;
R$_D^4$ is halogen, (C$_1$-C$_4$)-alkyl, (C$_1$-C$_4$)-alkoxy, CF$_3$;
m$_D$ is 1 or 2;
v$_D$ is 0, 1, 2 or 3;
and also to acylsulphamoylbenzamides, for example of the formula (S4$^b$) below, which are known, for example, from WO-A-99/16744,

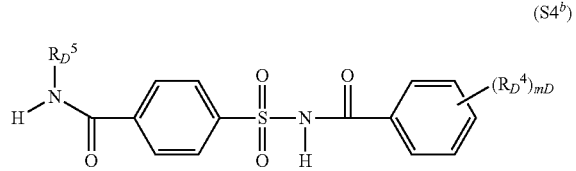

(S4$^b$)

for example those in which
R$_D^5$=cyclopropyl and (R$_D^4$)=2-OMe ("cyprosulfamide", S4-1),
R$_D^5$=cyclopropyl and (R$_D^4$)=5-Cl-2-OMe (S4-2),
R$_D^5$=ethyl and (R$_D^4$)=2-OMe (S4-3),
R$_D^5$=isopropyl and (R$_D^4$)=5-Cl-2-OMe (S4-4) and
R$_D^5$=isopropyl and (R$_D^4$)=2-OMe (S4-5)
and to compounds of the N-acylsulphamoylphenylurea type, of the formula (S4$^c$), which are known, for example, from EP-A-365484,

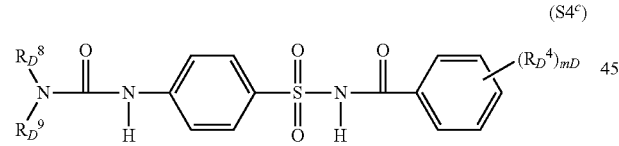

(S4$^c$)

in which
R$_D^8$ and R$_D^9$ are each independently hydrogen, (C$_1$-C$_8$)-alkyl, (C$_3$-C$_8$)-cycloalkyl, (C$_3$-C$_6$)-alkenyl, (C$_3$-C$_6$)-alkynyl,
R$_D^4$ is halogen, (C$_1$-C$_4$)-alkyl, (C$_1$-C$_4$)-alkoxy, CF$_3$,
m$_D$ is 1 or 2;
for example
1-[4-(N-2-methoxybenzoylsulphamoyl)phenyl]-3-methylurea, 1-[4-(N-2-methoxybenzoylsulphamoyl)phenyl]-3,3-dimethylurea, 1-[4-(N-4,5-dimethylbenzoylsulphamoyl)phenyl]-3-methylurea.
S5) Active compounds from the class of the hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.
S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydroquinoxalin-2-one, as described in WO-A-2005/112630.
S7) Compounds of the formula (S7), as described in WO-A-1998/38856,

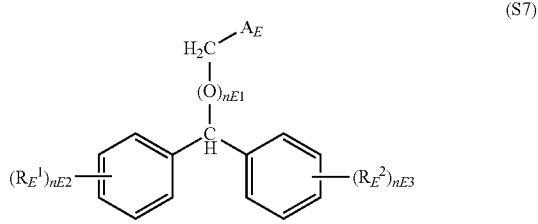

(S7)

where the symbols and indices have the following meanings:
R$_E^1$, R$_E^2$ are each independently halogen, (C$_1$-C$_4$)-alkyl, (C$_1$-C$_4$)-alkoxy, (C$_1$-C$_4$)-haloalkyl, (C$_1$-C$_4$)-alkylamino, di(C$_1$-C$_4$)-alkylamino, nitro;
A$_E$ is COOR$_E^3$ or COSR$_E^4$
R$_E^3$, R$_E^4$ are each independently hydrogen, (C$_1$-C$_4$)-alkyl, (C$_2$-C$_6$)-alkenyl, (C$_2$-C$_4$)-alkynyl, cyanoalkyl, (C$_1$-C$_4$)-haloalkyl, phenyl, nitrophenyl, benzyl, halobenzyl, pyridinylalkyl and alkylammonium,
n$_E^1$ is 0 or 1
n$_E^2$, n$_E^3$ are each independently of one another 0, 1 or 2,
preferably diphenylmethoxyacetic acid, ethyl diphenylmethoxyacetate, methyl diphenylmethoxyacetate (CAS reg. no. 41858-19-9) (S7-1).
S8) Compounds of the formula (S8), as described in WO-A-98/27049,

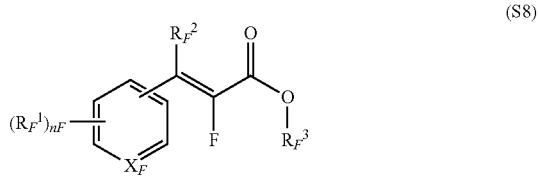

(S8)

in which
X$_F$ is CH or N,
n$_F$ in the case that X$_F$=N is an integer from 0 to 4 and
in the case that X$_F$=CH is an integer from 0 to 5,
R$_F^1$ is halogen, (C$_1$-C$_4$)-alkyl, (C$_1$-C$_4$)-haloalkyl, (C$_1$-C$_4$)-alkoxy, (C$_1$-C$_4$)-haloalkoxy, nitro, (C$_1$-C$_4$)-alkylthio, (C$_1$-C$_4$)-alkylsulphonyl, (C$_1$-C$_4$)-alkoxycarbonyl, optionally substituted phenyl, optionally substituted phenoxy,
R$_F^2$ is hydrogen or (C$_1$-C$_4$)alkyl
R$_F^3$ is hydrogen, (C$_1$-C$_8$)-alkyl, (C$_2$-C$_4$)-alkenyl, (C$_2$-C$_4$)-alkynyl, or aryl, where each of the aforementioned carbon-containing radicals is unsubstituted or substituted by one or more, preferably up to three identical or different radicals from the group consisting of halogen and alkoxy; or salts thereof,
preferably compounds in which
X$_F$ is CH,
n$_F$ is an integer from 0 to 2, $R_F^1$ is halogen, $(C_1-C_4)$-alkyl, $(C_1-C_4)$-haloalkyl, $(C_1-C_4)$-alkoxy, $(C_1-C_4)$-haloalkoxy,
$R_F^2$ is hydrogen or $(C_1-C_4)$-alkyl
$R_F^3$ is hydrogen, $(C_1-C_8)$-alkyl, $(C_2-C_4)$-alkenyl, $(C_2-C_4)$-alkynyl, or aryl, where each of the aforementioned carbon-containing radicals is unsubstituted or substituted by one or more, preferably up to three identical or different radicals from the group consisting of halogen and alkoxy,
or salts thereof.
S9) Active compounds from the class of the 3-(5-tetrazolylcarbonyl)-2-quinolones (S9), e.g. 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no.: 95855-00-8), as described in WO-A-1999/000020.
S10) Compounds of the formulae (S10$^a$) or (S10$^b$)
as described in WO-A-2007/023719 and WO-A-2007/023764, (S10$^a$)

(S10$^b$)

in which
$R_G^1$ is halogen, $(C_1-C_4)$-alkyl, methoxy, nitro, cyano, $CF_3$, $OCF_3$,
$Y_G$, $Z_G$ are each independently of one another O or S,
$n_G$ is an integer from 0 to 4,
$R_G^2$ is $(C_1-C_{16})$-alkyl, $(C_2-C_6)$-alkenyl, $(C_3-C_6)$-cycloalkyl, aryl; benzyl, halobenzyl,
$R_G^3$ is hydrogen or $(C_1-C_6)$-alkyl.
S11) Active compounds of the oxyimino compounds type (S11), which are known as seed-dressing compositions, for example "oxabetrinil" ((Z)-1,3-dioxolan-2-yl-methoxyimino(phenyl)acetonitrile) (S11-1), which is known as a seed-dressing safener for millet/sorghum, against damage by metolachlor, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against damage by metolachlor, and "cyometrinil" or "CGA-43089" ((Z)-cyanomethoxyimino(phenyl)acetonitrile) (S11-3), which is known as a seed-dressing safener for millet/sorghum against damage by metolachlor.
S12) Active compounds from the class of the isothiochromanones (S12), for example methyl[(3-oxo-1H-2-benzothiopyran-4(3H)-ylidene)methoxy]acetate (CAS reg. no. 205121-04-6) (S12-1) and related compounds from WO-A-1998/13361.
S13) One or more compounds from group (S13): "naphthalic anhydride" (1,8-naphthalenedicarboxylic anhydride) (S13-1), which is known as a seed-dressing safener for maize against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against damage by alachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for maize against damage by imidazolinones, "MG 191" (CAS reg. no. 96420-72-3) (2-dichloromethyl-2-methyl-1,3-dioxolane) (S13-5) from Nitrokemia, which is known as a safener for maize, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methylcarbamate) (S13-9).
S14) Active compounds which, in addition to herbicidal action against harmful plants, also have safener action on crop plants such as rice, for example "dimepiperate" or "MY-93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC-940" (3-(2-chlorophenylmethyl)-1-(1-methyl-1-phenylethyl)urea, see JP-A-60087254), which is known as a safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulphonyl)benzene) from Kumiai, (CAS reg. no. 54091-06-4), which is known as a safener against damage by some herbicides in rice.
S15) Compounds of the formula (S15) or tautomers thereof as described in WO-A-2008/131861 and WO-A-2008/131860

(S15)

in which
$R_H^1$ is a $(C_1-C_6)$-haloalkyl radical and
$R_H^2$ is hydrogen or halogen and
$R_H^3$, $R_H^4$ are each independently of one another hydrogen, $(C_1-C_{16})$-alkyl, $(C_2-C_{16})$-alkenyl or $(C_2-C_{16})$-alkynyl, where each of the latter 3 radicals is unsubstituted or substituted by one or more radicals from the group consisting of halogen, hydroxy, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl which is fused on one side of the ring to a 4- to 6-membered saturated or unsaturated carbocyclic ring, or $(C_4-C_6)$-cycloalkenyl which is fused on one side of the ring to a 4- to 6-membered saturated or unsaturated carbocyclic ring, where each of the latter 4 radicals is unsubstituted or substituted by one or more radicals from the group consisting of halogen, hydroxy, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-alkylamino, di[($C_1$-$C_4$)-alkyl]amino, [($C_1$-$C_4$)-alkoxy]carbonyl, [($C_1$-$C_4$)-haloalkoxy]carbonyl, ($C_3$-$C_6$)-cycloalkyl which is unsubstituted or substituted, phenyl which is unsubstituted or substituted, and heterocyclyl which is unsubstituted or substituted, or $R_H^3$ is ($C_1$-$C_4$)-alkoxy, ($C_2$-$C_4$)-alkenyloxy, ($C_2$-$C_6$)-alkynyloxy or ($C_2$-$C_4$)-haloalkoxy and $R_H^4$ is hydrogen or ($C_1$-$C_4$)-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy and ($C_1$-$C_4$)-alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Substances which Influence Plant Maturity:

Combination partners usable for the compounds of the general formula (I) in mixture formulations or in a tankmix are, for example, known active compounds based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

Examples of known substances which influence plant maturity and can be combined with the compounds of the general formula (I) include the active compounds which follow (the compounds are designated either by the "common name" according to the International Organization for Standardization (ISO) or by the chemical name or by the code number) and always use forms, such as acids, salts, esters and isomers, such as stereoisomers and optical isomers. In this case, one or else, in some cases, more than one use form is mentioned by way of example:

rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl (isopropylidene)aminooxyacetate, 2-(hexyloxy)-2-oxoethyl (isopropylidene) aminooxyacetate, 2-(isopropyloxy)-2-oxoethyl (cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol, sodium cycloprop-1-en-1-ylacetate, sodium cycloprop-2-en-1-ylacetate, sodium 3-(cycloprop-2-en-1-yl)propanoate, sodium 3-(cycloprop-1-en-1-yl)propanoate, jasmonic acid, methyl jasmonate, ethyl jasmonate.

Substances which influence plant health and germination:

Examples of combination partners usable for the compounds of the general formula (I) in mixture formulations or in a tankmix include known active compounds which influence plant health (the compounds are designated by the "common name" according to the International Organization for Standardization (ISO) or by the chemical name or by the code number and always encompass all use forms, such as acids, salts, esters and isomers, such as stereoisomers and optical isomers): sarcosine, phenylalanine, tryptophan, N'-methyl-1-phenyl-1-N,N-diethylaminomethanesulphonamide, apio-galacturonans as described in WO2010017956, 4-oxo-4-[(2-phenylethyl)amino]butanoic acid, 4-{([2-(1H-indol-3-yl)ethyl]amino}-4-oxobutanoic acid, 4-[(3-methylpyridin-2-yl)amino]-4-oxobutanoic acid, allantoin, 5-aminolevulic acid, (2S,3R)-2-(3,4-dihydroxyphenyl)-3,4-dihydro-2H-chromene-3,5,7-triol and structurally related catechols as described in WO2010122956, 2-hydroxy-4-(methylsulphanyl)butanoic acid, (3α,3βR,8αS)-3-({[(2R)-4-methyl-5-oxo-2,5-dihydrofuran-2-yl]oxy}methylene)-3,3α,4, 8b-tetrahydro-2H-indeno[1,2-b]furan-2-one and analogous lactones as described in EP2248421, abscisic acid, (2Z,4E)-5-[(1R,6R)-6-ethynyl-1-hydroxy-2,6-dimethyl-4-oxocyclohex-2-en-1-yl]-3-methylpenta-2,4-dienoic acid, methyl (2Z,4E)-5-[(1R,6R)-6-ethynyl-1-hydroxy-2,6-dimethyl-4-oxocyclohex-2-en-1-yl]-3-methylpenta-2,4-dienoate, 4-phenylbutyric acid, sodium 4-phenylbutanoate, potassium 4-phenylbutanoate.

Herbicides or Plant Growth Regulators:

Combination partners usable for the compounds of the general formula (I) in mixture formulations or in a tankmix are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 14th edition, The British Crop Protection Council and the Royal Soc. of Chemistry, 2006 and literature cited therein.

Examples of known herbicides or plant growth regulators which can be combined with compounds of the general formula (I) include the active compounds which follow (the compounds are designated by the "common name" according to the International Organization for Standardization (ISO) or by the chemical name or by the code number) and always encompass all use forms, such as acids, salts, esters and isomers, such as stereoisomers and optical isomers. In this case, one or else, in some cases, more than one application form is mentioned:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulphamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ephephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulphonamide, F-7967, i.e. 3-[7-chloro-5-fluoro-2-(trifluoromethyl)-1H-benzimidazol-4-yl]-1-methyl-6-(trifluoromethyl) pyrimidine-2,4(1H,3H)-dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. o-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopralin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulphate, monolinuron, monosulfuron, monosulfuron esters, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluoron, thiazopyr, thidiazimin, thidiazuron, thiencarbazone, thiencarbazone-methyl, thifensulfuron, thifensulfuron-methyl, thiobencarb, thiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

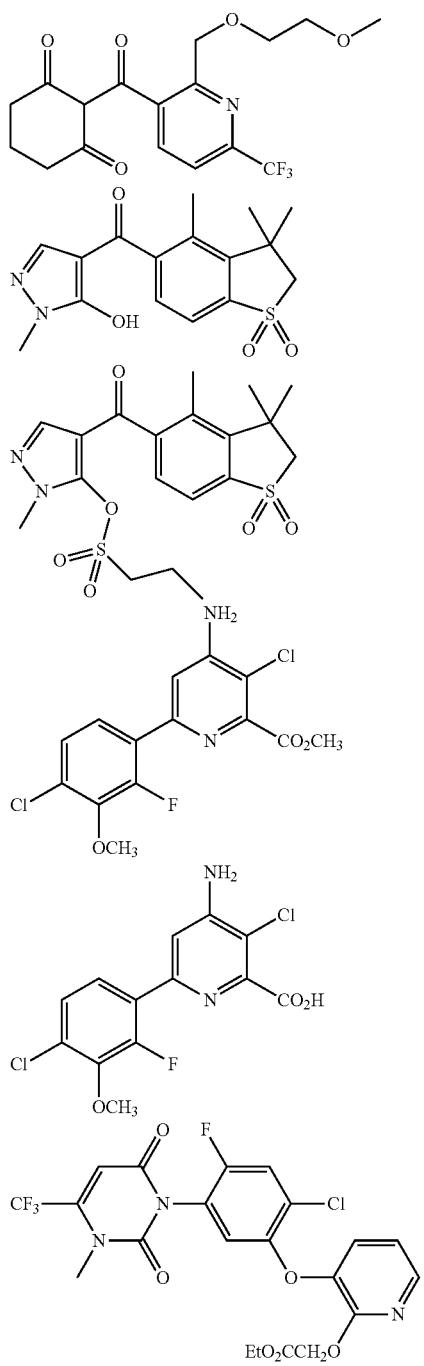

The invention is to be illustrated by the biological examples which follow, but without restricting it thereto.

Biological Examples

Seeds of monocotyledonous and dicotyledonous crop plants were laid out in sandy loam in wood-fiber pots, covered with soil and cultivated in a greenhouse under good growth conditions. The test plants were treated at the early leaf stage (BBCH10-BBCH13). To ensure uniform water supply before commencement of stress, the potted plants were supplied with the maximum amount of water immediately beforehand by dam irrigation and, after application, transferred into plastic inserts in order to prevent subsequent, excessively rapid drying. The compounds according to the invention, formulated in the form of wettable powders (WP), wettable granules (WG), suspension concentrates (SC) or emulsion concentrates (EC), were sprayed onto the green parts of the plants as an aqueous suspension at an equivalent water application rate of 600 I/ha with addition of 0.2% wetting agent (agrotin). Substance application is followed immediately by stress treatment of the plants (cold or drought stress). For cold stress treatment, the plants were kept under the following controlled conditions:

"day": 12 hours with illumination at 8° C.

"night": 12 hours without illumination at 1° C.

Drought stress was induced by gradual drying out under the following conditions:

"day": 14 hours with illumination at 26° C.

"night": 10 hours without illumination at 18° C.

The duration of the respective stress phases was guided mainly by the state of the untreated (=treated with blank formulation but without test compound), stressed control plants and thus varied from crop to crop. It was ended (by re-irrigating or transfer to a greenhouse with good growth conditions) as soon as irreversible damage was observed on the untreated, stressed control plants. In the case of dicotyledonous crops, for example oilseed rape and soybeans, the duration of the drought stress phase varied between 3 and 5 days; in the case of monocotyledonous crops, for example wheat, barley or maize, it varied between 6 and 10 days. The duration of the cold stress phase varied between 12 and 14 days.

The end of the stress phase was followed by an approx. 5-7-day recovery phase, during which the plants were once again kept under good growth conditions in a greenhouse. In order to rule out any influence of the effects observed by any fungicidal action of the test compounds, it was additionally ensured that the tests proceeded without fungal infection and without infection pressure.

After the recovery phase had ended, the intensities of damage were rated visually in comparison to untreated, unstressed controls of the same age (in the case of drought stress) or the same growth stage (in the case of cold stress). The intensity of damage was first recorded as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: Efficacy (%)

$DV_{us}$: damage value of the untreated, stressed control $DV_{ts}$: damage value of the plants treated with test compound The tables A-1 and B-1 to B-4 below list mean values in each case from three results of the same test.

Effects of selected compounds of the general formula (I) under cold stress using the example of ZEAMX:

TABLE A-1

| No. | Substance | Dosage | Unit | EF (ZEAMX) |
|---|---|---|---|---|
| 1 | I.1-197 | 250 | g/ha | >5 |
| 2 | I.2-21 | 500 | g/ha | >5 |
| 3 | I.2-23 | 500 | g/ha | >5 |
| 4 | I.5-52 | 250 | g/ha | >5 |
| 5 | I.9-32 | 25 | g/ha | >5 |

Effects of selected compounds of the general formula (I) under drought stress using the example of HORVS, BRSNS, ZEAMX and TRZAS:

TABLE B-1

| No. | Substance | Dosage | Unit | EF (HORVS) |
|---|---|---|---|---|
| 1 | I.1-176 | 500 | g/ha | >5 |
| 2 | I.1-179 | 500 | g/ha | >5 |
| 3 | I.1-183 | 500 | g/ha | >5 |
| 4 | I.1-184 | 50 | g/ha | >5 |
| 5 | I.1-218 | 50 | g/ha | >5 |
| 6 | I.2-17 | 100 | g/ha | >5 |
| 7 | I.2-21 | 500 | g/ha | >5 |
| 8 | I.2-53 | 1000 | g/ha | >5 |
| 9 | I.7-2 | 100 | g/ha | >5 |

TABLE B-2

| No. | Substance | Dosage | Unit | EF (BRSNS) |
|---|---|---|---|---|
| 1 | I.1-153 | 250 | g/ha | >5 |
| 2 | I.1-184 | 50 | g/ha | >5 |
| 3 | I.1-206 | 50 | g/ha | >5 |
| 4 | I.1-211 | 50 | g/ha | >5 |
| 5 | I.1-218 | 50 | g/ha | >5 |
| 6 | I.1-220 | 250 | g/ha | >5 |
| 7 | I.1-252 | 25 | g/ha | >5 |
| 8 | I.5-42 | 250 | g/ha | >5 |
| 9 | I.9-3 | 250 | g/ha | >5 |
| 10 | I.9-5 | 250 | g/ha | >5 |

TABLE B-3

| No. | Substance | Dosage | Unit | EF (ZEAMX) |
|---|---|---|---|---|
| 1 | I.1-153 | 25 | g/ha | >5 |
| 2 | I.1-155 | 25 | g/ha | >5 |
| 3 | I.1-175 | 500 | g/ha | >5 |
| 4 | I.1-176 | 500 | g/ha | >5 |
| 5 | I.1-183 | 500 | g/ha | >5 |
| 6 | I.1-184 | 50 | g/ha | >5 |
| 7 | I.1-205 | 500 | g/ha | >5 |
| 8 | I.1-206 | 50 | g/ha | >5 |
| 9 | I.1-207 | 500 | g/ha | >5 |
| 10 | I.1-211 | 500 | g/ha | >5 |
| 11 | I.1-218 | 50 | g/ha | >5 |
| 12 | I.1-220 | 25 | g/ha | >5 |
| 13 | I.1-224 | 500 | g/ha | >5 |
| 14 | I.2-14 | 250 | g/ha | >5 |
| 15 | I.2-22 | 50 | g/ha | >5 |
| 16 | I.2-30 | 500 | g/ha | >5 |
| 17 | I.3-8 | 25 | g/ha | >5 |
| 18 | I.5-42 | 10 | g/ha | >5 |
| 19 | I.7-15 | 250 | g/ha | >5 |
| 20 | I.7-18 | 500 | g/ha | >5 |

TABLE B-4

| No. | Substance | Dosage | Unit | EF (TRZAS) |
|---|---|---|---|---|
| 1 | I.1-252 | 25 | g/ha | >5 |
| 2 | I.3-8 | 25 | g/ha | >5 |
| 3 | I.9-3 | 250 | g/ha | >5 |
| 4 | I.9-20 | 25 | g/ha | >5 |

In the above tables:
BRSNS=*Brassica napus*
HORVS=*Hordeum vulgare*
TRZAS=*Triticum aestivum*
ZEAMX=*Zea mays*

Similar results were also achieved with further compounds of the general formula (I), also in the case of application to different plant species.

The invention claimed is:
1. A substituted isoquinolinone of formula (I) and/or a respective salt thereof

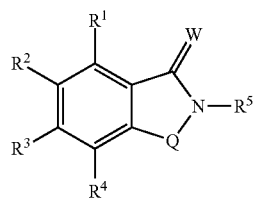

(I)

capable of being used for increasing tolerance to abiotic stress in a plant, where Q represents

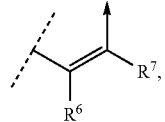

Q-1 where the arrow represents a bond to the group N—$R^5$,
W represents oxygen or sulphur,
$R^1$, $R^2$, and $R^3$ independently of one another represent hydrogen, nitro, amino, hydroxyl, cyano, alkyl, cycloalkyl, alkenyl, alkynyl, optionally halogen-, alkyl-, alkoxy-, or haloalkyl-substituted phenyl, arylalkyl, heteroaryl, cycloalkylalkyl, haloalkyl, alkoxyalkyl, alkoxy, haloalkoxy, cycloalkyloxy, arylalkoxy, alkoxycarbonyl, alkylthio, haloalkylthio, aryloxy, or aminoalkyl,
$R^4$ represents hydrogen, nitro, amino, hydroxyl, cyano, alkyl, cycloalkyl, alkenyl, alkynyl, arylalkyl, cycloalkylalkyl, haloalkyl, alkoxyalkyl, alkoxy, haloalkoxy, cycloalkyloxy, arylalkoxy, alkoxycarbonyl, alkylthio, haloalkylthio, heterocyclyl-N-alkoxy, aryloxy, or aminoalkyl,
$R^5$ represents hydrogen, hydroxyl, alkyl, cycloalkyl, halogen, haloalkyl, alkoxyalkyl, alkynyl, alkenyl, cycloalkylalkyl, cyanoalkyl, arylalkyl, heteroarylalkyl, aryl, alkylcarbonyl, cycloalkylcarbonyl, haloalkylcarbonyl, alkoxycarbonyl, alkylsulphonyl, arylsulphonyl, or a negative charge,
$R^6$ represents hydrogen, hydroxyl, halogen, amino, alkyl, cycloalkyl, alkylcarbonyl, arylcarbonyl, alkylaminocarbonyl, bisalkylaminocarbonyl, cycloalkylaminocarbonyl, arylaminocarbonyl, cyanoalkylaminocarbonyl, hydroxycarbonyl, alkoxycarbonyl, cycloalkyloxycarbonyl, cycloalkylalkoxycarbonyl, haloalkoxycarbonyl, arylaminocarbonylamino, alkylaminocarbonylamino, heteroarylaminocarbonylamino, alkoxy, alkylcarbonyloxy, arylcarbonyloxy, haloalkyl, alkoxyalkyl, alkynyl, alkenyl, aryl, heteroaryl, heterocyclyl, alkylamino, bisalkylamino, cycloalkylamino, or arylalkylamino, and $R^7$ represents hydrogen, halogen, amino, alkyl, haloalkyl, cycloalkyl, alkylcarbonyl, arylcarbonyl, heteroarylcarbonyl, cycloalkylcarbonyl, alkoxycarbonyl, hydroxycarbonyl, cycloalkylalkoxycarbonyl, alkylcarbonyloxy, arylaminocarbonyl, alkylaminocarbonyl, bisalkylaminocarbonyl, cycloalkylaminocarbonyl, cyanoalkylaminocarbonyl, alkylamino, arylamino, cycloalkylamino, or bisalkylamino.

2. A substituted isoquinolinone of formula (I) and/or a respective salt thereof, according to claim 1, where, in formula (I), Q represents

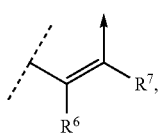

Q-1 where the arrow represents a bond to the group N—$R^5$, W represents oxygen or sulphur, $R^1$, $R^2$, and $R^3$ are each independently hydrogen, nitro, amino, hydroxyl, cyano, $(C_1-C_8)$-alkyl, $(C_3-C_8)$-cycloalkyl, $(C_2-C_8)$-alkenyl, $(C_2-C_8)$-alkynyl, optionally halogen-, $(C_1-C_8)$-alkyl-, $(C_1-C_8)$-alkoxy-, or $(C_1-C_7)$-haloalkyl-substituted phenyl, aryl-$(C_1-C_8)$-alkyl, heteroaryl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, aryloxy, or amino-$(C_1-C_8)$-alkyl, $R^4$ represents hydrogen, nitro, amino, hydroxyl, cyano, $(C_1-C_8)$-alkyl, $(C_3-C_8)$-cycloalkyl, $(C_2-C_8)$-alkenyl, $(C_2-C_8)$-alkynyl, aryl-$(C_1-C_8)$-alkyl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, heterocyclyl-N-alkoxy, aryloxy, or amino-$(C_1-C_8)$-alkyl, $R^5$ represents hydrogen, hydroxy, $(C_1-C_8)$-alkyl, $(C_3-C_8)$-cycloalkyl, halogen, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, $(C_3-C_8)$-cycloalkyl-$(C_1-C_8)$-alkyl, cyano-$(C_1-C_8)$-alkyl, aryl-$(C_1-C_8)$-alkyl, heteroaryl-$(C_1-C_8)$-alkyl, aryl, $(C_1-C_8)$-alkylcarbonyl, $(C_3-C_8)$-cycloalkylcarbonyl, $(C_1-C_8)$-haloalkylcarbonyl, $(C_1-C_8)$-alkoxycarbonyl, $(C_1-C_8)$-alkylsulphonyl, arylsulphonyl, or a negative charge, $R^6$ represents hydrogen, hydroxy, nitro, halogen, amino, $(C_1-C_8)$-alkyl, $(C_3-C_8)$-cycloalkyl, $(C_1-C_8)$-alkylcarbonyl, arylcarbonyl, $(C_1-C_8)$-alkylaminocarbonyl, bis-$(C_1-C_8)$-alkylaminocarbonyl, $(C_3-C_8)$-cycloalkylaminocarbonyl, arylaminocarbonyl, cyano-$(C_1-C_8)$-alkylaminocarbonyl, $(C_1-C_8)$-alkoxycarbonylamino, hydroxycarbonyl, $(C_1-C_8)$-alkoxycarbonyl, $(C_1-C_8)$-cycloalkoxycarbonyl, $(C_1-C_8)$-cycloalkyl-$(C_1-C_8)$-alkoxycarbonyl, $(C_1-C_8)$-haloalkoxycarbonyl, arylaminocarbonylamino, $(C_1-C_8)$-alkylaminocarbonylamino, heteroarylaminocarbonylamino, $(C_1-C_8)$-alkoxy, $(C_1-C_8)$-alkylcarbonyloxy, arylcarbonyloxy, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, aryl, heteroaryl, $(C_1-C_8)$-alkylamino, bis-$(C_1-C_8)$-alkylamino, $(C_3-C_8)$-cycloalkylamino, or aryl-$(C_1-C_8)$-alkylamino, and $R^7$ represents hydrogen, halogen, amino, $(C_1-C_8)$-alkyl, $(C_1-C_8)$-haloalkyl, $(C_3-C_8)$-cycloalkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, hydroxycarbonyl, $(C_3-C_8)$-cycloalkyl-$(C_1-C_8)$-alkoxycarbonyl, $(C_1-C_8)$-alkylcarbonyloxy, arylaminocarbonyl, $(C_1-C_8)$-alkylaminocarbonyl, bis-$(C_1-C_8)$-alkylaminocarbonyl, $(C_3-C_8)$-cycloalkylaminocarbonyl, cyano-$(C_1-C_8)$-alkylaminocarbonyl, $(C_1-C_8)$-alkylamino, arylamino, $(C_3-C_8)$-cycloalkylamino, or bis-$(C_1-C_8)$-alkylamino.

3. A substituted isoquinolinone of formula (I) and/or a respective salt thereof according to claim 1, where, in formula (I), Q represents

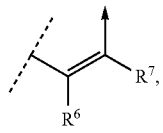

Q-1 where the arrow represents a bond to the group N—$R^5$, W represents oxygen or sulphur, $R^1$, $R^2$, and $R^3$ are each independently hydrogen, nitro, amino, hydroxyl, cyano, $(C_1-C_7)$-alkyl, $(C_3-C_7)$-cycloalkyl, $(C_2-C_7)$-alkenyl, $(C_2-C_7)$-alkynyl, optionally halogen-, $(C_1-C_8)$-alkyl-, $(C_1-C_8)$-alkoxy-, or $(C_1-C_7)$-haloalkyl-substituted phenyl, aryl-$(C_1-C_7)$-alkyl, $(C_3-C_7)$-cycloalkyl-$(C_1-C_7)$-alkyl, $(C_1-C_7)$-haloalkyl, $(C_1-C_7)$-alkoxy-$(C_1-C_7)$-alkyl, $(C_1-C_7)$-alkoxy, $(C_1-C_7)$-haloalkoxy, $(C_3-C_7)$-cycloalkyloxy, aryl-$(C_1-C_7)$-alkoxy, $(C_1-C_7)$-alkoxycarbonyl, $(C_1-C_7)$-alkylthio, $(C_1-C_7)$-haloalkylthio, or amino-$(C_1-C_7)$-alkyl, $R^4$ represents hydrogen, nitro, amino, hydroxyl, cyano, $(C_1-C_8)$-alkyl, $(C_3-C_8)$-cycloalkyl, $(C_2-C_8)$-alkenyl, $(C_2-C_8)$-alkynyl, aryl-$(C_1-C_8)$-alkyl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, heterocyclyl-N-alkoxy, aryloxy, or amino-$(C_1-C_8)$-alkyl, $R^5$ represents hydrogen, hydroxy, $(C_1-C_7)$-alkyl, $(C_3-C_7)$-cycloalkyl, halogen, $(C_1-C_7)$-haloalkyl, $(C_1-C_7)$-alkoxy-$(C_1-C_7)$-alkyl, $(C_2-C_7)$-alkynyl, $(C_2-C_7)$-alkenyl, $(C_3-C_7)$-cycloalkyl-$(C_1-C_7)$-alkyl, cyano-$(C_1-C_7)$-alkyl, aryl-$(C_1-C_7)$-alkyl, heteroaryl-$(C_1-C_7)$-alkyl, optionally substituted phenyl, $(C_1-C_7)$-alkylcarbonyl, $(C_3-C_7)$-cycloalkylcarbonyl, $(C_1-C_7)$-haloalkylcarbonyl, $(C_1-C_7)$-alkoxycarbonyl, $(C_1-C_7)$-alkylsulphonyl, arylsulphonyl, or a negative charge, $R^6$ represents hydrogen, hydroxy, nitro, halogen, amino, $(C_1-C_7)$-alkyl, $(C_3-C_7)$-cycloalkyl, $(C_1-C_7)$-alkylcarbonyl, arylcarbonyl, $(C_1-C_7)$-alkylaminocarbonyl, bis- ($C_1$-$C_7$)-alkylaminocarbonyl, ($C_3$-$C_7$)-cycloalkylaminocarbonyl, arylaminocarbonyl, cyano-($C_1$-$C_7$)-alkylaminocarbonyl, ($C_1$-$C_7$)-alkoxycarbonylamino, hydroxycarbonyl, ($C_1$-$C_7$)-alkoxycarbonyl, ($C_1$-$C_7$)-cycloalkoxycarbonyl, ($C_1$-$C_7$)-cycloalkyl-($C_1$-$C_7$)-alkoxycarbonyl, ($C_1$-$C_7$)-haloalkoxycarbonyl, arylaminocarbonylamino, ($C_1$-$C_7$)-alkylaminocarbonylamino, heteroarylaminocarbonylamino, ($C_1$-$C_7$)-alkoxy, ($C_1$-$C_7$)-alkylcarbonyloxy, arylcarbonyloxy, ($C_1$-$C_7$)-haloalkyl, ($C_1$-$C_7$)-alkoxy-($C_1$-$C_7$)-alkyl, ($C_2$-$C_7$)-alkynyl, ($C_2$-$C_7$)-alkenyl, optionally substituted phenyl, heteroaryl, ($C_1$-$C_7$)-alkylamino, bis-($C_1$-$C_7$)-alkylamino, ($C_3$-$C_7$)-cycloalkylamino, or aryl-($C_1$-$C_7$)-alkylamino, and $R^7$ represents hydrogen, halogen, amino, ($C_1$-$C_7$)-alkyl, ($C_1$-$C_7$)-haloalkyl, ($C_3$-$C_7$)-cycloalkyl, ($C_1$-$C_7$)-alkylcarbonyl, arylcarbonyl, heteroarylcarbonyl, ($C_3$-$C_7$)-cycloalkylcarbonyl, ($C_1$-$C_7$)-alkoxycarbonyl, hydroxycarbonyl, ($C_3$-$C_7$)-cycloalkyl-($C_1$-$C_7$)-alkoxycarbonyl, ($C_1$-$C_7$)-alkylcarbonyloxy, arylaminocarbonyl, ($C_1$-$C_7$)-alkylaminocarbonyl, bis-($C_1$-$C_7$)-alkylaminocarbonyl, ($C_3$-$C_7$)-cycloalkylaminocarbonyl, cyano-($C_1$-$C_7$)-alkylaminocarbonyl, ($C_1$-$C_7$)-alkylamino, arylamino, ($C_3$-$C_7$)-cycloalkylamino, or bis-($C_1$-$C_7$)-alkylamino.

4. A method of treatment for a plant comprising applying to a plant an effective nontoxic amount of at least one compound of formula (I) and/or a respective salt thereof

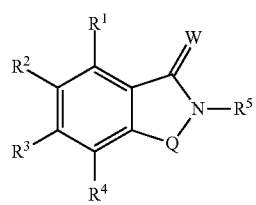

where
Q represents

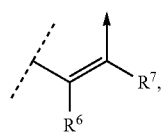

where the arrow represents a bond to the group N—$R^5$,
W represents oxygen or sulphur,
$R^1$, $R^2$, and $R^3$ independently of one another represent hydrogen, nitro, amino, hydroxyl, halogen, cyano, alkyl, cycloalkyl, alkenyl, alkynyl, optionally halogen-, alkyl-, alkoxy-, or haloalkyl-substituted phenyl, arylalkyl, heteroaryl, cycloalkylalkyl, haloalkyl, alkoxyalkyl, alkoxy, haloalkoxy, cycloalkyloxy, arylalkoxy, alkoxycarbonyl, alkylthio, haloalkylthio, aryloxy, or aminoalkyl,
$R^4$ represents hydrogen, nitro, amino, hydroxyl, halogen, cyano, alkyl, cycloalkyl, alkenyl, alkynyl, arylalkyl, cycloalkylalkyl, haloalkyl, alkoxyalkyl, alkoxy, haloalkoxy, cycloalkyloxy, arylalkoxy, alkoxycarbonyl, alkylthio, haloalkylthio, heterocyclyl-N-alkoxy, aryloxy, or aminoalkyl, $R^5$ represents hydrogen, hydroxyl, alkyl, cycloalkyl, halogen, haloalkyl, alkoxyalkyl, alkynyl, alkenyl, cycloalkylalkyl, cyanoalkyl, arylalkyl, heteroarylalkyl, aryl, alkylcarbonyl, cycloalkylcarbonyl, haloalkylcarbonyl, alkoxycarbonyl, alkylsulphonyl, arylsulphonyl, or a negative charge, $R^6$ represents hydrogen, hydroxyl, halogen, amino, alkyl, cycloalkyl, alkylcarbonyl, arylcarbonyl, alkylaminocarbonyl, bisalkylaminocarbonyl, cycloalkylaminocarbonyl, arylaminocarbonyl, cyanoalkylaminocarbonyl, hydroxycarbonyl, alkoxycarbonyl, cycloalkyloxycarbonyl, cycloalkylalkoxycarbonyl, haloalkoxycarbonyl, arylaminocarbonylamino, alkylaminocarbonylamino, heteroarylaminocarbonylamino, alkoxy, alkylcarbonyloxy, arylcarbonyloxy, haloalkyl, alkoxyalkyl, alkynyl, alkenyl, aryl, heteroaryl, heterocyclyl, alkylamino, bisalkylamino, cycloalkylamino, or arylalkylamino, and $R^7$ represents hydrogen, halogen, amino, alkyl, haloalkyl, cycloalkyl, alkylcarbonyl, arylcarbonyl, heteroarylcarbonyl, cycloalkylcarbonyl, alkoxycarbonyl, hydroxycarbonyl, cycloalkylalkoxycarbonyl, alkylcarbonyloxy, arylaminocarbonyl, alkylaminocarbonyl, bisalkylaminocarbonyl, cycloalkylaminocarbonyl, cyanoalkylaminocarbonyl, alkylamino, arylamino, cycloalkylamino, or bisalkylamino, to increase resistance of the plant to at least one abiotic stress factor.

5. A method of treatment according to claim 4, wherein the abiotic stress factor corresponds to at least one condition selected from the group consisting of drought, cold and hot conditions, aridity stress, osmotic stress, waterlogging, elevated soil salinity, elevated exposure to minerals, ozone conditions, strong light conditions, limited availability of nitrogen nutrients, and limited availability of phosphorus nutrients.

6. A compound of formula (I) and/or a respective salt thereof according to claim 1, capable of being used in spray application to a plant and/or a plant part in combination with at least one active compound selected from the group consisting of insecticides, attractants, acaricides, fungicides, nematicides, herbicides, growth regulators, safeners, substances which modulate a plant maturity and bactericides.

7. A compound of formula (I) and/or a respective salt thereof according to claim 1, capable of being used in spray application to a plant and/or a plant part in combination with a fertilizer.

8. A compound of formula (I) and/or a respective salt thereof according to claim 1 capable of being used for application to a genetically modified cultivar, a seed thereof, and/or to a cultivated area on which a cultivar grows.

9. A spray solution which comprises at least one compound of formula (I) and/or a respective salt thereof according to claim 1 capable of being used for enhancing resistance of a plant to an abiotic stress factor.

10. A method for increasing stress tolerance in a plant selected from the group of consisting of useful plants, ornamental plants, turfgrasses and trees, which comprises applying a sufficient, nontoxic amount of at least one compound of formula (I) and/or a respective salt thereof according to claim 1 to a plant, a seed thereof and/or to an area on which a plant grows.

11. The method according to claim 10, wherein resistance to abiotic stress of a plant thus treated is increased by at least 3% compared to an untreated plant under otherwise an identical physiological condition.

12. A substituted isoquinolinone of formula (I) and/or a respective salt thereof

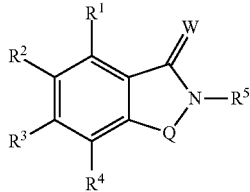

where
Q represents

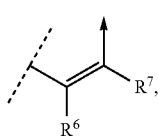

W represents oxygen, $R^1$ and $R^3$ are each independently hydrogen, halogen, cyano, $(C_1-C_7)$-alkyl, optionally substituted phenyl, $(C_1-C_7)$-alkoxy, $(C_1-C_7)$-haloalkoxy, $R^2$ represents phenyl optionally substituted with one or two halogen, $(C_1-C_8)$-alkyl, $(C_1-C_8)$-alkoxy, or $(C_1-C_7)$-haloalkyl, $R^4$ represents hydrogen, halogen, cyano, or $(C_1-C_8)$-haloalkoxy, $R^5$ represents hydrogen, $(C_1-C_7)$-alkyl, or a negative charge, $R^6$ represents hydrogen, hydroxy, $(C_1-C_7)$-alkyl, $(C_1-C_7)$-alkylaminocarbonyl, $(C_1-C_7)$-alkoxycarbonyl, $(C_1-C_7)$-cycloalkoxycarbonyl, $(C_1-C_7)$-alkoxy, or optionally substituted phenyl, and $R^7$ represents hydrogen, $(C_1-C_7)$-alkyl, $(C_1-C_7)$-alkylcarbonyl, or $(C_3-C_7)$-cycloalkylcarbonyl.

13. A substituted isoquinolinone of the formula

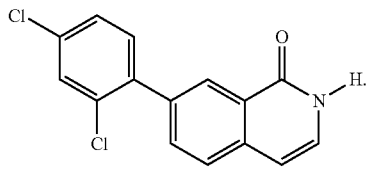

14. A method of treatment according to claim 4, wherein, in formula (I),
Q represents

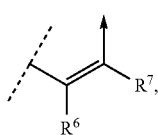

where the arrow represents a bond to the group N—$R^5$,
W represents oxygen or sulphur, $R^1$, $R^2$, and $R^3$ are each independently hydrogen, nitro, amino, hydroxyl, halogen, cyano, $(C_1-C_8)$-alkyl, $(C_3-C_8)$-cycloalkyl, $(C_2-C_8)$-alkenyl, $(C_2-C_8)$-alkynyl, optionally halogen-, $(C_1-C_8)$-alkyl-, $(C_1-C_8)$-alkoxy-, or $(C_1-C_7)$-haloalkyl-substituted phenyl, aryl-$(C_1-C_8)$-alkyl, heteroaryl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, aryloxy, or amino-$(C_1-C_8)$-alkyl, $R^4$ represents hydrogen, nitro, amino, hydroxyl, halogen, cyano, $(C_1-C_8)$-alkyl, $(C_3-C_8)$-cycloalkyl, $(C_2-C_8)$-alkenyl, $(C_2-C_8)$-alkynyl, aryl-$(C_1-C_8)$-alkyl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, heterocyclyl-N-alkoxy, aryloxy, or amino-$(C_1-C_8)$-alkyl, $R^5$ represents hydrogen, hydroxy, $(C_1-C_8)$-alkyl, $(C_3-C_8)$-cycloalkyl, halogen, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, $(C_3-C_8)$-cycloalkyl-$(C_1-C_8)$-alkyl, cyano-$(C_1-C_8)$-alkyl, aryl-$(C_1-C_8)$-alkyl, heteroaryl-$(C_1-C_8)$-alkyl, aryl, $(C_1-C_8)$-alkylcarbonyl, $(C_3-C_8)$-cycloalkylcarbonyl, $(C_1-C_8)$-haloalkylcarbonyl, $(C_1-C_8)$-alkoxycarbonyl, $(C_1-C_8)$-alkylsulphonyl, arylsulphonyl, or a negative charge, $R^6$ represents hydrogen, hydroxy, nitro, halogen, amino, $(C_1-C_8)$-alkyl, $(C_3-C_8)$-cycloalkyl, $(C_1-C_8)$-alkylcarbonyl, arylcarbonyl, $(C_1-C_8)$-alkylaminocarbonyl, bis-$(C_1-C_8)$-alkylaminocarbonyl, $(C_3-C_8)$-cycloalkylaminocarbonyl, arylaminocarbonyl, cyano-$(C_1-C_8)$-alkylaminocarbonyl, $(C_1-C_8)$-alkoxycarbonylamino, hydroxycarbonyl, $(C_1-C_8)$-alkoxycarbonyl, $(C_1-C_8)$-cycloalkoxycarbonyl, $(C_1-C_8)$-cycloalkyl-$(C_1-C_8)$-alkoxycarbonyl, $(C_1-C_8)$-haloalkoxycarbonyl, arylaminocarbonylamino, $(C_1-C_8)$-alkylaminocarbonylamino, heteroarylaminocarbonylamino, $(C_1-C_8)$-alkoxy, $(C_1-C_8)$-alkylcarbonyloxy, arylcarbonyloxy, $(C_1-C_8)$-haloalkyl, $(C_1-C_8)$-alkoxy-$(C_1-C_8)$-alkyl, $(C_2-C_8)$-alkynyl, $(C_2-C_8)$-alkenyl, aryl, heteroaryl, $(C_1-C_8)$-alkylamino, bis-$(C_1-C_8)$-alkylamino, $(C_3-C_8)$-cycloalkylamino, or aryl-$(C_1-C_8)$-alkylamino, and $R^7$ represents hydrogen, halogen, amino, $(C_1-C_8)$-alkyl, $(C_1-C_8)$-haloalkyl, $(C_3-C_8)$-cycloalkyl, $(C_1-C_8)$-alkylcarbonyl, arylcarbonyl, heteroarylcarbonyl, $(C_3-C_8)$-cycloalkylcarbonyl, $(C_1-C_8)$-alkoxycarbonyl, hydroxycarbonyl, $(C_3-C_8)$-cycloalkyl-$(C_1-C_8)$-alkoxycarbonyl, $(C_1-C_8)$-alkylcarbonyloxy, arylaminocarbonyl, $(C_1-C_8)$-alkylaminocarbonyl, bis-$(C_1-C_8)$-alkylaminocarbonyl, $(C_3-C_8)$-cycloalkylaminocarbonyl, cyano-$(C_1-C_8)$-alkylaminocarbonyl, $(C_1-C_8)$-alkylamino, arylamino, $(C_3-C_8)$-cycloalkylamino, or bis-$(C_1-C_8)$-alkylamino.

15. A method of treatment according to claim 4, wherein, in formula (I),

Q represents

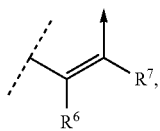

Q-1 where the arrow represents a bond to the group N—$R^5$,

W represents oxygen or sulphur, $R^1$, $R^2$, and $R^3$ are each independently hydrogen, nitro, amino, hydroxyl, halogen, cyano, $(C_1-C_7)$-alkyl, $(C_3-C_7)$-cycloalkyl, $(C_2-C_7)$-alkenyl, $(C_2-C_7)$-alkynyl, optionally halogen-, $(C_1-C_8)$-alkyl-, $(C_1-C_8)$-alkoxy-, or $(C_1-C_7)$-haloalkyl-substituted phenyl, aryl-$(C_1-C_7)$-alkyl, $(C_3-C_7)$-cycloalkyl-$(C_1-C_7)$-alkyl, $(C_1-C_7)$-haloalkyl, $(C_1-C_7)$-alkoxy-$(C_1-C_7)$-alkyl, $(C_1-C_7)$-alkoxy, $(C_1-C_7)$-haloalkoxy, $(C_3-C_7)$-cycloalkyloxy, aryl-$(C_1-C_7)$-alkoxy, $(C_1-C_7)$-alkoxycarbonyl, $(C_1-C_7)$-alkylthio, $(C_1-C_7)$-haloalkylthio, or amino-$(C_1-C_7)$-alkyl, $R^4$ represents hydrogen, nitro, amino, hydroxyl, halogen, cyano, $(C_1-C_8)$-alkyl, $(C_3-C_8)$-cycloalkyl, $(C_2-C_8)$-alkenyl, $(C_2-C_8)$-alkynyl, aryl-$(C_1-C_8)$-alkyl, $(C_3-C_8)$-cycloalkyl-$(C_1-C_8)$-alkyl, $(C_1-C_8)$-haloalkyl, $(C_1-C_8)$-alkoxy-$(C_1-C_8)$-alkyl, $(C_1-C_8)$-alkoxy, $(C_1-C_8)$-haloalkoxy, $(C_3-C_8)$-cycloalkyloxy, aryl-$(C_1-C_8)$-alkoxy, $(C_1-C_8)$-alkoxycarbonyl, $(C_1-C_8)$-alkylthio, $(C_1-C_8)$-haloalkylthio, heterocyclyl-N-alkoxy, aryloxy, or amino-$(C_1-C_8)$-alkyl, $R^5$ represents hydrogen, hydroxy, $(C_1-C_7)$-alkyl, $(C_3-C_7)$-cycloalkyl, halogen, $(C_1-C_7)$-haloalkyl, $(C_1-C_7)$-alkoxy-$(C_1-C_7)$-alkyl, $(C_2-C_7)$-alkynyl, $(C_2-C_7)$-alkenyl, $(C_3-C_7)$-cycloalkyl-$(C_1-C_7)$-alkyl, cyano-$(C_1-C_7)$-alkyl, aryl-$(C_1-C_7)$-alkyl, heteroaryl-$(C_1-C_7)$-alkyl, optionally substituted phenyl, $(C_1-C_7)$-alkylcarbonyl, $(C_3-C_7)$-cycloalkylcarbonyl, $(C_1-C_7)$-haloalkylcarbonyl, $(C_1-C_7)$-alkoxycarbonyl, $(C_1-C_7)$-alkylsulphonyl, arylsulphonyl, or a negative charge, $R^6$ represents hydrogen, hydroxy, nitro, halogen, amino, $(C_1-C_7)$-alkyl, $(C_3-C_7)$-cycloalkyl, $(C_1-C_7)$-alkylcarbonyl, arylcarbonyl, $(C_1-C_7)$-alkylaminocarbonyl, bis-$(C_1-C_7)$-alkylaminocarbonyl, $(C_3-C_7)$-cycloalkylaminocarbonyl, arylaminocarbonyl, cyano-$(C_1-C_7)$-alkylaminocarbonyl, $(C_1-C_7)$-alkoxycarbonylamino, hydroxycarbonyl, $(C_1-C_7)$-alkoxycarbonyl, $(C_1-C_7)$-cycloalkoxycarbonyl, $(C_1-C_7)$-cycloalkyl-$(C_1-C_7)$-alkoxycarbonyl, $(C_1-C_7)$-haloalkoxycarbonyl, arylaminocarbonylamino, $(C_1-C_7)$-alkylaminocarbonylamino, heteroarylaminocarbonylamino, $(C_1-C_7)$-alkoxy, $(C_1-C_7)$-alkylcarbonyloxy, arylcarbonyloxy, $(C_1-C_7)$-haloalkyl, $(C_1-C_7)$-alkoxy-$(C_1-C_7)$-alkyl, $(C_2-C_7)$-alkynyl, $(C_2-C_7)$-alkenyl, optionally substituted phenyl, heteroaryl, $(C_1-C_7)$-alkylamino, bis-$(C_1-C_7)$-alkylamino, $(C_3-C_7)$-cycloalkylamino, or aryl-$(C_1-C_7)$-alkylamino, and $R^7$ represents hydrogen, halogen, amino, $(C_1-C_7)$-alkyl, $(C_1-C_7)$-haloalkyl, $(C_3-C_7)$-cycloalkyl, $(C_1-C_7)$-alkylcarbonyl, arylcarbonyl, heteroarylcarbonyl, $(C_3-C_7)$-cycloalkylcarbonyl, $(C_1-C_7)$-alkoxycarbonyl, hydroxycarbonyl, $(C_3-C_7)$-cycloalkyl-$(C_1-C_7)$-alkoxycarbonyl, $(C_1-C_7)$-alkylcarbonyloxy, arylaminocarbonyl, $(C_1-C_7)$-alkylaminocarbonyl, bis-$(C_1-C_7)$-alkylaminocarbonyl, $(C_3-C_7)$-cycloalkylaminocarbonyl, cyano-$(C_1-C_7)$-alkylaminocarbonyl, $(C_1-C_7)$-alkylamino, arylamino, $(C_3-C_7)$-cycloalkylamino, or bis-$(C_1-C_7)$-alkylamino.

* * * * *